(12) United States Patent
Pastural et al.

(10) Patent No.: US 10,024,857 B2
(45) Date of Patent: Jul. 17, 2018

(54) SERUM-BASED BIOMARKERS OF PANCREATIC CANCER AND USES THEREOF FOR DISEASE DETECTION AND DIAGNOSIS

(75) Inventors: Elodie Pastural, Saskatoon (CA); Shawn Ritchie, Saskatoon (CA)

(73) Assignee: MED-LIFE DISCOVERIES LP, Saskatoon, Saskatchewan (CA)

( * ) Notice: Subject to any disclaimer, the term of this patent is extended or adjusted under 35 U.S.C. 154(b) by 812 days.

(21) Appl. No.: 13/499,369

(22) PCT Filed: Oct. 1, 2010

(86) PCT No.: PCT/CA2010/001565
§ 371 (c)(1),
(2), (4) Date: Mar. 30, 2012

(87) PCT Pub. No.: WO2011/038509
PCT Pub. Date: Apr. 7, 2011

(65) Prior Publication Data
US 2012/0202188 A1    Aug. 9, 2012

Related U.S. Application Data

(60) Provisional application No. 61/247,828, filed on Oct. 1, 2009.

(51) Int. Cl.
*G01N 24/00* (2006.01)
*G01N 33/574* (2006.01)
*G01N 33/92* (2006.01)

(52) U.S. Cl.
CPC ....... *G01N 33/57438* (2013.01); *G01N 33/92* (2013.01); *G01N 2405/04* (2013.01); *Y10T 436/163333* (2015.01)

(58) Field of Classification Search
CPC ........... C12Q 1/6886; C12Q 2600/118; G01N 33/57438; G01N 2800/52; G01N 33/574;
(Continued)

(56) References Cited

U.S. PATENT DOCUMENTS 7,349,809 B2    3/2008   Goodenowe
2009/0004671 A1   1/2009   Yamada et al.

FOREIGN PATENT DOCUMENTS

CA    2525740 A1    11/2004
CA    2619732 A1    3/2007
(Continued)

OTHER PUBLICATIONS

Fang et al. in "Discrimination of metabolic profiles of pancreatic cancer from chronic pancreatitis by high-resolution magic angle spinning 1H nuclear magnetic resonance and principal components analysis", Cancer Sci., 2007, v. 98, No. 11, pp. 1678-1682.*
(Continued)

*Primary Examiner* — Robert R Xu
(74) *Attorney, Agent, or Firm* — LeClairRyan PLLC

(57) ABSTRACT

Biomarkers of pancreatic cancer are described, as well as methods using these compounds for detecting pancreatic cancer. The methods can be used to diagnose a patient's health state, or change in health state, or for diagnosing risk of developing or the presence of pancreatic cancer. The method comprises analyzing a sample from a patient to obtain quantifying data for one or more than one of the metabolite markers; comparing the quantifying data to corresponding data obtained for one or more than one reference sample to identify abnormalities in the level of the metabolite marker(s) in the sample; and making a diagnosis if an abnormality is observed. Standards and kits for carrying out the method are also described.

8 Claims, 73 Drawing Sheets

(58) Field of Classification Search
CPC ....... G01N 33/57407; G01N 33/57484; G01N 33/6893; G01N 33/57488; G01N 33/6848; G01N 33/6851; G01N 2800/50; G01N 2201/1293
See application file for complete search history.

(56) References Cited

FOREIGN PATENT DOCUMENTS

| | | |
|---|---|---|
| CA | 2676109 A1 | 8/2008 |
| EP | 2770328 A3 | 8/2014 |
| WO | 98/43093 A1 | 10/1998 |
| WO | 2001057518 A2 | 8/2001 |
| WO | 2004/102189 A1 | 11/2004 |
| WO | 2006/044680 A1 | 4/2006 |
| WO | 2006/098087 A1 | 9/2006 |
| WO | 2007030928 A2 | 3/2007 |
| WO | 2007030948 A1 | 3/2007 |
| WO | 2007/062142 A2 | 5/2007 |
| WO | 2007098585 A1 | 9/2007 |
| WO | 2007/109881 A1 | 10/2007 |
| WO | 2007137410 A1 | 12/2007 |
| WO | 2008092280 A1 | 8/2008 |
| WO | 2008095275 A1 | 8/2008 |
| WO | 2008124916 A1 | 10/2008 |
| WO | 2009012595 A1 | 1/2009 |
| WO | 2009061404 A1 | 5/2009 |
| WO | 2009/088022 A1 | 7/2009 |
| WO | 2009/151967 A1 | 12/2009 |
| WO | 2010071988 A1 | 7/2010 |
| WO | 2011011882 A1 | 2/2011 |

OTHER PUBLICATIONS

Chen et al. "Proteomic Profiling of Pancreatic Cancer for Biomarker Discovery", Molecular & Cellular Proteomics, 2005, v. 4.4, pp. 523-533.*
Ritchie et al. "Metabolic system alterations in pancreatic cancer patient serum: potential for early detection", BMC Cancer 2013, 13:416, pp. 1-17.*
Ritchie et al. "Pancreatic cancer serum biomarker PC-594: Diagnostic performance and comparison to CA19-9", World J Gastroenterol 2015 Jun. 7; v. 21, no. 2, pp. 6604-6612.*
Ehmann et al., "Identification of Potential Markers for the Detection of Pancreatic Cancer through Comparative Serum Protein Expression Profiling," Pancreas 34(2):205-207 (2007).
Garcea et al., "Molecular Prognostic Markers in Pancreatic Cancer: A Systematic Review," Euro. J. Cancer 41:2213-2236 (2005).
Helmstaedter et al., "Pancreatic Cancer—EUS and Early Diagnosis," Langenbecks Arch. Surg. 393:923-927.
Khan et al., "Proton and Phosphorus-31 Nuclear Magnetic Resonance Spectroscopy of Human Bile in Hepatopancreaticobiliary Cancer," Eur. J. Gastroenterol. Hepatol. 17:733-738 (2005).
Peracaula et al., "Altered Glycosylation in Tumours Focused to Cancer Diagnosis," Disease Markers 25:207-218 (2008).
Szafranska et al., "MicroRNA Expression Alterations are Linked to Tumorigenesis and Non-Neoplasitc Processes in Pancreatic Ductal Adenocarcinoma," Oncogene 26:4442-4452 (2007).
Trougakos et al., "Clusterin/Apolipoprotein J in Human Aging and Cancer," Internat. J. Biochem. Cell Biol. 34:1430-1448 (2002).
Zuijdgeest-Van Leeuwen et al., "Fatty Acid Composition of Plasma Lipids in Patients with Pancreatic, Lung and Oesophageal Cancer in Comparison with Healthy Subjects," Clinical Nutrition 21(3):225-230 (2002).
Gemmel et al., "Pancreatic Cancer Screening: State of the Art," Exp. Rev. Gastroenterol. Hepatol. 3(1):89(8) (2009).
Boyle et al., "Cancer Incidence and Mortality in Europe, 2004," Annals Oncol. 16:481-488 (2005).
Miskiewicz et al., "Salivary Markers and Periodontal Symptoms in Pancreatic Cancer," Gastroenterol. Polska 18(3):115-119(2011).

Klapman et al., "Early Detection of Pancreatic Cancer: Why, Who, and How to Screen," Cancer Control 15(4):280-287 (2008).
Barrabes et al., "Glycosylation of Serum Ribonuclease 1 Indicates a Major Endothelial Origin and Reveals an Increase in Core Fucosylation in Pancreatic Cancer," Glycobiol. 17(4):388-400 (2007).
Koopman et al., "Serum Markers in Patients with Resectable Pancreatic Adenocarcinoma: Macrophage Inhibitory Cytokine 1 Versus CA19-9," Clin. Cancer Res. 12:442-446 (2006).
Rosty et al., "Identification of Hepatocarcinoma-Intestine-Pancreas/Pancreatitis-Associated Protein I as a Biomarker for Pancreatic Ductal Adenocarcinoma by Protein Biochip Technology," Cancer Res. 62:1868-1875 (2002).
Janardhan et al., "Choline Kinase: An Important Target for Cancer," Curr. Med. Chem. 13:1169-1186 (2006).
Bloomston et al., "MicroRNA Expression Patterns to Differentiate Pancreatic Adenocarcinoma from Normal Pancreas and Chronic Pancreatitis," JAMA 297(17):1901-1908 (2007).
Lee et al., "Expression Profiling Identifies MicroRNA Signature in Pancreatic Cancer," Int. J. Cancer 120(5):1046-1054 (2007).
Tian et al., "Proteomic Analysis Identifies MMP-9, DJ-I and AIBG as Overexpressed Proteins in Pancreatic Juice from Pancreatic Ductal Adenocarcinoma Patients," BMC Cancer 8:241-252 (2008).
Warden et al., "Evidence for Linkage of the Apolipoprotein A-II Locus to Plasma Apolipoprotein A-II and Free Fatty Acid Levels in Mice and Humans," Proc. Nat. Acad. Sci. U.S.A. 90:10886-10890 (1993).
Kolb et al., "Glucagon/Insulin Ratio as a Potential Biomarker for Pancreatic Cancer in Patients with New-Onset Diabetes Mellitus," Cancer Biol. Ther. 8(16):1527-1533 (2009).
Valerio et al. "Serum Protein Profiles of Patients with Pancreatic Cancer and Chronic Pancreatitis: Searching for a Diagnostic Protein Pattern," Rapid Comm. Mass Spectrom. 15:2420-2425 (2001).
Bhattacharyya et al. "Diagnosis of Pancreatic Cancer using Serum Proteomic Profiling," Neoplasia 6(5):674-686 (2004).
Honda et al. "Possible Detection of Pancreatic Cancer by Plasma Protein Profiling," Cancer Res. 65:10613-10622 (2005).
Ge et al. "Classification of Premalignant Pancreatic Cancer Mass-spectrometry Data using Decision Tree Ensembles," BMC Bioinformatics 9:275-286 (2008).
Conrads et al. "Cancer Diagnosis using Proteomic Patterns," Expert Rev. Mol. Diagn. 3(4):411-420 (2003).
Rao et al. "Lipid Composition and 3-hydroxy-3-methylglutaryl-CoA Reductase Activity of Acinar Cell Carcinoma of Rat Pancreas." Biochimica et Biophysica Acta 759:74-80 (1983).
Pawa et al. "Mass Spectrometry Based Proteomic Profiling for Pancreatic Cancer," J. Pancreas 11(5):423-426 (2010).
International Search Report for PCT/CA2010/001565 (dated Jan. 17, 2011).
International Written Opinion for PCT/CA2010/001565 (dated Jan. 17, 2011).
Hsu et al., "Electrospray Ionization with Low-Energy Collisionally Activated Dissociation Tandem Mass Spectrometry of Glycerophospholipids: Mechanisms of Fragmentation and Structural Characterization," J. Chromatog. B: Biomed. Sci. Appl. 877(26):2673-2695 (2009).
Misek et al., "Early Detection and Biomarkers in Pancreatic Cancer," J. Nat. Comp. Cancer Net. 5(10):1034-1041 (2007).
Supplemental European Search Report for corresponding EP 10819788, dated Feb. 15, 2013.
EPO Communication for EP Application No. 14164872.5, dated Jun. 29, 2016.
Beger et al., "Metabonomic Models of Human Pancreatic Cancer Using 1D Proton NMR Spectra of Lipids in Plasma," Metabolomics 2(3):125-134 (2006).
Micromass Quattro Micro LC/MS/MS Triple Quadrupole Mass Spectrometer—IET, http://ietltd.com/mass-spectrometers/quatro-micro/ (printed Mar. 3, 2015).
Pesticide Waste Analysis Laboratory, University Institute of Pesticides and Water Resources, http://www.uji.es/UK/serveis/iupa/larp/ins.html (printed Mar. 3, 2015).
Sugimoto et al., "Capillary Electrophoresis Mass Spectrometry-Based Saliva Metabolomics Identified Oral, Breast and Pancreatic Cancer-Specific Profiles," Metabolomics 6:78-95 (2010).

(56) References Cited

OTHER PUBLICATIONS

Urayama et al., "Comprehensive Mass Spectrometry Based Metabolic Profiling of Blood Plasma Reveals Potent Discriminatory Classifiers of Pancreatic Cancer," Rapid Communications in Mass Spectrometry 24:613-620 (2010).
Opposition Decision in EP 10819788.0 (dated Oct. 26, 2016).

* cited by examiner a)

b)

(a)

(b)

(c)

(d)

(e)

(f)

(a)

(b)

| Classification Table | | | | | | | | |
|---|---|---|---|---|---|---|---|---|
| Prob Level | Correct | | Incorrect | | Percentages | | | |
| | Non-Event | Event | Non-Event | Event | Correct | Sensi-tivity | Speci-ficity | FALSE | FALSE NEG |
| 0.05 | 38 | 36 | 14 | 2 | 82.2 | 95 | 72 | 26.9 | 5.3 |
| 0.1 | 38 | 40 | 10 | 2 | 86.7 | 95 | 80 | 20.8 | 4.8 |
| 0.15 | 38 | 41 | 9 | 2 | 87.8 | 95 | 82 | 19.1 | 4.7 |
| 0.2 | 38 | 42 | 8 | 2 | 88.9 | 95 | 84 | 17.4 | 4.5 |
| 0.25 | 38 | 42 | 8 | 2 | 88.9 | 95 | 84 | 17.4 | 4.5 |
| 0.3 | 38 | 42 | 8 | 2 | 88.9 | 95 | 84 | 17.4 | 4.5 |
| 0.35 | 38 | 42 | 8 | 2 | 88.9 | 95 | 84 | 17.4 | 4.5 |
| 0.4 | 37 | 43 | 7 | 3 | 88.9 | 92.5 | 86 | 15.9 | 6.5 |
| 0.45 | 37 | 43 | 7 | 3 | 88.9 | 92.5 | 86 | 15.9 | 6.5 |
| 0.5 | 37 | 44 | 6 | 3 | 90 | 92.5 | 88 | 14 | 6.4 |
| 0.55 | 36 | 44 | 6 | 4 | 88.9 | 90 | 88 | 14.3 | 8.3 |
| 0.6 | 34 | 45 | 5 | 6 | 87.8 | 85 | 90 | 12.8 | 11.8 |
| 0.65 | 34 | 45 | 5 | 6 | 87.8 | 85 | 90 | 12.8 | 11.8 |
| 0.7 | 33 | 46 | 4 | 7 | 87.8 | 82.5 | 92 | 10.8 | 13.2 |
| 0.75 | 33 | 48 | 2 | 7 | 90 | 82.5 | 96 | 5.7 | 12.7 |
| 0.8 | 33 | 48 | 2 | 7 | 90 | 82.5 | 96 | 5.7 | 12.7 |
| 0.85 | 31 | 48 | 2 | 9 | 87.8 | 77.5 | 96 | 6.1 | 15.8 |
| 0.9 | 28 | 48 | 2 | 12 | 84.4 | 70 | 96 | 6.7 | 20 |
| 0.95 | 25 | 49 | 1 | 15 | 82.2 | 62.5 | 98 | 3.8 | 23.4 |
| 1 | 0 | 50 | 0 | 40 | 55.6 | 0 | 100 | . | 44.4 |

(a)

(b)

(a)

(b)

(a)

(b)

(c)

(d)

(c)

(a)

(b)

(a)

(b)

(b)

(a)

(b)

(c)

(a)

(b)

(c)

(d)

a)

c)

(a)

(b)

(c)

(d)

(a)

(b)

(c)

(d)

SERUM-BASED BIOMARKERS OF PANCREATIC CANCER AND USES THEREOF FOR DISEASE DETECTION AND DIAGNOSIS

This application is a national stage application under 35 U.S.C. § 371 from PCT Application No. PCT/CA2010/001565, filed Oct. 1, 2010, which claims the priority benefit of U.S. Provisional Application No. 61/247,828, filed Oct. 1, 2009.

FIELD OF INVENTION

The present invention relates to biomarkers and methods of detecting diseases and physiological conditions. More specifically, the invention relates to biomarkers of pancreatic cancer and methods using these compounds for detecting diseases and physiological conditions, especially pancreatic cancer.

BACKGROUND OF THE INVENTION

The incidence of pancreatic cancer has increased during the past decades throughout the world, and ranks as the fourth and sixth leading causes of cancer in North America and the European Union respectively (1). This high rank is due to a very poor overall survival (OS) rate (less than 4%), which is illustrated by an annual incidence rate of pancreatic cancer almost identical to the mortality rate. In Canada for example, 3800 new cases were expected to be diagnosed in 2008 with 3700 anticipated deaths from this cancer.

Diagnosis is difficult because there are no noticeable symptoms in early stages, and signs are common with many other illnesses. Furthermore, pancreas location behind other organs renders its imaging more difficult. Diagnosis is usually performed when cancer has already disseminated to other organs. In combination with this late detection, pancreatic cancer displays a poor response to chemotherapy, radiation therapy, and surgery as conventionally used. For patients with advanced pancreatic cancer, the OS rate is less than 1% at five years, whereas for the rare patients diagnosed at an early stage, when surgery is possible, the after resection OS rate climbs to 20% (2). These numbers emphasize the need for an early detection and a new treatment concept of pancreatic cancer.

Current detection methods mostly rely on imaging and are summarized in Table 1.

TABLE 1

Current pancreatic cancer detection methods (adapted from cancer.gov)

| | |
|---|---|
| Imaging | Computed Tomography (CT) Scan |
| | Ultrasonography    Transabdominal Ultrasound |
| |                   Endoscopic Ultrasound |
| | Magnetic Resonance Imaging (MRI) |
| | Endoscopic Retrograde Cholangiopancreatography |
| | Percutaneous Transhepatic Cholangiography |
| Biopsies | Fine-Needle Aspiration (FNA) Biopsy |
| | Brush Biopsy |
| | Laparoscopy |
| Lab tests | Bilirubin and other substances |

The most sensitive and specific screening tool currently available seems to be the endoscopic ultrasound (3, 4), but its invasive features restrict its use to the screening of high risk populations, namely kindred with minimum two affected first-degree relatives or with known hereditary pancreatic cancer. Another inconvenience of endoscopic ultrasound is that its use is recommended to be associated to other methods such as computed tomography and endoscopic retrograde cholangiopancreatography (5). Diagnosis is confirmed exclusively on analysis of a biopsy. Thus, in addition to being invasive, this multi-step detection and diagnosis process only establishes the presence of an already developed tumor and does not identify risks of developing cancer.

New technologies such as genomics, proteomics, metabolomics and glycomics, have been used in the search for blood-based tumor markers, and have identified glycoproteins, more specifically highly glycosylated mucins, as main tumor markers in all kinds of cancer (6). Among these highly glycosylated mucins, which can be detected by specific monoclonal antibodies, the Cancer Antigen 19-9 (CA 19-9) is present primarily in pancreatic and biliary tract cancers, but also in patients with other malignancies (e.g. colorectal cancer) and benign conditions such as cirrhosis and pancreatitis. CA 19-9 is detected in most proteomics studies in pancreatic cancer serum samples (such as (7)), but its low specificity does not recommend it as a pancreatic cancer biomarker. Anecdotally so far, another glycosylation-related potential biomarker of pancreatic cancer is the core fusylation of biantennary glycans of RNase I, which displayed a 40% increase in the serum of two pancreatic cancer patients relative to two healthy controls (8).

Another well-known serum marker of pancreatic cancer is CEA (carcinoembryonic antigen), with an average reported sensitivity and specificity of both 65% (7). HIP/PAP-I and MIC-1 (macrophage inhibitory cytokine I) are also classical serum markers (9, 10). According to one study, MIC-1 and CA19-9 seem the markers with the highest sensitivity and specificity, in the sense of specificity vs. chronic pancreatitis (and not vs. colon cancer for example), when compared to osteopontin, TIMP-1 and HIP/PAP-I (9).

The use of CA19-9 as a marker is now recommended in combination with other markers, such as the mutation status of pancreatic cancer-related oncogenes like K-ras (2). K-ras is reported to be mutated in 78% of pancreatic adenocarcinomas (11). Molecular events in pancreatic carcinogenesis have been extensively studied (12), and beside K-ras, p53, p21, p16, p27, SMAD4, and cyclin D1 are a few of these genes whose mutations or alterations in expression have been associated to pancreatic cancer (12). However, evidence regarding their application as prognostic indicators is conflicting. For instance, there is no consensus on the association between mutation in p53 and decreased survival (12).

MicroRNA profiling has also been performed for pancreatic cancer, with the identification of some common microRNAs specifically altered (13-15).

Protein markers show the advantage of simple screening through an ELISA (Enzyme-linked immunosorbent assay) method, and research in this field is therefore very intensive. Newer proteomics studies have identified additional protein markers, such as apolipoproteins A-I and A-II, and transthyretin (7), all decreased in serum of pancreatic cancer patients, as well as MMP-9, DJ-1 and A1BG, each of which is overexpressed in pancreatic juice from cancer patients (16).

The involvement of apolipoproteins is interesting since they participate in lipid metabolism (17) and other members of this family have been associated to cancer (18).

The fatty acid composition of lipids in plasma and bile from patients with pancreatic cancer has also been analyzed (19, 20), even though neither of these studies has detailed the chemical subfamilies of the altered lipids. Plasma from pancreatic patients showed significantly lower levels of phospholipids that contain the side chain 18:2(ω6), 20:5(ω3) or 22:5(ω3), without distinction of lipid classes (19). Bile from hepatopancreaticobiliary cancer patients was found to contain a much lower level of phosphatidylcholines without distinction of side chains (20).

Since diabetes mellitus (DM) has a high prevalence in pancreatic cancer patients and is frequently of new onset, research has also been aimed at determining whether DM can be utilized as an early pancreatic cancer marker (21). A 2-fold increase of the glucagon/insulin ratio was found in the blood of pancreatic cancer patients relative to healthy controls, and at a cut-off of 7.4 ng/mU glucagon/insulin, pancreatic cancer induced new-onset DM could be discriminated from type 2 DM with 77% sensitivity and 69% specificity (21).

Overall, the methods described above are not ideally suited for large-scale population screening (either for low compliance or low sensitivity and specificity except in the case of a still-to-optimize multiple method combination), and most are capable of detecting pancreatic cancer after the formation of a tumor only. As a result, there still remains a need for accurate methods of detection, particularly for methods to detect early stages of the disease.

SUMMARY OF THE INVENTION

It is an object of the invention to provide diagnostic methods and diagnostic markers useful for detecting cancer in a subject.

Accordingly, the invention relates to methods and diagnostic markers for detecting or diagnosing cancer. Such methods and diagnostic markers are particularly useful for detecting pancreatic cancer.

As an aspect of the invention, a method is provided for diagnosing a subject's pancreatic cancer health state or change in health state, or for diagnosing pancreatic cancer or the risk of pancreatic cancer in a subject, comprising steps of:
  a) analyzing a sample from the patient by high resolution mass spectrometry to obtain accurate mass intensity data;
  b) comparing the accurate mass intensity data to corresponding data obtained from one or more than one reference sample to identify an increase or decrease in accurate mass intensity; and
  c) using the increase or decrease in accurate mass intensity for diagnosing the patient's pancreatic cancer health state, or change in pancreatic cancer health state, or for diagnosing risk of developing pancreatic cancer or the presence of pancreatic cancer in the patient,
wherein the accurate mass intensity is measured, in Daltons, at or substantially equivalent to a hydrogen and electron adjusted accurate mass, or neutral accurate mass as described in further detail herein, for example in Table 5.

In an embodiment, the accurate mass intensity is measured at one or more of the following masses: 78.0516; 84.0575; 112.0974; 116.5696; 191.5055; 197.0896; 200.1389; 202.045; 203.1155; 214.1204; 214.1205; 232.1309; 233.1345; 240.0997; 243.0714; 244.0554; 254.1127; 255.1161; 256.2403; 260.0033; 262.0814; 268.1284; 270.0323; 270.0867; 276.0948; 280.2403; 280.2404; 281.2432; 281.2435; 282.2558; 282.2559; 283.2591; 283.2595; 284.9259; 300.1186; 300.2067; 302.0945; 302.222; 302.2457; 304.2375; 304.2407; 317.9613; 318.0931; 326.2048; 326.2458; 327.9902; 328.2403; 328.2408; 328.2627; 329.2439; 329.2658; 330.2559; 332.1473; 338.0189; 348.1191; 350.2222; 360.1782; 360.1792; 361.1828; 366.3593; 368.1057; 382.1083; 382.1601; 418.2204; 428.2404; 428.3647; 446.2526; 446.3395; 468.2336; 468.3581; 468.3807; 469.237; 469.3616; 481.315; 484.3527; 485.904; 494.4321; 495.3325; 496.3373; 505.3146; 508.2256; 517.3141; 518.321; 519.3295; 520.448; 522.4638; 522.4639; 523.3661; 523.4675; 538.4237; 540.4381; 541.3134; 541.3361; 542.3394; 545.3454; 562.4962; 564.5121; 565.3373; 566.3403; 569.3682; 570.372; 572.4798; 573.4833; 574.4952; 575.4985; 576.4751; 576.5113; 577.5149; 578.5169; 578.5284; 579.5313; 587.3214; 588.3269; 589.3368; 590.3408; 592.4709; 594.4852; 594.4863; 595.4892; 595.4897; 596.5017; 596.5027; 597.5066; 598.4955; 599.4993; 600.5117; 601.5151; 602.5269; 603.5297; 606.5591; 609.3259; 613.3379; 615.3535; 627.5656; 628.5438; 630.799; 631.798; 633.3245; 635.7525; 636.7532; 645.7958; 657.7337; 658.7372; 670.5696; 671.5731; 681.5858; 702.5709; 715.6959; 719.6256; 720.6272; 721.5035; 723.5203; 723.521; 724.5252; 724.5477; 725.7228; 733.5054; 735.6582; 743.5396; 744.5425; 745.5631; 746.5128; 746.5705; 748.527; 749.5374; 749.5388; 750.5425; 751.5511; 751.5539; 752.5574; 755.5497; 757.556; 757.5587; 758.562; 758.5626; 759.5383; 759.5733; 760.5792; 763.5578; 765.5678; 766.4792; 771.5699; 773.5276; 774.5419; 775.5522; 775.5532; 775.5532; 777.0402; 777.5709; 779.5405; 779.5416; 780.5452; 780.5454; 781.5029; 781.5566; 782.5612; 783.569; 783.5755; 784.5742; 784.5806; 785.5913; 785.5929; 785.5931; 786.593; 786.5972; 787.5989; 791.5841; 793.7091; 795.5181; 796.5212; 801.5147; 801.5262; 801.5523; 802.5291; 803.5373; 803.5414; 803.5677; 804.5422; 804.5456; 804.5714; 804.7208; 805.5549; 806.5632; 807.5734; 807.5739; 807.5764; 808.5783; 808.5791; 809.5796; 810.5867; 811.5729; 811.608; 812.6774; 813.5888; 819.5177; 823.5411; 824.69; 825.5522; 826.5561; 826.7047; 827.5401; 827.5678; 827.7082; 828.5397; 828.5721; 829.5516; 829.5532; 829.5843; 830.5591; 830.5879; 831.5652; 831.572; 831.5997; 832.6031; 833.5864; 834.5868; 835.598; 837.7209; 838.7284; 838.7435; 839.7464; 847.531; 850.7061; 850.7326; 851.6694; 851.7107; 851.7337; 852.7368; 853.573; 854.7358; 854.7397; 855.5721; 855.7392; 855.7436; 856.7505; 856.754; 857.6923; 857.7543; 857.7574; 858.7644; 861.749; 865.752; 866.7585; 867.7649; 868.7704; 871.5547; 873.7819; 874.7066; 874.787; 875.7108; 879.7629; 889.7537; 889.8147; 894.7911; 898.7043; 898.7325; 902.7629; 903.7636; 907.7847; 908.7907; 909.7882; 910.7272; 916.7735; 919.6496; 921.813; 922.7081; 922.7285; 922.8222; 923.7295; 924.7233; 925.727; 933.8137; 937.7542; 946.8194; 947.8263; 948.836; 950.7364; 960.7432; 970.733; 972.7481; 973.7482; 984.7406; 986.7568; 996.7518; 997.7397; 998.7566; 999.7632; 1010.765; 1011.669; 1011.77; 1012.781; 1016.931; 1017.935; 1018.944; 1019.951; 1020.957; 1038.915; 1039.705; 1039.921; 1040.933; 1041.935; 1199.084;

1200.088; 1201.09; 1202.098; 1223.09; 1224.096; 1225.096; 1226.599; 1227.112; 1228.117; 1229.12; 1230.125; 1247.084; 1249.105; 1250.108; 1251.119; 1252.12; 1253.123; 1253.134; 1254.137 and 1255.153.

In a further non-limiting embodiment of the invention, the accurate mass intensity is measured at an accurate mass of 519.3295, 523.3661, 541.3134, 702.5709, 724.5477, 757.556, 779.5405, 783.569, 785.5913, 803.5373, 805.5549, 807.5734, 809.5796, 812.6774, 829.5516, 833.5864, 576.4751, 594.4863, 596.5017 or combinations thereof. In such embodiments a decrease in accurate mass intensity is generally identified in the comparing step (b).

In a further exemplary embodiment, the accurate mass is measured at an accurate mass of 600.5117. In such an embodiment an increase in accurate mass intensity is identified in the comparing step (b).

In the above-described method, the term "substantially equivalent" may in certain non-limiting embodiments refer to ±5 ppm of the hydrogen and electron adjusted accurate mass, or neutral accurate mass, and in further embodiments, ±1 ppm of the hydrogen and electron adjusted accurate mass, or neutral accurate mass.

As a further aspect of the invention, there is provided a method for diagnosing a patient's pancreatic cancer health state, or change in pancreatic cancer health state, or for diagnosing risk of developing pancreatic cancer or the presence of pancreatic cancer in a patient, comprising the steps of:
 a) analyzing a sample from the patient to obtain quantifying data for one or more than one metabolite marker;
 b) comparing the quantifying data for the one or more than one metabolite marker to corresponding data obtained for one or more than one reference sample to identify an increase or decrease in the level of the one or more than one metabolite marker in the sample; and
 c) using the increase or decrease in the level of the one or more than one metabolite marker in the sample for diagnosing the patient's pancreatic cancer health state, or change in pancreatic cancer health state, or for diagnosing risk of developing pancreatic cancer or the presence of pancreatic cancer in the patient,
wherein the one or more metabolite marker is as described herein.

In an embodiment, the one or more metabolite marker comprises one or more molecule having a molecular formula as follows: $C_{36}H_{62}O_4$, $C_{36}H_{62}O_5$, $C_{36}H_{64}O_5$, $C_{36}H_{66}O_5$, $C_{36}H_{64}O_6$, $C_{36}H_{66}O_6$, $C_{36}H_{68}O_6$, $C_{22}H_{46}NO_7P$, $C_{22}H_{48}NO_7P$, $C_{24}H_{50}NO_7P$, $C_{24}H_{48}NO_7P$, $C_{24}H_{46}NO_7P$, $C_{26}H_{54}NO_7P$, $C_{26}H_{52}NO_7P$, $C_{26}H_{50}NO_7P$, $C_{26}H_{48}NO_7P$, $C_{28}H_{56}NO_7P$, $C_{28}H_{54}NO_7P$, $C_{28}H_{52}NO_7P$, $C_{28}H_{50}NO_7P$, $C_{28}H_{48}NO_7P$, $C_{28}H_{46}NO_7P$, $C_{30}H_{56}NO_7P$, $C_{30}H_{54}NO_7P$, $C_{30}H_{52}NO_7P$, $C_{30}H_{50}NO_7P$, $C_{32}H_{58}NO_7P$, $C_{32}H_{54}NO_7P$, $C_{38}H_{76}NO_7P$, $C_{40}H_{82}NO_7P$, $C_{40}H_{80}NO_7P$, $C_{40}H_{78}NO_7P$, $C_{40}H_{70}NO_7P$, $C_{42}H_{78}NO_8P$, $C_{42}H_{80}NO_8P$, $C_{42}H_{82}NO_8P$, $C_{42}H_{84}NO_8P$, $C_{44}H_{78}NO_8P$, $C_{44}H_{80}NO_8P$, $C_{44}H_{82}NO_8P$, $C_{44}H_{84}NO_8P$, $C_{44}H_{86}NO_8P$, $C_{44}H_{88}NO_8P$, $C_{46}H_{78}NO_8P$, $C_{46}H_{80}NO_8P$, $C_{46}H_{82}NO_8P$, $C_{46}H_{84}NO_8P$, $C_{48}H_{80}NO_8P$, $C_{48}H_{82}NO_8P$, $C_{48}H_{84}NO_8P$, $C_{48}H_{86}NO_8P$, $C_{42}H_{80}NO_7P$, $C_{42}H_{82}NO_7P$, $C_{42}H_{84}NO_7P$, $C_{44}H_{82}NO_7P$, $C_{44}H_{84}NO_7P$, $C_{44}H_{86}NO_7P$, $C_{44}H_{88}NO_7P$, $C_{46}H_{82}NO_7P$, $C_{46}H_{84}NO_7P$, $C_{46}H_{86}NO_7P$, $C_{48}H_{84}NO_7P$, $C_{48}H_{86}NO_7P$, $C_{39}H_{79}N_2O_6P$ (or $C_{39}H_{80}N_2O_6P^+$), or $C_{41}H_{81}N_2O_6P$ (or $C_{41}H_{82}N_2O_6P$), or $C_{41}H_{83}N_2O_6P$ (or $C_{41}H_{84}N_2O_6P^+$), or $C_{47}H_{93}N_2O_6P$ (or $C_{47}H_{94}N_2O_6P^+$), or $C_{47}H_{95}N_2O_6P$ (or $C_{47}H_{96}N_2O_6P^+$), including combinations thereof.

In further non-limiting embodiments, the metabolite marker may be a diacylphosphatidylcholine, plasmanylphosphocholine or plasmenylphosphocholine as defined in Formula (I):

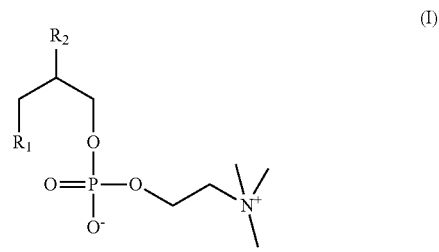

(I)

including adducts or salts thereof, wherein $R_1$ is a 16:0, 16:1, 18:0, 18:1, 18:2, 18:3, 20:3, 20:4, 20:5, 22:5 or 22:6 fatty acid or alcohol moiety bonded to the glycerol backbone, the bond being an acyl linkage when the metabolite marker is a diacylphosphatidylcholine, an ether linkage when the metabolite marker is a plasmanylphosphocholine, or a vinyl-ether linkage when the metabolite marker is a plasmenylphosphocholine; and $R_2$ is a 16:0, 16:1, 18:0, 18:1, 18:2, 18:3, 20:3, 20:4, 20:5, 22:5, or 22:6 fatty acid moiety bonded to the glycerol backbone through an acyl linkage.

In further embodiments, the metabolite marker may be a 2-lysophosphatidylcholine as defined in Formula (II) or a 1-lysophosphatidylcholine as defined in Formula (III):

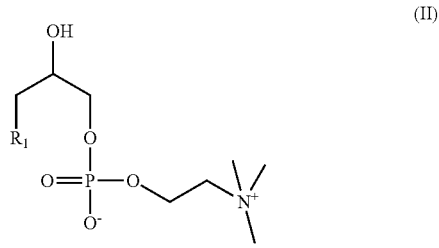

(II)

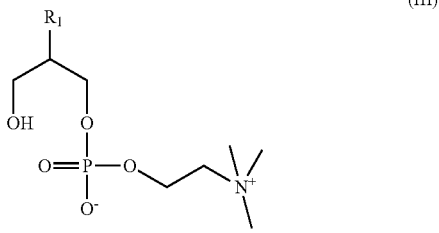

(III)

including adducts or salts thereof, wherein $R_1$ is a 14:0, 14:1, 16:0, 16:1, 16:2, 18:0, 18:1, 18:2, 18:3, 20:1, 20:2, 20:3, 20:4, 20:5, 20:6, 22:3, 22:4, 22:5, 22:6, 24:4, 24:6, 30:1, 32:0, 32:1, 32:2 or 32:6 fatty acid moiety bonded to the glycerol backbone through an acyl linkage.

In other non-limiting embodiments, the metabolite marker may be a sphingomyelin as defined in Formula (IV):

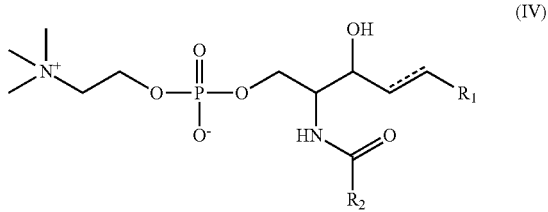

(IV)

including adducts or salts thereof, wherein the dashed line represents an optional double bond;

$R_1$ is a $C_{1-3}$ alkyl group; and $R_2$ is a $C_{11}$ to $C_{25}$ alkyl or alkenyl group, the alkenyl group having from 1 to 3 double bonds.

In certain non-limiting embodiments, $R_2$ of the sphingomyelin of Formula (IV) may be a $C_{11}$ alkyl group, a $C_{13}$ alkyl group, a $C_{15}$ alkyl group, a $C_{17}$ alkyl group, a $C_{17}$ alkenyl group with 3 double bonds, a $C_{19}$ alkyl group, a $C_{21}$ alkyl group, a $C_{23}$ alkenyl group with 1 double bond, a $C_{23}$ alkyl group, a $C_{24}$ alkyl group, a $C_{25}$ alkenyl group with 1 double bond, a $C_{25}$ alkyl group.

The above described methods may further include steps of: analyzing a sample from the patient to obtain quantifying data for one or more than one internal standard molecule; and obtaining a ratio for each of the levels of the one or more than one metabolite marker to the level obtained for the one or more than one internal standard molecule; wherein the comparing step (b) comprises comparing each ratio to one or more corresponding ratios obtained for the one or more than one reference sample.

Without wishing to be limiting in any way, it will be appreciated that the above-described methods can be carried out, at least in part, with the assistance of a computer. In such embodiments the computer may be integrated with the instrument used to perform the analysis, or it may be a separate computer adapted to receive data output from the instrument according to the knowledge and skill of those in the art. The analyzing step (a) will typically be carried out using the instrument, for example but not limited to a mass spectrometer, and the comparing step (b) carried out using the computer or other processing means programmed to receive the accurate mass intensity data or quantifying data from the instrument and perform the calculations required to identify an increase or decrease in the level of the one or more than one metabolite marker in the sample. This data from step (b) may be output for use by an individual trained to identify the noted increase or decrease and make the diagnosis of step (c), or alternatively the computer or processing means may be further programmed to generate an output of a diagnosis. In the latter case, the output may comprise a positive or negative diagnosis factor, and may optionally include additional details including but not limited to statistical data, threshold data, patient data and other details. The data may be output to a display, such as a monitor, to a printer for generating a copy of the details of diagnosis, to a data receiving centre or directly to a service provider, or in any other way as would be understood by one skilled in the art.

In certain embodiments, the metabolite may be a lysophosphatidylcholine (LysoPC), including LysoPC 14:0, LysoPC 14:1, LysoPC 16:0, LysoPC 16:1, LysoPC 16:2, LysoPC 18:0, LysoPC 18:1, LysoPC 18:2, LysoPC 18:3, LysoPC 20:1, LysoPC 20:2, LysoPC 20:3, LysoPC 20:4, LysoPC 20:5, LysoPC 20:6, LysoPC 22:3, LysoPC 22:4, LysoPC 22:5, LysoPC 22:6, LysoPC 24:4, LysoPC 24:6, LysoPC 30:1, LysoPC 32:0, LysoPC 32:1, LysoPC 32:2, LysoPC 32:6, or combinations thereof.

In other embodiments the metabolite may be a phosphatidylcholine, including phosphatidylcholine molecules having a molecular formula of $C_{42}H_{78}NO_8P$, $C_{42}H_{80}NO_8P$, $C_{42}H_{82}NO_8P$, $C_{42}H_{84}NO_8P$, $C_{44}H_{78}NO_8P$, $C_{44}H_{80}NO_8P$, $C_{44}H_{82}NO_8P$, $C_{44}H_{84}NO_8P$, $C_{44}H_{86}NO_8P$, $C_{44}H_{88}NO_8P$, $C_{46}H_{78}NO_8P$, $C_{46}H_{80}NO_8P$, $C_{46}H_{82}NO_8P$, $C_{46}H_{84}NO_8P$, $C_{48}H_{80}NO_8P$, $C_{48}H_{82}NO_8P$, $C_{48}H_{84}NO_8P$, $C_{48}H_{86}NO_8P$, or combinations thereof.

In other embodiments the metabolite may be a plasmenylphosphocholine, including plasmenylphosphocholine molecules having a formula of $C_{42}H_{80}NO_7P$, $C_{42}H_{82}NO_7P$, $C_{42}H_{84}NO_7P$, $C_{44}H_{82}NO_7P$, $C_{44}H_{84}NO_7P$, $C_{44}H_{86}NO_7P$, $C_{44}H_{88}NO_7P$, $C_{46}H_{82}NO_7P$, $C_{46}H_{84}NO_7P$, $C_{46}H_{86}NO_7P$, $C_{48}H_{84}NO_7P$, $C_{48}H_{86}NO_7P$, or combinations thereof.

In yet further embodiments the metabolite may be a sphingomyelin, including sphingomyelin molecules having a molecular formula of $C_{39}H_{79}N_2O_6P$ (or $C_{39}H_{80}N_2O_6P$), $C_{41}H_{81}N_2O_6P$ (or $C_{41}H_{82}N_2O_6P$), or $C_{41}H_{83}N_2O_6P$ (or $C_{41}H_{84}N_2O_6P$), or $C_{47}H_{93}N_2O_6P$ (or $C_{47}H_{94}N_2O_6P^+$), or $C_{47}H_{95}N_2O_6P$ (or $C_{47}H_{96}N_2O_6P^+$), or combinations thereof.

As described herein, alterations in the levels of the metabolite markers may be detected by MS/MS transition. For instance, a metabolite marker of molecular formula $C_{36}H_{64}O_5$ may be monitored for level fluctuations of organic extracts in negative ionization mode (such as atmospheric pressure chemical ionization (APCI)) at a MS/MS transition of 575.5/513.5, 575.5/557.5, 575.5/539.5, 575.5/531.5, 575.5/499.5, 575.5/495.5, 575.5/459.4, 575.5/417.4, 575.5/415.3, 575.5/413.3, 575.5/403.3, 575.5/295.2, 575.5/279.2, 575.5/260.2, 575.5/251.2, 575.5/197.9, 575.5/119.4, 575.5/113.1, and 575.5/97.0, or combinations thereof.

Other useful MS/MS transitions for organic extracts in negative ionization mode (e.g. APCI mode) for the metabolite markers described herein include: 593.5/557.5, 593.5/575.4, 593.5/549.4, 593.5/531.5, 593.5/513.4, 593.5/495.4, 593.5/433.3, 593.5/421.4, 593.5/415.2, 593.5/391.4, 593.5/371.3, 593.5/315.3, 593.5/311.1, 593.5/297.2, 593.5/281.2, 593.5/277.2, 593.5/251.2, 593.5/201.1, 593.5/195.3, 593.5/171.1, 593.5/139.1 and 593.5/133.5, or combinations thereof for $C_{36}H_{66}O_6$; 595.5/559.5, 595.5/577.4, 595.5/551.4, 595.5/533.4, 595.5/515.5, 595.5/497.4, 595.5/478.4, 595.5/433.3, 595.5/423.4, 595.5/391.3, 595.5/372.3, 595.5/595.5/315.3, 595.5/313.2, 595.5/298.2, 595.5/297.2, 595.5/281.2, 595.5/279.2, 595.5/239.2, 595.5/232.9, 595.5/171.1, 595.5/169.1 and 595.5/141.1, or combinations thereof for $C_{36}H_{68}O_6$; 557.4/495.4, 557.4/539.4, 557.4/513.3, 557.4/279.2, 557.4/277.2, 557.4/220.7 and 557.4/111.2, or combinations thereof for $C_{36}H_{62}O_4$; 573.5/511.4, 573.5/555.3, 573.5/537.4, 573.5/529.4, 573.5/519.4, 573.5/493.3, 573.5/457.4, 573.5/455.3, 573.5/443.4, 573.5/415.4, 573.5/413.3, 573.5/411.3, 573.5/399.3, 573.5/397.3, 573.5/389.7, 573.5/295.2, 573.5/279.2, 573.5/277.2, 573.5/251.2, 573.5/231.1, 573.5/223.1, 573.5/201.1, 573.5/171.1, 573.5/169.1, 573.5/125.1 and 573.5/113.1, or combinations thereof for $C_{36}H_{62}O_5$; 577.5/515.4, 577.5/559.4, 577.5/546.5, 577.5/533.5, 577.5/497.4, 577.5/419.4, 577.5/405.5, 577.5/297.2 and 577.5/281.2, or combinations thereof for $C_{36}H_{66}O_5$; 591.5/573.4, 591.5/555.4, 591.5/528.3, 591.5/511.2, 591.5/476.1, 591.5/419.3, 591.5/403.1, 591.5/387.3, 591.5/297.2, 591.5/295.2, 591.5/274.0, 591.5/255.3, 591.5/223.6, 591.5/

203.5, 591.5/201.1, 591.5/171.0 and 591.5/125.3, or combinations thereof for $C_{36}H_{64}O_6$.

Other useful MS/MS transitions for aqueous extracts in positive ionization mode (e.g. positive Electrospray Ionization (ESI)) for the metabolite markers described herein include: 520.3/184.2 for $C_{26}H_{50}NO_7P$; 524.3/184.2 for $C_{26}H_{54}NO_7P$; 542.3/184.2 for $C_{28}H_{48}NO_7P$; 758.6/184.2 for $C_{42}H_{80}NO_8P$; 784.6/184.2 for $C_{44}H_{82}NO_8P$; 786.6/184.2 for $C_{44}H_{84}NO_8P$; 788.6/184.2 for $C_{44}H_{86}NO_8P$; 790.6/184.2 for $C_{44}H_{88}NO_8P$; 806.6/184.2 for $C_{46}H_{80}NO_8P$; 808.6/184.2 for $C_{46}H_{82}NO_8P$; 810.6/184.2 for $C_{46}H_{84}NO_8P$; 834.6/184.2 for $C_{48}H_{84}NO_8P$; 836.6/184.2 for $C_{48}H_{86}NO_8P$; 703.6/184.2 for $C_{39}H_{79}N_2O_6P$; 729.6/184.2 for $C_{41}H_{81}N_2O_6P$; 731.6/184.2 for $C_{41}H_{83}N_2O_6P$; 813.6/184.2 for $C_{47}H_{93}N_2O_6P$; or 815.6/184.2 for $C_{47}H_{95}N_2O_6P$. Additional MS/MS transition details and other features of the metabolites described herein are evident from the following detailed description of the invention and may also be used in further non limiting embodiments of the invention.

Other useful MS/MS transitions for aqueous extracts in negative ionization mode (e.g. negative ESI) for the metabolite markers described herein include: 564.3/504.3/279.3 for $C_{26}H_{50}NO_7P$; 568.3/508.4/283.3 for $C_{26}H_{54}NO_7P$; 586.3/526.3/301.2 for $C_{28}H_{48}NO_7P$; 802.6/742.6/279.2, 802.6/742.6/281.2, 802.6/742.6/253.2 or 802.6/742.6/255.2 for $C_{42}H_{80}NO_8P$; 828.6/768.6/305.3, 828.6/768.6/279.2, 828.6/768.6/281.2 or 828.6/768.6/255.2 for $C_{44}H_{82}NO_8P$; 830.6/770.6/279.2, 830.6/770.6/281.2 or 830.6/770.6/283.2 for $C_{44}H_{84}NO_8P$; 832.6/772.6/281.2 or 832.6/772.6/283.2 for $C_{44}H_{86}NO_8P$; 834.6/774.6/283.2 for $C_{44}H_{88}NO_8P$; 850.6/790.6/327.3, 850.6/790.6/279.2, 850.6/790.6/303.2 or 850.6/790.6/255.2 for $C_{46}H_{80}NO_8P$; 852.6/792.6/329.3, 852.6/792.6/301.3, 852.6/792.6/303.2, 852.6/792.6/281.2, 852.6/792.6/283.2 or 852.6/792.6/255.2 for $C_{46}H_{82}NO_8P$; 854.6/794.6/331.3, 854.6/794.6/303.2, 854.6/794.6/283.2 or 854.6/794.6/255.2 for $C_{46}H_{84}NO_8P$; 878.6/818.6/327.3 or 878.6/818.6/283.2 for $C_{48}H_{84}NO_8P$; 880.6/820.6/329.3 or 880.6/820.6/283.2 for $C_{44}H_{86}NO_8P$; 747.6/687.6/168.1 for $C_{39}H_{79}N_2O_6P$; 773.6/713.6/168.1 for $C_{41}H_{81}N_2O_6P$; 775.6/715.6/168.1 for $C_{41}H_{83}N_2O_6P$; 857.6/797.6/168.1 for $C_{47}H_{93}N_2O_6P$; or 859.6/799.6/168.1 for $C_{47}H_{95}N_2O_6P$. Additional MS/MS transition details and other features of the metabolites described herein are evident from the following detailed description of the invention and may also be used in further non limiting embodiments of the invention.

In the above-described methods, the step of comparing accurate mass intensity data to reference data to identify an increase or decrease in accurate mass intensity; or the step of comparing quantifying data for a metabolite marker to reference data to identify an increase or decrease in the level of the metabolite marker, can in certain non-limiting embodiments comprise or otherwise relate to a step of determining the level of the specified markers, metabolites or molecules, either by determining a change in accurate mass intensity or by other analytical means.

The invention further relates to an assay standard comprising a metabolite marker as described herein labeled with a detection agent. The standard will be useful for carrying out a diagnostic method as described herein, and may include one or more of the following non-limiting detection agents: a stable isotope, an enzyme, or a protein that enables detection in vitro.

In certain non-limiting embodiments, the assay standard may comprise as the metabolite marker a diacylphosphatidylcholine, plasmanylphosphocholine or plasmenylphosphocholine as defined in Formula (I):

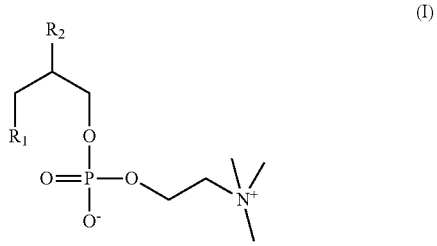

(I)

including adducts or salts thereof, wherein $R_1$ is a 16:0, 16:1, 18:0, 18:1, 18:2, 18:3, 20:3, 20:4, 20:5, 22:5 or 22:6 fatty acid or alcohol moiety bonded to the glycerol backbone, the bond being an acyl linkage when the metabolite marker is a diacylphosphatidylcholine, an ether linkage when the metabolite marker is a plasmanylphosphocholine, or a vinyl-ether linkage when the metabolite marker is a plasmenylphosphocholine; and $R_2$ is a 16:0, 16:1, 18:0, 18:1, 18:2, 18:3, 20:3, 20:4, 20:5, 22:5, or 22:6 fatty acid moiety bonded to the glycerol backbone through an acyl linkage.

In further embodiments, the assay standard may comprise as the metabolite marker a 2-lysophosphatidylcholine as defined in Formula (II) and a 1-lysophosphatidylcholine in Formula (III):

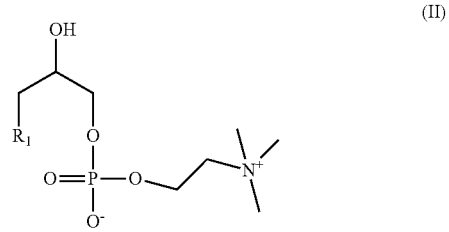

(II)

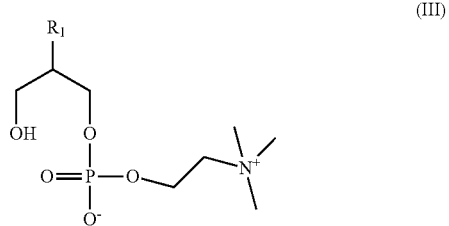

(III)

including adducts or salts thereof, wherein $R_1$ is a 14:0, 14:1, 16:0, 16:1, 16:2, 18:0, 18:1, 18:2, 18:3, 20:1, 20:2, 20:3, 20:4, 20:5, 20:6, 22:3, 22:4, 22:5, 22:6, 24:4, 24:6, 30:1, 32:0, 32:1, 32:2 or 32:6 fatty acid moiety bonded to the glycerol backbone through an acyl linkage.

In other non-limiting embodiments, the assay standard may comprise as the metabolite marker a sphingomyelin as defined in Formula (IV):

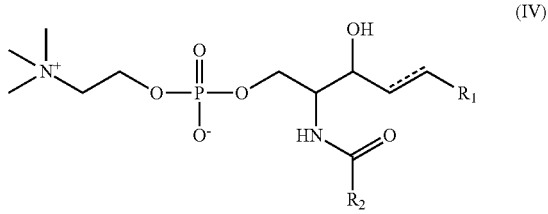

(IV)

including adducts or salts thereof, wherein the dashed line represents an optional double bond, $R_1$ is a $C_{13}$ alkyl group; and $R_2$ is a $C_{11}$ to $C_{25}$ alkyl or alkenyl group, the alkenyl group having from 1 to 3 double bonds.

In certain non-limiting embodiments, $R_2$ of the sphingomyelin of Formula (IV) may be a $C_{11}$ alkyl group, a $C_{13}$ alkyl group, a $C_{15}$ alkyl group, a $C_{17}$ alkyl group, a $C_{17}$ alkenyl group with 3 double bonds, a $C_{19}$ alkyl group, a $C_{21}$ alkyl group, a $C_{23}$ alkenyl group with 1 double bond, a $C_{23}$ alkyl group, a $C_{24}$ alkyl group, a $C_{25}$ alkenyl group with 1 double bond, or a $C_{25}$ alkyl group.

In further embodiments of the standard, which are also considered to be non-limiting, the assay standard may comprise as the metabolite marker a lysophosphatidylcholine (LysoPC, either 1-LysoPC or 2-LysoPC) including LysoPC 14:0, LysoPC 14:1, LysoPC 16:0, LysoPC 16:1, LysoPC 16:2, LysoPC 18:0, LysoPC 18:1, LysoPC 18:2, LysoPC 18:3, LysoPC 20:1, LysoPC 20:2, LysoPC 20:3, LysoPC 20:4, LysoPC 20:5, LysoPC 20:6, LysoPC 22:3, LysoPC 22:4, LysoPC 22:5, LysoPC 22:6, LysoPC 24:4, LysoPC 24:6, LysoPC 30:1, LysoPC 32:0, LysoPC 32:1, LysoPC 32:2, or LysoPC 32:6.

The invention further relates to a kit or commercial package comprising the above-described standard and instructions for quantitating an analyte or performing a diagnostic test as described herein.

BRIEF DESCRIPTION OF THE DRAWINGS

These and other features of the invention will become more apparent from the following description in which reference is made to the following figures.

in one pattern (a) and one main side chain, 18:1 (m/z 281.2) in the other (b). "785.6" is therefore PtdCho 18:0/18:2 and PtdCho18:1/18:1.

Figure 31:
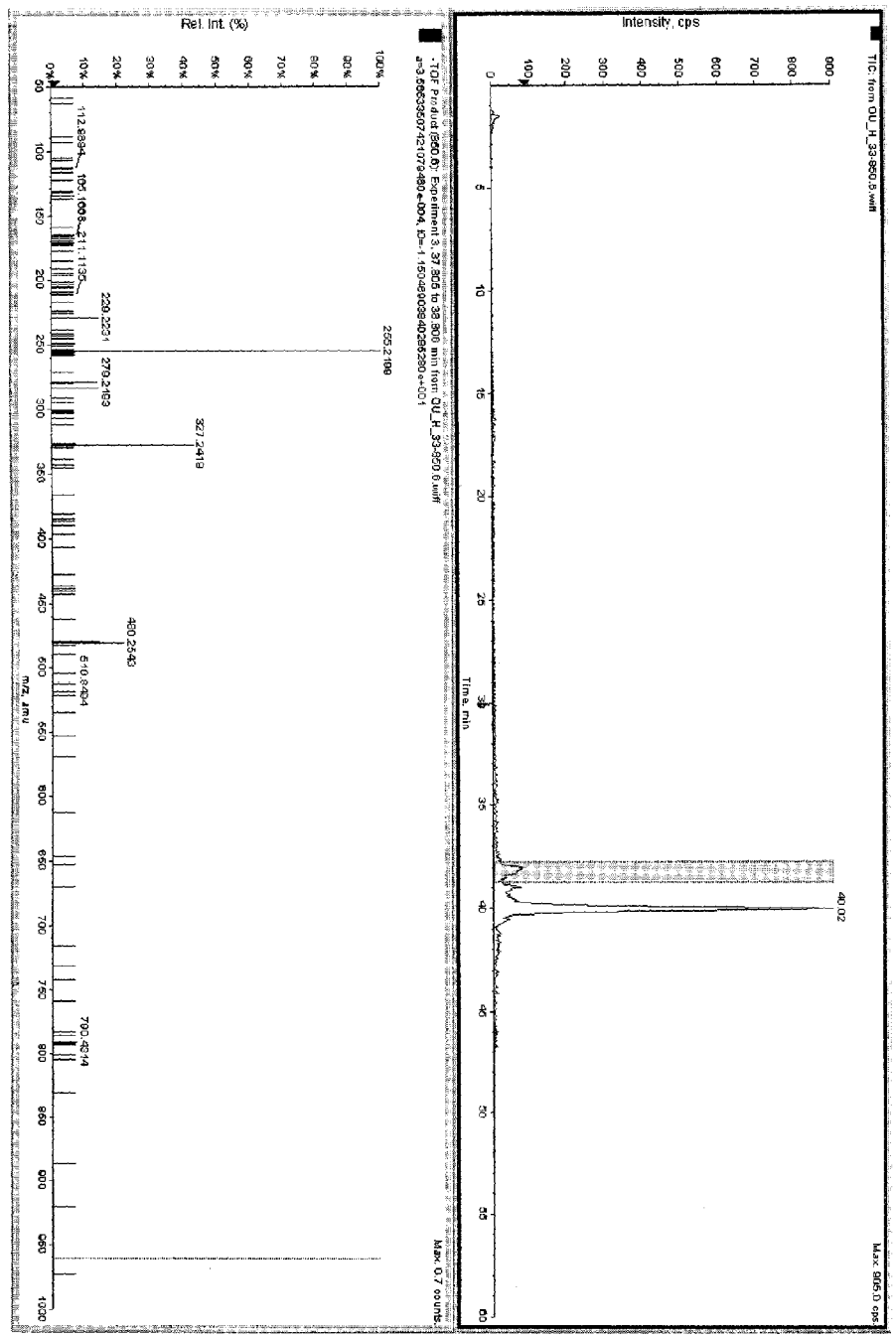
Figure 31:
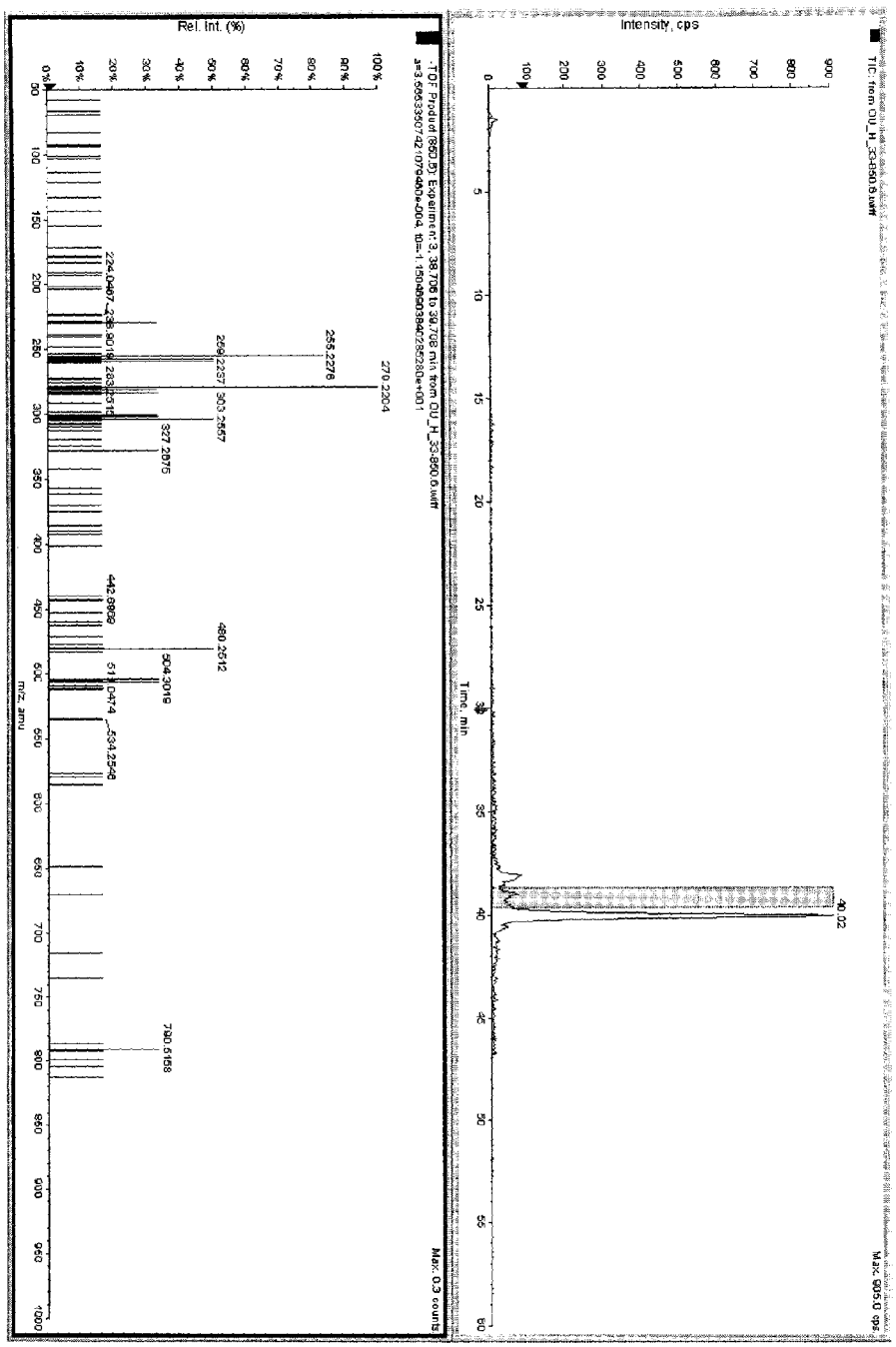
Figure 31:
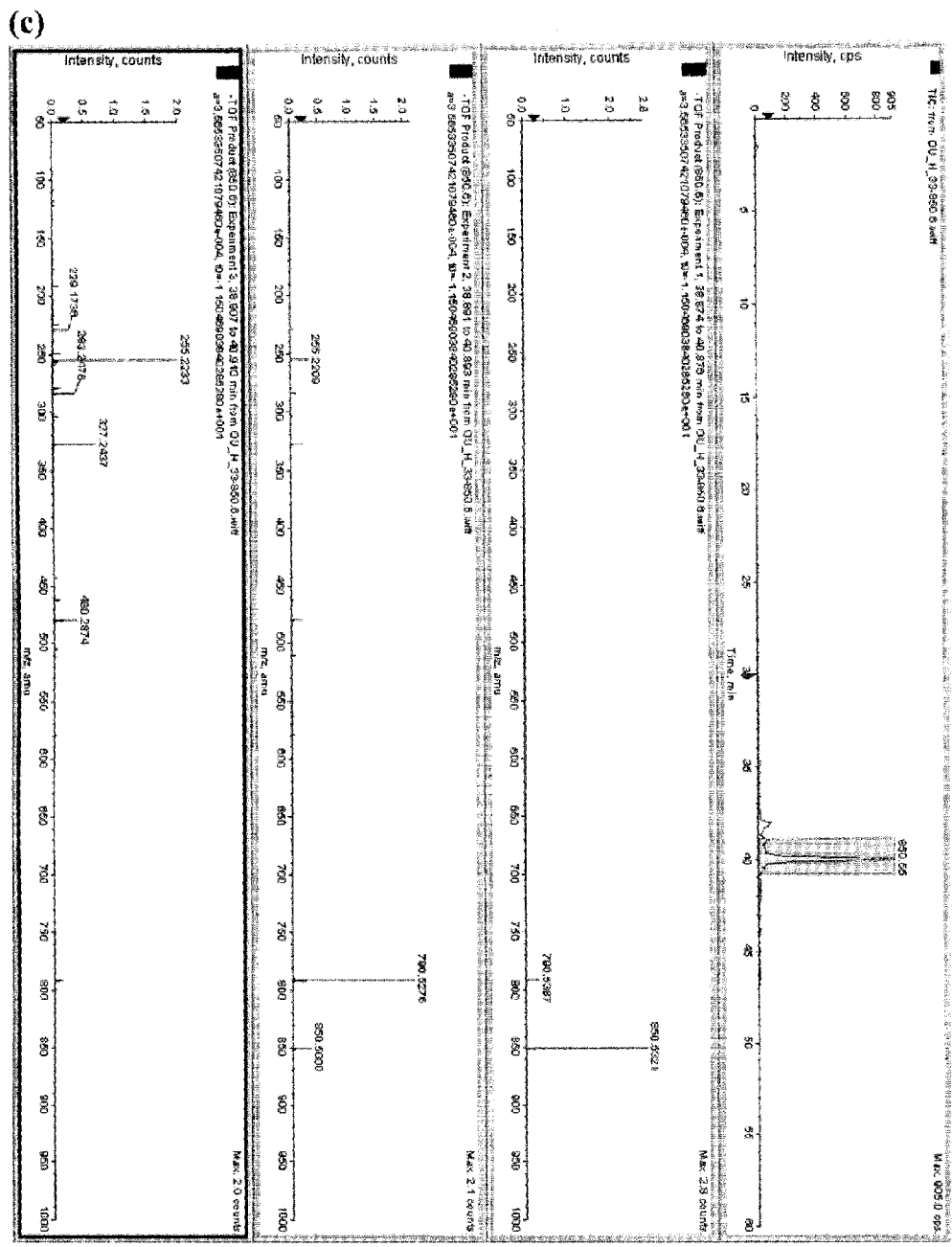
Figure 31:
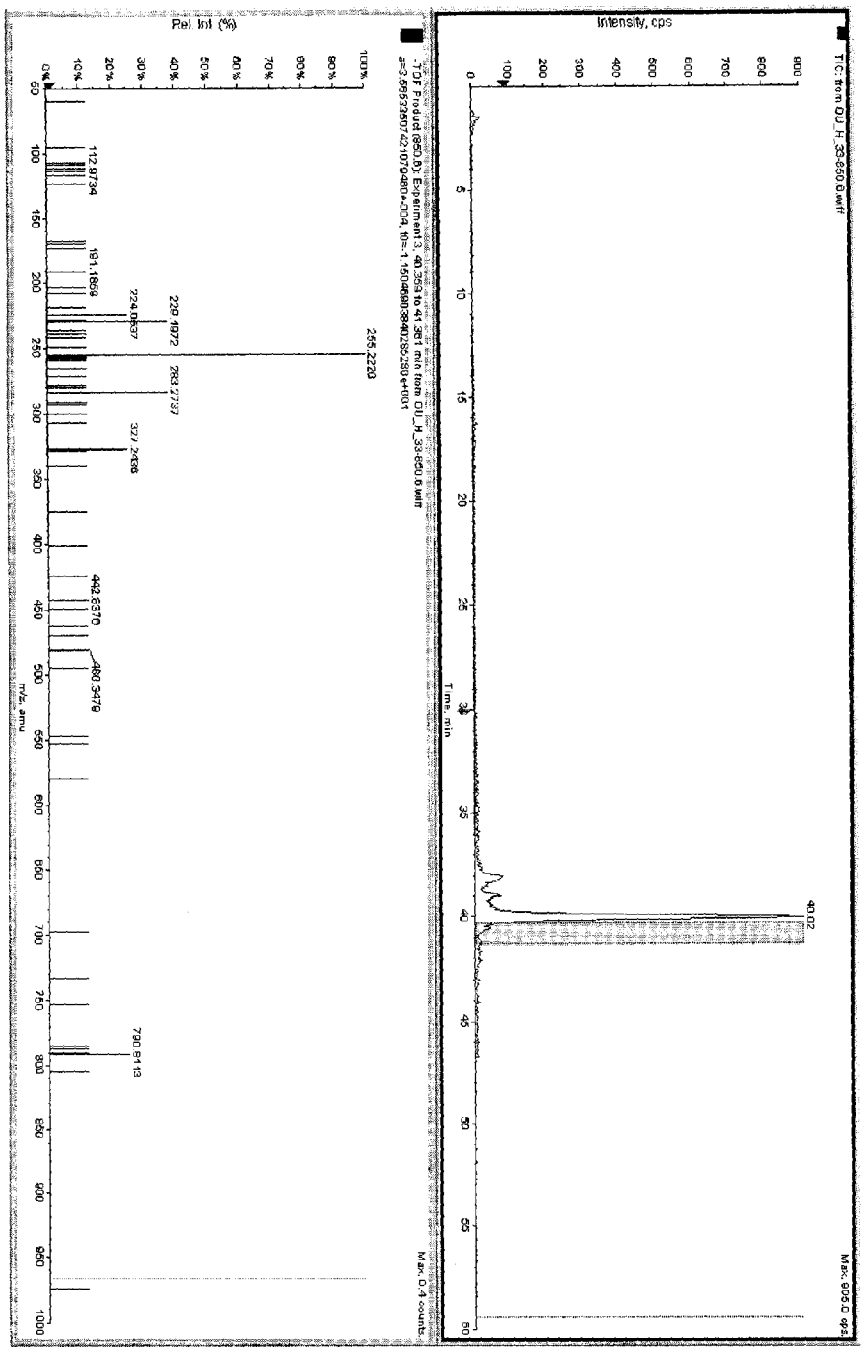

FIG. 31 illustrates the fragmentation pattern of "805.6" as a formic acid adduct in negative aqueous ESI mode at different retention times (a-d). The different side chains, 16:0 (m/z 255.2), 22:6 (m/z 327.3), 18:2 (m/z 279.3) and 20:4 (m/z 303.2), identify "805.6" as PtdCho 22:6/16:0 and, PtdCho 20:4/18:2).

Figure 32:
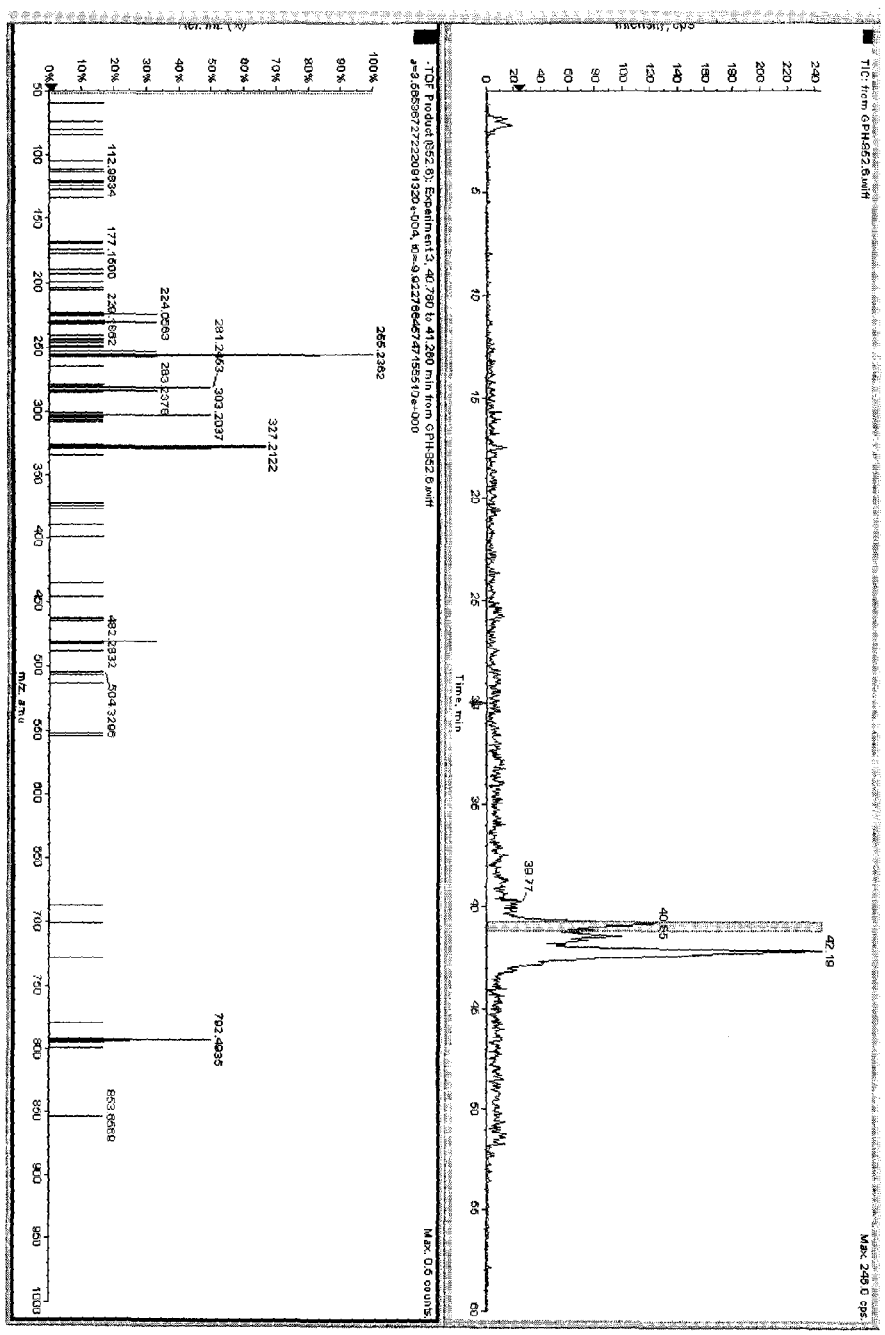
Figure 32:
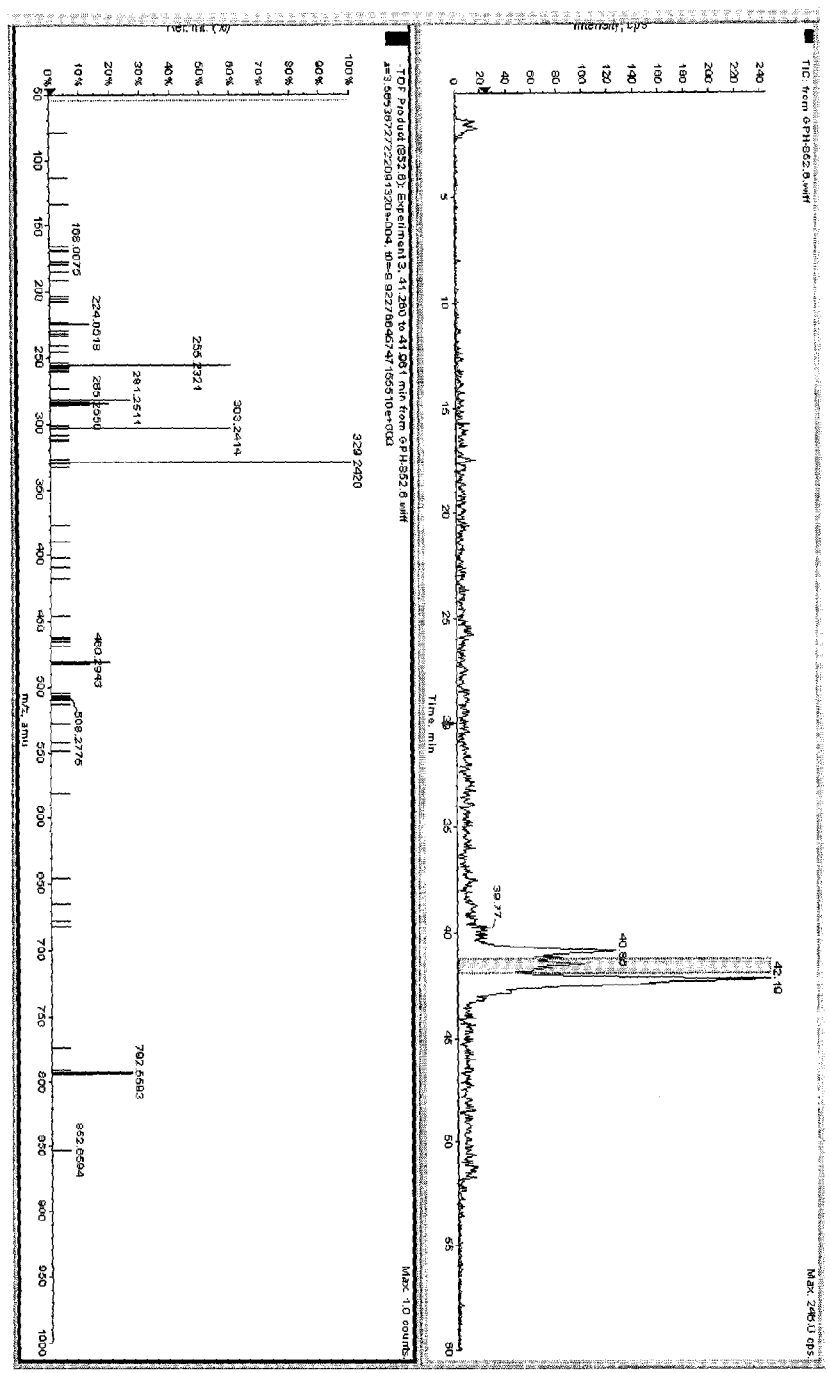
Figure 32:
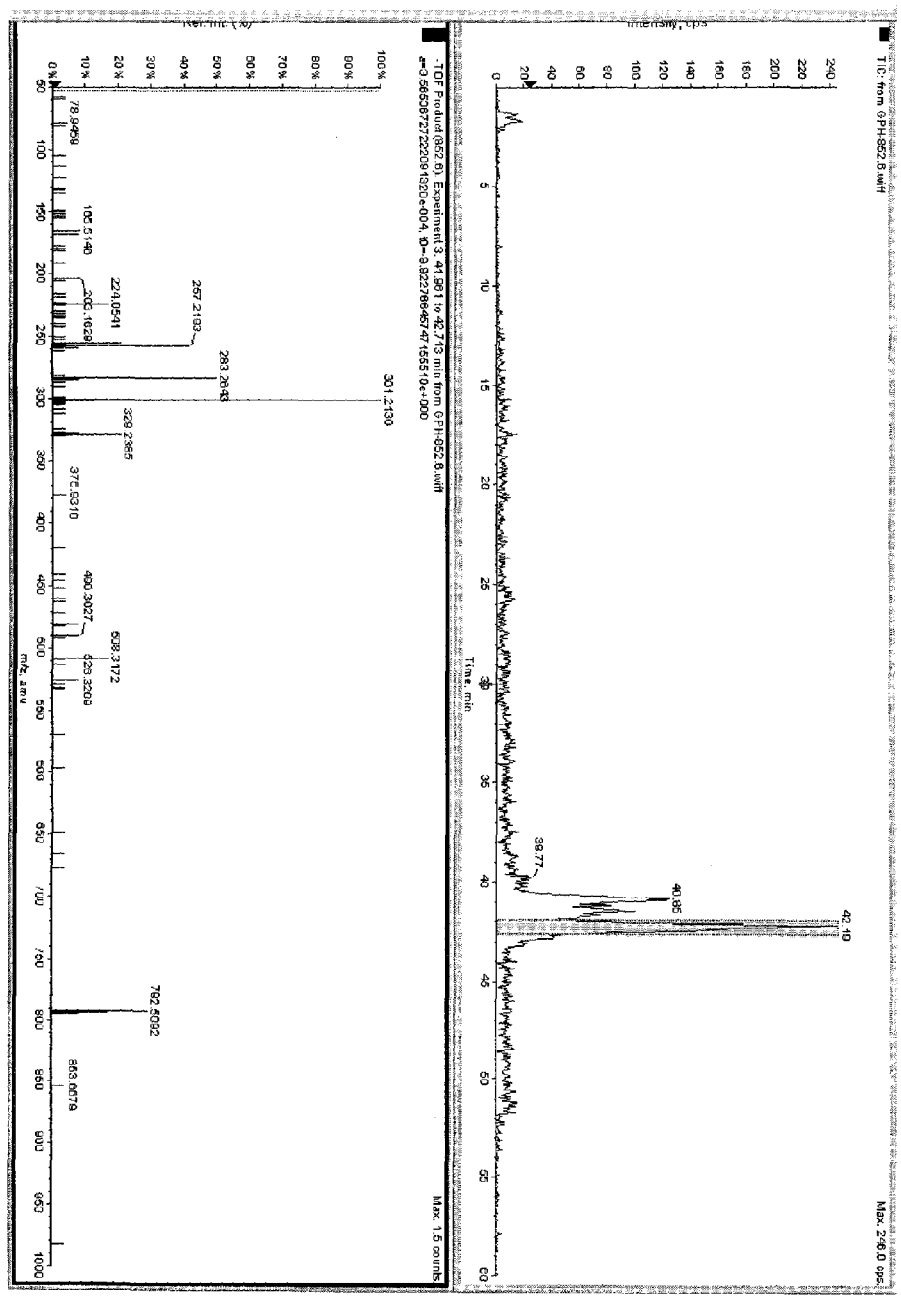

FIG. 32 illustrates the fragmentation patterns of "807.6" as a formic acid adduct in negative aqueous ESI mode at different retention times (a-c). The different side chains, 18:0 (m/z 283.2), 20:5 (m/z 301.2), 16:0 (m/z 255.2), 22:5 (m/z 329.3), 18:1 (m/z 281.3) and 20:4 (m/z 303.2) identify "807.6" as PtdCho 18:0/20:5, PtdCho 16:0/22:5, PtdCho 22:5/16:0 and PtdCho 18:1/20:4.

Figure 33:
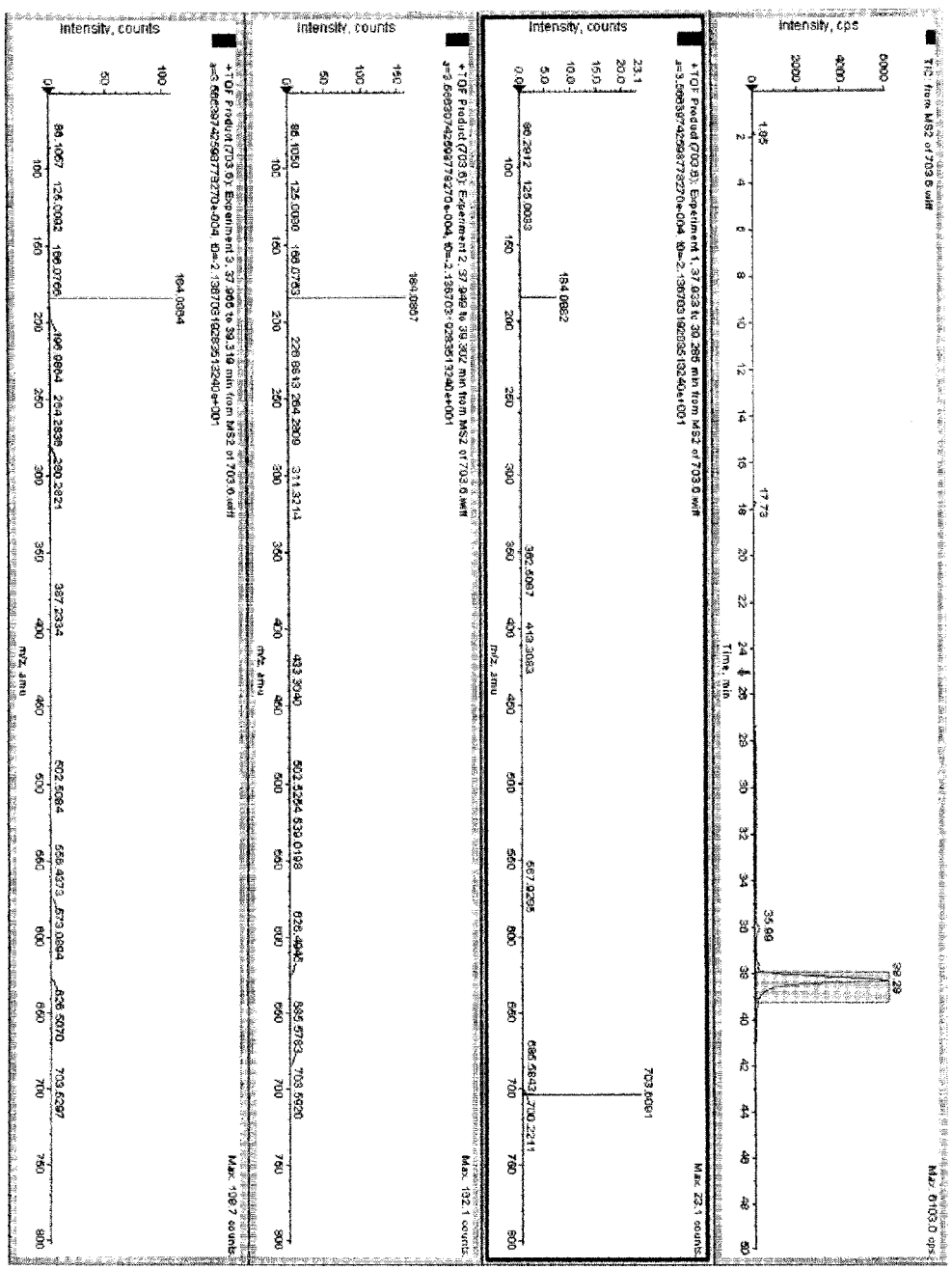

FIG. 33 illustrates the fragmentation pattern of 702.6 in positive aqueous ESI mode.

Figure 34:
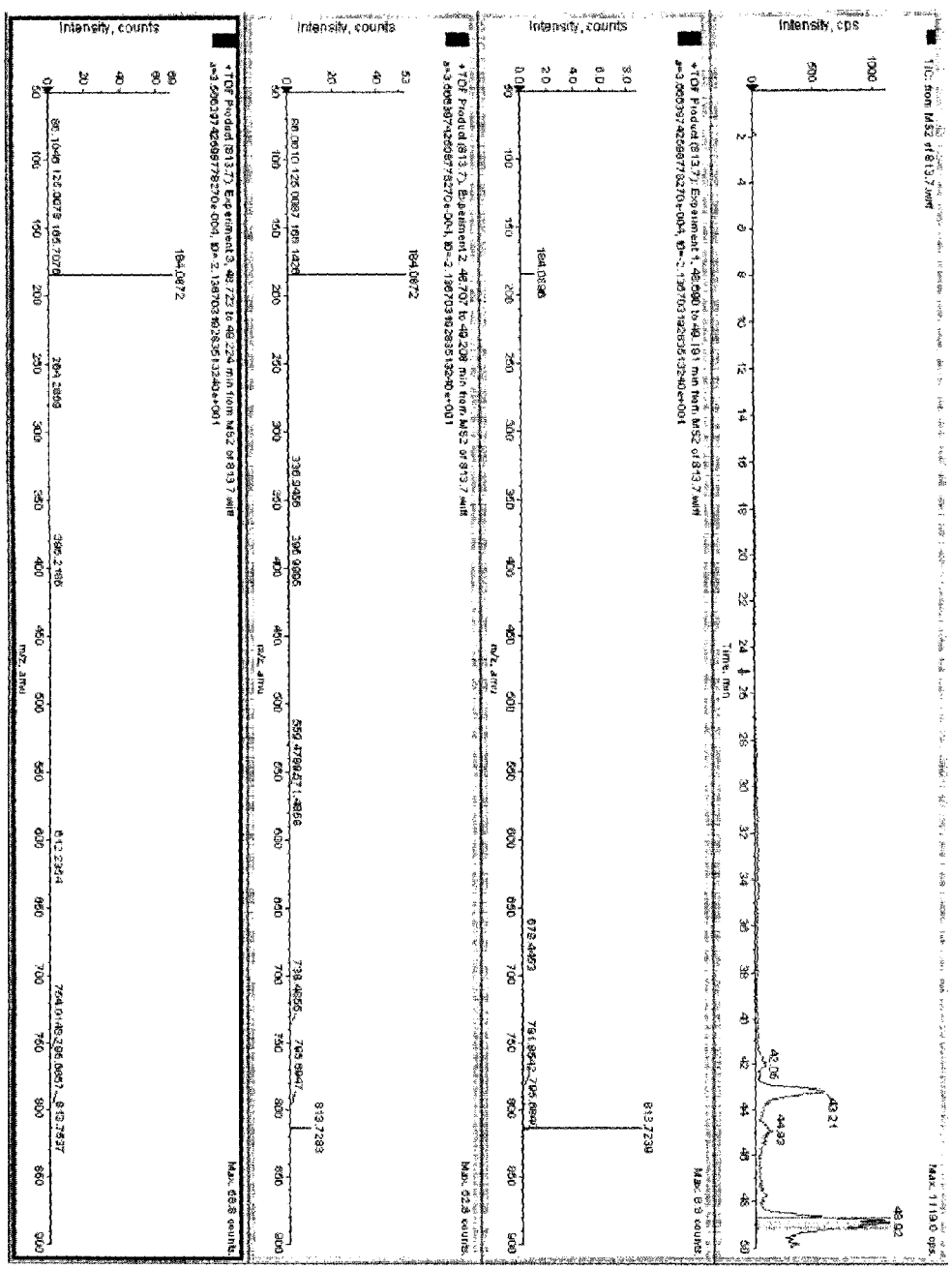

FIG. 34 illustrates the fragmentation pattern of 812.7 in positive aqueous ESI mode.

Figure 35:
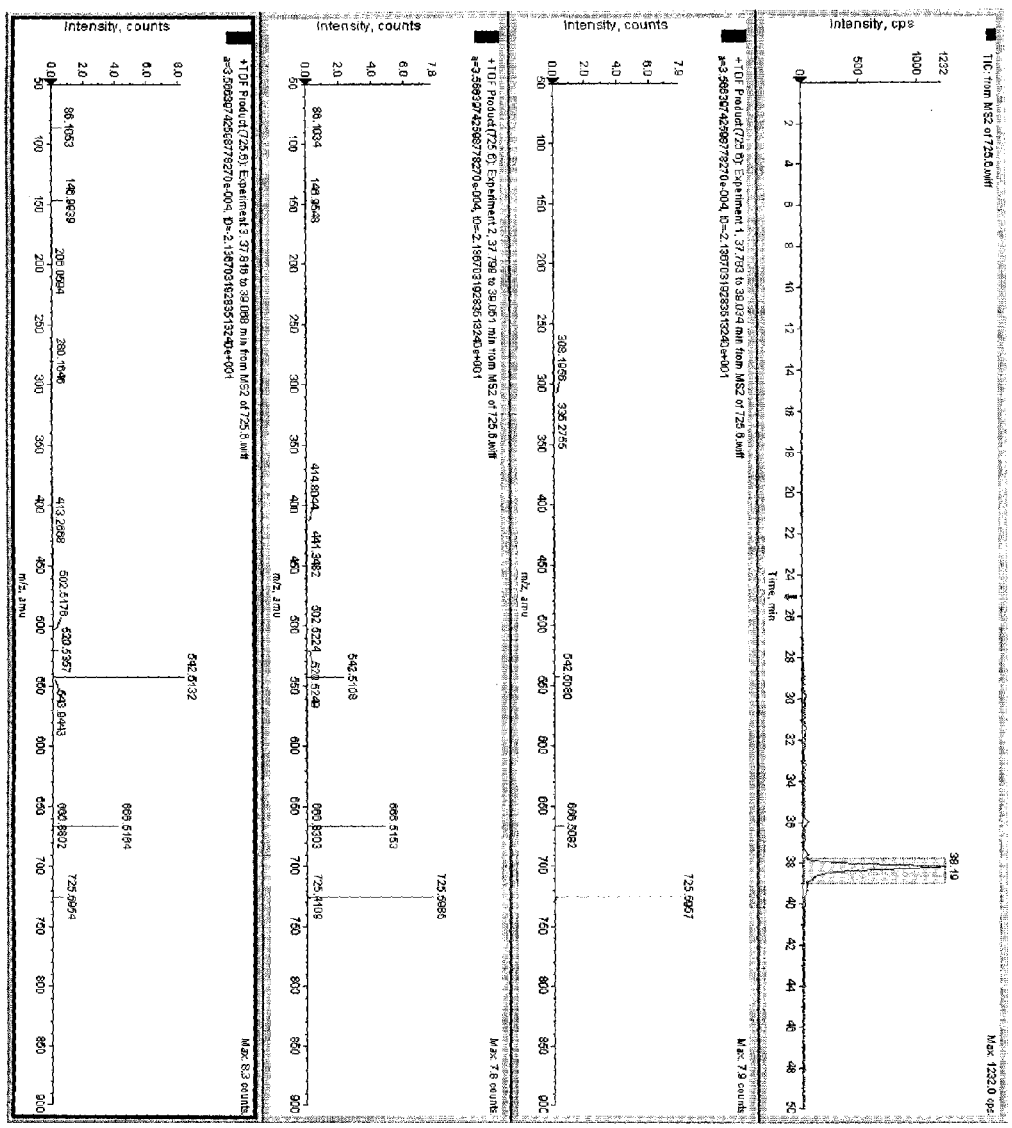
Figure 36:
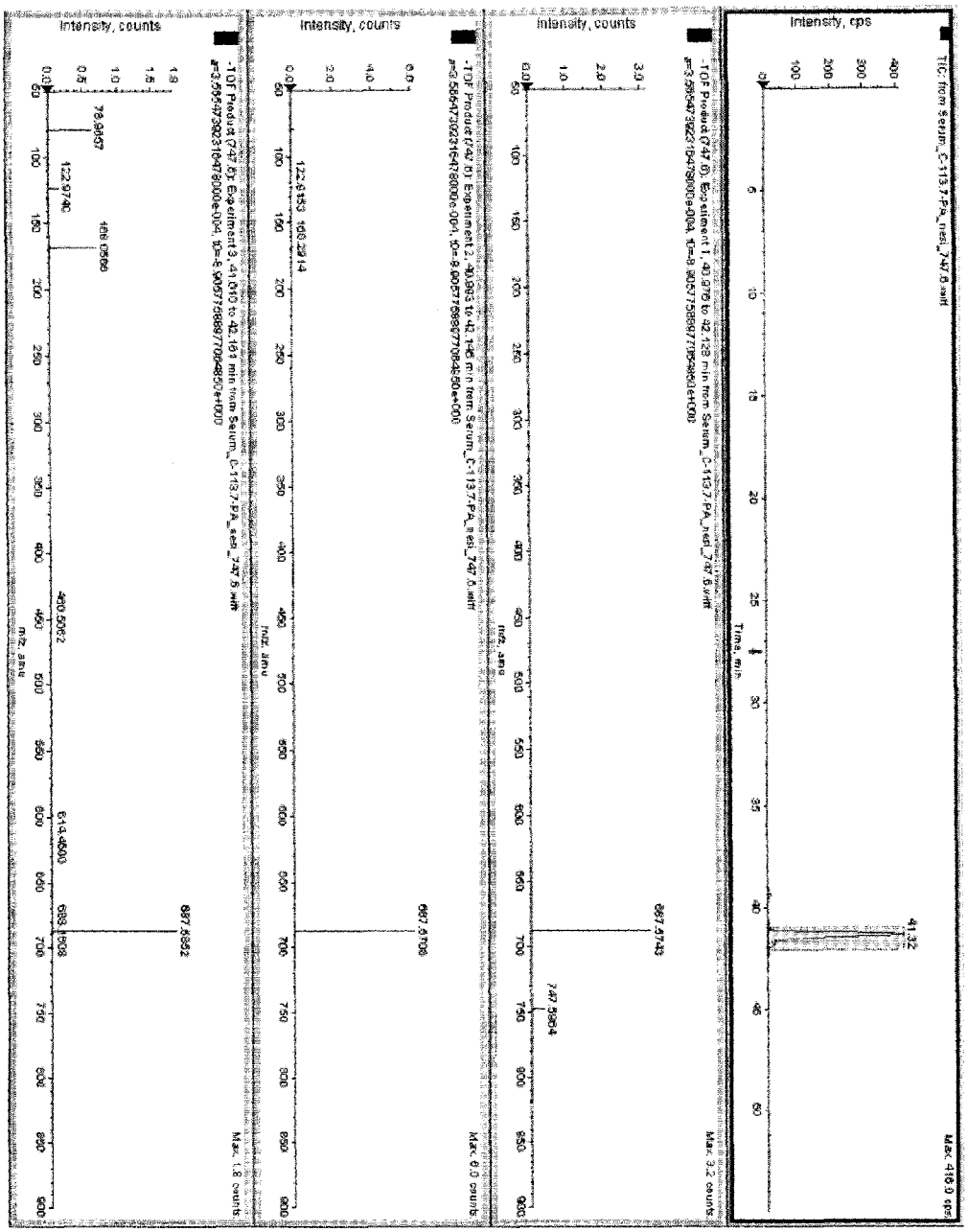

FIG. 35 illustrates the fragmentation pattern of 724.6 in positive aqueous ESI mode FIG. 36 illustrates the fragmentation pattern of 702.6 as a formic acid adduct in negative ESI analysis mode in control sample aqueous extracts (m/z 747.6).

Figure 37:
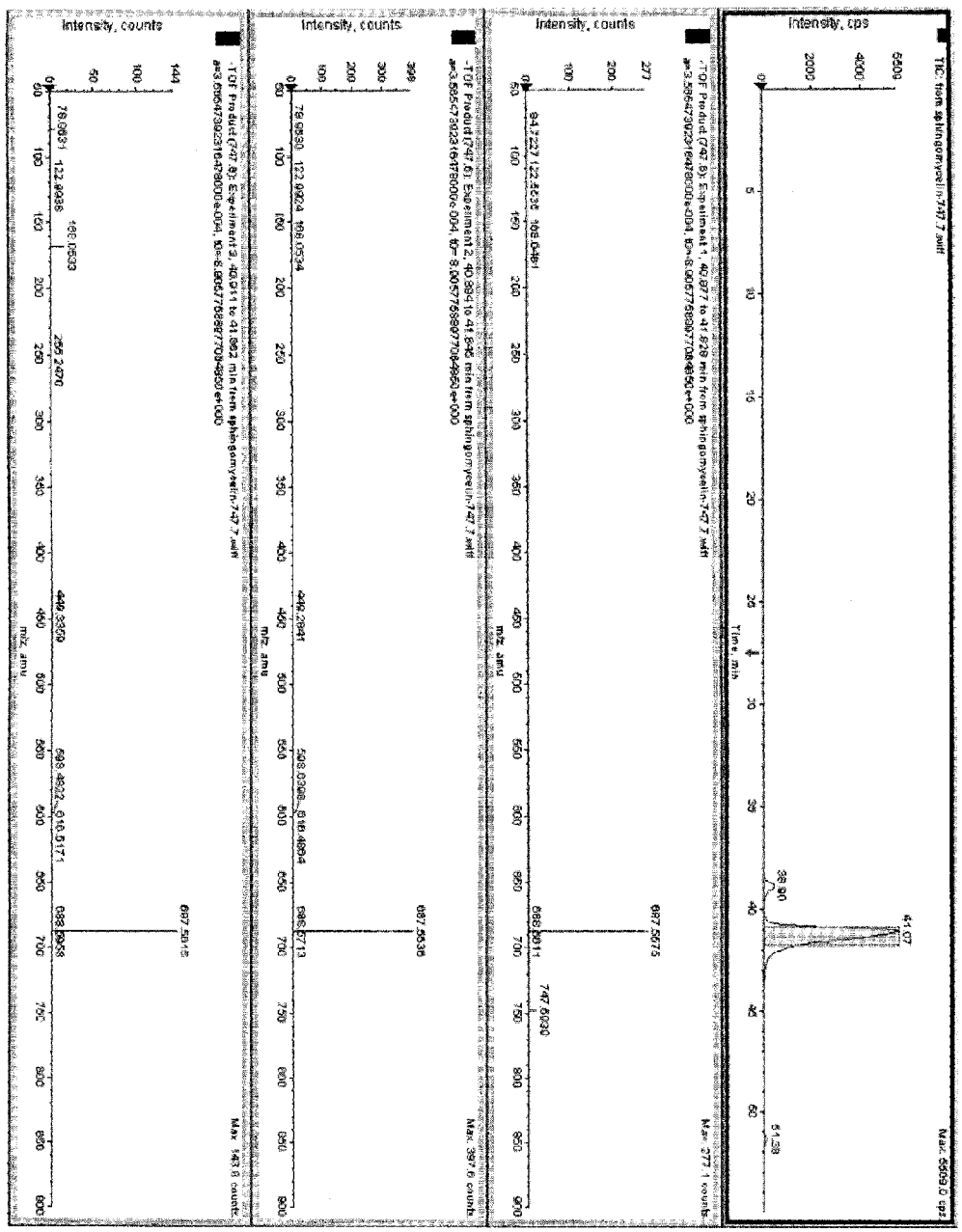

FIG. 37 illustrates the fragmentation pattern of synthetic SM(d18:1/16:0) (from Avanti Polar Lipids, cat. 860584) as a formic acid adduct in negative ESI analysis mode (m/z 747.6).

Figure 38:
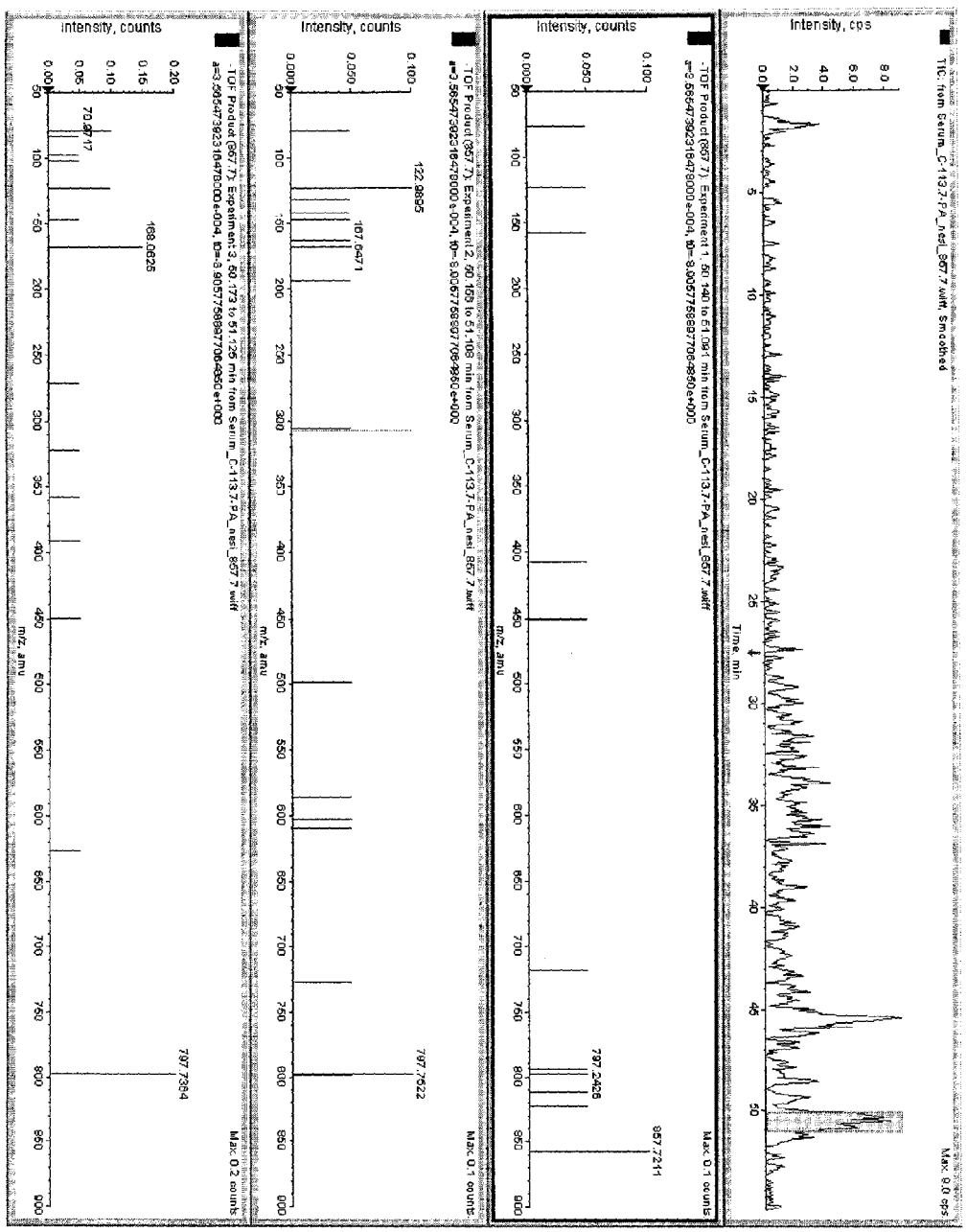

FIG. 38 illustrates the fragmentation pattern of 812.7 as a formic acid adduct in negative ESI analysis mode in control sample aqueous extracts (m/z 857.7).

Figure 39:
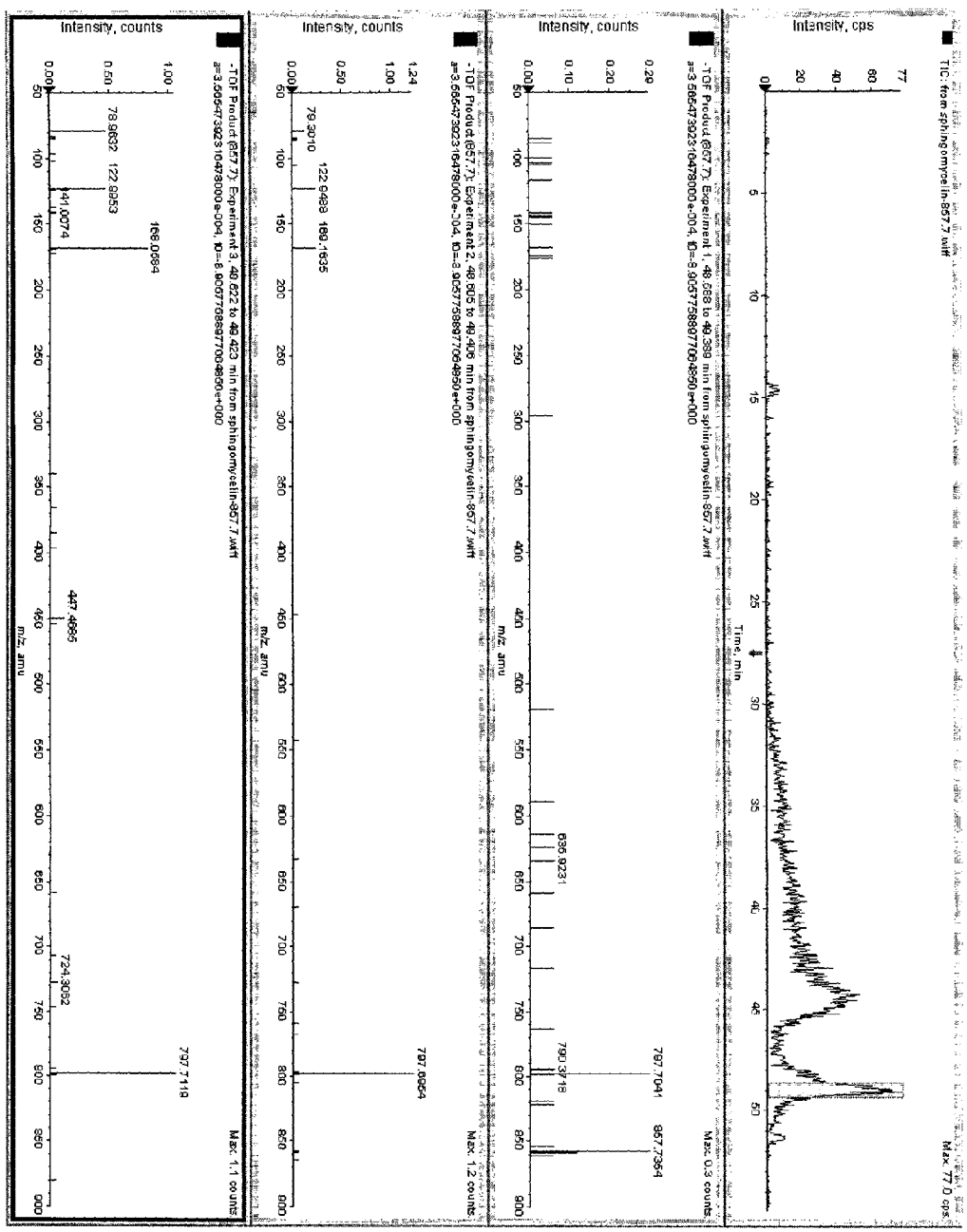

FIG. 39 illustrates the fragmentation pattern of synthetic SM(d18:1/24:1(15Z)) (from Avanti Polar Lipids, cat. 860593) as a formic acid adduct in negative ESI analysis mode (m/z 857.7).

Figure 40:
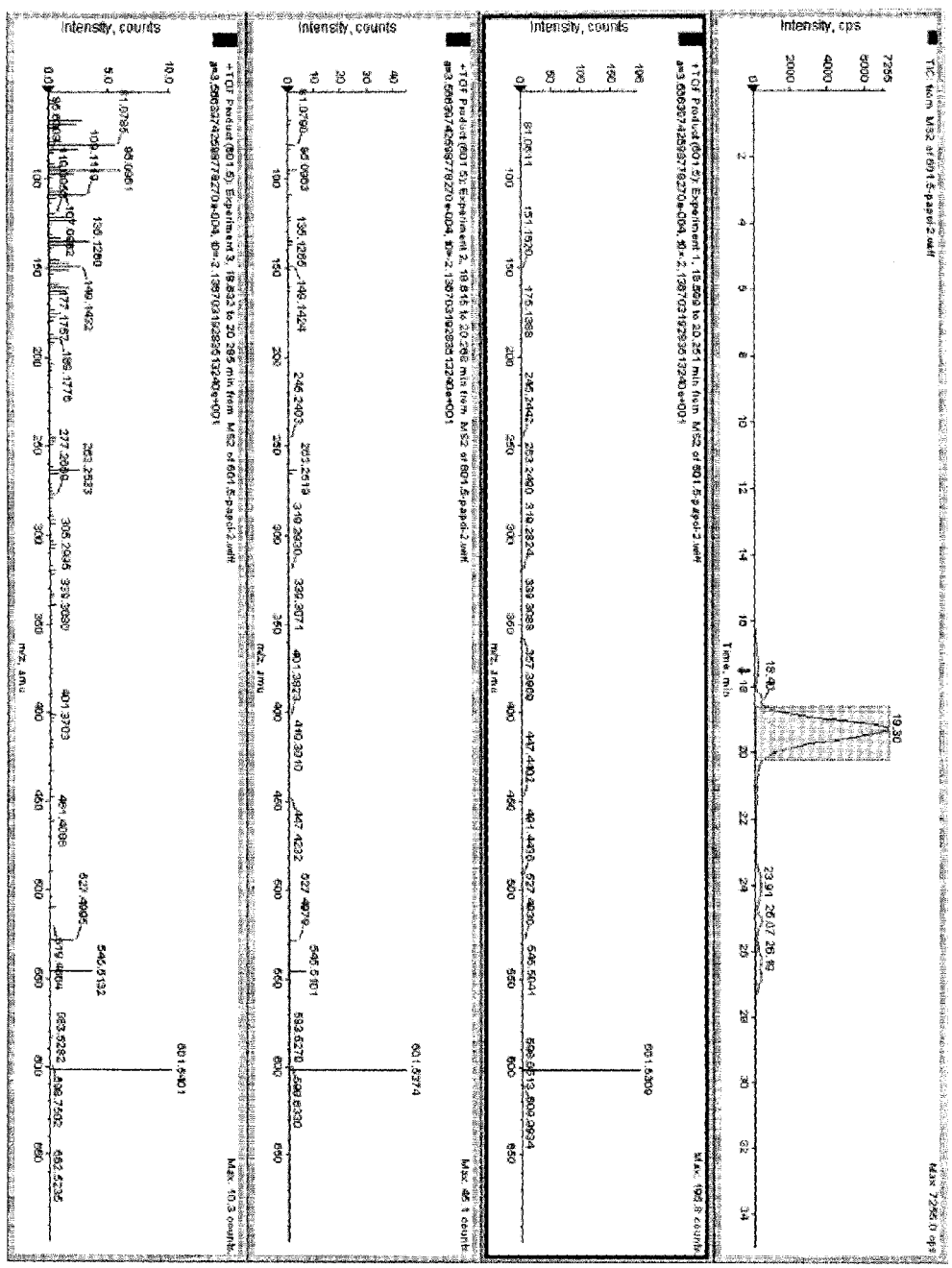

FIG. 40 illustrates the fragmentation of 600.5117 organic extract in positive APCI.

Figure 41:
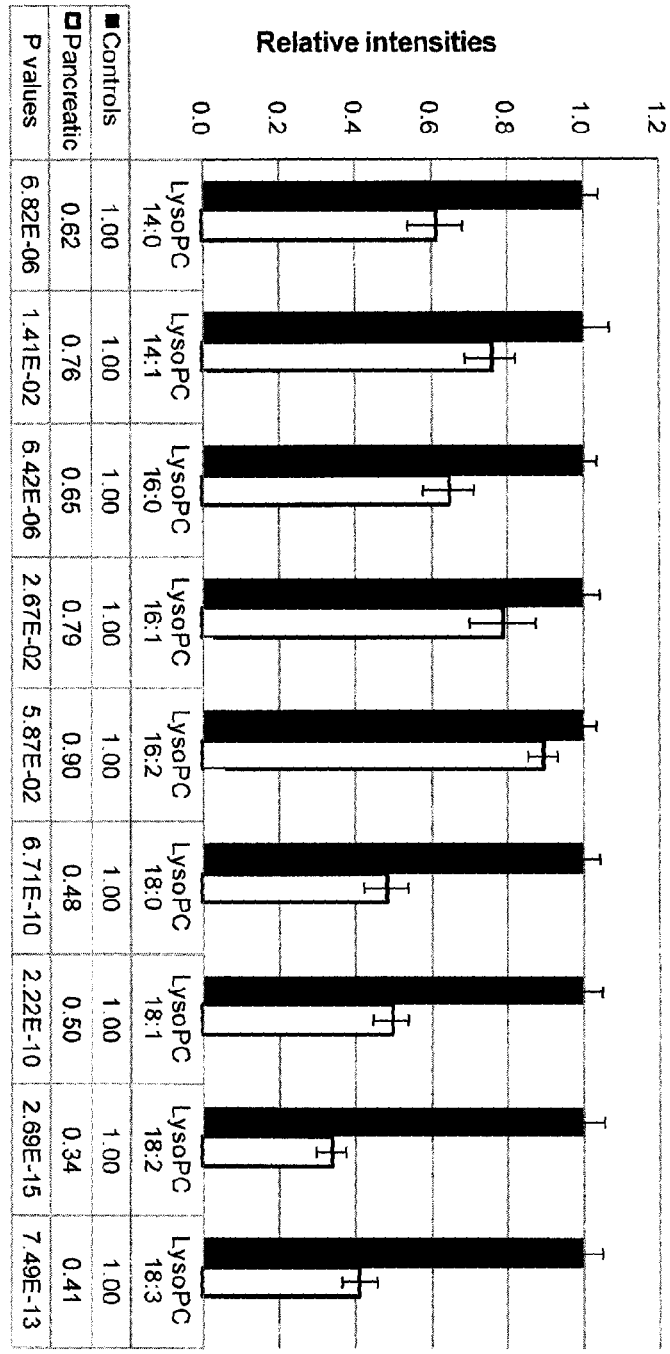
Figure 41:
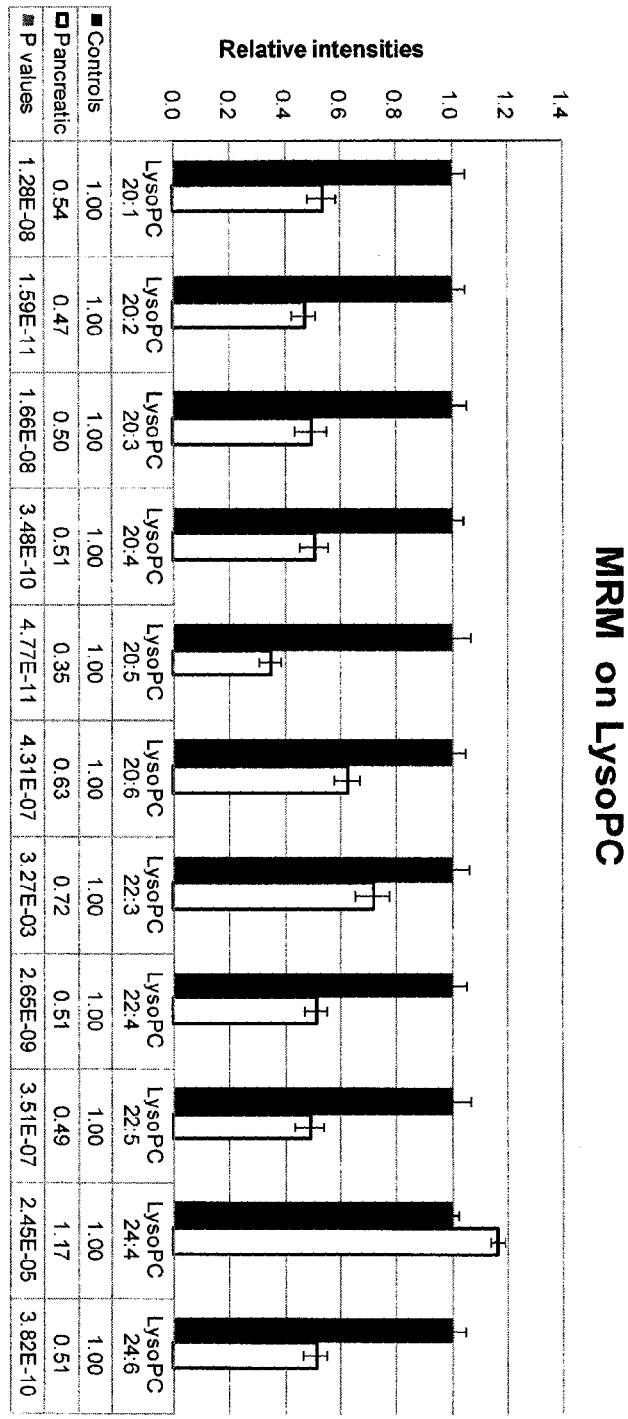
Figure 41:
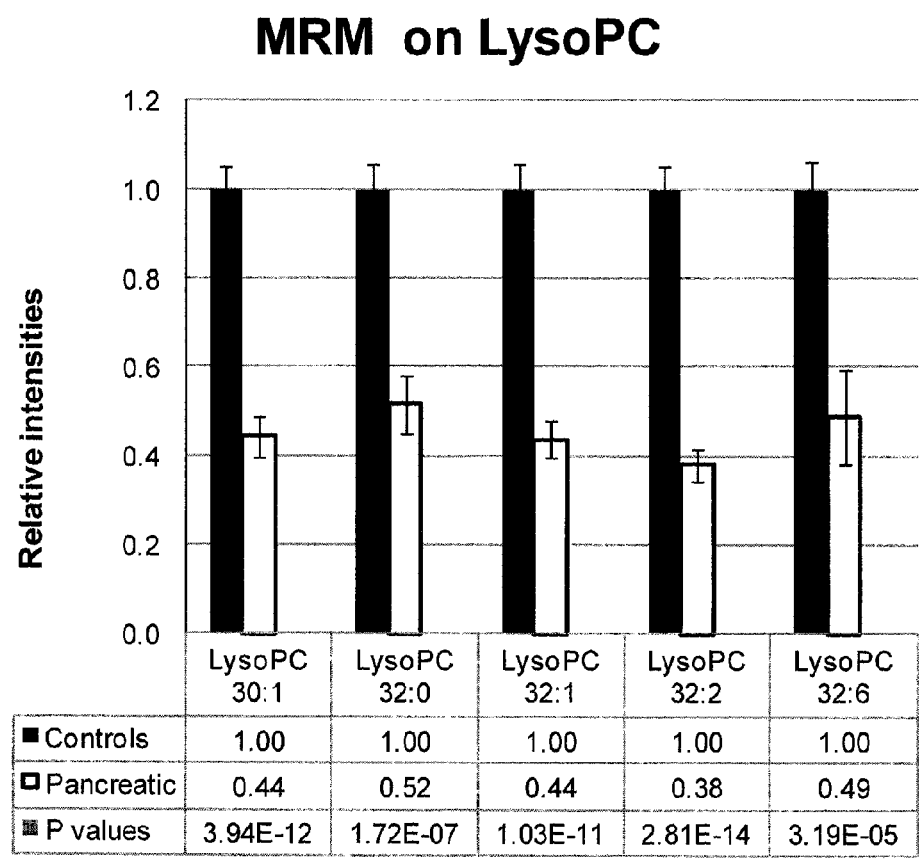
Figure 41:
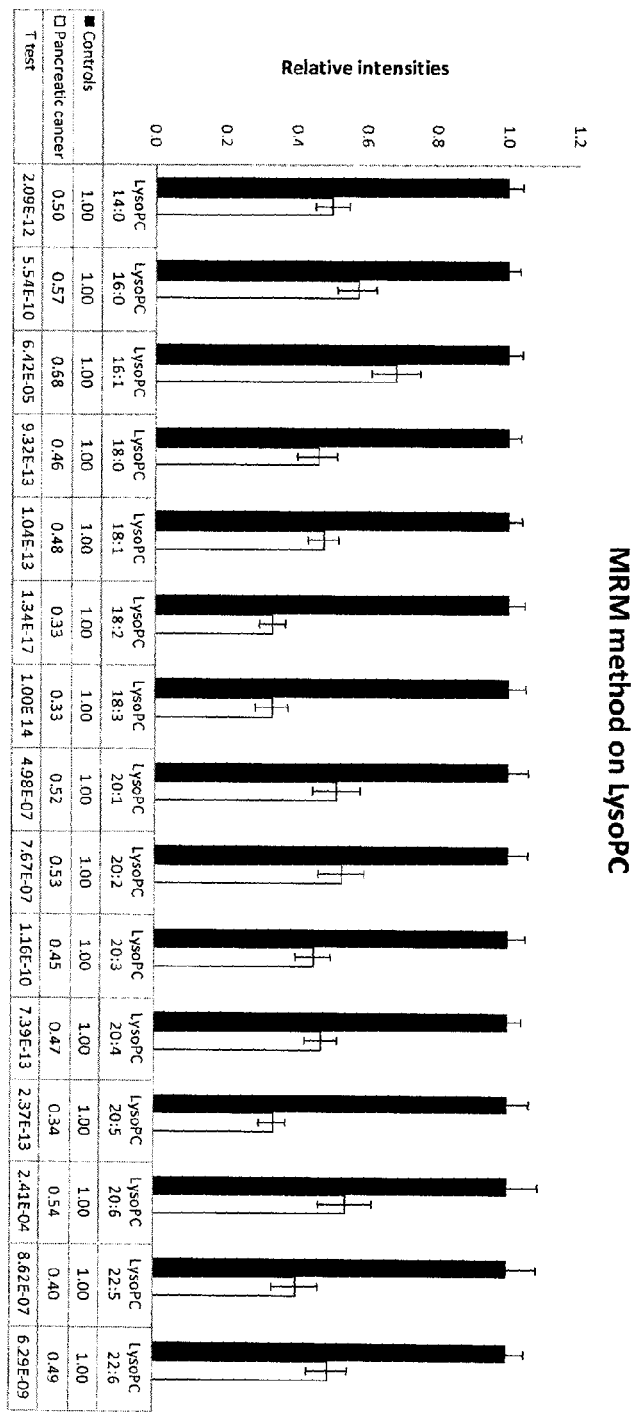

FIG. 41 shows the relative levels of LysoPC 18:0 (mass 523.4), LysoPC18:2 (mass 519.3) and LysoPC20:5 (mass 541.3) and of additional LysoPC in the serum of pancreatic cancer patients relative to controls by Electrospray Ionization (ESI) analysis. (a) LysoPC with 14, 16 and 18 carbons on the side chain, (b) LysoPC with 20, 22 and 24 carbons on the side chain, (c) LysoPC with 30 and 32 carbons on the side chain, and (d) LysoPC with 14, 16, 18, 20 and 22 carbons on the side chain. (a) to (c) in positive ESI analysis mode and (d) in negative ESI analysis mode.

Figure 42:
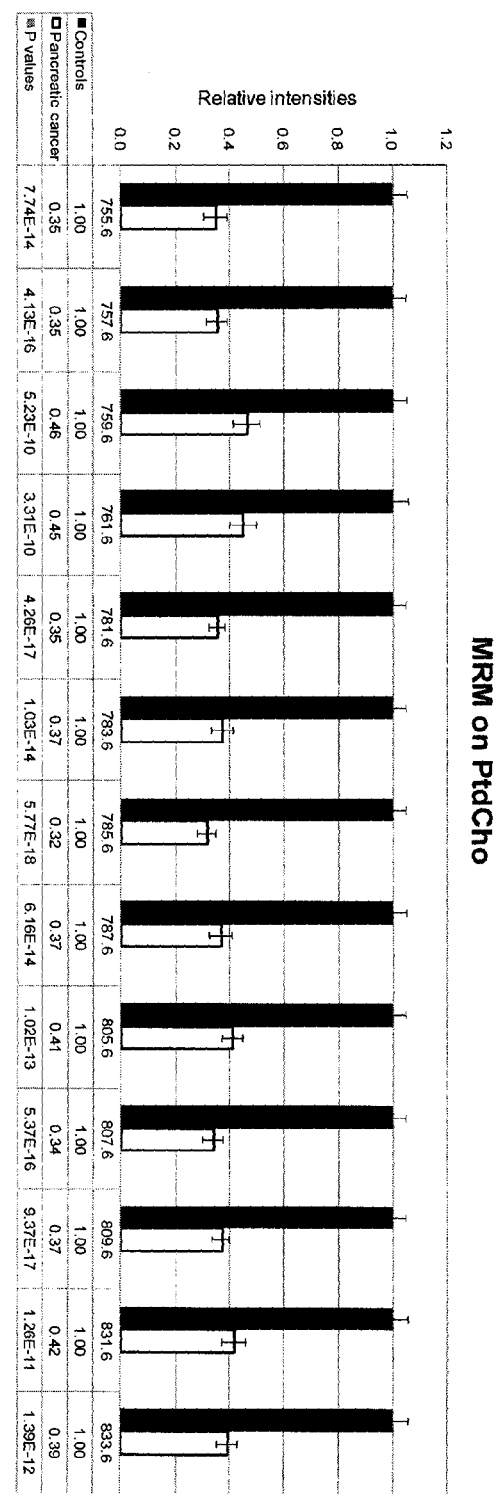
Figure 42:
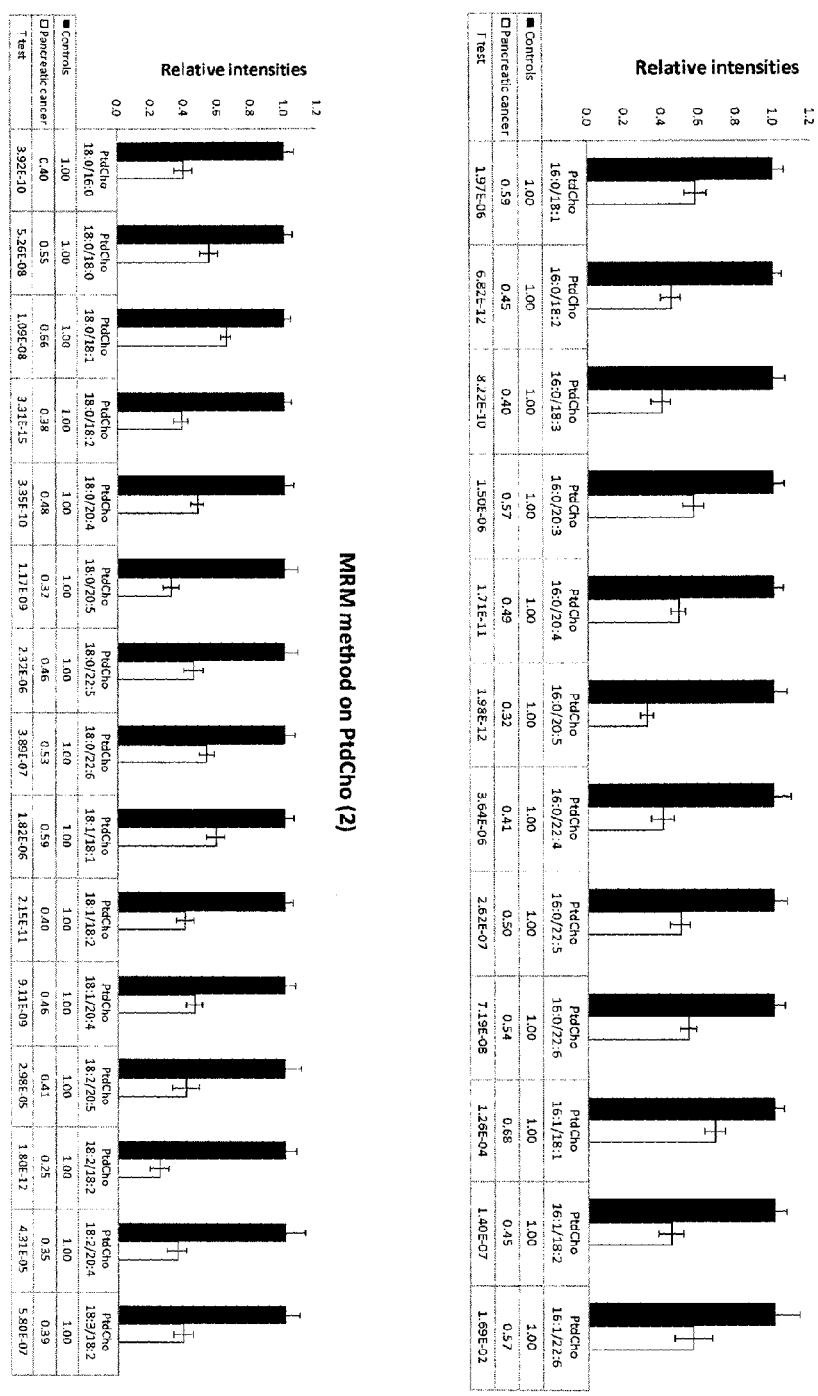
Figure 42:
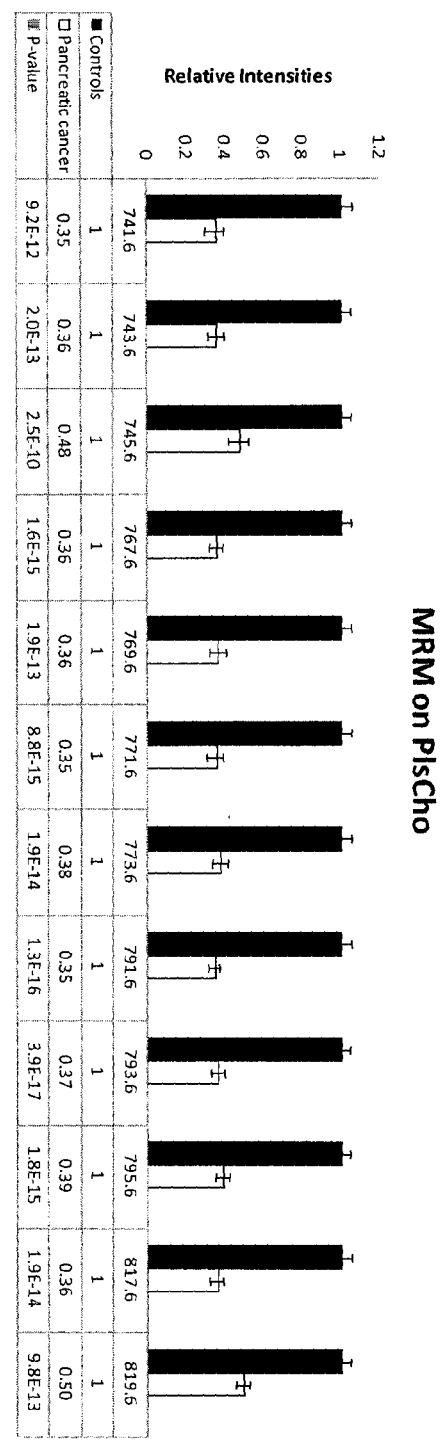

FIG. 42 shows the relative MRM levels of 13 PtdCho named by their parent mass in positive ESI analysis mode (a) 27 PtdCho in negative ESI mode (b), and 12 PlsCho named by their parent mass in positive ESI mode (c) in the serum of pancreatic cancer patients relative to controls.

Figure 43:
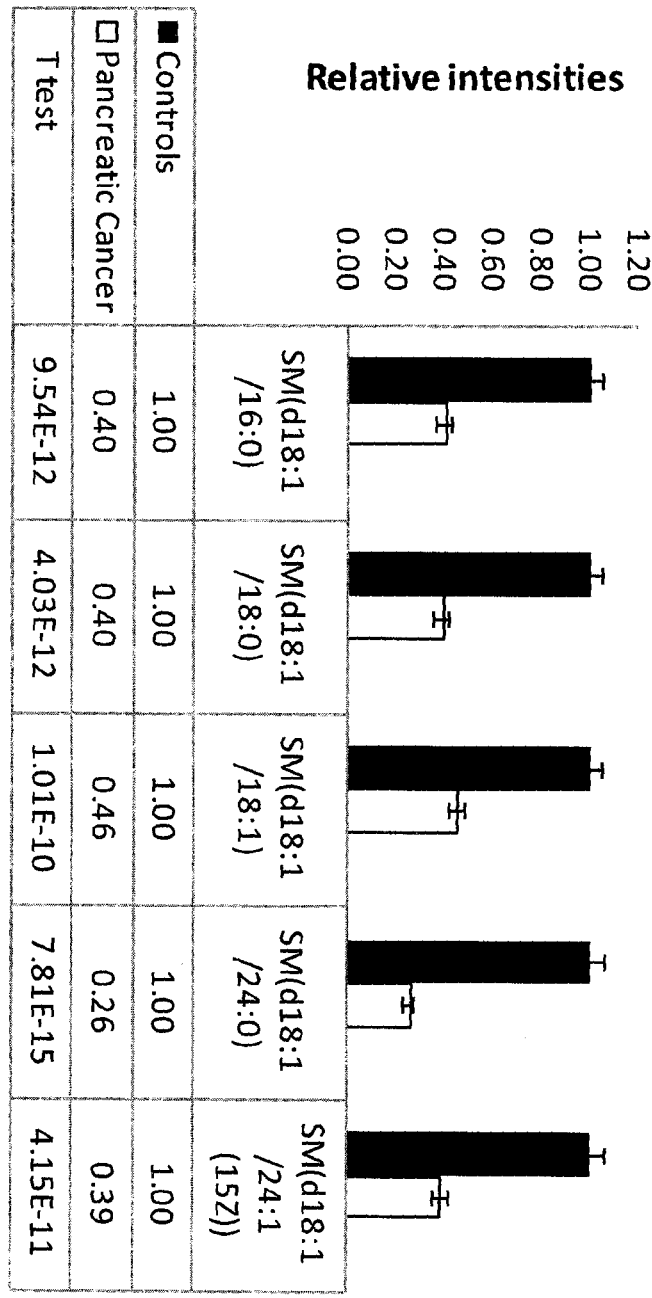

FIG. 43 shows the relative MRM levels of five sphingomyelins in the serum of pancreatic cancer patients relative to controls.

Figure 44:
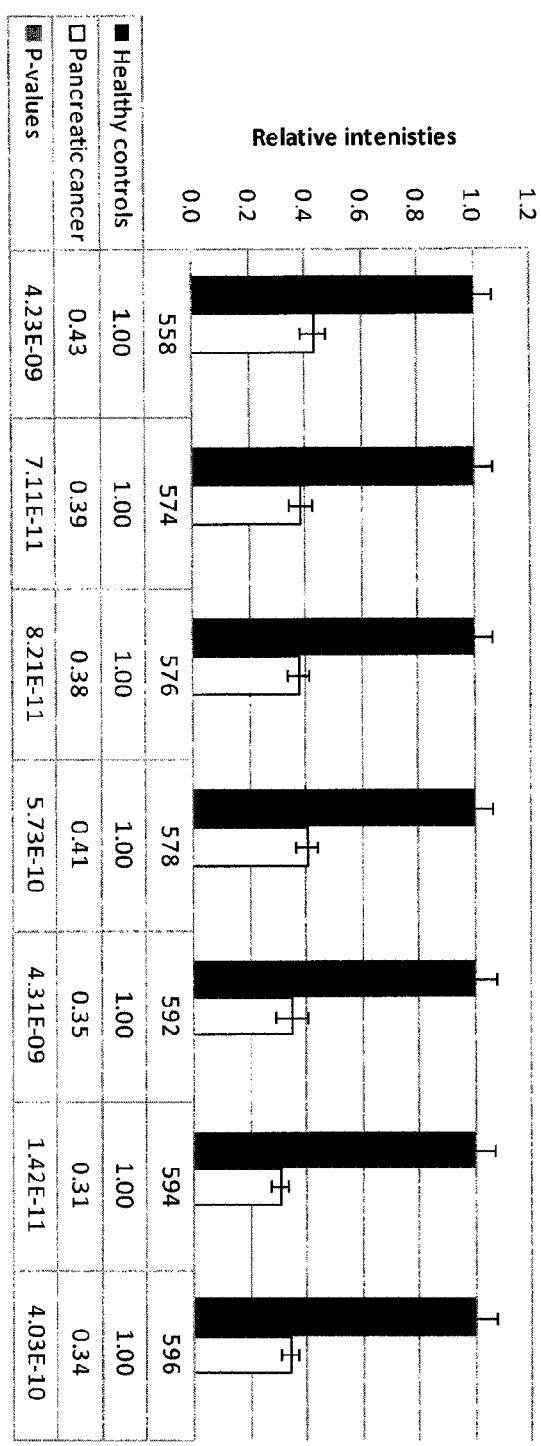

FIG. 44 shows the relative levels of C36 markers in the serum of pancreatic cancer patients relative to controls.

Figure 45:
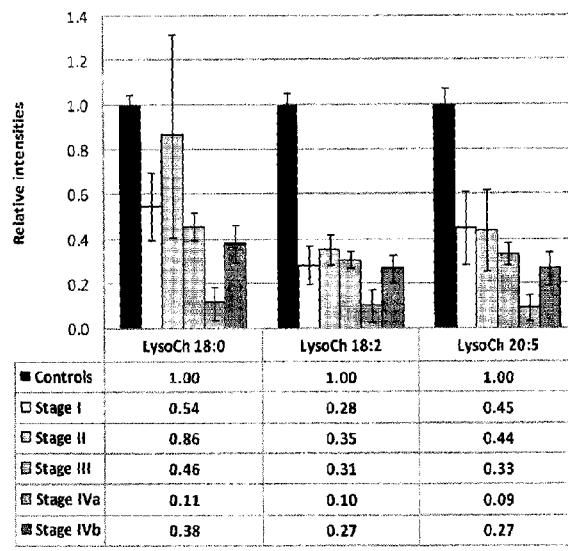
Figure 45:
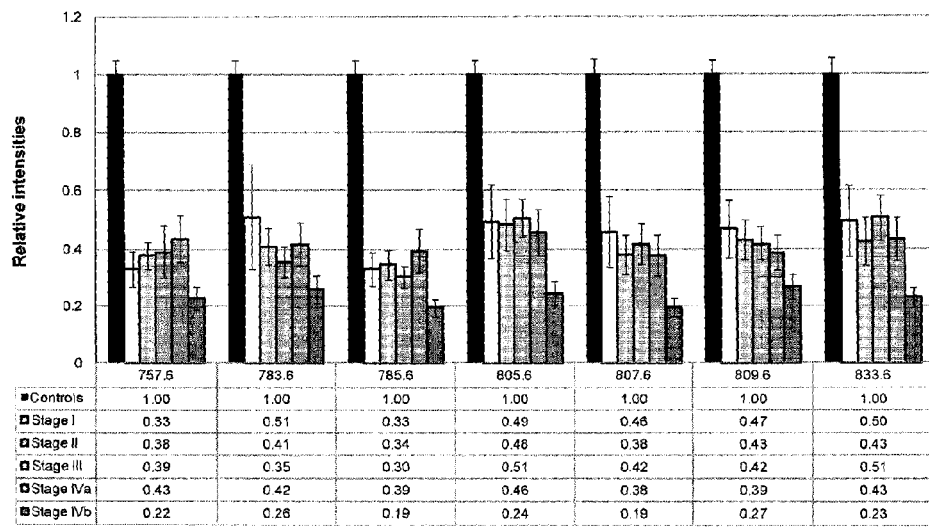
Figure 45:
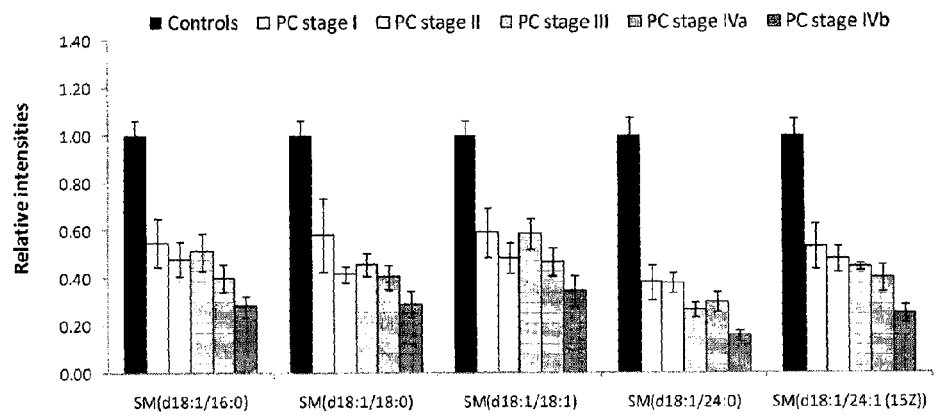
Figure 45:
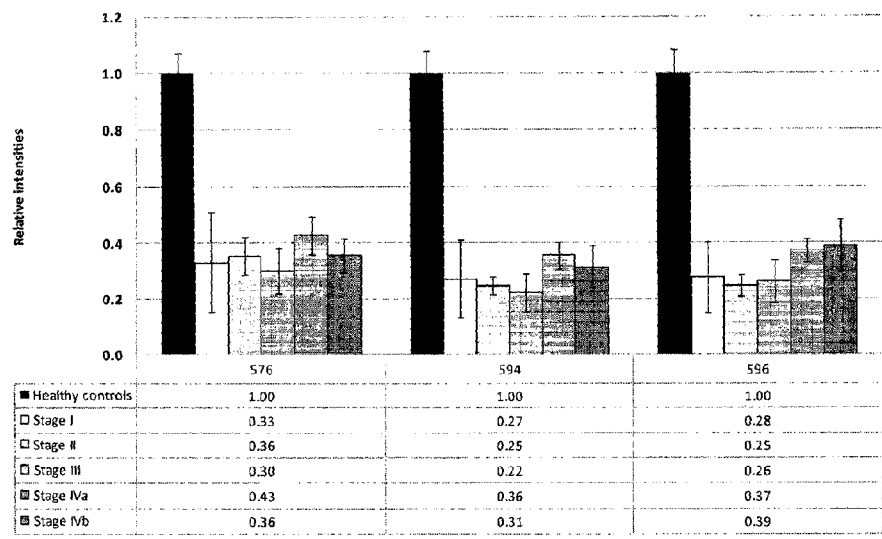

FIG. 45 shows the relative intensities of biomarkers for pancreatic cancer at different stages in three LysoPC (a), seven PtdCho (b), five sphingomyelins (c) and three C36 markers (d).

Figure 46:
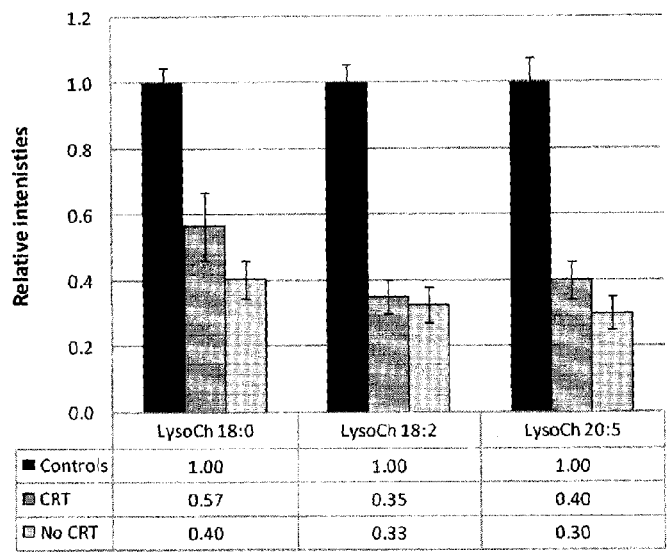
Figure 46:
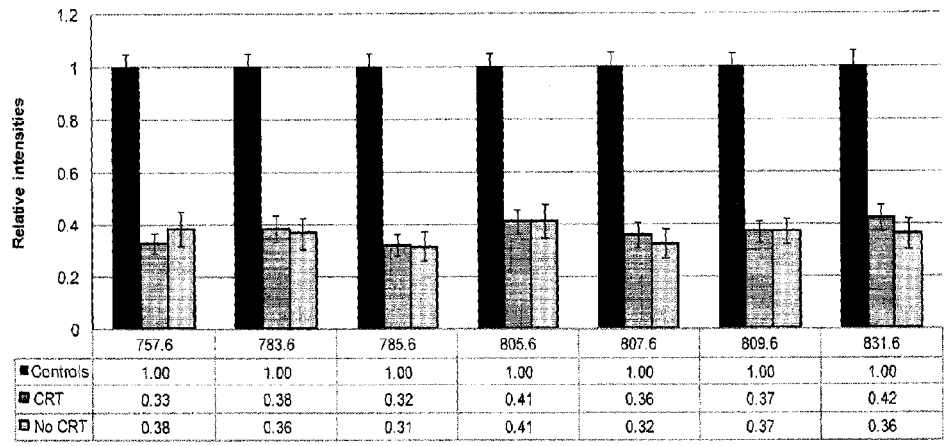
Figure 46:
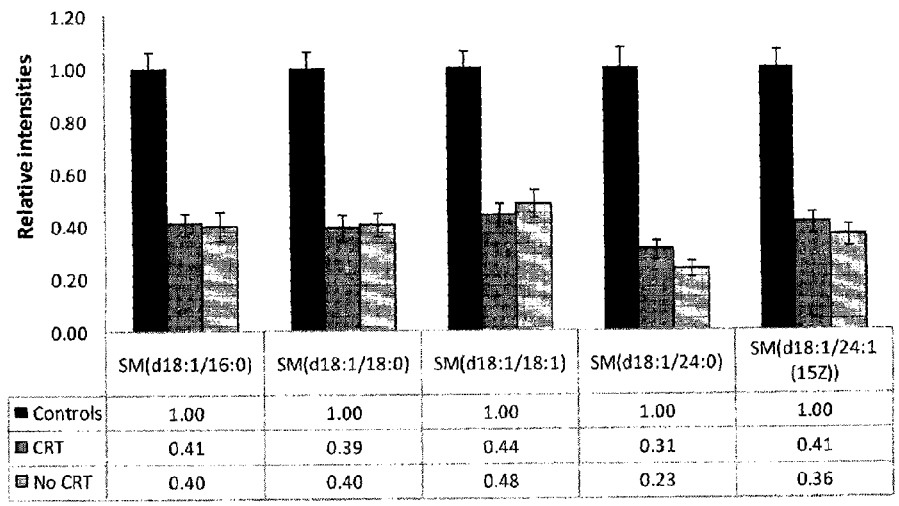
Figure 46:
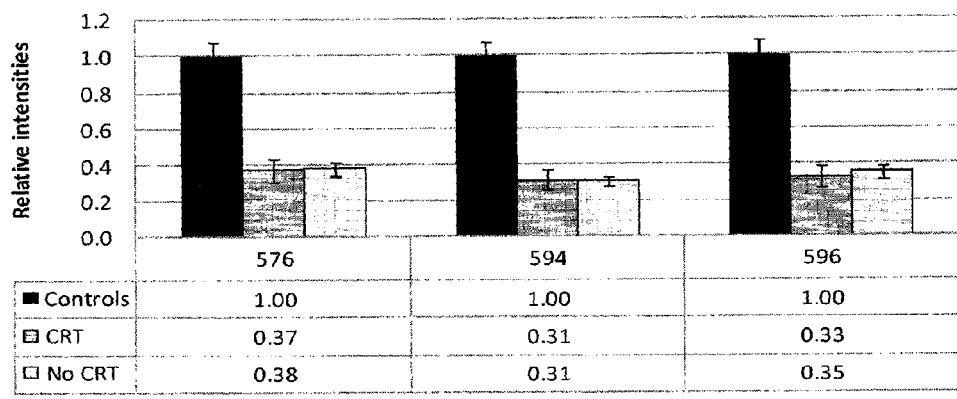

FIG. 46 shows the relative intensities of biomarkers for pancreatic cancer chemoradiation therapy status in three LysoPC (a), seven PtdCho (b), five sphingomyelins (c) and three C36 markers (d).

DETAILED DESCRIPTION

The present inventors have identified cancer-specific biomarkers in human serum, and accordingly present herein a non-invasive cancer detection method that is useful for monitoring an individual's susceptibility to disease, and that may be used either alone or in combination with other known diagnostic methods. The methods described are particularly useful for detecting or diagnosing pancreatic cancer.

A "non-targeted" approach was developed for the identification of biomarkers specific to pancreatic cancer. This discovery platform incorporated the use of Fourier transform ion cyclotron resonance mass spectrometry (FTICR-MS), which is capable of detecting ions with mass accuracy below 1 part per million (ppm). Using this method, liquid sample extracts can be directly infused, for instance using electrospray ionization (ESI) and atmospheric pressure chemical ionization (APCI), without chromatographic separation. Ions with differing mass to charge (M/Z) ratios are then simultaneously resolved using a Fourier transformation. This combination of liquid extraction, flow injection, high resolution and informatics affords a unique opportunity to broadly characterize the biochemical composition of samples without a priori knowledge.

When analyzing the serum metabolomic profiles of pancreatic cancer patients and healthy asymptomatic subjects included in their study, the inventors identified specific biomarkers that had significantly altered serum levels in pancreatic cancer patients when compared to controls in a set of 90 samples. Structural characterization was performed by MS/MS technology, and some of the markers were found to be choline-related compounds. Alterations in the serum levels of these biomarkers were confirmed by targeted mass spectrometry using a targeted high-throughput triple-quadrupole MRM (TQ-MRM) method on the same samples.

The inventors have accordingly developed methods to monitor levels of these biomarkers in a subject in a specific and sensitive manner, and to use this information as a useful tool for the early detection and screening of pancreatic cancer.

The present invention accordingly relates to a method of diagnosing cancer by measuring the levels of specific biomarkers present in human serum and comparing them to "normal" reference levels. The described method may be used for the early detection and diagnosis of cancer as well as for monitoring the effects of treatment on cancer patients.

The method also may be incorporated into a high-throughput screening method for testing large numbers of individuals, and further enables longitudinal screening throughout the lifetime of a subject to assess risk and detect disease early on. The method therefore has the potential to detect disease progression prior to that detectable by conventional methods, which is critical to positive treatment outcome.

According to the described method, biological samples taken from one or more subjects of a particular health-state category are compared to the same samples taken from the normal population to identify differences in the levels of the described biomarkers. The samples are extracted and analyzed using various analytical platforms including, but not limited to, Fourier transform ion cyclotron resonance mass spectrometry (FTMS) and liquid chromatography mass spectrometry (LC-MS).

The biological samples could originate from anywhere within the body, for example but not limited to, blood (serum/plasma), cerebral spinal fluid (CSF), bile, urine, stool, breath, saliva, or biopsy of any solid tissue including tumor, adjacent normal, smooth and skeletal muscle, adipose tissue, liver, skin, hair, brain, kidney, pancreas, lung, colon, stomach, or other. Of particular interest are samples that are serum or CSF. While the term "serum" is used herein, those skilled in the art will recognize that plasma or whole blood or a sub-fraction of whole blood may be used.

When a blood sample is drawn from a patient there are several ways in which the sample can be processed. The range of processing can be as little as none (i.e. frozen whole blood) or as complex as the isolation of a particular cell type. The most common and routine procedures involve the preparation of either serum or plasma from whole blood. All blood sample processing methods, including spotting of blood samples onto solid-phase supports, such as filter paper or other immobile materials, are also contemplated by the invention.

Without wishing to be limiting, the processed blood or plasma sample described above may then be further processed to make it compatible with the methodical analysis technique to be employed in the detection and measurement of the metabolites contained within the processed blood sample. The types of processing can range from as little as no further processing to as complex as differential extraction and chemical derivatization. Extraction methods may include sonication, soxhlet extraction, microwave assisted extraction (MAE), supercritical fluid extraction (SFE), accelerated solvent extraction (ASE), pressurized liquid extraction (PLE), pressurized hot water extraction (PHWE) and/or surfactant assisted extraction (PHWE) in common solvents such as methanol, ethanol, mixtures of alcohols and water, or organic solvents such as ethyl acetate or hexane. A method of particular interest for extracting metabolites for FTMS non-targeted analysis and for flow injection LC-MS/MS analysis is to perform a liquid/liquid extraction whereby non-polar metabolites dissolve in an organic solvent and polar metabolites dissolve in an aqueous solvent.

The extracted samples may be analyzed using any suitable method including those known in the art. For example, and without wishing to be limiting, extracts of biological samples are amenable to analysis on essentially any mass spectrometry platform, either by direct injection or following chromatographic separation. Typical mass spectrometers are comprised of a source that ionizes molecules within the sample, and a detector for detecting the ionized molecules or fragments of molecules. Non-limiting examples of common sources include electron impact, electrospray ionization (ESI), atmospheric pressure chemical ionization (APCI), atmospheric pressure photo ionization (APPI), matrix assisted laser desorption ionization (MALDI), surface enhanced laser desorption ionization (SELDI), and derivations thereof. Common mass separation and detection systems can include quadrupole, quadrupole ion trap, linear ion trap, time-of-flight (TOF), magnetic sector, ion cyclotron (FTMS), Orbitrap, and derivations and combinations thereof. The advantage of FTMS over other MS-based platforms is its high resolving capability that allows for the separation of metabolites differing by only hundredths of a Dalton, many of which would be missed by lower resolution instruments.

By the term "metabolite", it is meant specific small molecules, the levels or intensities of which are measured in a sample, and that may be used as markers to diagnose a disease state. These small molecules may also be referred to herein as "metabolite marker", "metabolite component", "biomarker", or "biochemical marker".

The metabolites are generally characterized by their accurate mass, as measured by mass spectrometry technique. The accurate mass may also be referred to as "accurate neutral mass" or "neutral mass". The accurate mass of a metabolite is given herein in Daltons (Da), or a mass substantially equivalent thereto. By "substantially equivalent thereto", it is meant that a +/−5 ppm difference in the accurate mass would indicate the same metabolite. The accurate mass is given as the mass of the neutral metabolite. During the ionization of the metabolites, which occurs during analysis of the sample, the metabolite will cause either a loss or gain of one or more hydrogen atoms and a loss or gain of an electron. This changes the accurate mass to the "ionized mass", which differs from the accurate mass by the mass of hydrogen atoms and electrons lost or gained during ionization. Unless otherwise specified, the accurate neutral mass will be referred to herein.

Similarly, when a metabolite is described by its molecular formula, the molecular formula of the neutral metabolite will be given. Naturally, the molecular formula of the ionized metabolite will differ from the neutral molecular formula by the number of hydrogen atoms lost or gained during ionization or due to the addition of a non-hydrogen adduct ion.

Data is collected during analysis and quantifying data for one or more than one metabolite is obtained. "Quantifying data" is obtained by measuring the levels or intensities of specific metabolites present in a sample.

The quantifying data is compared to corresponding data from one or more than one reference sample. The "reference sample" is any suitable reference sample for the particular disease state. For example, and without wishing to be limiting in any manner, the reference sample may be a sample from a control individual, i.e., a person not suffering from cancer with or without a family history of cancer (also referred to herein as a "'normal' counterpart"); the reference sample may also be a sample obtained from a patient clinically diagnosed with cancer. As would be understood by a person of skill in the art, more than one reference sample may be used for comparison to the quantifying data. For example and without wishing to be limiting, the one or more than one reference sample may be a first reference sample obtained from a non-cancer control individual. In the case of monitoring a subject's change in disease state, the reference sample may include a sample obtained at an earlier time period either pre-therapy or during therapy to compare the change in disease state as a result of therapy.

An "internal control metabolite" refers to an endogenous metabolite naturally present in the patient. Any suitable endogenous metabolite that does not vary over the disease states can be used as the internal control metabolite.

Use of a ratio of the metabolite marker to the internal control metabolite offers measurement that is more stable and reproducible than measurement of absolute levels of the metabolite marker. As the internal control metabolite is naturally present in all samples and does not appear to vary significantly over disease states, the sample-to-sample variability (due to handling, extraction, etc) is minimized.

As discussed above the biomarkers described herein were identified by a method known as non-targeted analysis. Non-targeted analysis involves the measurement of as many molecules in a sample as possible, without any prior knowledge or selection of the components prior to the analysis (see WO 01/57518, published Aug. 9, 2001). Therefore, the potential for non-targeted analysis to discover novel metabolite biomarkers is high versus targeted methods, which detect a predefined list of molecules. The present inventors used a non-targeted method to identify metabolite components that differ between cancer-positive and healthy individuals, followed by the development of a high-throughput targeted assay for a subset of the metabolites identified from the non-targeted analysis.

According to this analysis small molecules, metabolites, or metabolite fragments were identified that have differential abundances between cancer-positive serum and normal serum. As listed in Table 5, the inventors found 362 metabolite masses to have statistically significant differential abundances between cancer-positive serum and normal serum. All of these features, which differ statistically between the two populations, have potential diagnostic utility. However, the incorporation of 362 signals into a commercially diagnostic assay is in many cases impractical, so an optimum diagnostic set of markers or metabolites may be selected, for instance in a panel for a high-throughput screening (HTS) assay.

There are multiple types of HTS assay platform options currently available depending on the molecules being detected. These include, but are not limited to, colorimetric chemical assays (UV, or other wavelength), antibody-based enzyme-linked immunosorbant assays (ELISAs), chip-based and polymerase-chain reaction for nucleic acid detection assays, bead-based nucleic-acid detection methods, dipstick chemical assays, image analysis such as MRI, petscan, CT scan, and various mass spectrometry-based systems.

In a non-limiting embodiment, the HTS assay is based upon conventional triple-quadrupole mass spectrometry technology. The HTS assay works by directly injecting a serum extract into the triple-quad mass spectrometer, which then individually isolates each of the parent molecules by single-ion monitoring (SIM). This is followed by the fragmentation of each molecule using an inert gas (called a collision gas, collectively referred to as collision-induced dissociation or CID). The intensity of a specific fragment from each parent biomarker is then measured and recorded, through a process called multiple-reaction monitoring (MRM). In addition, an internal standard molecule is also added to each sample and subjected to fragmentation as well. This internal standard fragment should have the same intensity in each sample if the method and instrumentation is operating correctly. When all biomarker fragment intensities, as well as the internal standard fragment intensities are collected, a ratio of the biomarker to IS fragment intensity is calculated, and the ratio log-transformed. The values for each patient sample are then compared to a previously determined distribution of disease-positive and controls, to determine the relative likelihood that the person is positive or negative for the disease.

A commercial method for screening patients for cancer using the described assay methods is also envisioned. There are numerous options for the deployment of the assay world-wide. These include, but are not limited to: 1, the development of MS/MS methods compatible with current laboratory instrumentation and triple-quadrupole mass spectrometers which are readily in place in many labs around the world, and/or 2, the establishment of a testing facility where samples could be shipped and analyzed at one location, and the results sent back to the patient or patient's physician.

Structural elucidation of the identified metabolites was carried out using a series of physical and chemical property investigations. The principal characteristics that are normally used for this identification are accurate mass and molecular formula determination, polarity, acid/base properties, NMR spectra, and MS/MS or MSn spectra.

One group of diagnostic biomarkers, referred to herein as the C36 markers (558.4, 574.5, 576.5, 578.5, 592.5, 594.5, 596.5), were determined to have the following molecular formulae, respectively: $C_{36}H_{62}O_4$, $C_{36}H_{62}O_5$, $C_{36}H_{64}O_5$, $C_{36}H_{66}O_5$, $C_{36}H_{64}O_6$, $C_{36}H_{66}O_6$, and $C_{36}H_{68}O_6$. MS/MS transitions for each of these biomarkers for organic extracts in negative APCI were observed as follows: $C_{36}H_{62}O_4$: 557.4/495.4, 557.4/539.4, 557.4/513.3, 557.4/279.2, 557.4/277.2, 557.4/220.7 and 557.4/111.2; $C_{36}H_{62}O_5$: 573.5/511.4, 573.5/555.3, 573.5/537.4, 573.5/529.4, 573.5/519.4, 573.5/493.3, 573.5/457.4, 573.5/455.3, 573.5/443.4, 573.5/415.4, 573.5/413.3, 573.5/411.3, 573.5/399.3, 573.5/397.3, 573.5/389.7, 573.5/295.2, 573.5/279.2, 573.5/277.2, 573.5/251.2, 573.5/231.1, 573.5/223.1, 573.5/201.1, 573.5/171.1, 573.5/169.1, 573.5/125.1 and 573.5/113.1; $C_{36}H_{64}O_5$: 575.5/513.5, 575.5/557.5, 575.5/531.5, 575.5/499.5, 575.5/495.4, 575.5/447.3, 575.5/417.4, 575.5/415.4, 575.5/413.3, 575.5/371.3, 575.5/295.2, 575.5/279.2, 575.5/260.2, 575.5/251.2, 575.5/459.4, 575.5/403.3, 575.5/197.9, 575.5/119.4, 575.5/113.1, 575.5/97.0 and 575.5/539.5; $C_{36}H_{66}O_5$: 577.5/515.4, 577.5/559.4, 577.5/546.5, 577.5/533.5, 577.5/497.4, 577.5/419.4, 577.5/405.5, 577.5/297.2 and 577.5/281.2; $C_{36}H_{64}O_6$: 591.5/573.4, 591.5/555.4, 591.5/528.3, 591.5/511.2, 591.5/476.1, 591.5/419.3, 591.5/403.1, 591.5/387.3, 591.5/297.2, 591.5/295.2, 591.5/274.0, 591.5/255.3, 591.5/223.6, 591.5/203.5, 591.5/201.1, 591.5/171.0 and 591.5/125.3; $O_{36}H_{66}O_6$: 593.5/557.5, 593.5/513.4, 593.5/495.4, 593.5/371.3, 593.5/315.3, and 593.5/277.2; $C_{36}H_{68}O_6$: 595.5/577.5, 595.5/559.5, 595.5/551.5, 595.5/549.7, 595.5/533.5, 595.5/279.2, 595.5/391.3, 595.5/515.4, 595.5/478.4, 595.5/423.4, 595.5/372.5, 595.5/315.3, 595.5/313.2, 595.5/433.3, 595.5/298.2, 595.5/239.2, 595.5/232.9, 595.5/171.1, 595.5/169.1, 595.5/141.1 and 595.5/497.4.

A second group of choline-related diagnostic biomarkers, including lysophosphatidylcholines, phosphatidylcholines and sphingomyelins were also identified. The lysophosphatidylcholines include: LysoPC 14:0; LysoPC 14:1; LysoPC 16:0; LysoPC 16:1; LysoPC 16:2; LysoPC 18:0; LysoPC 18:1; LysoPC 18:2; LysoPC 18:3; LysoPC 20:1; LysoPC 20:2; LysoPC 20:3; LysoPC 20:4; LysoPC 20:5; LysoPC 20:6; LysoPC 22:3; LysoPC 22:4; LysoPC 22:5; LysoPC 22:6; LysoPC 24:4; LysoPC 24:6; LysoPC 30:1; LysoPC 32:0; LysoPC 32:1; LysoPC 32:2; and LysoPC 32:6. The molecular weight, formulae and MS/MS transitions for each of these biomarkers are described in further detail below.

The phosphatidylcholines (755.55; 757.56; 759.58; 761.59; 779.54; 781.56; 783.58; 785.59; 787.61; 803.54; 805.56; 807.58; 809.59; 829.55; 831.58; and 833.59), were determined to have the following molecular formulae, respectively: $C_{42}H_{78}NO_8P$; $C_{42}H_{80}NO_8P$; $C_{42}H_{82}NO_8P$; $C_{42}H_{84}NO_8P$; $C_{44}H_{78}NO_8P$; $C_{44}H_{80}NO_8P$; $C_{44}H_{82}NO_8P$; $C_{44}H_{84}NO_8P$; $C_{44}H_{86}NO_8P$; $C_{46}H_{78}NO_8P$; $C_{46}H_{80}NO_8P$; $C_{46}H_{82}NO_8P$; $C_{46}H_{84}NO_8P$; $C_{48}H_{80}NO_8P$; $C_{48}H_{82}NO_8P$; and $C_{48}H_{84}NO_8P$. The molecular weight, formulae and MS/MS transitions for each of these biomarkers are described in further detail below.

The sphingomyelins 702.57 and 812.68 were determined to have the respective formulae $C_{39}H_{72}N_2O_6P$ and $C_{47}H_{93}N_2O_6P$. The molecular weight, formulae and MS/MS transitions for each of these biomarkers are described in further detail below.

The present invention is further defined with reference to the following examples that are not to be construed as limiting.

EXAMPLES

Materials & Methods:
1. Patient Sample Selection

Clinical samples were obtained from Osaka Medical University, Japan. Samples were collected, processed and stored in a consistent manner by teams of physicians. All samples were properly consented and were accompanied by detailed pathology reports.

The samples included 50 controls and 40 pancreatic cancer patients, among them 20 had undergone chemoradiation therapy (CRT) and 20 had not at the time of sampling. Four patients were in stage I, four in stage II, five in stage III, 16 in stage IVa and 11 in stage IVb (Table 2).

TABLE 2

Clinical characteristics of the studied population.

| | Stage I | Stage II | Stage III | Stage IVa | Stage IVb |
|---|---|---|---|---|---|
| CRT | 4 | 2 | 2 | 7 | 5 |
| no CRT | 0 | 2 | 3 | 9 | 6 |

All samples were processed and analyzed in a randomized manner and the results unblinded following analysis.

2. Sample Extraction

Serum samples were stored at −80° C. until thawed for analysis, and were only thawed once. All extractions were performed on ice. Serum samples were prepared for FTICR-MS analysis by first sequentially extracting equal volumes of serum with 1% ammonium hydroxide and ethyl acetate (EtOAc) in the ratio of 1:1:5 respectively three times. Samples were centrifuged between extractions at 4° C. for 10 min at 3500 rpm, and the organic layer removed and transferred to a new tube (extract A). After the third EtOAc extraction, 0.33% formic acid was added, followed by two more EtOAc extractions. Following the final organic extraction, the remaining aqueous component was further extracted twice with water, and protein removed by precipitation with 3:1 acetonitrile (extract B). A 1:5 ratio of EtOAc to butanol (BuOH) was then evaporated under nitrogen to the original BuOH starting volume (extract C). All extracts were stored at −80° C. until FTICR-MS analysis.

3. FTICR-MS Analysis

Extracts were diluted either three or six-fold in methanol:0.1% (v/v) ammonium hydroxide (50:50, v/v) for negative ionization modes, or in methanol:0.1% (v/v) formic acid (50:50, v/v) for positive ionization modes. For APCI, sample extracts were directly injected without diluting. All analyses were performed on a Bruker Daltonics APEX III Fourier transform ion cyclotron resonance mass spectrometer equipped with a 7.0 T actively shielded superconducting magnet (Bruker Daltonics, Billerica, Mass.). Samples were directly injected using electrospray ionization (ESI) and atmospheric pressure chemical ionization (APCI) at a flow rate of 600 µL per hour. Details of instrument tuning and calibration conditions have been previously reported (22). Although different sample extracts were analyzed separately, the mass spectral data for each sample were combined following spectral processing. All sample peaks were calibrated using internal standards such that each internal standard mass peak had a mass error of <1 ppm relative to the theoretical mass.

4. Full-Scan Q-TOF and HPLC-Coupled Tandem Mass Spectrometry 4.1 Organic Extracts 500 µL of ethyl acetate extracts of serum from five pancreatic cancer samples and five normal samples were evaporated separately under nitrogen gas and each reconstituted in 50 µl, of isopropanol:methanol:formic acid (10:89.9:0.1, v/v/v). For both LC/MS full scan and MS/MS, 20 µL of the reconstituted samples were subjected to HPLC (Agilent 1100, Agilent Technologies) analyses with Hypersil ODS column (5 µm, 150×4.6 mm), mobile phase: Solvent A: 94.9% $H_2O$, 5% MeOH and 0.1% Formic acid, Solvent B: 100% MeOH, gradient 100% A to 79% A and 21% B at 15 min, then to 100% B at 25 min, and then held up to 30 min at a flow rate of 1 mL/min. Eluate from the HPLC was analyzed using an ABI QSTAR® XL mass spectrometer fitted with an APCI source and data were collected in negative mode. The scan type in full scan mode was time-of-flight (TOF-MS) with a scan time of 1.0000 second, mass range between 50 and 1500 Da, and duration time of 30 min. Source parameters were as follows: Ion source gas 1 (GS1) 80; Ion source gas 2 (GS2) 10; Curtain gas (CUR) 30; Nebulizer Current (NC)-3.0; Temperature 400° C.; Declustering Potential (DP)-60; Focusing Potential (FP)-265; Declustering Potential 2 (DP2)-15. In MS/MS mode, scan type was Product Ion, scan time was 1.0000 second, scan range was 50 to 1500 Da and duration time was 30 min. All source parameters are the same as above, with collision energies (CE) of −35 V and collision gas (CAD, nitrogen) of 5.

4.2 Aqueous Extracts

10 µL of C-ACN fractions (aqueous extracts) of serum from five pancreatic cancer samples and five normal samples were directly injected into HPLC (Agilent 1100) equipped with a Meta Sil AQ column (3 µm, 100×2.0 mm, Varian) for full scan and product ion scan (MS/MS) at a flow rate of 0.18 mL/min. Solvent A: $H_2O$-MeOH-formic acid (94.9:5:0.1, v/v/v) and solvent B: MeOH-formic acid (99.9:0.1, v/v) were used as the mobile phase; the gradient solvent program was applied starting from 100% of A to 80% of B and 20% of A at 11 min, then held up to 20 min, then to 100% of B at 30 min, then held up to 45 min Eluate from the HPLC was analyzed in negative and positive modes, using an Applied Biosystem (AB) QSTAR® XL mass spectrometer fitted with an ESI source. The scan type in full scan mode was time-of-flight (TOF-MS) with a scan time of 1.0000 second, mass range between 50 and 1500 Da, and duration time of 60 min. Source parameters are as follows: Ion source gas 1 (GS1), 65; Ion source gas 2 (GS2), 75; Curtain gas (CUR), 30; Temperature 425° C.; for negative mode: Ion Spray (IS), −4200V; Declustering Potential (DP), −60; Focusing Potential (FP), −265; Declustering Potential 2 (DP2), −15; and for positive mode: Ion Spray (IS), 5500V; Declustering Potential (DP), 60; Focusing Potential (FP), 265; Declustering Potential 2 (DP2), 15. In MS/MS mode, the scan type was Product Ion, scan time was set as 1.0000 second, scan range was 50 to 1500 Da and duration time was 60 min. All source parameters are the same as above, with collision energy (CE) of −30 V and +30V, respectively, and collision gas (CAD, nitrogen) of 5.

5. LC-MS/MS Flow Injection Analyses.

All LC-MS/MS analyses were performed according to Goodenowe et al. (23) with the following modifications. Specifically, analyses were performed using a triple quadrupole mass spectrometer (4000 Q TRAP, Applied Biosystems) coupled with an Agilent 1100 LC system.

5.1 MRM for C36 Markers

Sample was prepared by adding 15 µL, of internal standard (0.1 µg/mL of (24-$^{13}$C)-Cholic Acid (Cambridge Isotope Laboratories, Andover, Mass.) in methanol) to 120 µL ethyl acetate fraction of each sample. 100 µL of sample was injected by flow injection analysis (FIA), and monitored under negative Atmospheric Pressure Chemical Ionization (APCI) mode. The method was based on multiple reaction monitoring (MRM) of one parent/fragment transition for each metabolite and (24-$^{13}$C)-Cholic Acid (Table 3).

TABLE 3

List of C36 markers monitored in negative mode (organic fraction) with their formulae and transitions

| Name | Mass | Predicted formula | MRM transitions |
|---|---|---|---|
| "558" | 558.4 | C36H62O4 | 557.4/495.4 |
| "574" | 574.5 | C36H62O5 | 573.5/511.4 |
| "576" | 576.5 | C36H64O5 | 575.5/513.5 |
| "578" | 578.5 | C36H66O5 | 577.5/515.5 |
| "592" | 592.5 | C36H64O6 | 591.5/555.4 |
| "594" | 594.5 | C36H66O6 | 593.5/557.5 |
| "596" | 596.5 | C36H68O6 | 595.5/559.5 |

Each transition was scanned for 70 ms. 100% MeOH at a flow rate of 360 µL/min was used as the mobile phase. The source parameters were set as follows: CUR: 10.0, CAD: 8.0, NC: −4.0, TEM: 400, GS1:30, GS2:50, interface heater on. A standard curve was generated for all analytes to verify instrument linearity by serial dilution of (24-$^{13}$C)-Cholic Acid in extracted commercial serum matrix (ethyl acetate fraction). All samples were analyzed in a randomized blinded manner and were bracketed by known serum standard dilutions. All standard curves had $r^2$ values >0.98.

5.2 MRM for Choline-Related Compounds

12 µL of C-ACN fraction was mixed with 108 µL mobile phase and 15 µL reserpine as an internal standard. Mobile phase consists of 75% acetonitrile and 25% of 1% formic acid in ddH$_2$O. 100 µL of sample was injected by flow injection analysis (FIA), and monitored under positive or negative Ion Electrospray (ESI) mode. The method was based on multiple reaction monitoring (MRM) of one parent/fragment transition for each metabolite and reserpine (Table 4). The negative ESI mode transitions for phosphatidylcholines have been selected as follows: formate adduct and qualifier (both common to same mass phosphatidylcholines), and sn-2 fatty acid (specific to individual phosphatidylcholines).

TABLE 4

List of choline-related markers with their formulae and transitions monitored in positive mode (a) and in negative mode (b), both with aqueous fractions (a)

| | Name | Mass (neutral) | Formula | MRM transitions (M + H) |
|---|---|---|---|---|
| Lysophosphatidylcholines | LysoPC 14:0 | 467.3 | C22H46NO7P | 468.3/184.2 |
| | LysoPC 14:1 | 465.3 | C22H48NO7P | 466.3/184.2 |
| | LysoPC 16:0 | 495.3 | C24H50NO7P | 496.3/184.2 |
| | LysoPC 16:1 | 493.3 | C24H48NO7P | 494.3/184.2 |
| | LysoPC 16:2 | 491.3 | C24H46NO7P | 492.3/184.2 |
| | LysoPC 18:0 | 523.3 | C26H54NO7P | 524.3/184.2 |
| | LysoPC 18:1 | 521.3 | C26H52NO7P | 522.3/184.2 |
| | LysoPC 18:2 | 519.3 | C26H50NO7P | 520.3/184.2 |
| | LysoPC 18:3 | 517.3 | C26H48NO7P | 518.3/184.2 |
| | LysoPC 20:1 | 549.4 | C28H56NO7P | 550.4/184.2 |
| | LysoPC 20:2 | 547.4 | C28H54NO7P | 548.4/184.2 |
| | LysoPC 20:3 | 545.3 | C28H52NO7P | 546.3/184.2 |
| | LysoPC 20:4 | 543.3 | C28H50NO7P | 544.3/184.2 |
| | LysoPC 20:5 | 541.3 | C28H48NO7P | 542.3/184.2 |
| | LysoPC 20:6 | 539.3 | C28H46NO7P | 540.3/184.2 |
| | LysoPC 22:3 | 573.4 | C30H56NO7P | 574.4/184.2 |
| | LysoPC 22:4 | 571.4 | C30H54NO7P | 572.4/184.2 |
| | LysoPC 22:5 | 569.4 | C30H52NO7P | 570.4/184.2 |
| | LysoPC 22:6 | 567.3 | C30H50NO7P | 568.3/184.2 |
| | LysoPC 24:4 | 599.4 | C32H58NO7P | 600.4/184.2 |
| | LysoPC 24:6 | 595.4 | C32H54NO7P | 596.4/184.2 |
| | LysoPC 30:1 | 689.5 | C38H76NO7P | 690.5/184.2 |
| | LysoPC 32:0 | 719.6 | C40H82NO7P | 720.6/184.2 |
| | LysoPC 32:1 | 717.6 | C40H80NO7P | 718.6/184.2 |
| | LysoPC 32:2 | 715.6 | C40H78NO7P | 716.6/184.2 |
| | LysoPC 32:6 | 707.5 | C40H70NO7P | 708.5/184.2 |
| Phosphatidylcholines | 755.6 | 755.55 | C42H78NO8P | 756.6/184.2 |
| | 757.6 | 757.56 | C42H80NO8P | 758.6/184.2 |
| | 759.6 | 759.58 | C42H82NO8P | 760.6/184.2 |
| | 761.6 | 761.59 | C42H84NO8P | 762.6/184.2 |
| | 781.6 | 781.56 | C44H80NO8P | 782.6/184.2 |
| | 783.6 | 783.58 | C44H82NO8P | 784.6/184.2 |
| | 785.6 | 785.59 | C44H84NO8P | 786.6/184.2 |
| | 787.6 | 787.61 | C44H86NO8P | 788.6/184.2 |
| | 805.6 | 805.56 | C46H80NO8P | 806.6/184.2 |
| | 807.6 | 807.58 | C46H82NO8P | 808.6/184.2 |
| | 809.6 | 809.59 | C46H84NO8P | 810.6/184.2 |
| | 831.6 | 831.58 | C48H82NO8P | 832.6/184.2 |
| | 833.6 | 833.59 | C48H84NO8P | 834.6/184.2 |

TABLE 4-continued

List of choline-related markers with their formulae and transitions monitored in
positive mode (a) and in negative mode (b), both with aqueous fractions

| | | | | |
|---|---|---|---|---|
| Plasmenylcholines | 742.6 | 741.57 | C42H80NO7P | 742.6/184.2 |
| | 744.6 | 743.58 | C42H82NO7P | 744.6/184.2 |
| | 746.6 | 745.60 | C42H84NO7P | 746.6/184.2 |
| | 768.6 | 767.58 | C44H82NO7P | 768.6/184.2 |
| | 770.6 | 769.60 | C44H84NO7P | 770.6/184.2 |
| | 772.6 | 771.61 | C44H86NO7P | 772.6/184.2 |
| | 774.6 | 773.63 | C44H88NO7P | 774.6/184.2 |
| | 792.6 | 791.58 | C46H82NO7P | 792.6/184.2 |
| | 794.6 | 793.60 | C46H84NO7P | 794.6/184.2 |
| | 796.6 | 795.61 | C46H86NO7P | 796.6/184.2 |
| | 818.6 | 817.60 | C48H84NO7P | 818.6/184.2 |
| | 820.6 | 819.61 | C48H86NO7P | 820.6/184.2 |

| | Metabolite Name | Molecular Formula | Mass (neutral) | MRM Transition |
|---|---|---|---|---|
| Sphingomyelins | SM(d18:1/16:0) | $C_{39}H_{79}N_2O_6P$ | 702.6 | 703.6/184.2 |
| | SM(d18:1/18:1) | $C_{41}H_{81}N_2O_6P$ | 728.6 | 729.6/184.2 |
| | SM(d18:1/18:0) | $C_{41}H_{83}N_2O_6P$ | 730.6 | 731.6/184.2 |
| | SM(d18:1/24:1 (15Z)) | $C_{47}H_{93}N_2O_6P$ | 812.6 | 813.6/184.2 |
| | SM(d18:1/24:0) | $C_{47}H_{95}N_2O_6P$ | 814.6 | 815.6/184.2 |

(b)

| | Metabolite Name | Molecular Formula | Parent Mass (neutral) | [M + FA − H] Mass | MRM Transitions |
|---|---|---|---|---|---|
| Lysophosphatidylcholines | LysoPC 14:0 | C22H46NO7P | 467.3 | 512.3 | 512.3/452.3/227.2 |
| | LysoPC 14:1 | C22H44NO7P | 465.3 | 510.3 | 510.3/450.3/225.2 |
| | LysoPC 16:0 | C24H50NO7P | 495.3 | 540.3 | 540.3/480.3/255.2 |
| | LysoPC 16:1 | C24H48NO7P | 493.3 | 538.3 | 538.3/478.3/253.2 |
| | LysoPC 16:2 | C24H46NO7P | 491.3 | 536.3 | 536.3/476.3/251.2 |
| | LysoPC 18:0 | C26H54NO7P | 523.4 | 568.4 | 568.4/508.4/283.3 |
| | LysoPC 18:1 | C26H52NO7P | 521.3 | 566.3 | 566.3/506.3/281.3 |
| | LysoPC 18:2 | C26H50NO7P | 519.3 | 564.3 | 564.3/504.3/279.3 |
| | LysoPC 18:3 | C26H48NO7P | 517.3 | 562.3 | 562.3/502.3/277.3 |
| | LysoPC 20:1 | C28H56NO7P | 549.4 | 594.4 | 594.4/534.4/309.3 |
| | LysoPC 20:2 | C28H54NO7P | 547.4 | 592.4 | 592.4/532.4/307.3 |
| | LysoPC 20:3 | C28H52NO7P | 545.3 | 590.3 | 590.3/530.3/305.2 |
| | LysoPC 20:4 | C28H50NO7P | 543.3 | 588.3 | 588.3/528.3/303.2 |
| | LysoPC 20:5 | C28H48NO7P | 541.3 | 586.3 | 586.3/526.3/301.2 |
| | LysoPC 20:6 | C28H46NO7P | 539.3 | 584.3 | 584.3/524.3/299.2 |
| | LysoPC 22:3 | C30H56NO7P | 573.4 | 618.4 | 618.4/558.4/333.3 |
| | LysoPC 22:4 | C30H54NO7P | 571.4 | 616.4 | 616.4/556.4/331.3 |
| | LysoPC 22:5 | C30H52NO7P | 569.3 | 614.3 | 614.3/554.3/329.2 |
| | LysoPC 22:6 | C30H50NO7P | 567.3 | 612.3 | 612.3/552.3/327.2 |
| | LysoPC 24:4 | C32H58NO7P | 599.4 | 644.4 | 644.4/584.4/359.3 |
| | LysoPC 24:6 | C32H54NO7P | 595.4 | 640.4 | 640.4/580.4/355.3 |
| | LysoPC 30:1 | C38H76NO7P | 689.5 | 734.5 | 734.5/674.5/449.4 |
| | LysoPC 32:0 | C40H82NO7P | 719.6 | 764.6 | 764.6/703.6/479.5 |
| | LysoPC 32:1 | C40H80NO7P | 717.6 | 762.6 | 762.6/702.6/477.4 |
| | LysoPC 32:2 | C40H78NO7P | 715.6 | 760.6 | 760.6/700.6/475.4 |
| | LysoPC 32:6 | C40H70NO7P | 707.5 | 752.5 | 752.5/692.5/467.4 |

| | Metabolite Name | Parent Mass | Molecular Formula | [Parent + FA − H] | MRM Transitions |
|---|---|---|---|---|---|
| Phosphatidylcholines | PtdCho 16:0/18:3 | 755.6 | C42H78NO8P | 800.6 | 800.6/740.6/277.2 |
| | PtdCho 16:1/18:2 | 755.6 | C42H78NO8P | 800.6 | 800.6/740.6/279.2 |
| | PtdCho 18:2/16:1 | 755.6 | C42H78NO8P | 800.6 | 800.6/740.6/253.2 |
| | PtdCho 18:3/16:0 | 755.6 | C42H78NO8P | 800.6 | 800.6/740.6/255.2 |
| | PtdCho 16:0/18:2 | 757.6 | C42H80NO8P | 802.6 | 802.6/742.6/279.2 |
| | PtdCho 16:1/18:1 | 757.6 | C42H80NO8P | 802.6 | 802.6/742.6/281.2 |
| | PtdCho 18:1/16:1 | 757.6 | C42H80NO8P | 802.6 | 802.6/742.6/253.2 |
| | PtdCho 18:2/16:0 | 757.6 | C42H80NO8P | 802.6 | 802.6/742.6/255.2 |
| | PtdCho 16:0/18:1 | 759.6 | C42H82NO8P | 804.6 | 804.6/744.6/281.2 |
| | PtdCho 18:1/16:0 | 759.6 | C42H82NO8P | 804.6 | 804.6/744.6/255.2 |
| | PtdCho 18:0/16:1 | 761.6 | C42H84NO8P | 806.6 | 806.6/746.6/255.2 |
| | PtdCho 16:0/18:0 | 761.6 | C42H84NO8P | 806.6 | 806.6/746.6/281.2 |
| | PtdCho 16:0/20:5 | 779.6 | C44H78NO8P | 824.6 | 824.6/764.6/301.2 |
| | PtdCho 18:3/18:2 | 779.6 | C44H78NO8P | 824.6 | 824.6/764.6/279.2 |
| | PtdCho 20:5/16:0 | 779.6 | C44H78NO8P | 824.6 | 824.6/764.6/255.2 |
| | PtdCho 16:0/20:4 | 781.6 | C44H80NO8P | 826.6 | 826.6/766.6/303.2 |
| | PtdCho 18:2/18:2 | 781.6 | C44H80NO8P | 826.6 | 826.6/766.6/279.2 |
| | PtdCho 20:4/16:0 | 781.6 | C44H80NO8P | 826.6 | 826.6/766.6/255.2 |
| | PtdCho 16:0/20:3 | 783.6 | C44H82NO8P | 828.6 | 828.6/768.6/305.3 |

TABLE 4-continued

List of choline-related markers with their formulae and transitions monitored in
positive mode (a) and in negative mode (b), both with aqueous fractions

| | | | | | |
|---|---|---|---|---|---|
| | PtdCho 18:1/18:2 | 783.6 | C44H82NO8P | 828.6 | 828.6/768.6/279.2 |
| | PtdCho 18:2/18:1 | 783.6 | C44H82NO8P | 828.6 | 828.6/768.6/281.2 |
| | PtdCho 20:3/16:0 | 783.6 | C44H82NO8P | 828.6 | 828.6/768.6/255.2 |
| | PtdCho 18:0/18:2 | 785.6 | C44H84NO8P | 830.6 | 830.6/770.6/279.2 |
| | PtdCho 18:1/18:1 | 785.6 | C44H84NO8P | 830.6 | 830.6/770.6/281.2 |
| | PtdCho 18:2/18:0 | 785.6 | C44H84NO8P | 830.6 | 830.6/770.6/283.2 |
| | PtdCho 18:0/18:1 | 787.6 | C44H86NO8P | 832.6 | 832.5/772.6/281.2 |
| | PtdCho 18:1/18:0 | 787.6 | C44H86NO8P | 832.6 | 832.5/772.6/283.2 |
| | PtdCho 18:0/18:0 | 789.6 | C44H88NO8P | 834.6 | 834.6/774.6/283.2 |
| | PtdCho 16:1/22:6 | 803.6 | C46H78NO8P | 848.6 | 848.6/788.6/327.3 |
| | PtdCho 20:5/18:2 | 803.6 | C46H78NO8P | 848.6 | 848.6/788.6/279.2 |
| | PtdCho 16:0/22:6 | 805.6 | C46H80NO8P | 850.6 | 850.6/790.6/327.3 |
| | PtdCho 18:2/20:4 | 805.6 | C46H80NO8P | 850.6 | 850.6/790.6/303.2 |
| | PtdCho 20:4/18:2 | 805.6 | C46H80NO8P | 850.6 | 850.6/790.6/279.2 |
| | PtdCho 22:6/16:0 | 805.6 | C46H80NO8P | 850.6 | 850.6/790.6/255.2 |
| | PtdCho 16:0/22:5 | 807.6 | C46H82NO8P | 852.6 | 852.6/792.6/329.3 |
| | PtdCho 18:0/20:5 | 807.6 | C46H82NO8P | 852.6 | 852.6/792.6/301.3 |
| | PtdCho 18:1/20:4 | 807.6 | C46H82NO8P | 852.6 | 852.6/792.6/303.2 |
| | PtdCho 20:4/18:1 | 807.6 | C46H82NO8P | 852.6 | 852.6/792.6/281.2 |
| | PtdCho 20:5/18:0 | 807.6 | C46H82NO8P | 852.6 | 852.6/792.6/283.2 |
| | PtdCho 22:5/16:0 | 807.6 | C46H82NO8P | 852.6 | 852.6/792.6/255.2 |
| | PtdCho 16:0/22:4 | 809.6 | C46H84NO8P | 854.6 | 854.6/794.6/331.3 |
| | PtdCho 18:0/20:4 | 809.6 | C46H84NO8P | 854.6 | 854.6/794.6/303.2 |
| | PtdCho 20:4/18:0 | 809.6 | C46H84NO8P | 854.6 | 854.6/794.6/283.2 |
| | PtdCho 22:4/16:0 | 809.6 | C46H84NO8P | 854.6 | 854.6/794.6/255.2 |
| | PtdCho 18:1/22:6 | 831.6 | C48H82NO8P | 876.6 | 876.6/916.6/327.3 |
| | PtdCho 22:6/18:1 | 831.6 | C48H82NO8P | 876.6 | 876.6/916.6/281.2 |
| | PtdCho 18:0/22:6 | 833.6 | C48H84NO8P | 878.6 | 878.6/818.6/327.3 |
| | PtdCho 22:6/18:0 | 833.6 | C48H84NO8P | 878.6 | 878.6/818.6/283.2 |
| | PtdCho 18:0/22:5 | 835.6 | C48H86NO8P | 880.6 | 880.6/820.6/329.3 |
| | PtdCho 22:5/18:0 | 835.6 | C48H86NO8P | 880.6 | 880.6/820.6/283.2 |

| | Metabolite Name | Molecular Formula | Parent Mass | [M + FA − H] Mass | MRM Transitions |
|---|---|---|---|---|---|
| Sphingomyelins | SM(d18:1/16:0) | $C_{39}H_{79}N_2O_6P$ | 702.6 | 747.6 | 747.6/687.6/168.1 |
| | SM(d18:1/18:1) | $C_{41}H_{81}N_2O_6P$ | 728.6 | 773.6 | 773.6/713.6/168.1 |
| | SM(d18:1/18:0) | $C_{41}H_{83}N_2O_6P$ | 730.6 | 775.6 | 775.6/715.6/168.1 |
| | SM(d18:1/24:1 (15Z)) | $C_{47}H_{93}N_2O_6P$ | 812.6 | 857.6 | 857.6/797.6/168.1 |
| | SM(d18:1/24:0) | $C_{47}H_{95}N_2O_6P$ | 814.6 | 859.6 | 859.6/799.6/168.1 |

Each transition was scanned for 70 ms. Mobile phase was used at a flow rate of 60 µL/min. The source parameters were set as follows: CUR: 10.0, IS: 5500.0, CAD: 10.0, TEM: 500, GS1:30, GS2:50, interface heater on. A standard curve was generated for all analytes to verify instrument linearity by serial dilution of C-ACN fraction of Randox (Human Serum Precision Control Level II) with constant concentration of reserpine. All samples were analyzed in a randomized blinded manner and were bracketed by known serum standard dilutions. All standard curves had $r^2$ values >0.98. For sphingomyelins, both MRM transitions were run and similarity was verified; the MRM transitions with m/z 168 were selected for the graphs reported.

6. Statistical Analysis

FTICR-MS accurate mass array alignments were performed using DISCOVAmetrics™ (Phenomenome Discoveries Inc., Saskatoon). Initial statistical analysis and graphs of FTICR-MS data were carried out using Microsoft Office Excel 2007. Two-tailed unpaired Student's t-tests were used for determination of significant difference between pancreatic cancer and controls. P-values of less than 0.05 were considered significant. ROC curves were generated from logistic regression analysis using SAS Enterprise Guide 4.2.

Results

FTICR Metabolomic Profiling

1A. FTICR Data Analysis

Figure 1:
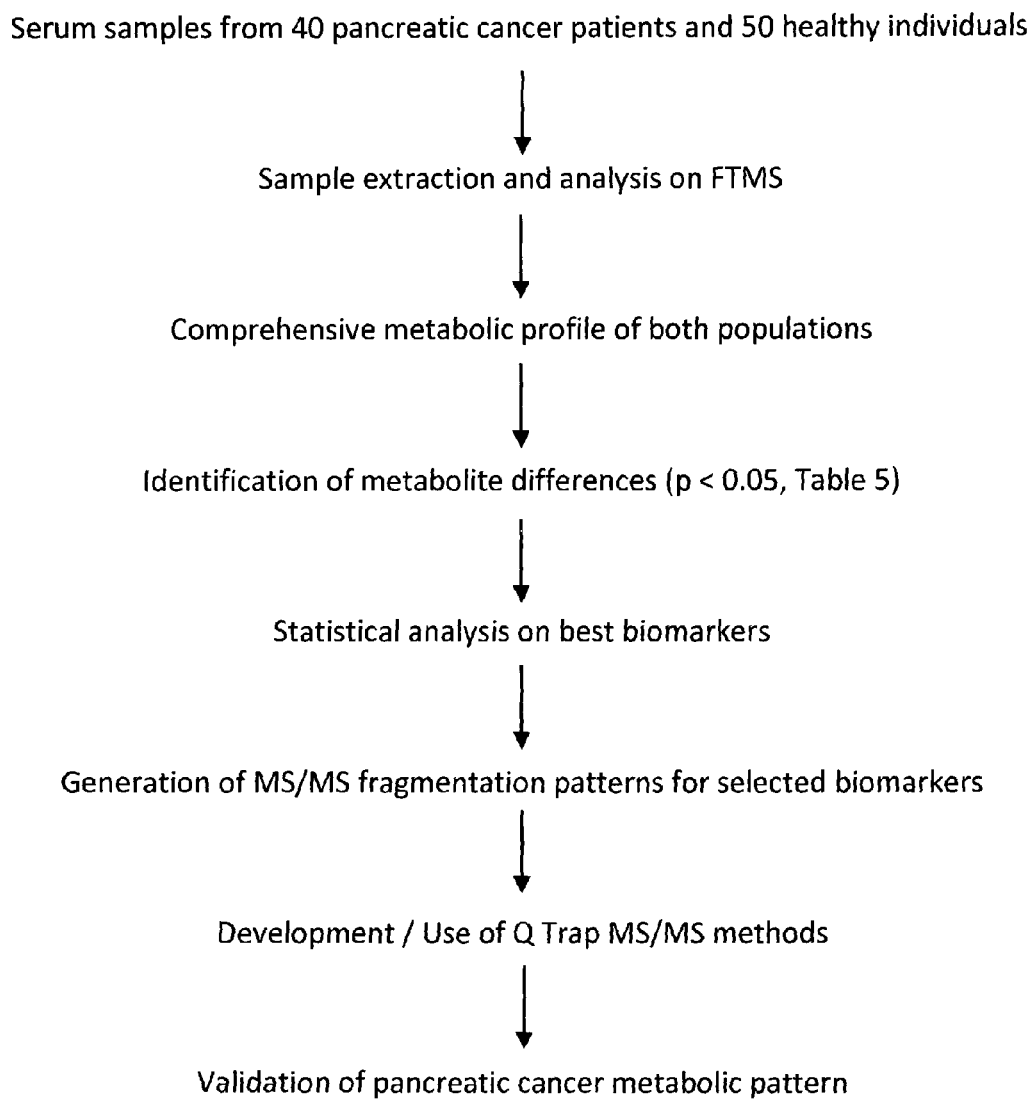
FIG. 1 provides a schematic description of the studies performed.

The experimental workflow generated for the studies described here is summarized in FIG. 1.

Serum metabolites were captured through a liquid extraction process (see methods) and extracts were directly infused by electrospray ionization (ESI) or atmospheric pressure chemical ionization (APCI) on an FTICR mass spectrometer. In total six separate analyses comprising combinations of extracts and ionization modes were obtained for each sample:

Aqueous Extract
1. Positive ESI (analysis mode 1101)
2. Negative ESI (analysis mode 1102)

Organic Extract
3. Positive ESI (analysis mode 1201)
4. Negative ESI (analysis mode 1202)
5. Positive APCI (analysis mode 1203)
6. Negative APCI (analysis mode 1204)

Separately for each project, the resulting spectral data of all the subjects was aligned within 1 ppm mass accuracy, background peaks were subtracted, and a two-dimensional array table comprising the intensities of each of the sample-specific spectral peaks was created using custom informatics software DISCOVAmetrics™

In the metabolomic profile thus created, a Boolean filtering sorted the masses that differentiate the "pancreatic cancer" condition from the "control" condition. Table 5 lists the 362 masses that discriminate the pancreatic cancer samples from the control samples with a p-value lower than 0.05.

TABLE 5

Accurate mass features differing between clinically diagnosed pancreatic cancer patients and controls ($p < 0.05$).

| Detected Mass | Analysis Mode | P value | Ratio pancreatic cancer/ control | AVG controls | AVG pancreatic cancer |
|---|---|---|---|---|---|
| 786.593 | 1101 | 5.24E−14 | 0.30 | 15.59 | 4.61 |
| 595.4897 | 1202 | 7.48E−14 | 0.36 | 5.30 | 1.88 |
| 594.4863 | 1202 | 9.91E−14 | 0.31 | 14.02 | 4.40 |
| 785.5913 | 1101 | 1.39E−13 | 0.27 | 33.03 | 8.93 |
| 808.5783 | 1101 | 1.63E−13 | 0.30 | 15.62 | 4.75 |
| 702.5709 | 1101 | 2.39E−13 | 0.47 | 9.60 | 4.48 |
| 780.5452 | 1101 | 3.57E−13 | 0.30 | 22.48 | 6.68 |
| 807.5734 | 1101 | 5.49E−13 | 0.28 | 34.47 | 9.70 |
| 576.4751 | 1202 | 5.61E−13 | 0.40 | 4.85 | 1.93 |
| 541.3134 | 1101 | 6.66E−13 | 0.37 | 6.27 | 2.30 |
| 804.5422 | 1101 | 2.04E−12 | 0.34 | 6.56 | 2.26 |
| 779.5405 | 1101 | 2.66E−12 | 0.26 | 53.60 | 13.93 |
| 812.6774 | 1101 | 3.81E−12 | 0.54 | 5.11 | 2.77 |
| 758.5626 | 1101 | 1.17E−11 | 0.31 | 23.80 | 7.28 |
| 783.569 | 1101 | 1.19E−11 | 0.36 | 13.94 | 4.98 |
| 596.5017 | 1202 | 2.03E−11 | 0.36 | 11.29 | 4.04 |
| 803.5373 | 1101 | 2.11E−11 | 0.33 | 13.46 | 4.48 |
| 810.5867 | 1101 | 3.75E−11 | 0.39 | 7.46 | 2.90 |
| 724.5477 | 1101 | 3.75E−11 | 0.49 | 8.07 | 3.98 |
| 519.3295 | 1101 | 7.30E−11 | 0.41 | 6.62 | 2.71 |
| 757.556 | 1101 | 1.04E−10 | 0.27 | 58.48 | 16.01 |
| 600.5117 | 1203 | 2.61E−10 | 1.40 | 124.61 | 174.25 |
| 809.5796 | 1101 | 2.67E−10 | 0.43 | 15.81 | 6.73 |
| 829.5516 | 1101 | 2.82E−10 | 0.41 | 7.32 | 2.98 |
| 523.3661 | 1101 | 3.97E−10 | 0.49 | 4.95 | 2.44 |
| 784.5742 | 1101 | 4.29E−10 | 0.42 | 6.06 | 2.54 |
| 806.5632 | 1101 | 4.47E−10 | 0.37 | 13.07 | 4.77 |
| 601.5151 | 1203 | 5.26E−10 | 1.39 | 52.15 | 72.62 |
| 805.5549 | 1101 | 6.17E−10 | 0.35 | 27.28 | 9.66 |
| 833.5864 | 1101 | 9.05E−10 | 0.43 | 9.23 | 4.01 |
| 723.5203 | 1202 | 1.35E−09 | 0.55 | 6.92 | 3.80 |
| 749.5374 | 1202 | 1.36E−09 | 0.46 | 11.63 | 5.39 |
| 782.5612 | 1101 | 1.71E−09 | 0.37 | 19.17 | 7.08 |
| 827.5401 | 1101 | 1.73E−09 | 0.39 | 12.52 | 4.83 |
| 801.5147 | 1101 | 2.21E−09 | 0.39 | 6.00 | 2.34 |
| 834.5868 | 1101 | 2.61E−09 | 0.45 | 4.76 | 2.16 |
| 781.5566 | 1101 | 4.33E−09 | 0.33 | 44.71 | 14.95 |
| 828.5397 | 1101 | 4.68E−09 | 0.41 | 6.34 | 2.61 |
| 831.5652 | 1101 | 4.96E−09 | 0.51 | 8.53 | 4.33 |
| 592.4709 | 1202 | 5.85E−09 | 0.37 | 4.97 | 1.85 |
| 759.5383 | 1101 | 9.35E−09 | 0.53 | 11.72 | 6.21 |
| 240.0997 | 1202 | 1.36E−08 | 0.45 | 15.83 | 7.05 |
| 1038.915 | 1203 | 1.58E−08 | 0.39 | 6.28 | 2.45 |
| 588.3269 | 1202 | 1.79E−08 | 0.54 | 6.01 | 3.25 |
| 587.3214 | 1202 | 2.93E−08 | 0.50 | 19.54 | 9.71 |
| 545.3454 | 1101 | 4.01E−08 | 0.54 | 4.67 | 2.53 |
| 382.1601 | 1201 | 4.69E−08 | 1.94 | 12.90 | 24.98 |
| 326.2048 | 1202 | 5.08E−08 | 2.58 | 3.05 | 7.87 |
| 360.1782 | 1201 | 7.10E−08 | 1.52 | 5.83 | 8.85 |
| 280.2404 | 1202 | 7.61E−08 | 2.44 | 16.22 | 39.65 |
| 281.2432 | 1202 | 9.00E−08 | 2.38 | 3.68 | 8.77 |
| 214.1204 | 1203 | 1.01E−07 | 1.67 | 6.67 | 11.12 |
| 302.222 | 1201 | 1.19E−07 | 2.58 | 13.20 | 34.07 |
| 282.2558 | 1202 | 1.47E−07 | 2.40 | 31.82 | 76.36 |
| 575.4985 | 1203 | 1.73E−07 | 1.25 | 61.51 | 76.85 |
| 855.5721 | 1101 | 1.74E−07 | 0.39 | 4.56 | 1.77 |
| 283.2591 | 1202 | 1.89E−07 | 2.45 | 6.15 | 15.06 |
| 759.5733 | 1101 | 2.33E−07 | 0.39 | 31.65 | 12.32 |
| 760.5792 | 1101 | 2.65E−07 | 0.45 | 13.99 | 6.28 |
| 574.4952 | 1203 | 2.84E−07 | 1.25 | 162.04 | 201.84 |
| 517.3141 | 1101 | 4.79E−07 | 0.57 | 16.74 | 9.61 |
| 283.2595 | 1204 | 5.17E−07 | 1.41 | 11.22 | 15.84 |
| 262.0814 | 1201 | 5.40E−07 | 0.44 | 10.65 | 4.71 |
| 811.5729 | 1202 | 5.45E−07 | 0.65 | 6.67 | 4.34 |
| 1040.933 | 1203 | 6.01E−07 | 0.58 | 10.18 | 5.93 |
| 328.2627 | 1202 | 6.71E−07 | 2.06 | 16.89 | 34.73 |
| 326.2458 | 1202 | 7.57E−07 | 2.06 | 7.72 | 15.91 |
| 282.2559 | 1204 | 8.36E−07 | 1.46 | 56.00 | 81.98 |
| 564.5121 | 1202 | 9.99E−07 | 3.32 | 3.17 | 10.53 |
| 276.0948 | 1201 | 1.00E−06 | 1.22 | 9.93 | 12.12 |
| 775.5522 | 1202 | 1.02E−06 | 0.51 | 7.83 | 4.02 |
| 811.608 | 1101 | 1.38E−06 | 0.49 | 4.23 | 2.09 |
| 824.69 | 1203 | 1.74E−06 | 0.61 | 5.01 | 3.03 |
| 495.3325 | 1101 | 2.06E−06 | 0.58 | 17.63 | 10.17 |
| 508.2256 | 1201 | 2.26E−06 | 1.43 | 4.64 | 6.65 |
| 562.4962 | 1202 | 2.46E−06 | 2.91 | 3.06 | 8.90 |
| 329.2658 | 1202 | 2.48E−06 | 1.99 | 3.85 | 7.68 |
| 518.321 | 1101 | 2.57E−06 | 0.63 | 4.70 | 2.95 |
| 1016.931 | 1203 | 3.03E−06 | 0.57 | 58.00 | 32.85 |
| 1017.935 | 1203 | 3.05E−06 | 0.57 | 45.70 | 26.16 |
| 360.1792 | 1202 | 5.30E−06 | 1.49 | 36.91 | 54.94 |
| 566.3403 | 1202 | 5.63E−06 | 0.67 | 29.61 | 19.78 |
| 565.3373 | 1202 | 5.77E−06 | 0.65 | 118.24 | 77.43 |
| 300.2067 | 1201 | 6.14E−06 | 2.41 | 2.57 | 6.20 |
| 771.5699 | 1202 | 7.10E−06 | 0.69 | 6.90 | 4.76 |
| 116.5696 | 1202 | 7.19E−06 | 1.22 | 5.54 | 6.78 |
| 468.3807 | 1202 | 8.42E−06 | 0.64 | 5.22 | 3.33 |
| 361.1828 | 1202 | 8.72E−06 | 1.50 | 7.05 | 10.58 |
| 428.3647 | 1201 | 9.73E−06 | 0.66 | 10.24 | 6.78 |
| 1255.153 | 1203 | 1.04E−05 | 0.59 | 7.38 | 4.36 |
| 1200.088 | 1203 | 1.52E−05 | 0.55 | 8.45 | 4.64 |
| 540.4381 | 1202 | 1.58E−05 | 0.61 | 5.38 | 3.27 |
| 851.7107 | 1203 | 1.63E−05 | 0.72 | 8.61 | 6.17 |
| 1018.944 | 1203 | 1.71E−05 | 0.64 | 38.50 | 24.48 |
| 505.3146 | 1202 | 1.95E−05 | 0.73 | 6.13 | 4.50 |
| 496.3373 | 1101 | 2.20E−05 | 0.65 | 4.79 | 3.10 |
| 569.3682 | 1202 | 2.30E−05 | 0.72 | 39.22 | 28.31 |
| 330.2559 | 1202 | 2.43E−05 | 2.07 | 4.21 | 8.70 |
| 808.5791 | 1201 | 2.54E−05 | 0.71 | 46.64 | 33.33 |
| 572.4798 | 1203 | 3.15E−05 | 1.20 | 18.65 | 22.42 |
| 765.5678 | 1201 | 3.27E−05 | 0.77 | 5.30 | 4.06 |
| 786.5972 | 1201 | 3.39E−05 | 0.72 | 29.54 | 21.13 |
| 1228.117 | 1203 | 3.63E−05 | 0.64 | 24.71 | 15.87 |
| 791.5841 | 1201 | 4.14E−05 | 0.75 | 5.81 | 4.35 |
| 1229.12 | 1203 | 4.19E−05 | 0.61 | 13.11 | 7.98 |
| 850.7061 | 1203 | 4.30E−05 | 0.72 | 13.39 | 9.66 |
| 830.5591 | 1201 | 4.47E−05 | 0.70 | 13.41 | 9.34 |
| 1201.09 | 1203 | 4.63E−05 | 0.50 | 9.82 | 4.92 |
| 802.5291 | 1201 | 4.75E−05 | 0.60 | 12.32 | 7.38 |
| 1041.935 | 1203 | 5.64E−05 | 0.65 | 7.35 | 4.79 |
| 260.0033 | 1101 | 6.07E−05 | 1.35 | 7.68 | 10.34 |
| 785.5929 | 1201 | 6.59E−05 | 0.71 | 70.58 | 50.30 |
| 1227.112 | 1203 | 6.68E−05 | 0.65 | 32.33 | 20.98 |
| 826.5561 | 1202 | 7.07E−05 | 0.50 | 15.42 | 7.74 |
| 1199.084 | 1203 | 7.39E−05 | 0.63 | 10.34 | 6.53 |
| 825.5522 | 1202 | 8.54E−05 | 0.47 | 32.08 | 15.06 |
| 244.0554 | 1101 | 8.97E−05 | 1.36 | 8.98 | 12.19 |
| 602.5269 | 1203 | 9.14E−05 | 1.26 | 208.79 | 262.81 |
| 570.372 | 1202 | 9.17E−05 | 0.76 | 11.10 | 8.43 |
| 599.4993 | 1203 | 9.78E−05 | 1.25 | 15.04 | 18.83 |
| 1019.951 | 1203 | 9.91E−05 | 0.67 | 21.64 | 14.54 |
| 1039.705 | 1201 | 1.01E−04 | 0.73 | 4.53 | 3.29 |
| 573.4833 | 1203 | 1.03E−04 | 1.19 | 7.23 | 8.57 |
| 801.5262 | 1201 | 1.06E−04 | 0.55 | 30.09 | 16.68 |
| 603.5297 | 1203 | 1.09E−04 | 1.25 | 86.64 | 108.65 |
| 1230.125 | 1203 | 1.10E−04 | 0.50 | 5.34 | 2.69 |
| 317.9613 | 1101 | 1.28E−04 | 1.39 | 5.16 | 7.18 |
| 807.5739 | 1201 | 1.34E−04 | 0.74 | 115.80 | 86.22 |
| 598.4955 | 1203 | 1.47E−04 | 1.25 | 37.42 | 46.65 |
| 368.1057 | 1202 | 1.61E−04 | 1.35 | 4.89 | 6.61 |
| 280.2403 | 1204 | 1.62E−04 | 1.24 | 31.44 | 39.14 |
| 823.5411 | 1201 | 1.65E−04 | 0.77 | 5.10 | 3.95 |
| 1039.921 | 1203 | 1.68E−04 | 0.52 | 4.79 | 2.48 |
| 284.9259 | 1203 | 1.69E−04 | 1.26 | 6.30 | 7.96 |
| 270.0867 | 1201 | 1.72E−04 | 1.19 | 20.78 | 24.82 |
| 578.5169 | 1203 | 1.75E−04 | 1.33 | 21.27 | 28.33 |
| 948.836 | 1204 | 1.83E−04 | 0.67 | 10.17 | 6.85 |
| 446.3395 | 1202 | 1.85E−04 | 0.70 | 5.27 | 3.69 |
| 577.5149 | 1203 | 1.90E−04 | 1.23 | 119.24 | 147.02 |
| 633.3245 | 1202 | 2.02E−04 | 0.68 | 8.26 | 5.63 |
| 590.3408 | 1202 | 2.15E−04 | 0.75 | 11.13 | 8.39 |
| 837.7209 | 1204 | 2.38E−04 | 0.61 | 6.81 | 4.19 |
| 469.3616 | 1201 | 2.44E−04 | 0.72 | 5.54 | 3.97 |
| 468.3581 | 1201 | 2.46E−04 | 0.69 | 17.82 | 12.36 |

TABLE 5-continued

Accurate mass features differing between clinically diagnosed pancreatic cancer patients and controls (p < 0.05).

| Detected Mass | Analysis Mode | P value | Ratio pancreatic cancer/control | AVG controls | AVG pancreatic cancer |
|---|---|---|---|---|---|
| 856.7505 | 1203 | 2.49E−04 | 1.22 | 205.07 | 250.07 |
| 576.5113 | 1203 | 2.52E−04 | 1.23 | 316.44 | 388.31 |
| 522.4639 | 1203 | 2.60E−04 | 0.62 | 16.82 | 10.39 |
| 787.5989 | 1101 | 2.64E−04 | 0.63 | 9.66 | 6.13 |
| 589.3368 | 1202 | 2.93E−04 | 0.74 | 35.28 | 26.06 |
| 300.1186 | 1202 | 3.03E−04 | 1.28 | 11.97 | 15.32 |
| 831.5997 | 1202 | 3.11E−04 | 0.66 | 72.40 | 47.60 |
| 270.0323 | 1101 | 3.20E−04 | 1.34 | 13.66 | 18.30 |
| 281.2435 | 1204 | 3.34E−04 | 1.23 | 6.03 | 7.44 |
| 84.0575 | 1202 | 3.34E−04 | 1.22 | 6.64 | 8.13 |
| 856.754 | 1204 | 3.41E−04 | 1.22 | 44.96 | 54.67 |
| 922.8222 | 1204 | 3.47E−04 | 0.53 | 8.16 | 4.32 |
| 832.6031 | 1202 | 3.48E−04 | 0.67 | 34.86 | 23.36 |
| 1202.098 | 1203 | 3.56E−04 | 0.58 | 7.40 | 4.27 |
| 829.5532 | 1201 | 3.74E−04 | 0.69 | 34.32 | 23.60 |
| 857.7543 | 1203 | 3.97E−04 | 1.21 | 114.80 | 138.68 |
| 327.9902 | 1101 | 4.25E−04 | 1.36 | 5.92 | 8.05 |
| 304.2407 | 1202 | 4.27E−04 | 1.46 | 8.00 | 11.67 |
| 538.4237 | 1202 | 4.40E−04 | 0.63 | 6.33 | 3.97 |
| 1020.957 | 1203 | 4.47E−04 | 0.69 | 7.99 | 5.52 |
| 1250.108 | 1203 | 4.49E−04 | 0.56 | 5.60 | 3.16 |
| 1253.134 | 1203 | 4.55E−04 | 0.63 | 11.69 | 7.34 |
| 847.531 | 1201 | 4.82E−04 | 0.78 | 5.86 | 4.56 |
| 200.1389 | 1202 | 5.57E−04 | 1.34 | 6.87 | 9.21 |
| 350.2222 | 1201 | 5.59E−04 | 1.74 | 4.00 | 6.97 |
| 857.7574 | 1204 | 5.87E−04 | 1.20 | 25.77 | 30.92 |
| 203.1155 | 1101 | 6.19E−04 | 1.49 | 7.01 | 10.46 |
| 197.0896 | 1101 | 7.68E−04 | 1.34 | 5.71 | 7.68 |
| 523.4675 | 1203 | 8.74E−04 | 0.64 | 5.97 | 3.84 |
| 191.5055 | 1203 | 9.26E−04 | 1.31 | 9.55 | 12.54 |
| 1011.669 | 1201 | 9.48E−04 | 0.78 | 6.76 | 5.27 |
| 838.7284 | 1204 | 9.60E−04 | 0.62 | 4.89 | 3.04 |
| 338.0189 | 1101 | 9.69E−04 | 1.34 | 7.96 | 10.70 |
| 202.045 | 1101 | 1.04E−03 | 1.32 | 33.71 | 44.61 |
| 302.0945 | 1201 | 1.06E−03 | 1.26 | 10.37 | 13.02 |
| 873.7819 | 1203 | 1.08E−03 | 1.23 | 8.50 | 10.45 |
| 1225.096 | 1203 | 1.15E−03 | 0.71 | 25.00 | 17.85 |
| 446.2526 | 1204 | 1.15E−03 | 2.33 | 2.87 | 6.69 |
| 898.7043 | 1203 | 1.31E−03 | 0.56 | 3.34 | 1.86 |
| 382.1083 | 1101 | 1.33E−03 | 1.56 | 5.59 | 8.70 |
| 970.733 | 1204 | 1.38E−03 | 0.55 | 6.35 | 3.49 |
| 715.6959 | 1101 | 1.42E−03 | 2.04 | 5.53 | 11.27 |
| 302.2457 | 1202 | 1.45E−03 | 1.23 | 9.18 | 11.33 |
| 851.7337 | 1204 | 1.56E−03 | 0.65 | 5.80 | 3.78 |
| 874.787 | 1203 | 1.64E−03 | 1.29 | 4.60 | 5.92 |
| 721.5035 | 1204 | 1.69E−03 | 0.48 | 3.57 | 1.70 |
| 630.799 | 1101 | 1.70E−03 | 2.32 | 25.23 | 58.48 |
| 1252.12 | 1203 | 1.70E−03 | 0.64 | 7.72 | 4.94 |
| 268.1284 | 1201 | 1.77E−03 | 1.34 | 8.63 | 11.54 |
| 780.5454 | 1201 | 1.80E−03 | 0.77 | 71.95 | 55.17 |
| 750.5425 | 1204 | 1.91E−03 | 0.46 | 8.04 | 3.67 |
| 749.5388 | 1204 | 1.96E−03 | 0.43 | 17.32 | 7.50 |
| 947.8263 | 1204 | 1.97E−03 | 0.77 | 15.18 | 11.72 |
| 853.573 | 1202 | 2.04E−03 | 0.67 | 26.48 | 17.62 |
| 779.5416 | 1201 | 2.06E−03 | 0.80 | 169.63 | 135.27 |
| 1224.096 | 1203 | 2.07E−03 | 0.70 | 9.01 | 6.26 |
| 838.7435 | 1203 | 2.13E−03 | 1.21 | 8.28 | 10.01 |
| 1226.599 | 1203 | 2.20E−03 | 0.73 | 20.59 | 15.07 |
| 635.7525 | 1101 | 2.21E−03 | 2.25 | 34.61 | 77.78 |
| 871.5547 | 1202 | 2.24E−03 | 0.80 | 8.04 | 6.45 |
| 743.5396 | 1202 | 2.25E−03 | 0.80 | 14.69 | 11.72 |
| 924.7233 | 1203 | 2.30E−03 | 0.61 | 9.77 | 5.92 |
| 801.5523 | 1202 | 2.44E−03 | 0.72 | 7.08 | 5.07 |
| 615.3535 | 1202 | 2.48E−03 | 0.77 | 7.10 | 5.50 |
| 541.3361 | 1202 | 2.58E−03 | 0.79 | 104.55 | 82.62 |
| 921.813 | 1204 | 2.60E−03 | 0.75 | 19.33 | 14.41 |
| 520.448 | 1203 | 2.72E−03 | 0.69 | 6.51 | 4.49 |
| 903.7636 | 1204 | 2.80E−03 | 1.19 | 105.15 | 125.04 |
| 744.5425 | 1202 | 2.99E−03 | 0.78 | 6.66 | 5.18 |
| 318.0931 | 1202 | 3.14E−03 | 0.82 | 20.17 | 16.54 |
| 758.562 | 1201 | 3.16E−03 | 0.77 | 64.96 | 49.94 |
| 1254.137 | 1203 | 3.19E−03 | 0.71 | 8.83 | 6.24 |
| 868.7704 | 1204 | 3.38E−03 | 0.68 | 3.94 | 2.67 |
| 606.5591 | 1203 | 3.47E−03 | 0.44 | 4.80 | 2.11 |
| 998.7566 | 1204 | 3.50E−03 | 0.74 | 10.82 | 7.99 |
| 329.2439 | 1202 | 3.53E−03 | 1.46 | 7.29 | 10.65 |
| 594.4852 | 1204 | 3.63E−03 | 0.59 | 11.81 | 7.00 |
| 757.5587 | 1201 | 3.64E−03 | 0.80 | 161.90 | 129.94 |
| 925.727 | 1203 | 3.69E−03 | 0.58 | 6.16 | 3.57 |
| 996.7518 | 1204 | 3.73E−03 | 0.67 | 11.29 | 7.51 |
| 804.5714 | 1202 | 3.76E−03 | 0.74 | 81.05 | 59.96 |
| 595.4892 | 1204 | 3.81E−03 | 0.61 | 4.70 | 2.86 |
| 328.2408 | 1202 | 3.92E−03 | 1.46 | 28.17 | 41.15 |
| 1223.09 | 1203 | 4.15E−03 | 0.73 | 9.81 | 7.16 |
| 803.5677 | 1202 | 4.22E−03 | 0.74 | 169.16 | 125.07 |
| 752.5574 | 1204 | 4.28E−03 | 0.54 | 7.20 | 3.87 |
| 328.2403 | 1204 | 4.36E−03 | 1.40 | 5.10 | 7.15 |
| 332.1473 | 1202 | 4.52E−03 | 1.21 | 7.74 | 9.34 |
| 631.798 | 1101 | 4.72E−03 | 1.92 | 3.52 | 6.76 |
| 775.5532 | 1204 | 5.06E−03 | 0.46 | 14.20 | 6.58 |
| 777.5709 | 1204 | 5.40E−03 | 0.54 | 6.39 | 3.44 |
| 636.7532 | 1101 | 5.40E−03 | 2.05 | 4.43 | 9.09 |
| 867.7649 | 1204 | 5.52E−03 | 0.71 | 7.81 | 5.51 |
| 597.5066 | 1204 | 5.52E−03 | 0.62 | 4.55 | 2.81 |
| 908.7907 | 1204 | 5.56E−03 | 0.68 | 9.63 | 6.54 |
| 763.5578 | 1204 | 5.62E−03 | 0.57 | 3.17 | 1.79 |
| 596.5027 | 1204 | 5.84E−03 | 0.60 | 11.58 | 6.97 |
| 777.0402 | 1204 | 6.01E−03 | 0.52 | 6.89 | 3.59 |
| 542.3394 | 1202 | 6.53E−03 | 0.83 | 23.67 | 19.76 |
| 723.521 | 1204 | 6.76E−03 | 0.57 | 7.41 | 4.19 |
| 627.5656 | 1203 | 6.89E−03 | 1.26 | 5.47 | 6.87 |
| 657.7337 | 1101 | 6.92E−03 | 2.06 | 20.13 | 41.54 |
| 255.1161 | 1201 | 7.01E−03 | 1.14 | 27.21 | 30.97 |
| 751.5511 | 1202 | 7.02E−03 | 0.64 | 7.10 | 4.57 |
| 751.5539 | 1204 | 7.02E−03 | 0.53 | 15.18 | 8.11 |
| 827.5678 | 1202 | 7.35E−03 | 0.71 | 67.73 | 47.91 |
| 658.7372 | 1101 | 7.35E−03 | 1.91 | 2.70 | 5.15 |
| 804.5456 | 1201 | 7.48E−03 | 0.79 | 26.05 | 20.68 |
| 670.5696 | 1203 | 7.50E−03 | 0.68 | 10.09 | 6.81 |
| 628.5438 | 1203 | 7.58E−03 | 1.18 | 7.10 | 8.39 |
| 613.3379 | 1202 | 7.62E−03 | 0.81 | 36.81 | 29.89 |
| 645.7958 | 1101 | 7.76E−03 | 2.00 | 3.94 | 7.88 |
| 850.7326 | 1204 | 7.89E−03 | 0.70 | 6.57 | 4.60 |
| 923.7295 | 1204 | 7.93E−03 | 0.83 | 13.51 | 11.27 |
| 579.5313 | 1203 | 8.30E−03 | 0.70 | 12.95 | 9.10 |
| 748.527 | 1204 | 8.77E−03 | 0.52 | 5.95 | 3.07 |
| 783.5755 | 1201 | 9.29E−03 | 0.79 | 37.00 | 29.41 |
| 828.5721 | 1202 | 9.38E−03 | 0.73 | 31.90 | 23.31 |
| 578.5284 | 1203 | 9.41E−03 | 0.71 | 33.06 | 23.56 |
| 894.7911 | 1204 | 9.58E−03 | 0.77 | 18.12 | 14.02 |
| 910.7272 | 1204 | 9.85E−03 | 0.83 | 10.17 | 8.45 |
| 112.0974 | 1201 | 1.01E−02 | 1.19 | 7.97 | 9.46 |
| 857.6923 | 1204 | 1.02E−02 | 0.49 | 2.58 | 1.26 |
| 1012.781 | 1204 | 1.03E−02 | 0.71 | 7.04 | 4.99 |
| 733.5054 | 1204 | 1.06E−02 | 1.35 | 6.61 | 8.91 |
| 829.5843 | 1202 | 1.08E−02 | 0.75 | 38.25 | 28.65 |
| 855.7436 | 1204 | 1.09E−02 | 1.15 | 12.81 | 14.70 |
| 997.7397 | 1204 | 1.09E−02 | 0.69 | 10.03 | 6.88 |
| 984.7406 | 1204 | 1.13E−02 | 0.73 | 7.01 | 5.09 |
| 735.6582 | 1204 | 1.13E−02 | 0.74 | 7.76 | 5.74 |
| 830.5879 | 1202 | 1.18E−02 | 0.77 | 18.18 | 13.95 |
| 775.5532 | 1203 | 1.19E−02 | 0.57 | 2.87 | 1.64 |
| 902.7629 | 1204 | 1.28E−02 | 1.16 | 113.63 | 131.44 |
| 874.7066 | 1203 | 1.29E−02 | 0.76 | 8.79 | 6.67 |
| 861.749 | 1203 | 1.30E−02 | 0.79 | 7.93 | 6.25 |
| 243.0714 | 1101 | 1.32E−02 | 1.24 | 7.52 | 9.33 |
| 256.2403 | 1202 | 1.33E−02 | 1.21 | 10.40 | 12.63 |
| 766.4792 | 1204 | 1.34E−02 | 0.70 | 5.88 | 4.13 |
| 214.1205 | 1201 | 1.34E−02 | 1.15 | 22.10 | 25.34 |
| 854.7397 | 1204 | 1.41E−02 | 1.15 | 19.42 | 22.33 |
| 1249.105 | 1203 | 1.45E−02 | 0.72 | 6.51 | 4.67 |
| 795.5181 | 1201 | 1.46E−02 | 0.84 | 11.33 | 9.57 |
| 854.7358 | 1203 | 1.48E−02 | 1.17 | 164.45 | 192.27 |
| 946.8194 | 1204 | 1.55E−02 | 0.81 | 26.05 | 21.20 |

TABLE 5-continued

Accurate mass features differing between clinically diagnosed pancreatic cancer patients and controls (p < 0.05).

| Detected Mass | Analysis Mode | P value | Ratio pancreatic cancer/control | AVG controls | AVG pancreatic cancer |
|---|---|---|---|---|---|
| 719.6256 | 1204 | 1.56E−02 | 1.30 | 8.46 | 10.99 |
| 919.6496 | 1101 | 1.56E−02 | 1.57 | 1.25 | 1.96 |
| 1251.119 | 1203 | 1.58E−02 | 0.72 | 9.37 | 6.76 |
| 855.7392 | 1203 | 1.60E−02 | 1.17 | 95.69 | 111.76 |
| 671.5731 | 1203 | 1.67E−02 | 0.72 | 5.22 | 3.74 |
| 839.7464 | 1203 | 1.71E−02 | 1.19 | 5.07 | 6.01 |
| 933.8137 | 1204 | 1.72E−02 | 0.80 | 21.43 | 17.14 |
| 725.7228 | 1101 | 1.74E−02 | 1.76 | 4.71 | 8.28 |
| 916.7735 | 1204 | 1.78E−02 | 1.15 | 137.59 | 158.45 |
| 468.2336 | 1201 | 1.80E−02 | 1.36 | 22.33 | 30.32 |
| 804.7208 | 1203 | 1.91E−02 | 0.70 | 5.47 | 3.81 |
| 304.2375 | 1201 | 1.92E−02 | 1.71 | 7.28 | 12.43 |
| 922.7285 | 1204 | 1.92E−02 | 0.81 | 15.80 | 12.85 |
| 609.3259 | 1202 | 1.93E−02 | 0.83 | 8.39 | 6.98 |
| 755.5497 | 1201 | 1.98E−02 | 0.84 | 5.36 | 4.49 |
| 972.7481 | 1204 | 2.01E−02 | 0.79 | 9.99 | 7.91 |
| 827.7082 | 1203 | 2.03E−02 | 0.85 | 9.17 | 7.79 |
| 494.4321 | 1203 | 2.04E−02 | 0.59 | 3.30 | 1.96 |
| 232.1309 | 1202 | 2.05E−02 | 1.09 | 227.50 | 248.81 |
| 803.5414 | 1201 | 2.06E−02 | 0.81 | 66.42 | 53.85 |
| 826.7047 | 1203 | 2.17E−02 | 0.85 | 15.48 | 13.19 |
| 720.6272 | 1204 | 2.20E−02 | 1.27 | 4.46 | 5.67 |
| 807.5764 | 1203 | 2.20E−02 | 0.71 | 3.47 | 2.46 |
| 922.7081 | 1203 | 2.29E−02 | 0.62 | 2.64 | 1.62 |
| 986.7568 | 1204 | 2.29E−02 | 0.83 | 9.18 | 7.65 |
| 348.1191 | 1201 | 2.29E−02 | 0.79 | 5.78 | 4.58 |
| 813.5888 | 1202 | 2.33E−02 | 0.84 | 5.27 | 4.43 |
| 233.1345 | 1202 | 2.41E−02 | 1.10 | 27.50 | 30.33 |
| 784.5806 | 1201 | 2.48E−02 | 0.85 | 14.21 | 12.08 |
| 973.7482 | 1204 | 2.50E−02 | 0.83 | 9.22 | 7.69 |
| 724.5252 | 1204 | 2.56E−02 | 0.69 | 3.95 | 2.71 |
| 1011.77 | 1204 | 2.62E−02 | 0.72 | 6.37 | 4.59 |
| 858.7644 | 1203 | 2.64E−02 | 1.15 | 121.34 | 139.48 |
| 835.598 | 1201 | 2.84E−02 | 0.86 | 6.87 | 5.90 |
| 469.237 | 1201 | 2.88E−02 | 1.28 | 5.11 | 6.54 |
| 773.5276 | 1204 | 2.94E−02 | 0.74 | 12.51 | 9.32 |
| 889.7537 | 1204 | 2.97E−02 | 1.13 | 79.81 | 90.07 |
| 819.5177 | 1201 | 3.10E−02 | 0.86 | 5.89 | 5.09 |
| 875.7108 | 1203 | 3.11E−02 | 0.78 | 5.01 | 3.89 |
| 781.5029 | 1204 | 3.18E−02 | 0.75 | 6.97 | 5.26 |
| 793.7091 | 1101 | 3.19E−02 | 1.68 | 4.56 | 7.67 |
| 866.7585 | 1204 | 3.28E−02 | 0.79 | 17.66 | 13.95 |
| 785.5931 | 1203 | 3.30E−02 | 0.78 | 5.98 | 4.67 |
| 485.904 | 1101 | 3.46E−02 | 1.14 | 7.86 | 8.96 |
| 1253.123 | 1201 | 3.47E−02 | 0.69 | 3.56 | 2.45 |
| 481.315 | 1202 | 3.56E−02 | 0.90 | 9.09 | 8.20 |
| 745.5631 | 1203 | 3.64E−02 | 1.47 | 7.05 | 10.35 |
| 851.6694 | 1101 | 3.64E−02 | 1.59 | 1.78 | 2.84 |
| 1010.765 | 1204 | 3.71E−02 | 0.72 | 8.26 | 5.97 |
| 999.7632 | 1204 | 3.72E−02 | 0.81 | 8.01 | 6.52 |
| 907.7847 | 1204 | 3.78E−02 | 0.81 | 23.16 | 18.73 |
| 254.1127 | 1201 | 3.80E−02 | 1.13 | 215.52 | 243.63 |
| 898.7325 | 1204 | 3.80E−02 | 0.88 | 13.60 | 11.95 |
| 418.2204 | 1204 | 4.01E−02 | 0.61 | 12.12 | 7.44 |
| 522.4638 | 1201 | 4.01E−02 | 0.67 | 3.86 | 2.59 |
| 937.7542 | 1204 | 4.06E−02 | 0.88 | 18.10 | 15.92 |
| 484.3527 | 1201 | 4.09E−02 | 0.74 | 11.34 | 8.43 |
| 366.3593 | 1101 | 4.15E−02 | 1.81 | 2.10 | 3.80 |
| 852.7368 | 1204 | 4.16E−02 | 0.88 | 7.42 | 6.52 |
| 831.572 | 1201 | 4.16E−02 | 0.84 | 30.16 | 25.20 |
| 746.5128 | 1204 | 4.27E−02 | 1.27 | 10.08 | 12.78 |
| 796.5212 | 1201 | 4.29E−02 | 0.85 | 4.71 | 3.98 |
| 1247.084 | 1203 | 4.37E−02 | 0.71 | 3.97 | 2.83 |
| 889.8147 | 1203 | 4.41E−02 | 0.65 | 1.97 | 1.28 |
| 681.5858 | 1204 | 4.42E−02 | 0.78 | 4.60 | 3.60 |
| 746.5705 | 1204 | 4.44E−02 | 1.31 | 7.89 | 10.30 |
| 865.752 | 1204 | 4.49E−02 | 0.81 | 28.03 | 22.72 |
| 960.7432 | 1204 | 4.59E−02 | 0.87 | 10.60 | 9.21 |
| 950.7364 | 1203 | 4.73E−02 | 0.72 | 14.31 | 10.32 |
| 78.0516 | 1202 | 4.75E−02 | 1.09 | 4.89 | 5.32 |
| 774.5419 | 1204 | 4.76E−02 | 0.72 | 6.38 | 4.61 |
| 428.2404 | 1201 | 4.93E−02 | 1.35 | 3.83 | 5.15 |
| 879.7629 | 1204 | 4.97E−02 | 0.79 | 24.59 | 19.43 |
| 909.7882 | 1203 | 4.98E−02 | 1.12 | 18.12 | 20.25 |

Figure 2:
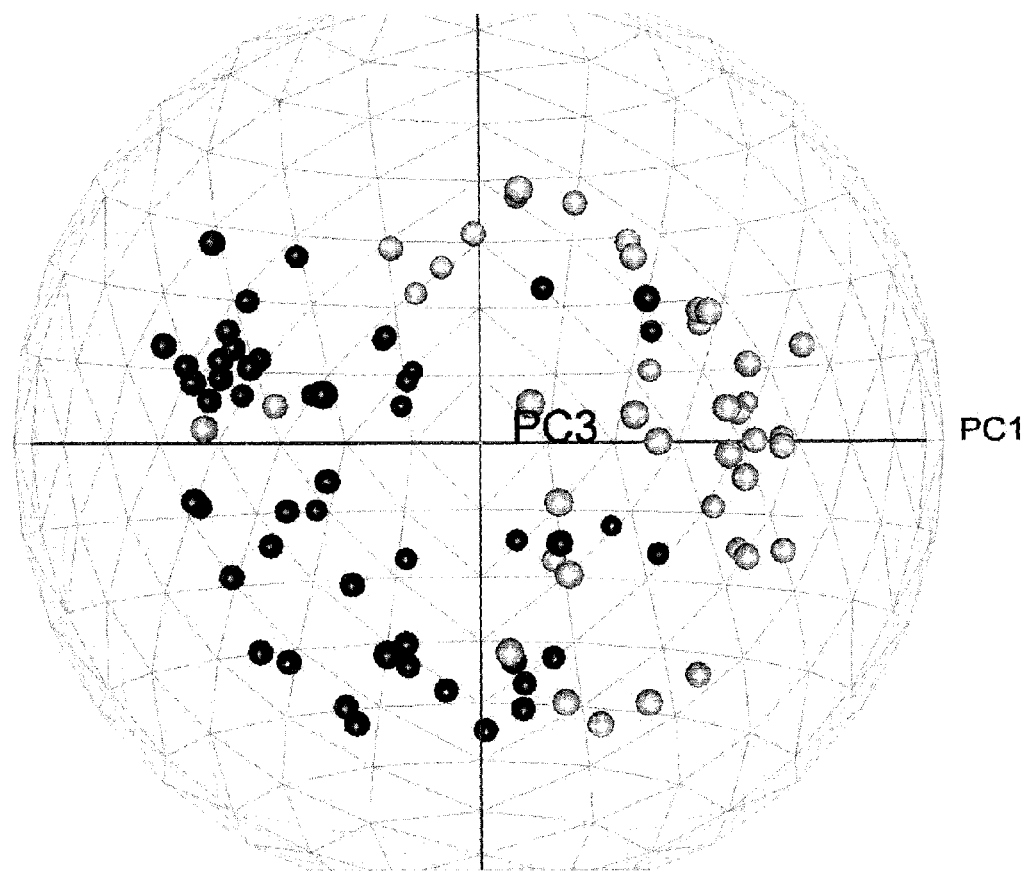
FIG. 2 illustrates a Principal Component Analysis on all masses differentiating pancreatic cancer from controls with p-value <0.05 showing a clear separation between pancreatic cancer samples (grey) and controls (black).

Principal Component Analysis was then performed on the whole populations (90 samples) upon the 362 markers through DISCOVAmetrics™. FIG. 2 illustrates the separation resulting from this unsupervised classification between pancreatic cancer (with individual samples in grey) and controls (in black).

$^{13}$C isotopic peaks were identified, such as the first two markers, 786.593 and 595.4897, which are the isotopic peaks of the fourth and third markers respectively, 785.5913 and 594.4863. Table 6 lists the 20 best biomarkers without $^{13}$C isotopic peaks. All of these markers except 600.5117 have decreased levels in the pancreatic cancer cohort relative to controls.

TABLE 6

List of the 20 best FTICR biomarkers of pancreatic cancer, sorted by mass within their analysis mode.

| Analysis Mode | Detected Mass | P value | Ratio pancreatic cancer/control |
|---|---|---|---|
| 1101 | 519.3295 | 7.30E−11 | 0.41 |
| | 523.3661 | 3.97E−10 | 0.49 |
| | 541.3134 | 6.66E−13 | 0.37 |
| | 702.5709 | 2.39E−13 | 0.47 |
| | 724.5477 | 3.75E−11 | 0.49 |
| | 757.556 | 1.04E−10 | 0.27 |
| | 779.5405 | 2.66E−12 | 0.26 |
| | 783.569 | 1.19E−11 | 0.36 |
| | 785.5913 | 1.39E−13 | 0.27 |
| | 803.5373 | 2.11E−11 | 0.33 |
| | 805.5549 | 6.17E−10 | 0.35 |
| | 807.5734 | 5.49E−13 | 0.28 |
| | 809.5796 | 2.67E−10 | 0.43 |
| | 812.6774 | 3.81E−12 | 0.54 |
| | 829.5516 | 2.82E−10 | 0.41 |
| | 833.5864 | 9.05E−10 | 0.43 |
| 1202 | 576.4751 | 5.61E−13 | 0.40 |
| | 594.4863 | 9.91E−14 | 0.31 |
| | 596.5017 | 2.03E−11 | 0.36 |
| 1203 | 600.5117 | 2.61E−10 | 1.40 |

Figure 3:
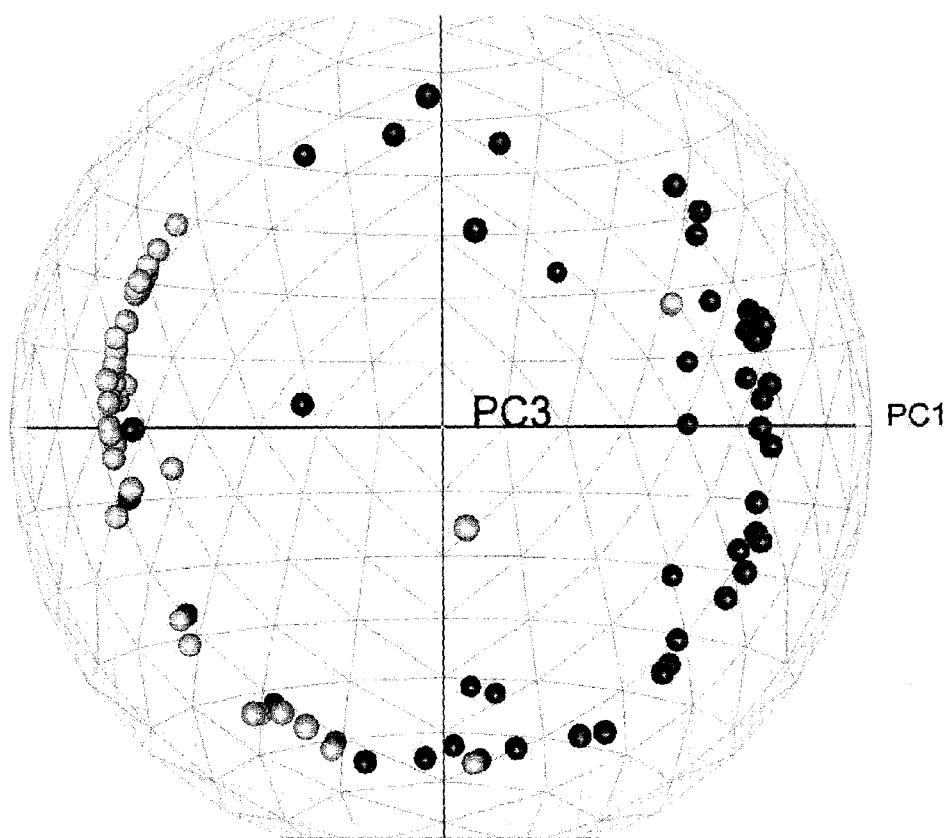
FIG. 3 illustrates a Principal Component Analysis on the 20 best biomarkers showing a clear separation between pancreatic cancer samples (grey) and controls (black) (a), and the relative level intensities of these 20 biomarkers in the serum of pancreatic cancer patients relative to controls (b).
Figure 3:
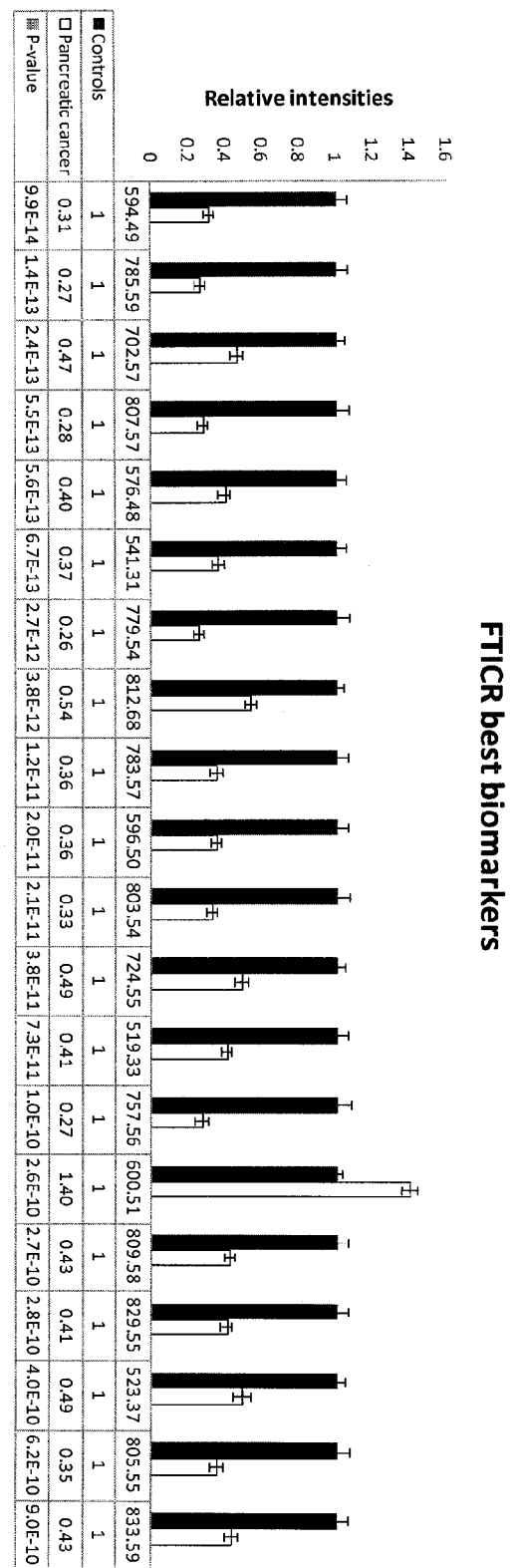

Principal Component Analysis was then performed on the whole populations upon these 20 markers through DISCOVAmetrics™. FIG. 3 illustrates (a) the separation resulting from this unsupervised classification between pancreatic cancer (with individual samples in grey) and controls (in black), as well as (b) the relative intensities of these 20 biomarkers in both populations.

1B. Logistic Regression Analysis

Receiver Operating Characteristic (ROC) analysis was performed on these 20 best FTICR biomarkers. Table 7 summarizes the resulting Areas Under the Curves (AUCs).

TABLE 7

List of FTICR biomarkers sorted by p-values with corresponding AUCs.

| Masses | P-value | Area Under the Curve |
|---|---|---|
| 594.4863 | 9.91E−14 | 0.961 |
| 785.5913 | 1.39E−13 | 0.932 |
| 702.5709 | 2.39E−13 | 0.909 |
| 807.5734 | 5.49E−13 | 0.933 |
| 576.4751 | 5.61E−13 | 0.925 |
| 541.3134 | 6.66E−13 | 0.921 |

TABLE 7-continued

List of FTICR biomarkers sorted by p-values with corresponding AUCs.

| Masses | P-value | Area Under the Curve |
|---|---|---|
| 779.5405 | 2.66E−12 | 0.934 |
| 812.6774 | 3.81E−12 | 0.895 |
| 783.569 | 1.19E−11 | 0.906 |
| 596.5017 | 2.03E−11 | 0.932 |
| 803.5373 | 2.11E−11 | 0.924 |
| 724.5477 | 3.75E−11 | 0.878 |
| 519.3295 | 7.30E−11 | 0.899 |
| 757.556 | 1.04E−10 | 0.916 |
| 600.5117 | 2.61E−10 | 0.855 |
| 809.5796 | 2.67E−10 | 0.895 |
| 829.5516 | 2.82E−10 | 0.877 |
| 523.3661 | 3.97E−10 | 0.877 |
| 805.5549 | 6.17E−10 | 0.897 |
| 833.5864 | 9.05E−10 | 0.888 |

Figure 4:
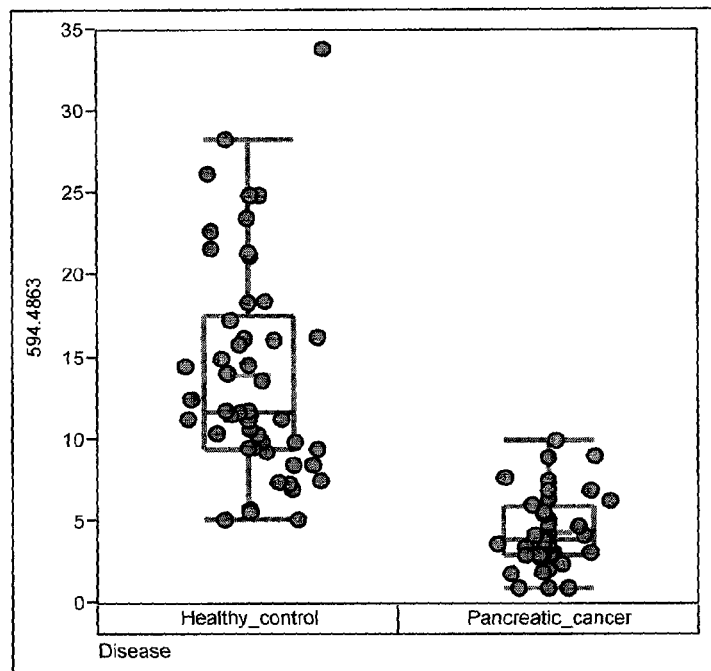
FIG. 4 illustrates a ROC and variability chart for the first six best biomarkers by FTICR, namely 594.4863 (AUC=0.96) (a), 785.5913 (AUC=0.93) (b), 702.5709 (AUC=0.91) (c), 807.5734 (AUC=0.93) (d), 576.4751 (AUC=0.93) (e) and 541.3134 (AUC=0.92) (f).
Figure 4:
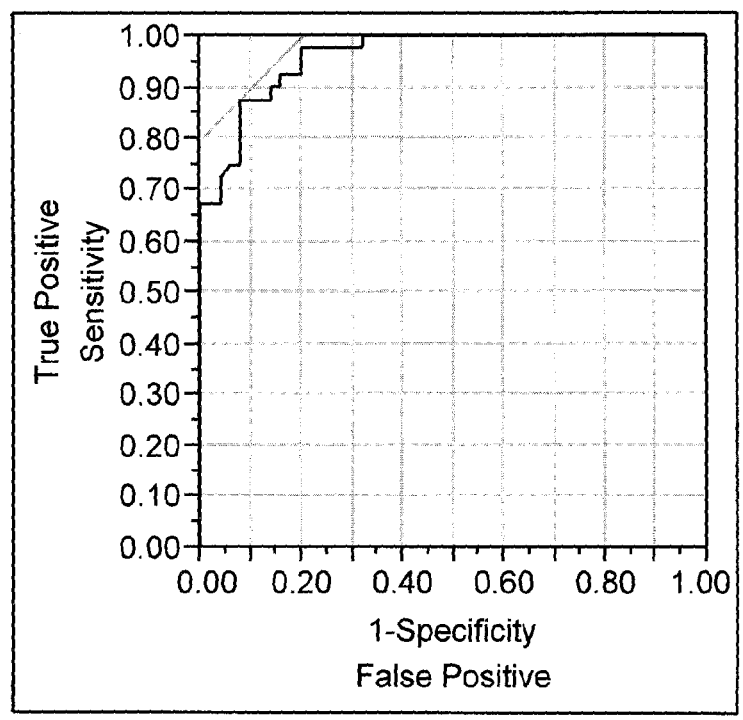
Figure 4:
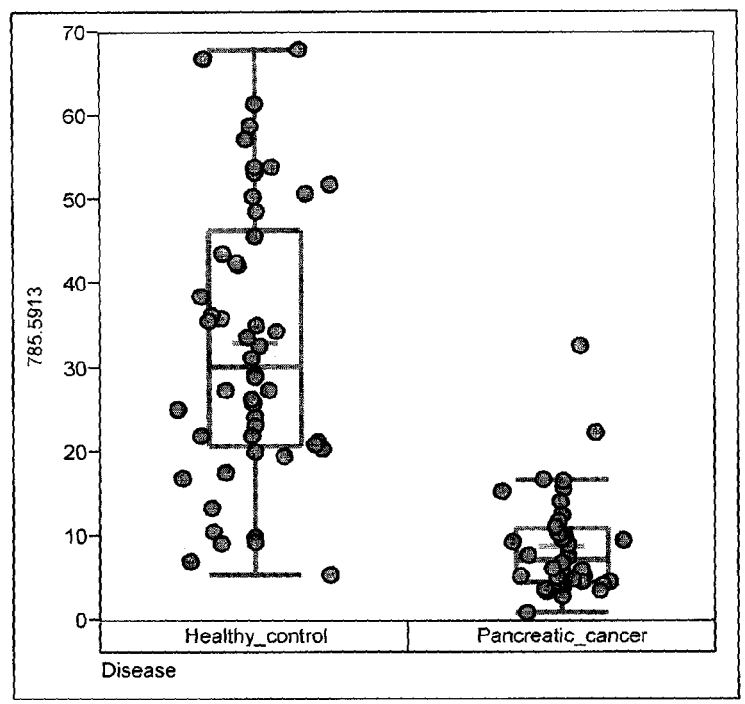
Figure 4:
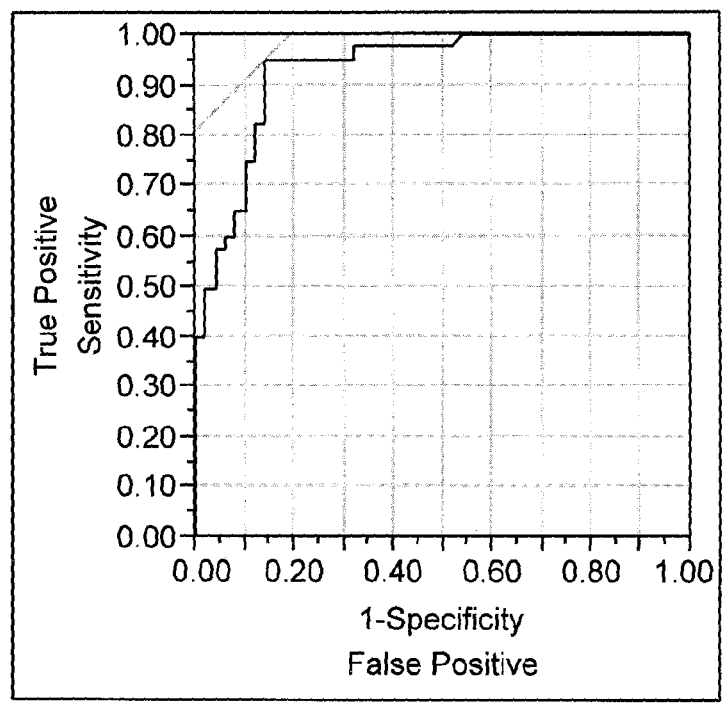
Figure 4:
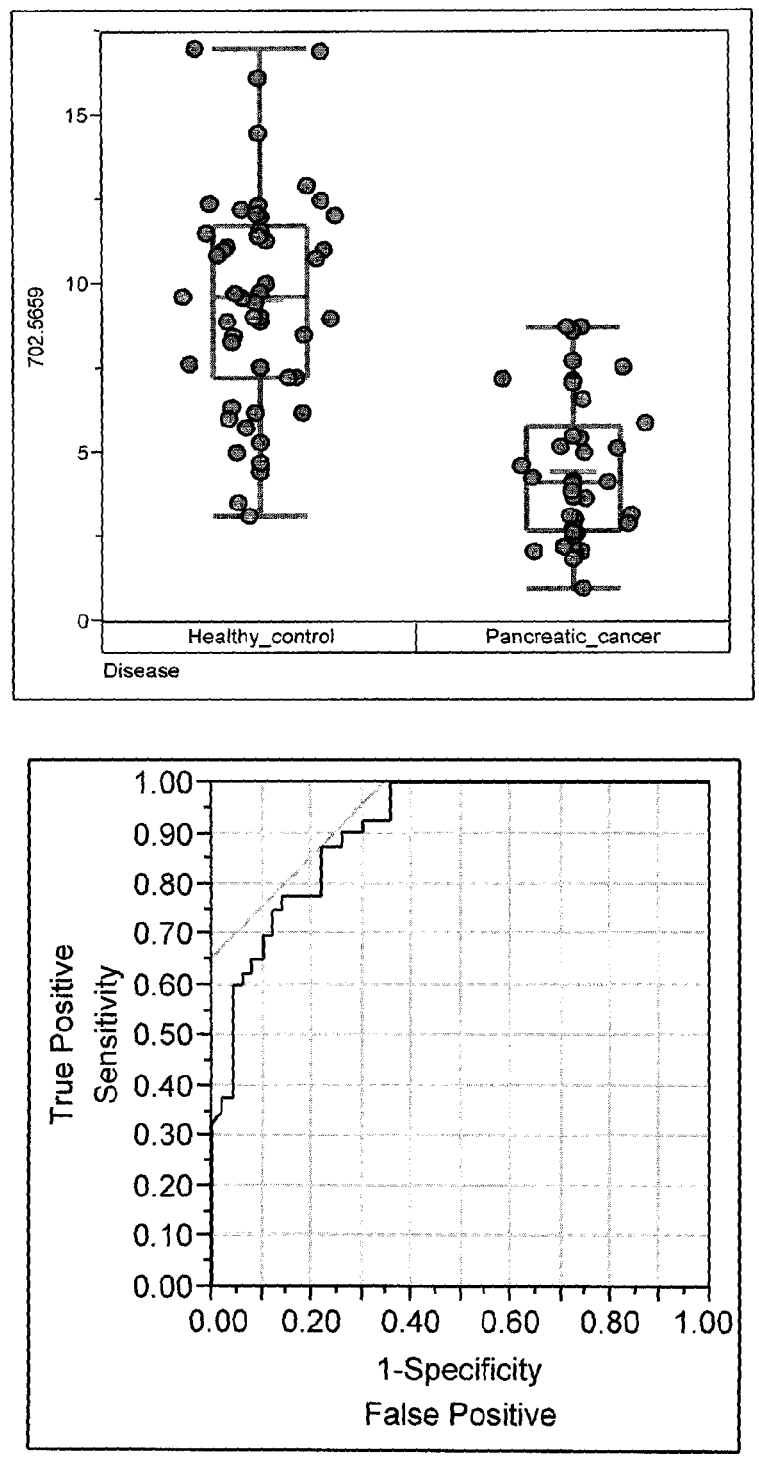
Figure 4:
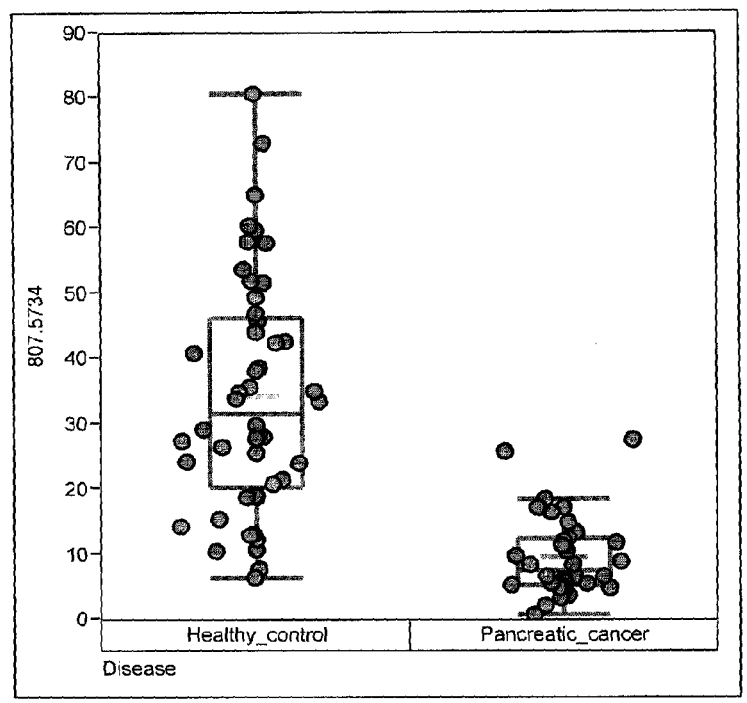
Figure 4:
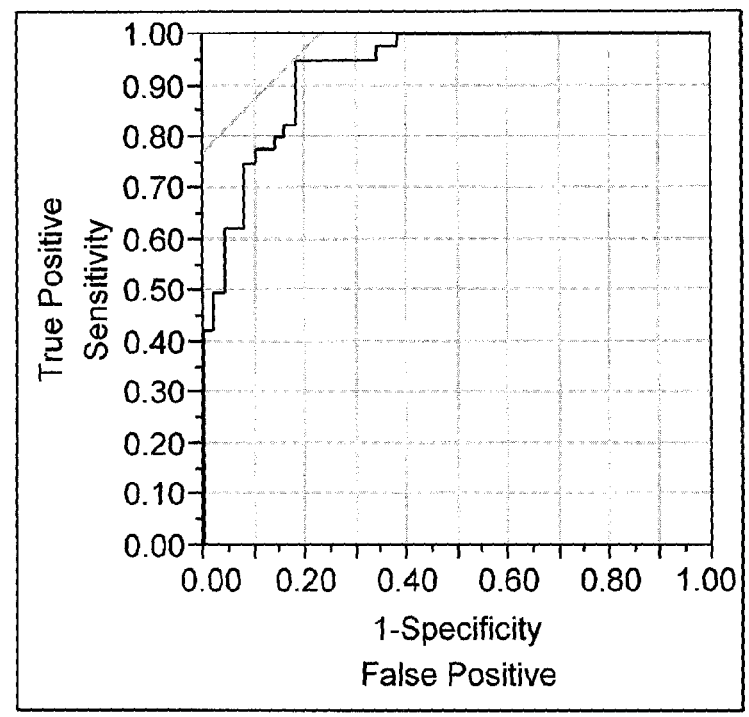
Figure 4:
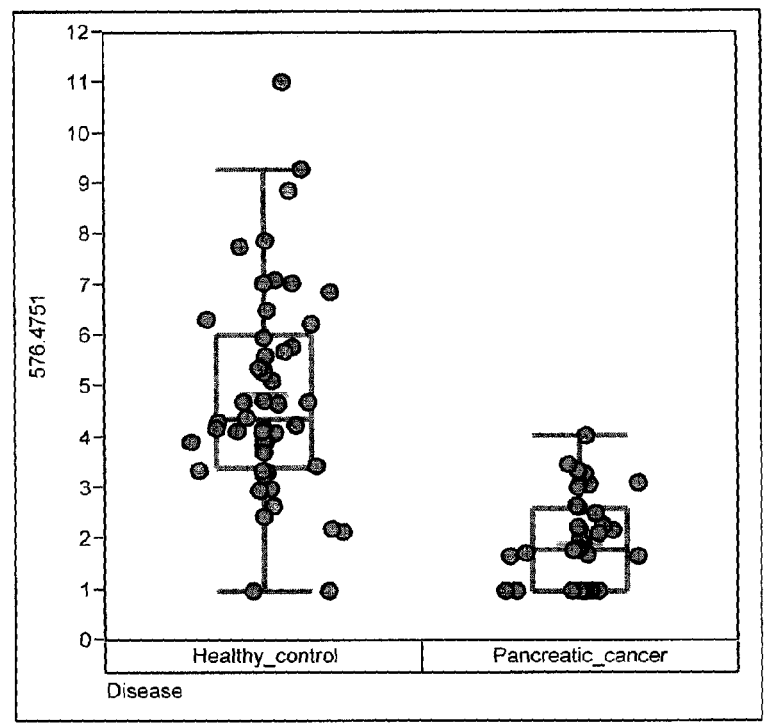
Figure 4:
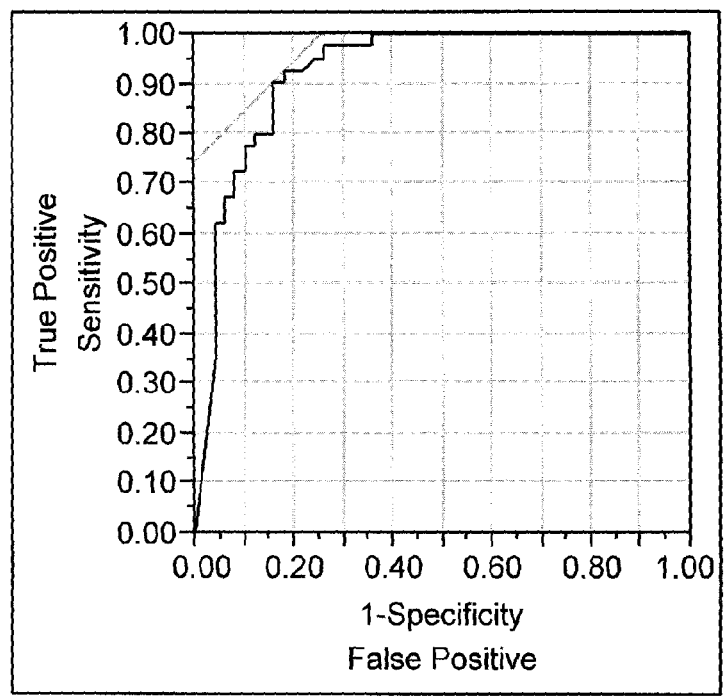
Figure 4:
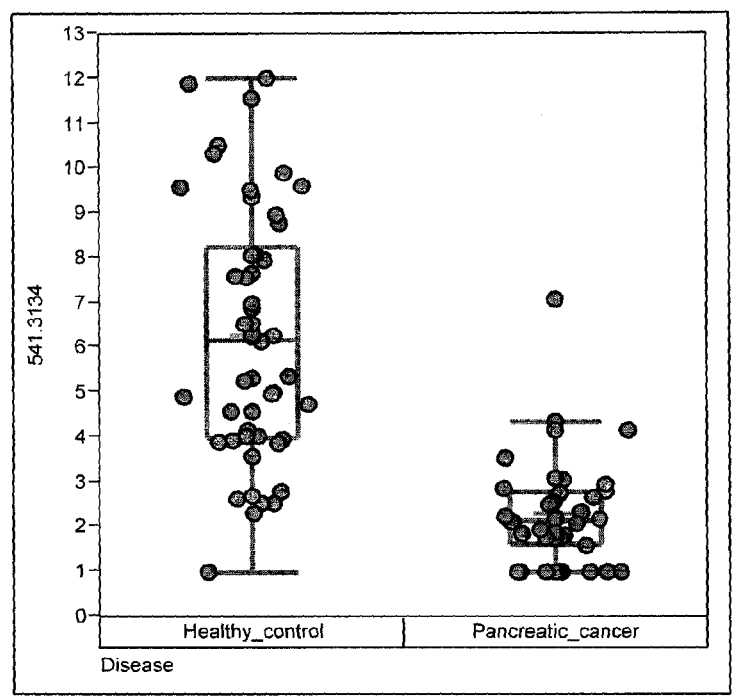
Figure 4:
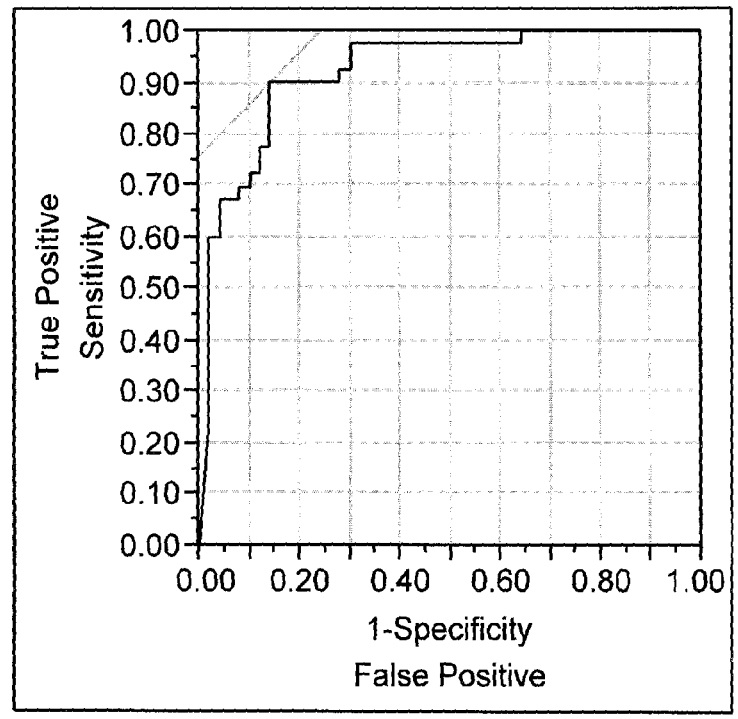

At least nine markers display AUC>0.90, which indicates an excellent specificity and sensitivity. FIG. 4 illustrates each ROC along with the distribution of sample values for the first six best biomarkers (p-value <E-12).

Figure 5:
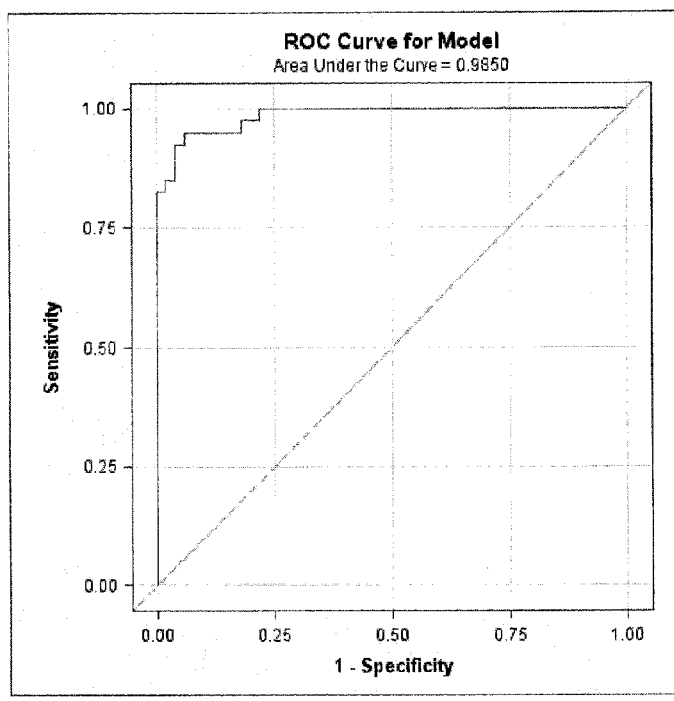
FIG. 5 shows a logistic regression analysis of the combination of the six FTICR best biomarkers, with ROC curve (a) and classification table (b).
Figure 6:
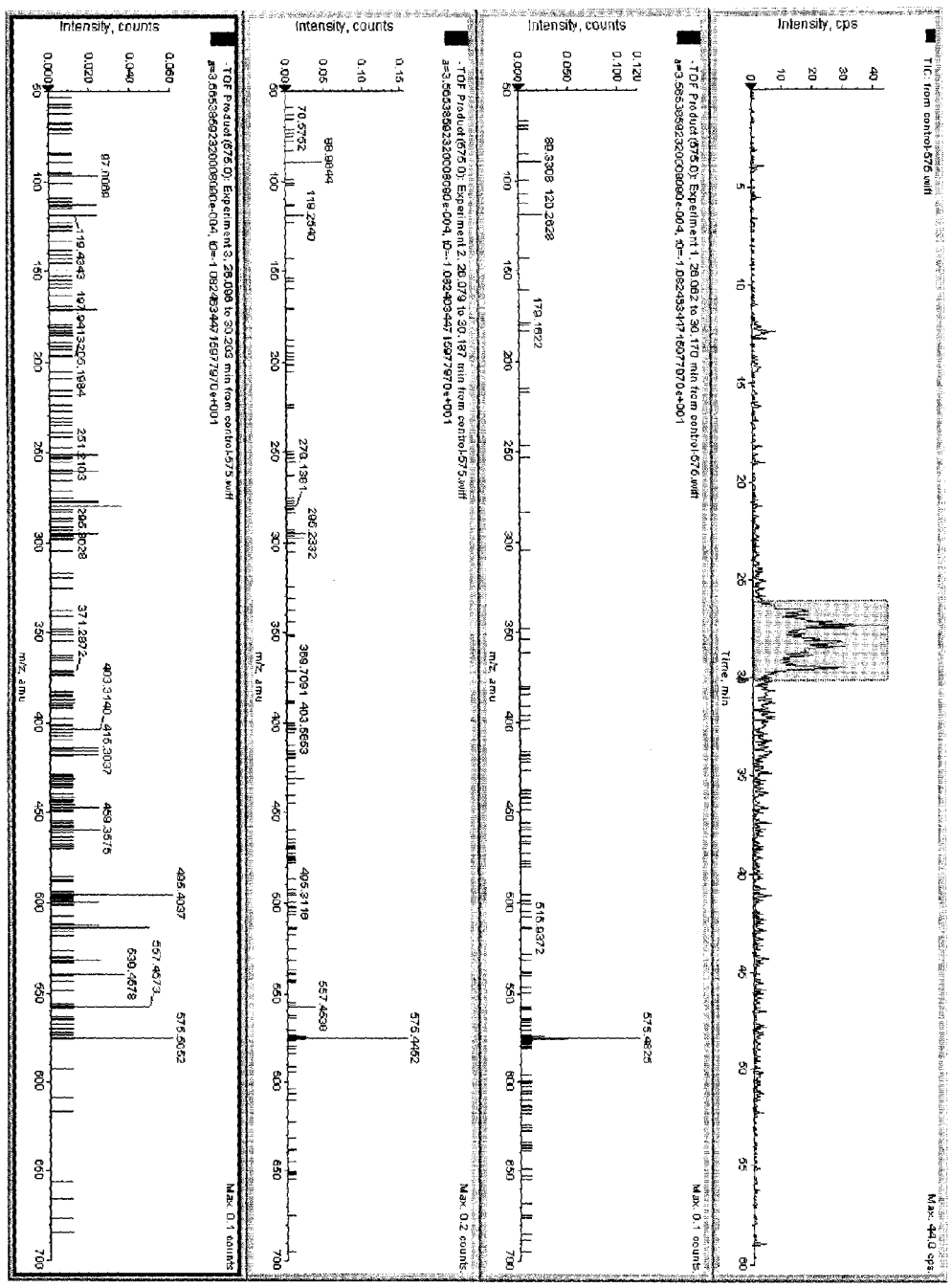
FIG. 6 illustrates the fragmentation pattern of C36 compound "576".
Figure 7:
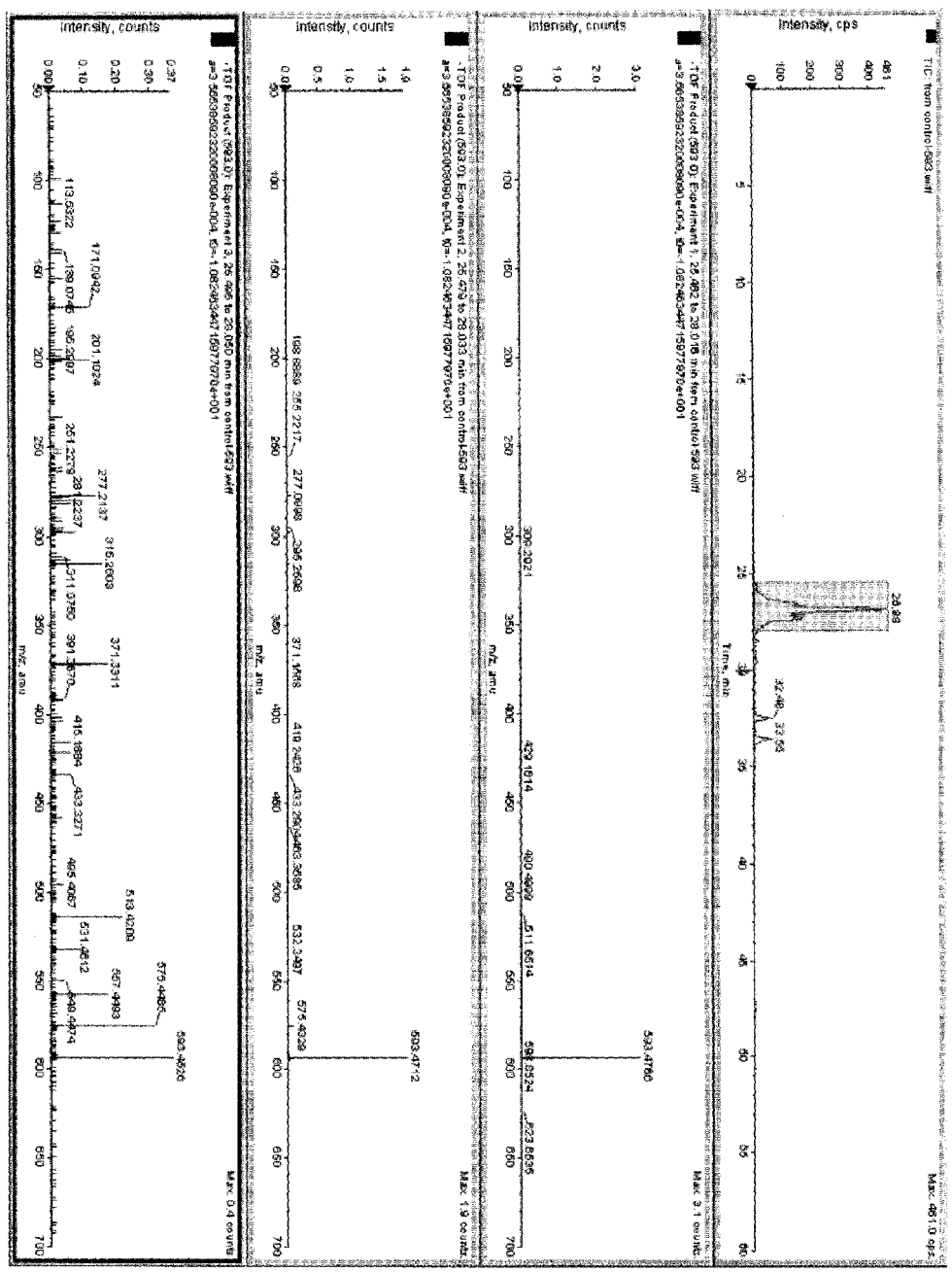
FIG. 7 illustrates the fragmentation pattern of C36 compound "594".
Figure 8:
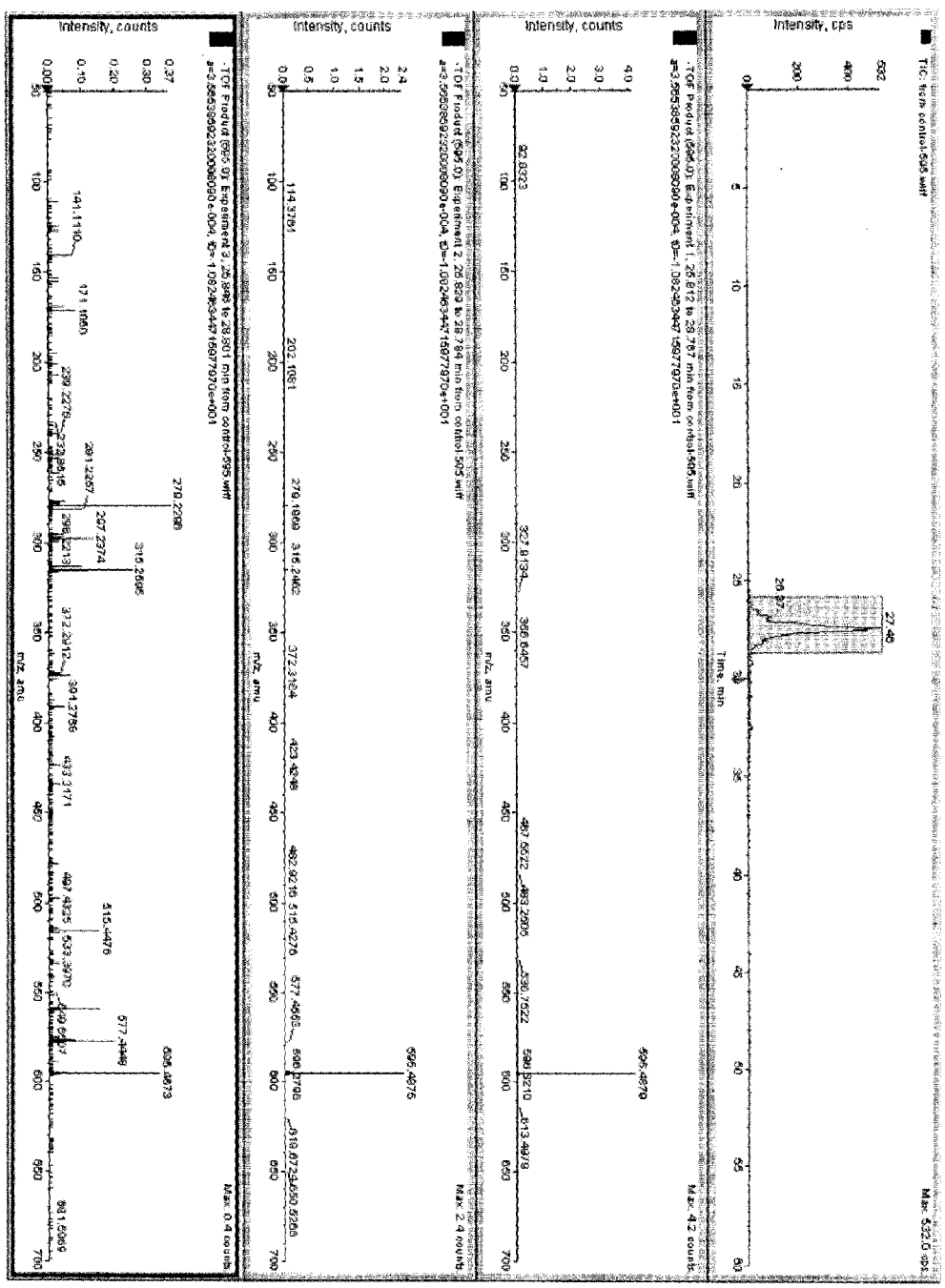
FIG. 8 illustrates the fragmentation pattern of C36 compound "596".
Figure 9:
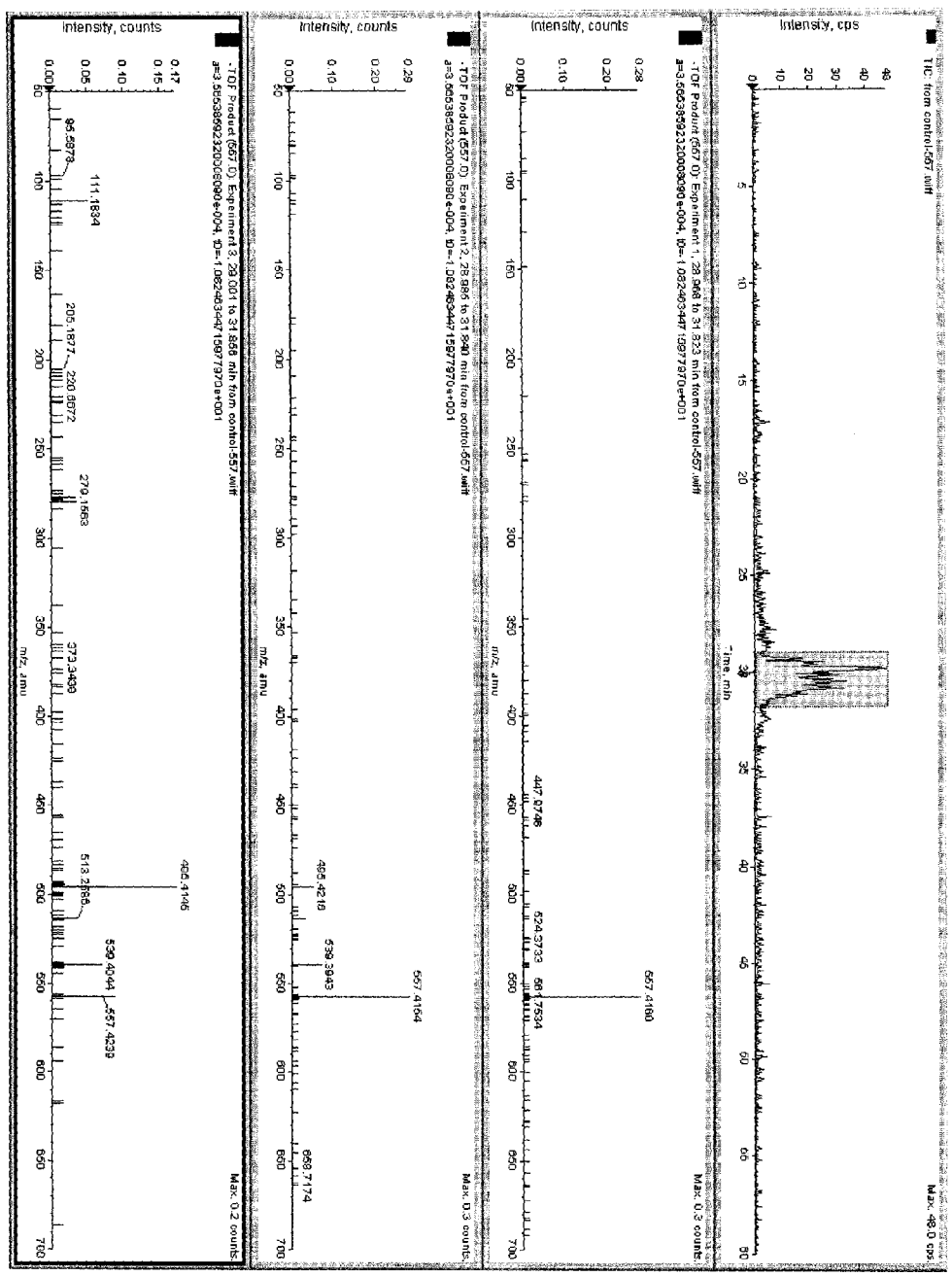
FIG. 9 illustrates the fragmentation pattern of C36 compound "558".
Figure 10:
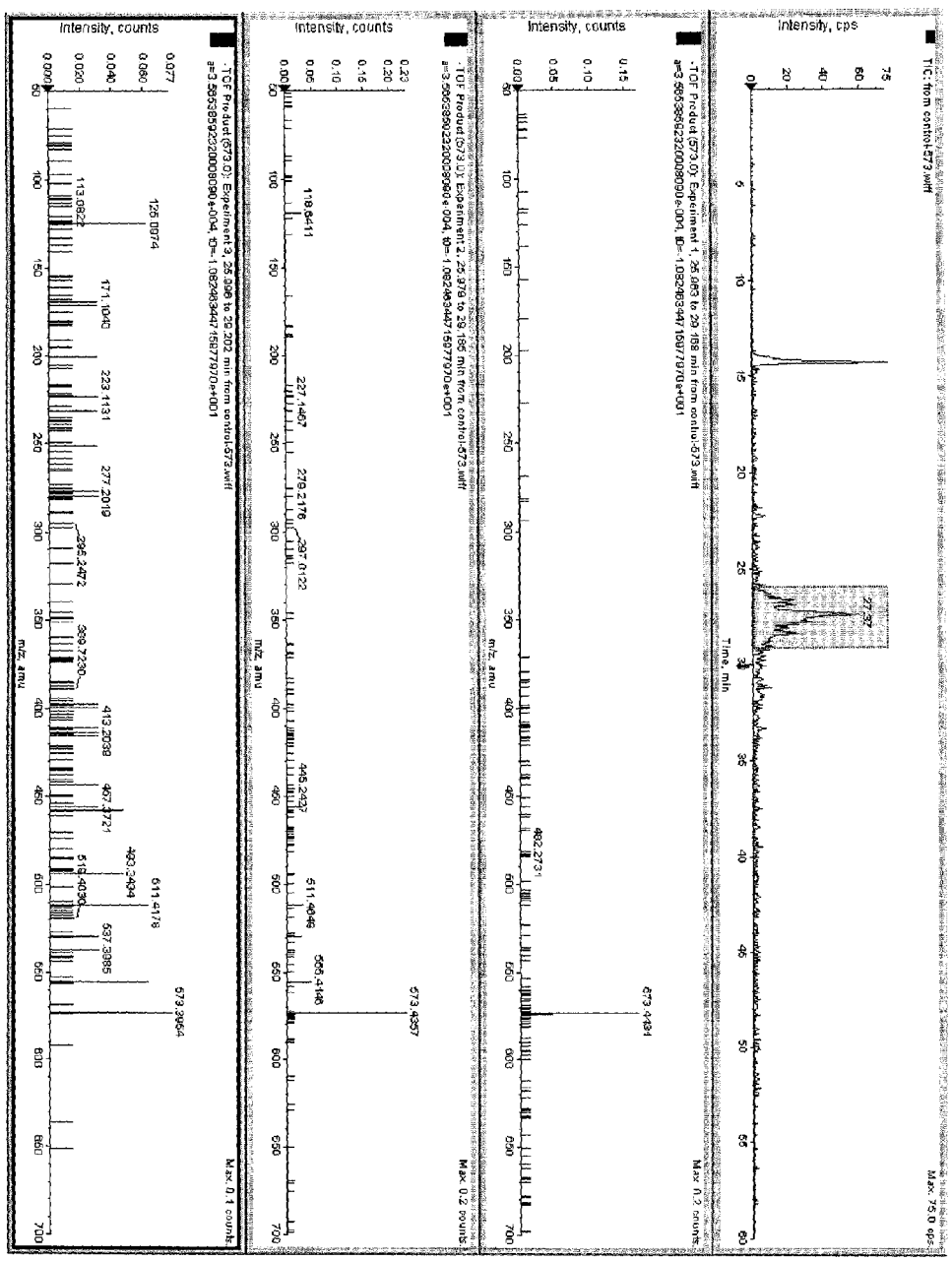
FIG. 10 illustrates the fragmentation pattern of C36 compound "574".
Figure 11:
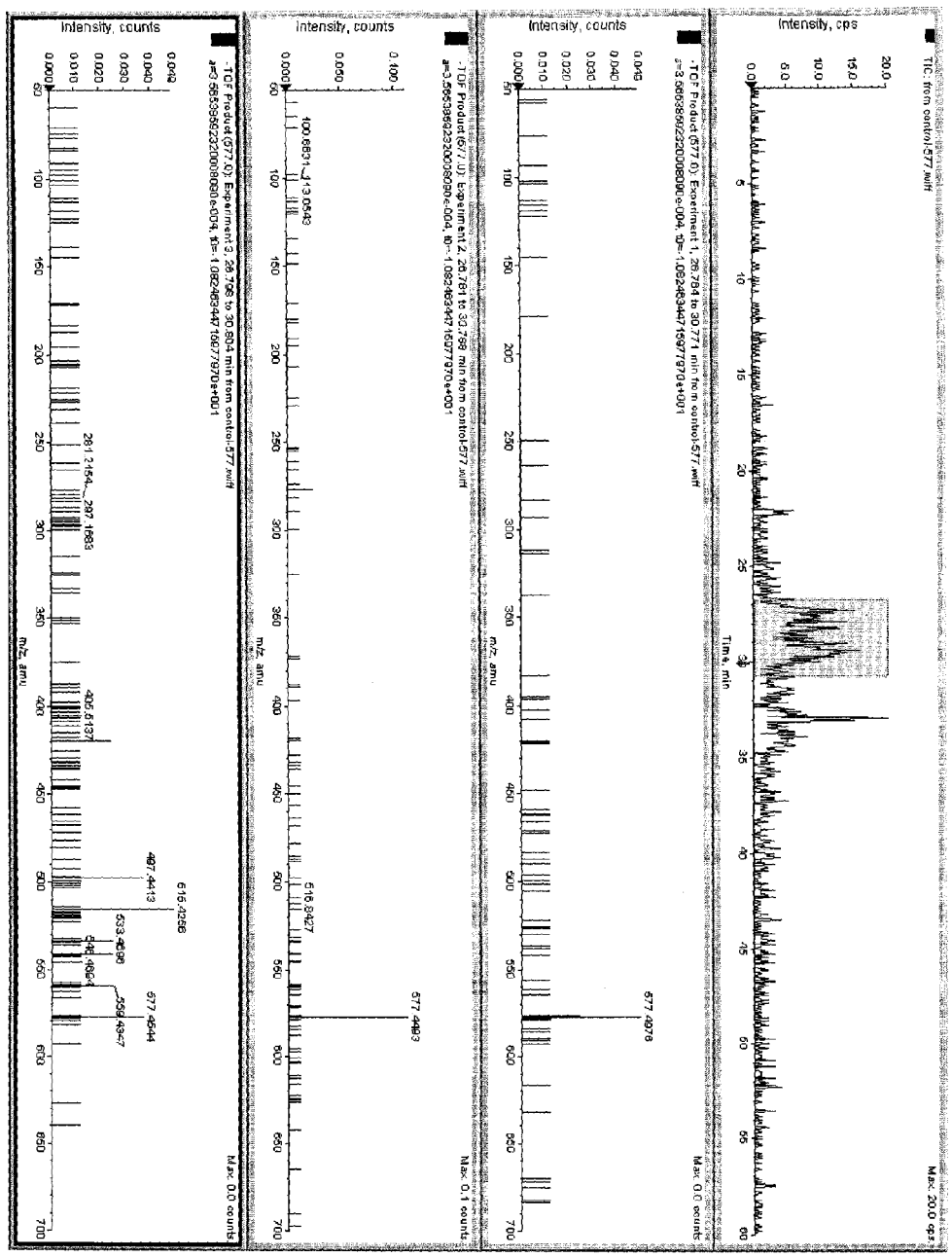
FIG. 11 illustrates the fragmentation pattern of C36 compound "578"
Figure 12:
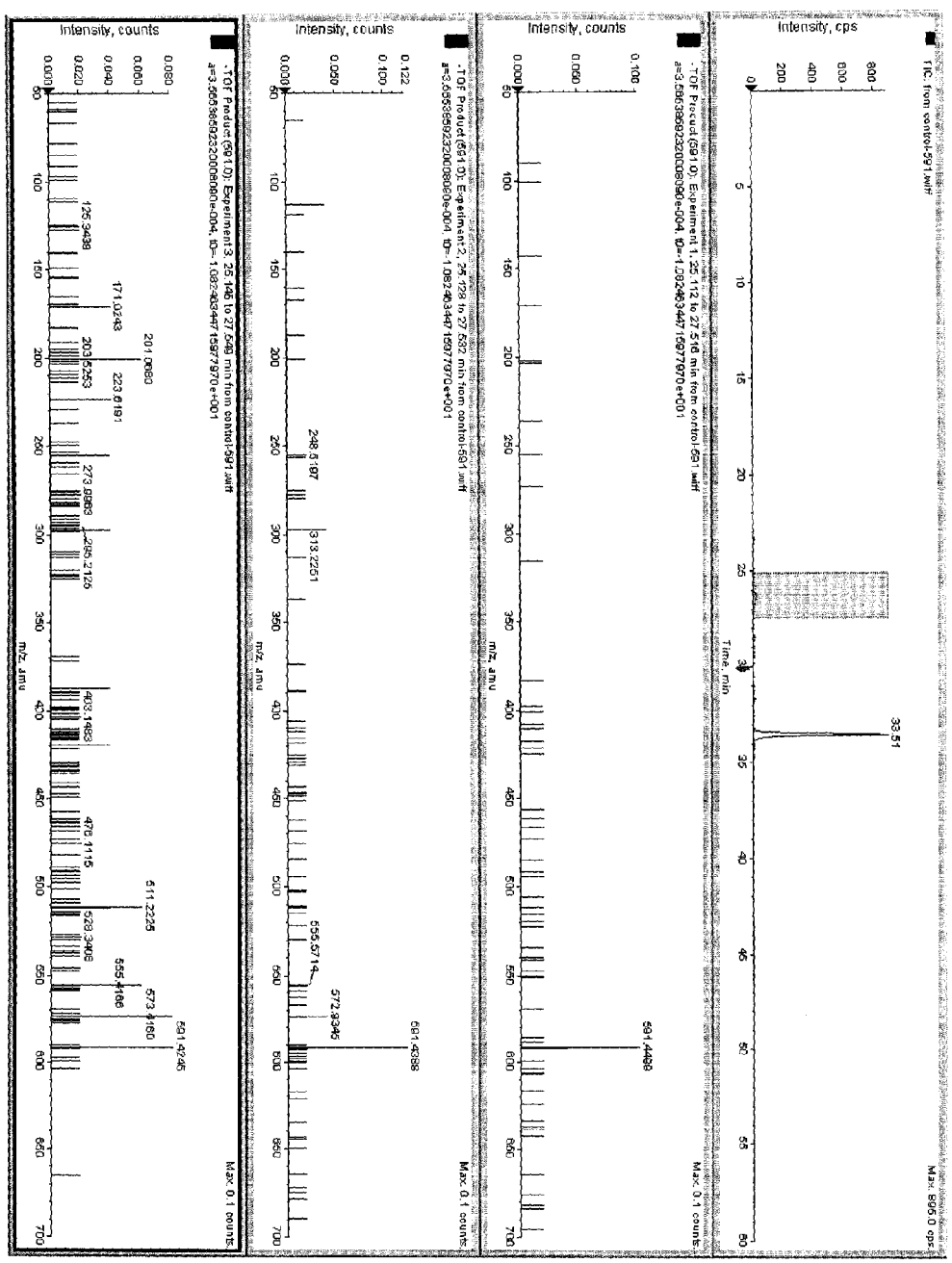
FIG. 12 illustrates the fragmentation pattern of C36 compound "592".

There are multiple ways of combining the best biomarkers in the perspective of obtaining a very high sensitivity and specificity with few of them. For example the combination of the six best biomarkers as classified by p-values displays an AUC of 0.985 (FIG. 5), with an optimal specificity and sensitivity pair of 92.5% and 88% respectively.

1C. Formula Prediction

Computational assignments of reasonable molecular formulae were performed for the 20 best biomarkers. The assignments were based on a series of mathematical and chemometric rules as previously described (24), which rely on high mass accuracy for precise prediction. The algorithm computes the number of carbons, hydrogens, oxygens, and other elements, based on their exact mass, which can be assigned to a detected accurate mass within defined constraints. Logical putative molecular formulae were computed in Table 8.

TABLE 8

Putative molecular formulae for the 20 best FTICR biomarkers.

| Analysis Mode | Detected Mass | Putative formula | P value | Ratio pancreatic cancer/control |
|---|---|---|---|---|
| 1101 | 519.3295 | $C_{26}H_{50}NO_7P$ | 7.30E−11 | 0.41 |
|  | 523.3661 | $C_{26}H_{54}NO_7P$ | 3.97E−10 | 0.49 |
|  | 541.3134 | $C_{28}H_{48}NO_7P$ or $C_{26}H_{49}NO_7PNa$ | 6.66E−13 | 0.37 |
|  | 702.5709 | $C_{39}H_{79}N_2O_6P$ | 2.39E−13 | 0.47 |
|  | 724.5477 | $C_{41}H_{77}N_2O_6P$ or $C_{39}H_{78}N_2O_6PNa$ | 3.75E−11 | 0.49 |
|  | 757.556 | $C_{42}H_{80}NO_8P$ | 1.04E−10 | 0.27 |
|  | 779.5405 | $C_{44}H_{78}NO_8P$ | 2.66E−12 | 0.26 |
|  | 783.569 | $C_{44}H_{82}NO_8P$ | 1.19E−11 | 0.36 |
|  | 785.5913 | $C_{44}H_{84}NO_8P$ | 1.39E−13 | 0.27 |
|  | 803.5373 | $C_{46}H_{78}NO_8P$ or $C_{44}H_{79}NO_8PNa$ | 2.11E−11 | 0.33 |
|  | 805.5549 | $C_{46}H_{80}NO_8P$ | 6.17E−10 | 0.35 |
|  | 807.5734 | $C_{46}H_{82}NO_8P$ | 5.49E−13 | 0.28 |
|  | 809.5796 | $C_{46}H_{84}NO_8P$ | 2.67E−10 | 0.43 |
|  | 812.6774 | $C_{47}H_{93}N_2O_6P$ | 3.81E−12 | 0.54 |
|  | 829.5516 | $C_{48}H_{80}NO_8P$ or $C_{46}H_{81}NO_8PNa$ | 2.82E−10 | 0.41 |
|  | 833.5864 | $C_{48}H_{84}NO_8P$ or $C_{46}H_{85}NO_8PNa$ | 9.05E−10 | 0.43 |
| 1202 | 576.4751 | $C_{36}H_{64}O_5$ | 5.61E−13 | 0.40 |
|  | 594.4863 | $C_{36}H_{66}O_6$ | 9.91E−14 | 0.31 |
|  | 596.5017 | $C_{36}H_{68}O_6$ | 2.03E−11 | 0.36 |
| 1203 | 600.5117 | $C_{39}H_{68}O_4$ | 2.61E−10 | 1.40 |

Four main families seem to emerge, three in 1101 analysis mode and one in 1202 analysis mode. In 1101 mode they are reminiscent of choline-related compounds, namely lysophosphatidylcholines for compounds in $NO_7P$, phosphatidylcholines for compounds in $NO_8P$, and sphingomyelins for compounds in $N_2O_6P$. The next step was the structural validation of these 16 putative choline-related compounds, the three compounds in C36 and the additional compound in 1203 mode.

HPLC-Coupled Tandem Mass Spectrometry

Tandem mass spectrometric fragmentation fingerprints were generated for the markers mentioned above.

2A. 1202/1204 Compounds in C36

Selected ethyl acetate extracts of serum from the control cohort used in the FTICR-MS work were re-analyzed using HPLC coupled to a quadrupole time-of-flight (Q-TOF) mass spectrometer in APCI negative ion mode (1202 mode) for the three C36 biomarkers, "576", "594" and "596". For a retention time around 25-27 minutes, the MS/MS and MS3 fragmentation data were dominated by peaks resulting from losses of $H_2O$ (m/z 557, 575 and 577 respectively) and losses of two molecules of $H_2O$ (m/z 539, 557 and 559 respectively), with smaller peaks corresponding to losses of $CO_2$ (m/z 531, 549 and 551 respectively) and losses of $CO_2$ and $H_2O$ (m/z 513, 531 and 533) (Table 9; FIGS. 6 to 12).

TABLE 9

Fragmentation pattern of biomarkers "576", "594" and "596"
in negative APCI mode (with m/z 575, 593 and 595 respectively),
with daughter ion relative abundance.

| Parent mass 576.5 Predicted formula C36H64O5 m/z 575 | | Parent mass 594.5 Predicted formula C36H66O6 m/z 593 | | Parent mass 596.5 Predicted formula C36H68O6 m/z 595 | |
|---|---|---|---|---|---|
| Mass | Intensity | Mass | Intensity | Mass | Intensity |
| 495.4234 | 100 | 593.4734 | 100 | 279.2176 | 100 |
| 575.5086 | 100 | 575.4275 | 94 | 595.4591 | 86 |
| 513.4442 | 80 | 513.4442 | 65 | 315.2409 | 64 |
| 557.4564 | 80 | 371.3305 | 53 | 577.4549 | 55 |
| 539.4565 | 60 | 557.4476 | 53 | 515.4361 | 41 |
| 575.3825 | 60 | 315.2542 | 47 | 297.2472 | 36 |
| 97.0558 | 40 | 277.2144 | 41 | 559.452 | 36 |
| 403.3057 | 40 | 171.1025 | 35 | 595.6056 | 36 |
| 415.3021 | 40 | 201.101 | 35 | 281.228 | 27 |
| 459.3655 | 40 | 575.5266 | 35 | 313.2118 | 27 |
| 531.4755 | 40 | 279.2113 | 29 | 171.0829 | 23 |
| 71.0055 | 20 | 297.2407 | 24 | 576.4453 | 23 |
| 89.0176 | 20 | 513.5378 | 24 | 141.1259 | 18 |
| 101.0108 | 20 | 531.4495 | 24 | 577.5812 | 18 |
| 113.0104 | 20 | 557.5539 | 24 | 169.1396 | 14 |
| 119.0578 | 20 | 593.638 | 24 | 251.2339 | 14 |
| 123.0715 | 20 | 200.091 | 18 | 277.2081 | 14 |
| 125.0865 | 20 | 281.2217 | 18 | 373.3293 | 14 |
| 185.1142 | 20 | 313.2716 | 18 | 391.3588 | 14 |
| 197.1239 | 20 | 415.2715 | 18 | 594.507 | 14 |
| 205.193 | 20 | 433.3294 | 18 | 594.6352 | 14 |
| 251.2101 | 20 | 113.0862 | 12 | 125.0949 | 9 |
| 277.2081 | 20 | 139.1091 | 12 | 127.1136 | 9 |
| 279.2301 | 20 | 155.1033 | 12 | 153.1139 | 9 |
| 295.2963 | 20 | 195.1371 | 12 | 155.1126 | 9 |
| 297.2213 | 20 | 199.0942 | 12 | 207.214 | 9 |
| 371.2799 | 20 | 233.2058 | 12 | 239.2276 | 9 |
| 373.3873 | 20 | 251.2279 | 12 | 253.2247 | 9 |
| 387.3672 | 20 | 261.2057 | 12 | 261.2179 | 9 |
| 389.3049 | 20 | 263.2417 | 12 | 278.2338 | 9 |
| 417.3544 | 20 | 295.1996 | 12 | 295.2189 | 9 |
| 429.3153 | 20 | 311.1893 | 12 | 298.2186 | 9 |
| 431.3005 | 20 | 391.3737 | 12 | 372.3292 | 9 |
| 441.3348 | 20 | 403.3434 | 12 | 423.3793 | 9 |
| 445.3017 | 20 | 421.3739 | 12 | 497.4302 | 9 |
| 463.2347 | 20 | 495.4067 | 12 | 514.4141 | 9 |
| 529.4355 | 20 | 549.4484 | 12 | 515.5639 | 9 |
| 539.352 | 20 | 111.0599 | 6 | 516.4506 | 9 |
| 557.5893 | 20 | 125.0949 | 6 | 533.424 | 9 |
|  |  | 127.1051 | 6 | 558.4582 | 9 |
|  |  | 141.0992 | 6 | 559.6117 | 9 |
|  |  | 169.1103 | 6 | 595.6698 | 9 |
|  |  | 183.0976 | 6 | 115.0181 | 5 |
|  |  | 185.1039 | 6 | 143.099 | 5 |
|  |  | 221.1523 | 6 | 185.1091 | 5 |
|  |  | 283.2708 | 6 | 201.1223 | 5 |
|  |  | 289.2268 | 6 | 202.1455 | 5 |
|  |  | 309.3185 | 6 | 233.2287 | 5 |
|  |  | 331.3406 | 6 | 235.147 | 5 |
|  |  | 353.3364 | 6 | 239.0883 | 5 |
|  |  | 373.322 | 6 | 249.1502 | 5 |
|  |  | 389.3346 | 6 | 249.2509 | 5 |
|  |  | 401.2808 | 6 | 263.2417 | 5 |
|  |  | 417.3774 | 6 | 265.2183 | 5 |
|  |  | 446.3477 | 6 | 281.3413 | 5 |
|  |  | 451.3569 | 6 | 314.2888 | 5 |
|  |  | 453.4963 | 6 | 361.3032 | 5 |
|  |  | 514.4737 | 6 | 371.3305 | 5 |
|  |  | 549.5451 | 6 | 373.5324 | 5 |
|  |  | 559.0969 | 6 | 387.3451 | 5 |
|  |  | 564.3806 | 6 | 405.3583 | 5 |
|  |  | 568.1941 | 6 | 407.3632 | 5 |
|  |  | 576.3011 | 6 | 433.306 | 5 |
|  |  | 592.3951 | 6 | 438.3753 | 5 |
|  |  | 594.26 | 6 | 483.4343 | 5 |
|  |  | 594.4887 | 6 | 497.5474 | 5 |
|  |  |  |  | 531.4495 | 5 |
|  |  |  |  | 532.5142 | 5 |
|  |  |  |  | 533.554 | 5 |
|  |  |  |  | 533.6667 | 5 |

TABLE 9-continued

Fragmentation pattern of biomarkers "576", "594" and "596" in negative APCI mode (with m/z 575, 593 and 595 respectively), with daughter ion relative abundance.

| Parent mass 576.5 Predicted formula C36H64O5 m/z575 | | Parent mass 594.5 Predicted formula C36H66O6 m/z593 | | Parent mass 596.5 Predicted formula C36H68O6 m/z595 | |
|---|---|---|---|---|---|
| Mass | Intensity | Mass | Intensity | Mass | Intensity |
| | | | | 540.2675 | 5 |
| | | | | 541.4458 | 5 |
| | | | | 549.6155 | 5 |
| | | | | 551.5353 | 5 |
| | | | | 558.3518 | 5 |
| | | | | 560.3933 | 5 |
| | | | | 561.2821 | 5 |
| | | | | 577.7255 | 5 |
| | | | | 594.9372 | 5 |

Figure 13:
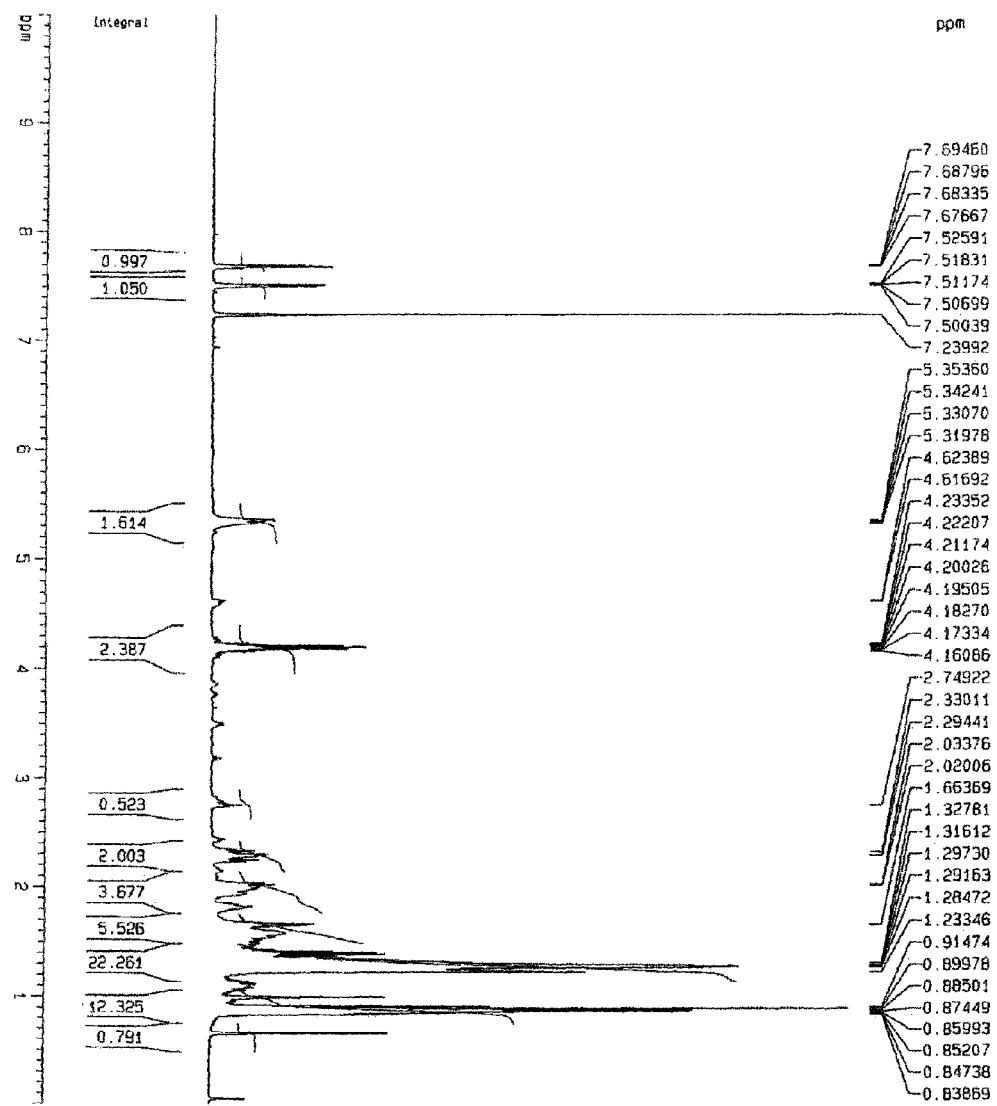
FIG. 13 shows the NMR spectrum of the fraction rich in C36 markers "594" and "596".

Among FTICR biomarkers in Table 5, the presence of other compounds in 1202 mode with a mass differing from the masses above only by two or four suggested that a whole family may be altered in pancreatic cancer. We therefore performed the same analysis as above for 574.5, 578.5, 592.5 and 558.4, respectively predicted to have a formula of $C_{36}H_{62}O_5$, $C_{36}H_{62}O_5$, $C_{36}H_{64}O_6$ and $C_{36}H_{62}O_4$ (Table 10; FIGS. 9 to 12).

gradient elution; acetonitrile—water 25:75 to 100% acetonitrile resulted in a fraction found to be very rich in two pancreatic cancer C36 markers (m/z 594 and 596) when analyzed by LC/MS and MS/MS. The proton nuclear magnetic resonance ($^1$H NMR) spectrum (FIG. 13) of this fraction showed resonances characteristic of compounds with condensed ring systems thought to be pregnane ring.

TABLE 10

Fragmentation pattern of biomarkers "558", "574", "578" and "592" in negative APCI mode, with daughter ion relative abundance.

| Parent mass 592.5 Predicted formula C36H64O6 m/z591 | | Parent mass 558.5 Predicted formula C36H62O4 m/z 557 | | Parent mass 574.5 Predicted formula C36H62O5 m/z573 | | Parent mass 578.5 Predicted formula C36H66O5 m/z577 | |
|---|---|---|---|---|---|---|---|
| Mass | Intensity | Mass | Intensity | Mass | Intensity | Mass | Intensity |
| 591.3998 | 100 | 495.4401 | 100 | 573.3857 | 100 | 515.402 | 100 |
| 171.0927 | 75 | 539.3868 | 40 | 125.0991 | 80 | 497.4302 | 67 |
| 201.0903 | 75 | 557.4298 | 40 | 511.3968 | 80 | 533.4673 | 67 |
| 511.3543 | 75 | 111.0836 | 30 | 555.3937 | 80 | 541.4196 | 67 |
| 573.4127 | 75 | 539.5089 | 30 | 171.1025 | 40 | 559.4431 | 67 |
| 125.0907 | 50 | 279.2176 | 20 | 223.1101 | 40 | 577.464 | 67 |
| 223.1661 | 50 | 97.0632 | 10 | 277.1956 | 40 | 251.1982 | 33 |
| 255.2113 | 50 | 205.1823 | 10 | 279.2301 | 40 | 283.2393 | 33 |
| 279.1987 | 50 | 221.1467 | 10 | 457.3247 | 40 | 297.1955 | 33 |
| 295.206 | 50 | 373.3365 | 10 | 493.3789 | 40 | 405.4037 | 33 |
| 403.3358 | 50 | 494.5049 | 10 | 511.5665 | 40 | 515.5469 | 33 |
| 497.4637 | 50 | 495.5737 | 10 | 529.3751 | 40 | 576.4904 | 33 |
| 515.4105 | 50 | 513.4187 | 10 | 537.3752 | 40 | | |
| 529.4701 | 50 | | | 555.5264 | 40 | | |
| 555.4025 | 50 | | | 113.0782 | 20 | | |
| 559.4253 | 50 | | | 205.1823 | 20 | | |
| 573.5834 | 50 | | | 295.2447 | 20 | | |
| 591.6189 | 50 | | | 385.3239 | 20 | | |
| 111.0639 | 25 | | | 389.3346 | 20 | | |
| 113.0263 | 25 | | | 401.3484 | 20 | | |
| 127.0882 | 25 | | | 415.3709 | 20 | | |
| 203.1713 | 25 | | | 429.3309 | 20 | | |
| 275.1623 | 25 | | | 443.3555 | 20 | | |
| 277.2144 | 25 | | | 519.3887 | 20 | | |
| 297.2213 | 25 | | | 574.2218 | 20 | | |
| 313.245 | 25 | | | | | | |

Several classes of metabolites, including various forms of steroids (or bile acids), fatty acids and fat soluble vitamins theoretically fit these elemental compositions.

Preliminary Isolation of C36 Markers and NMR Analysis

Ethyl acetate extracts of commercial serum subjected to reverse phase flash column chromatography with a step These two markers are thought to have a steroidal backbone and may probably belong to a class of compounds known as bile acids.

2B. Putative Choline-Related Compounds

In table 6, 16 compounds showed putative formulas belonging to three choline-related families, namely lysophosphatidylcholines (LysoPC) for 519.3, 523.3, and 541.3, phosphatidylcholines (PtdCho) for 757.6, 779.5, 783.6, 785.6, 803.5, 805.6, 807.6, 809.6, 829.6 and 833.6, and sphingomyelins for 702.6, 724.5 and 812.7.

Figure 14:
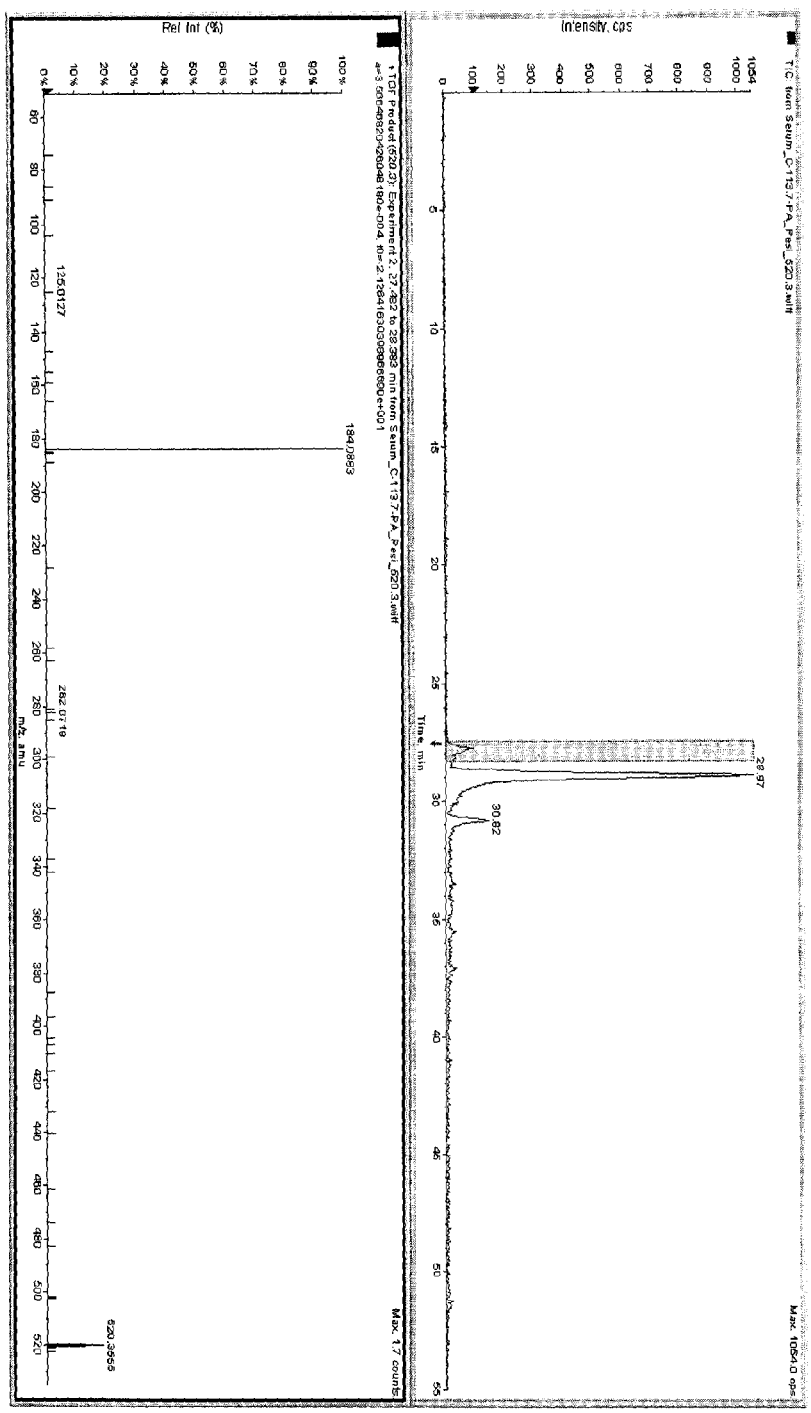
FIG. 14 illustrates the fragmentation patterns of 519.3 in positive aqueous ESI mode. (a) and (b) correspond to the fragmentation patterns at different retention times.
Figure 14:
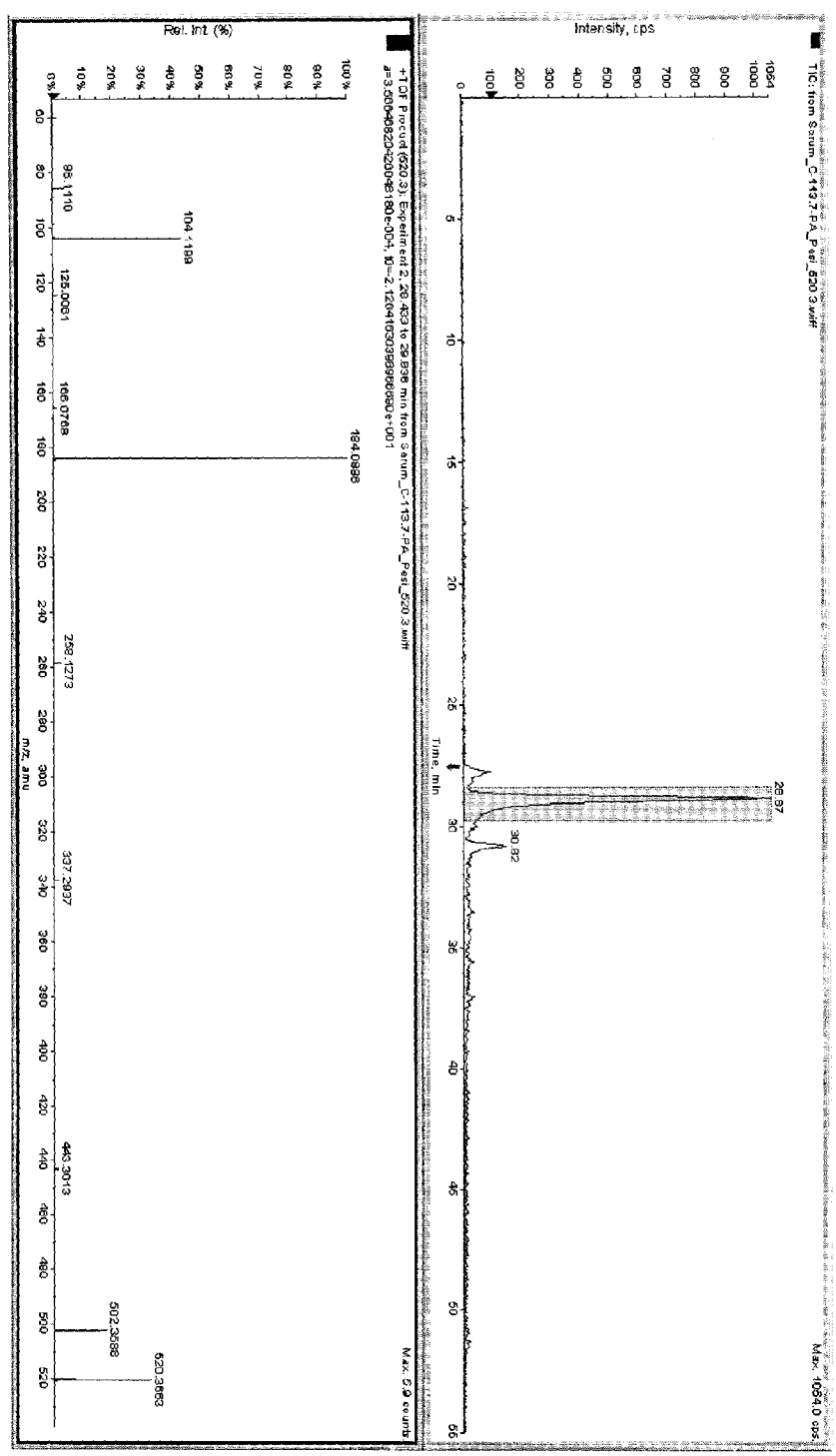
Figure 15:
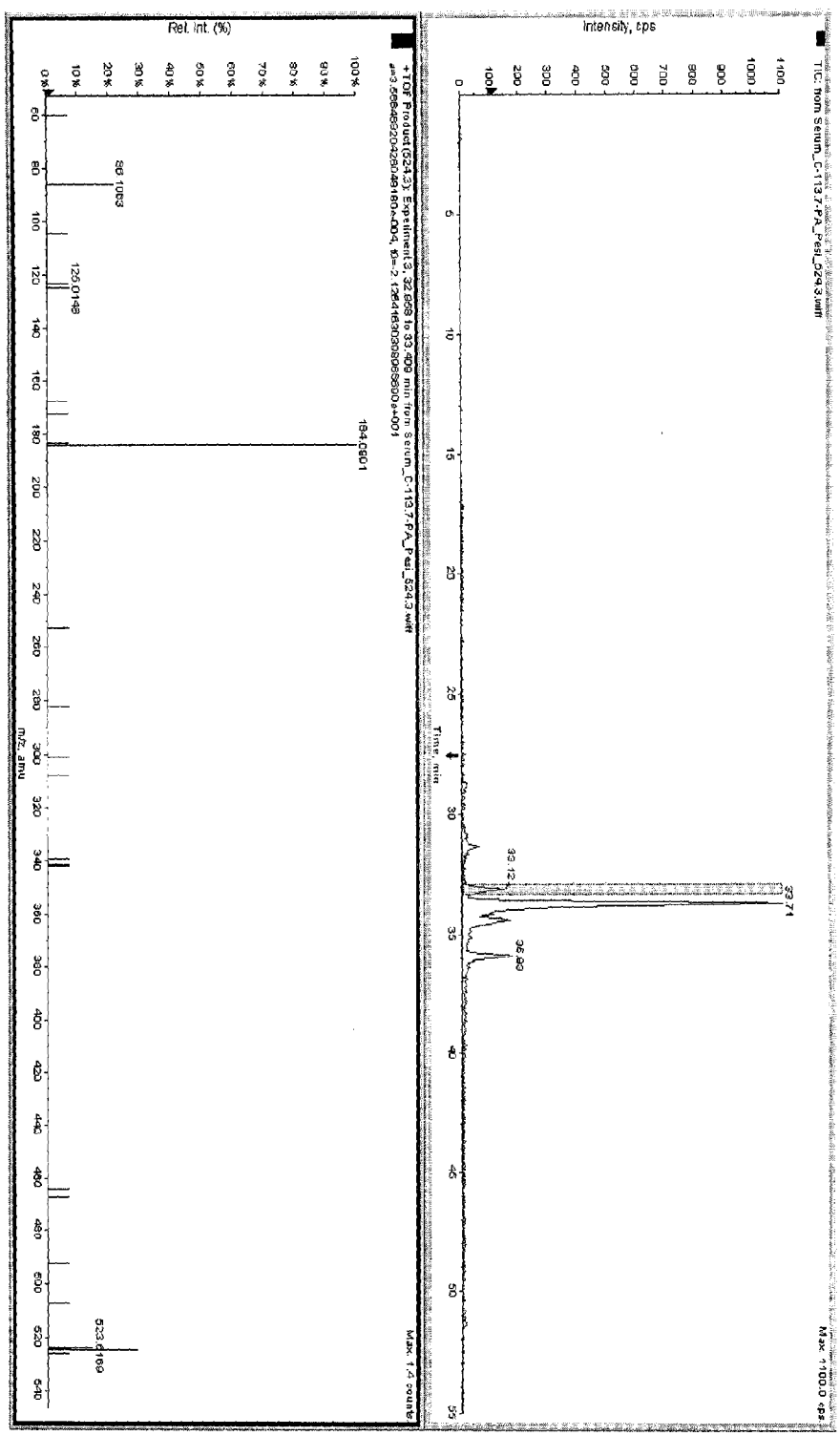
FIG. 15 illustrates the fragmentation patterns of 523.3 in positive aqueous ESI mode. (a) and (b) correspond to the fragmentation patterns at different retention times.
Figure 15:
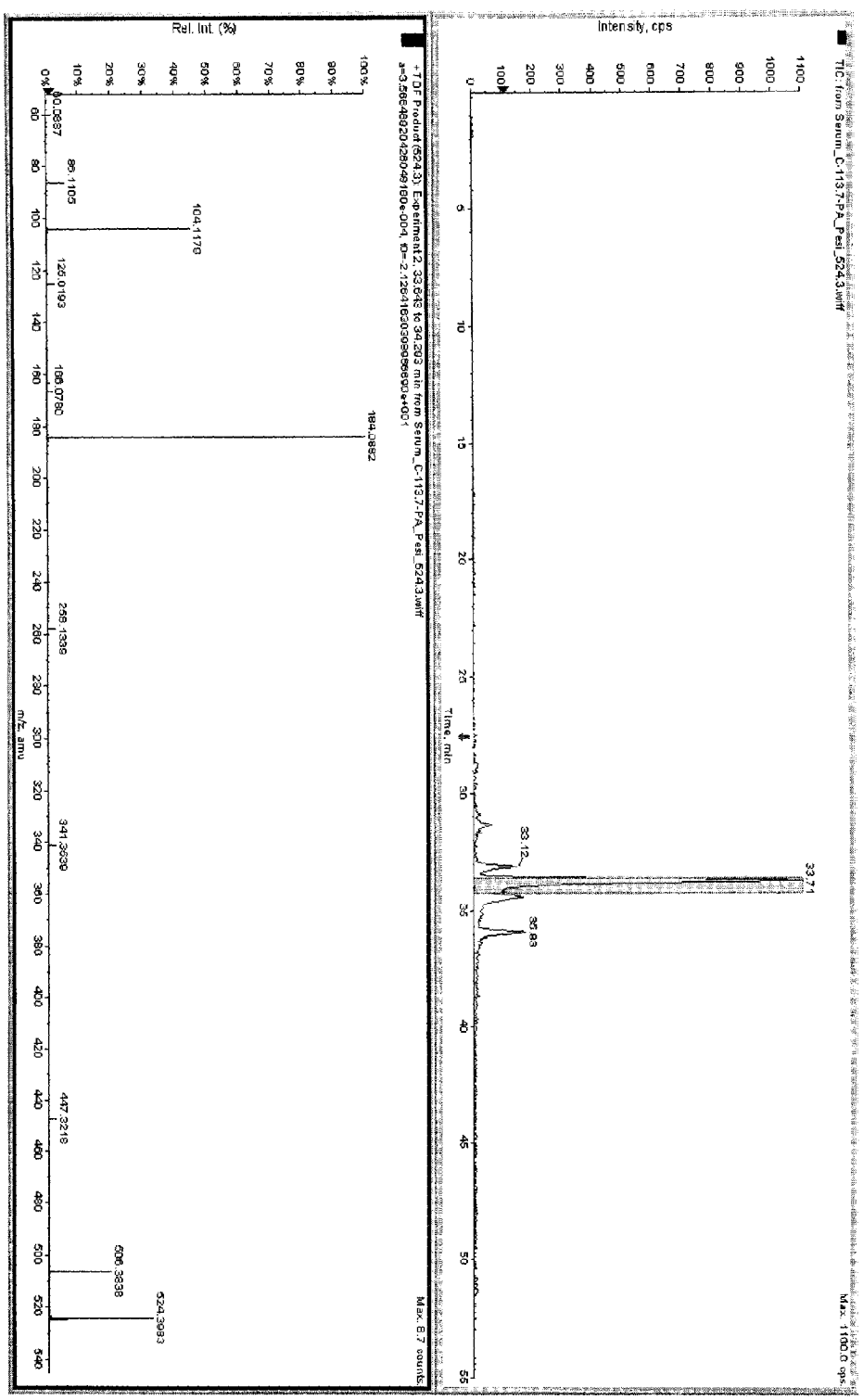
Figure 16:
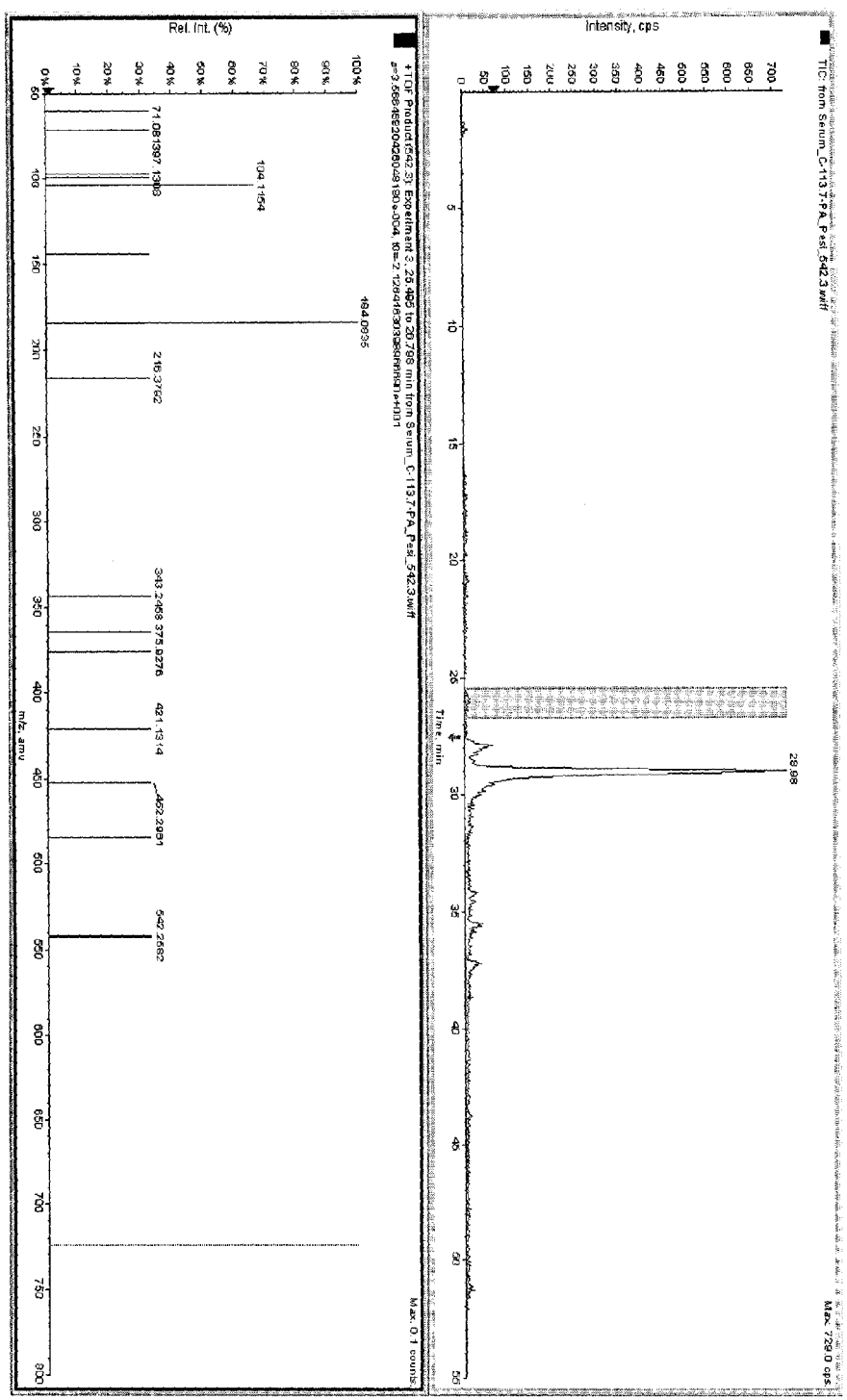
FIG. 16 illustrates the fragmentation patterns of 541.3 in positive aqueous ESI mode. (a), (b), (c) and (d) correspond to fragmentation patterns at different retention times.
Figure 16:
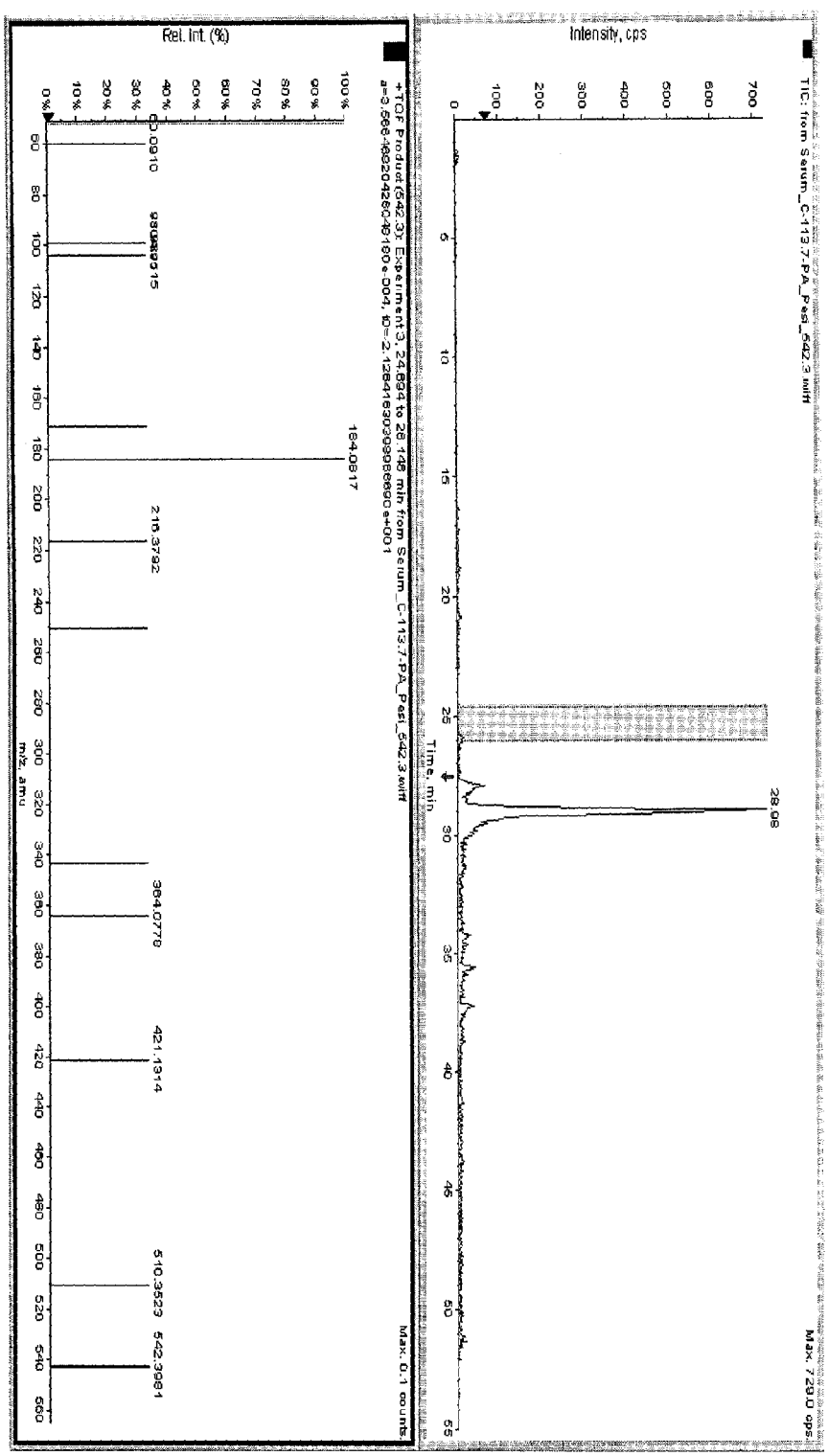
Figure 16:
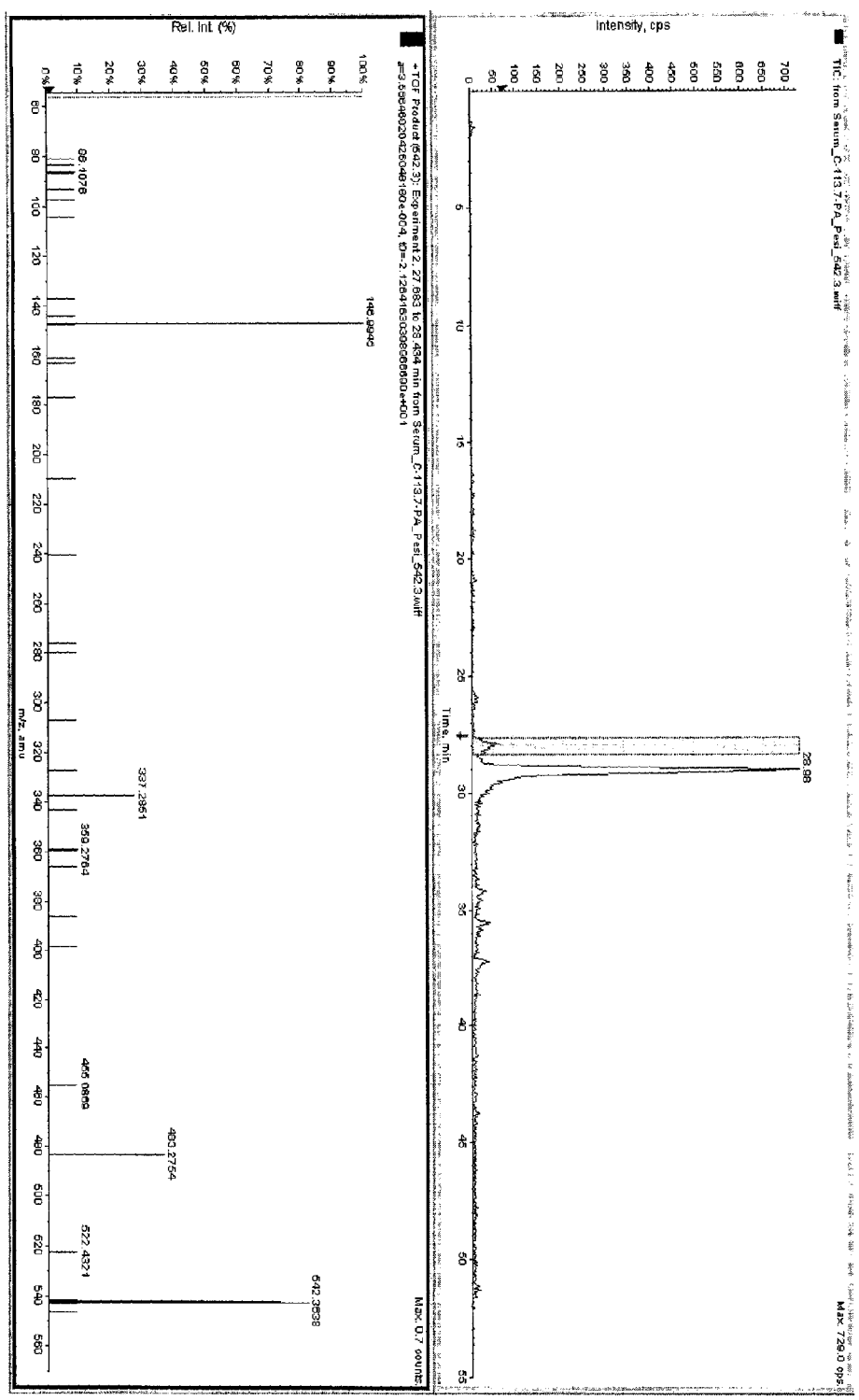
Figure 16:
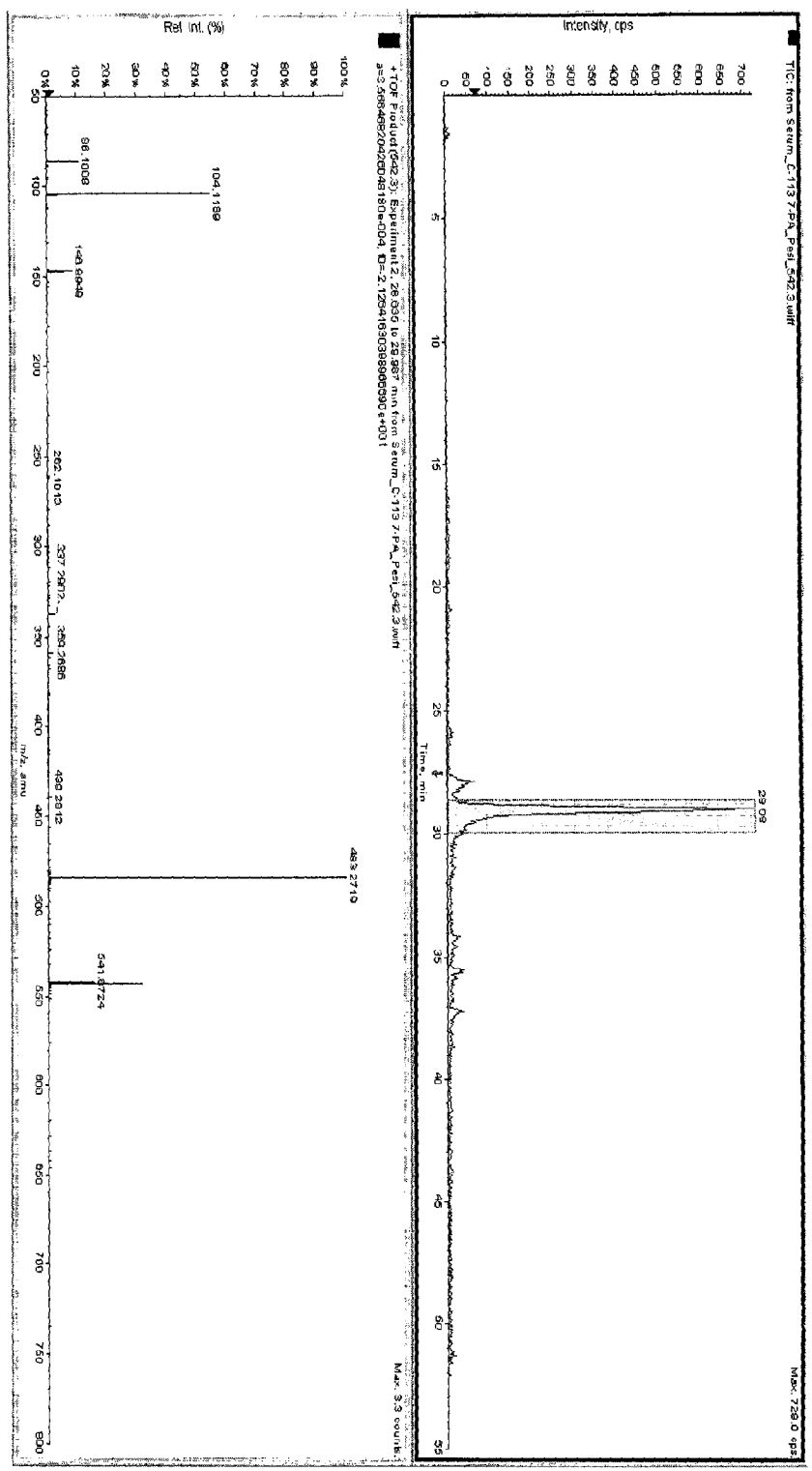
Figure 17:
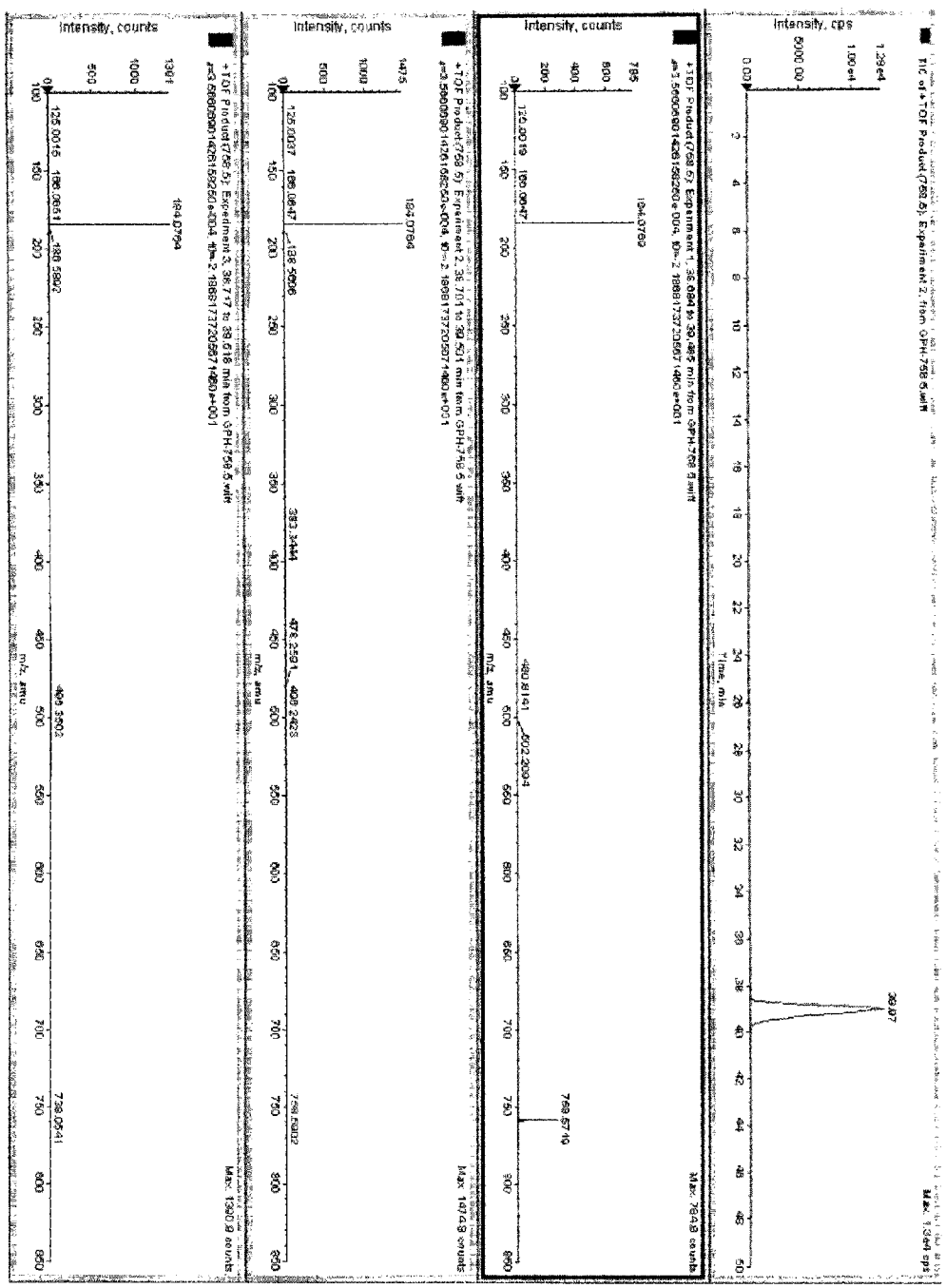
FIG. 17 illustrates the fragmentation pattern of 757.6 in positive aqueous ESI mode.
Figure 18:
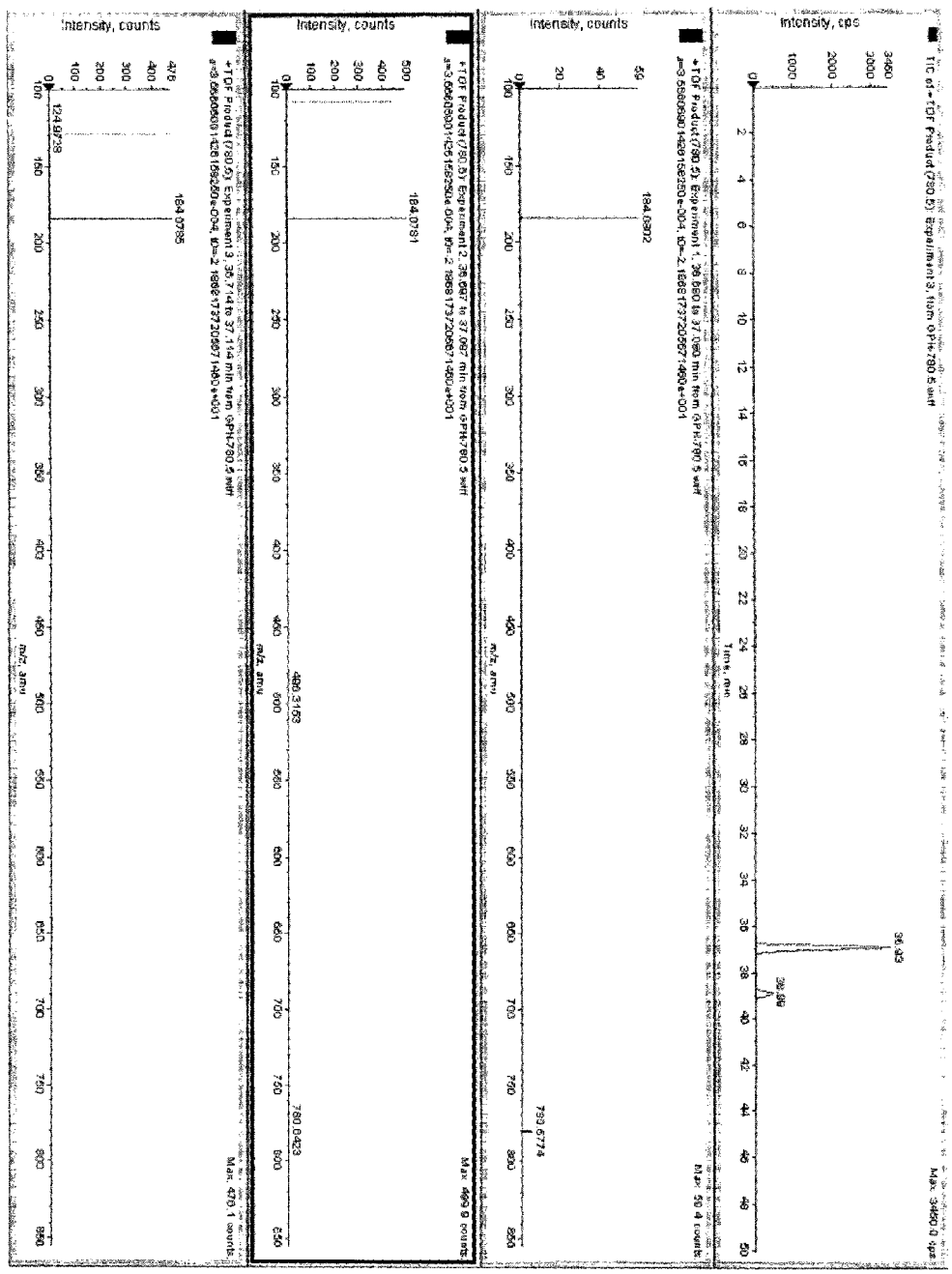
FIG. 18 illustrates the fragmentation pattern of 779.5 in positive aqueous ESI mode.
Figure 19:
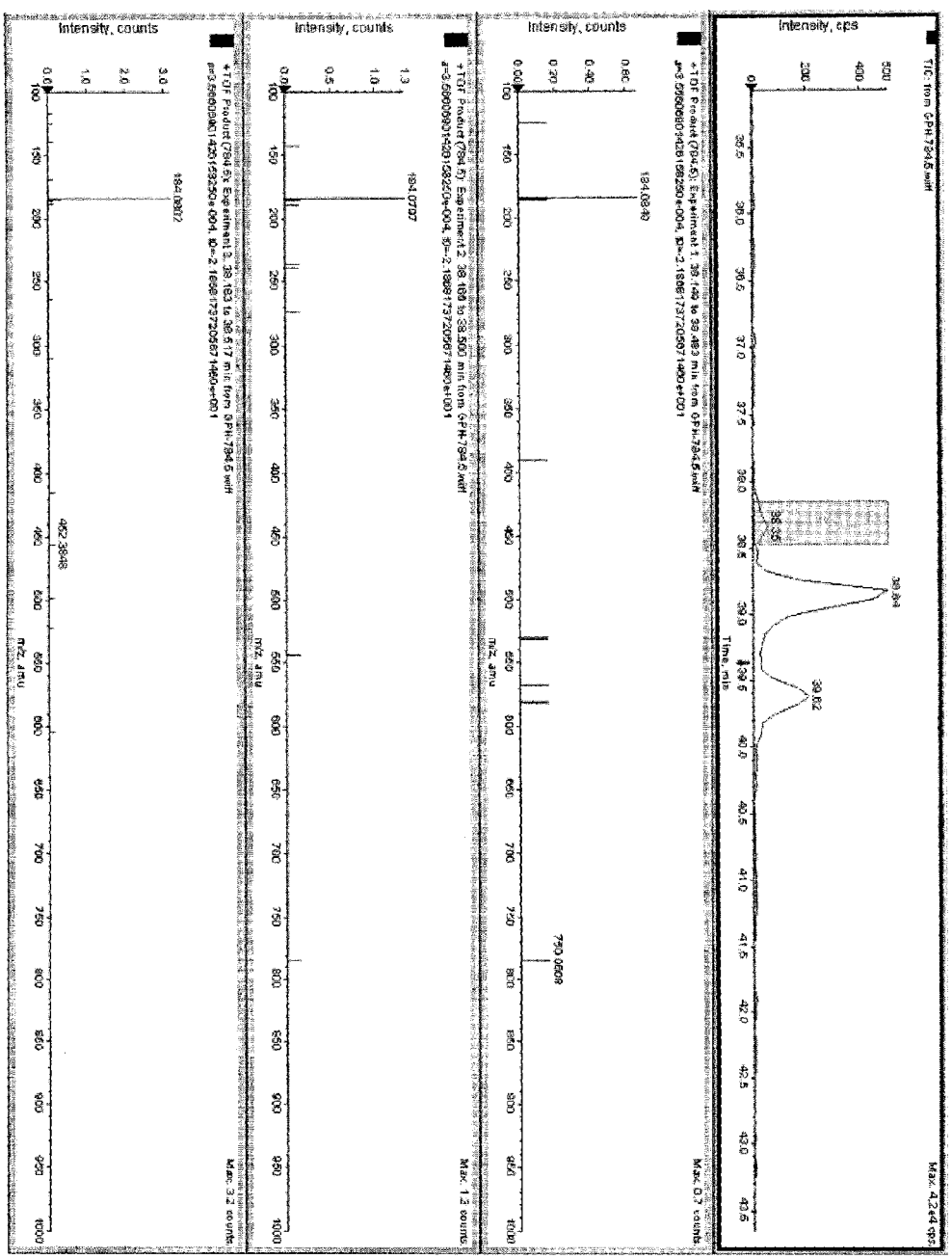
FIG. 19 illustrates the fragmentation pattern of 783.6 in positive aqueous ESI mode, showing three retention times with choline fragments (a), (b), (c).
Figure 19:
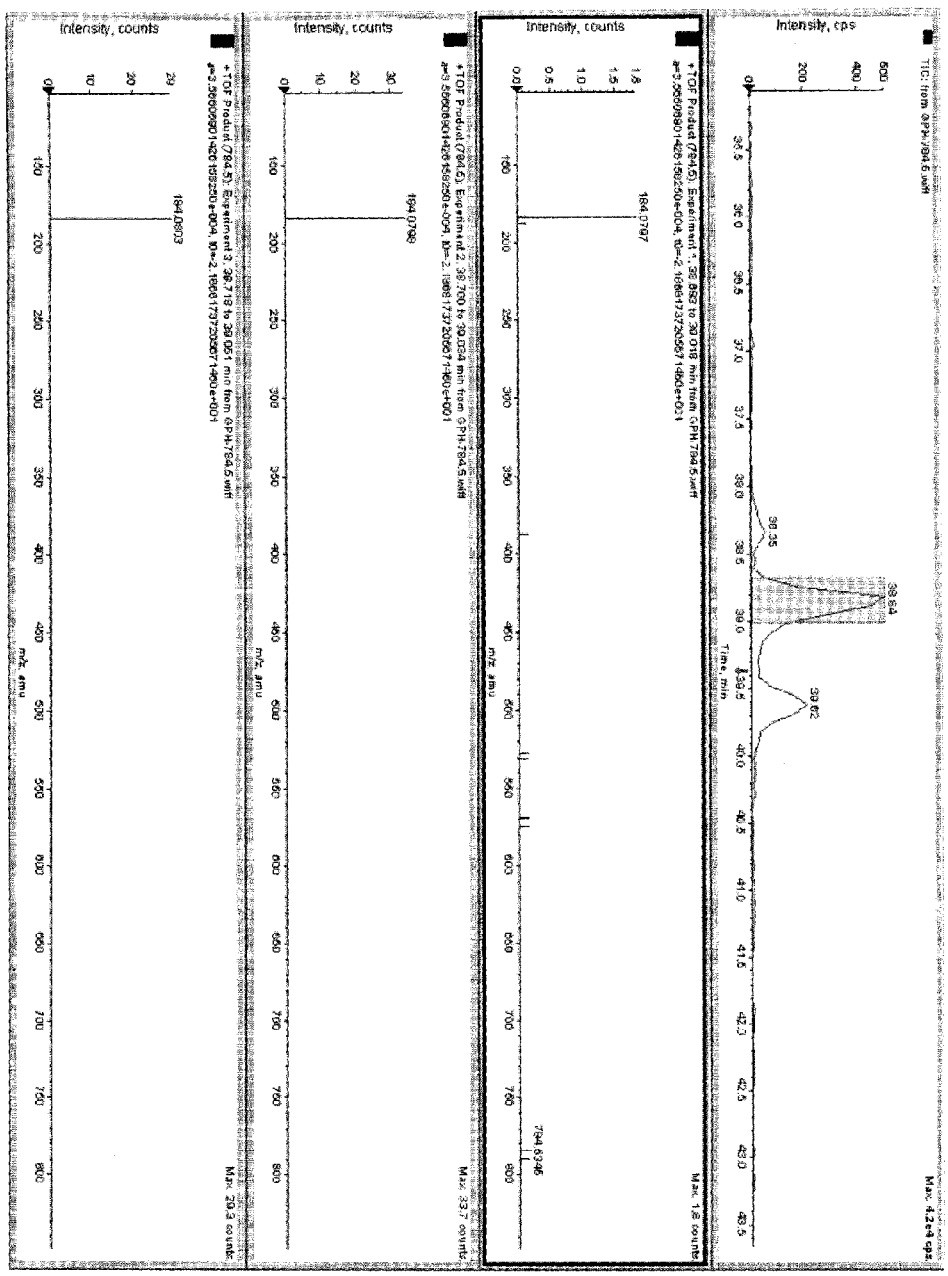
Figure 19:
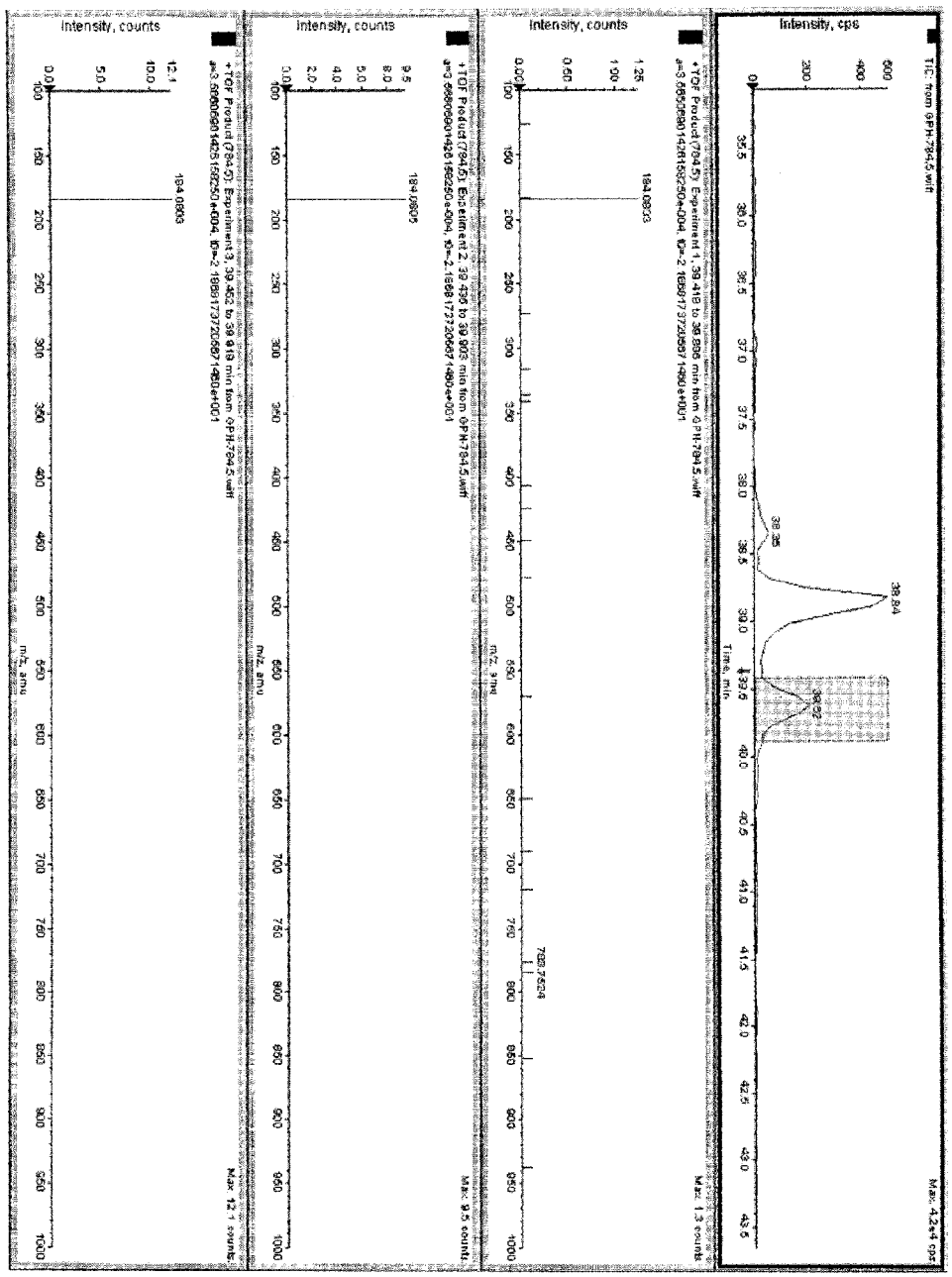
Figure 20:
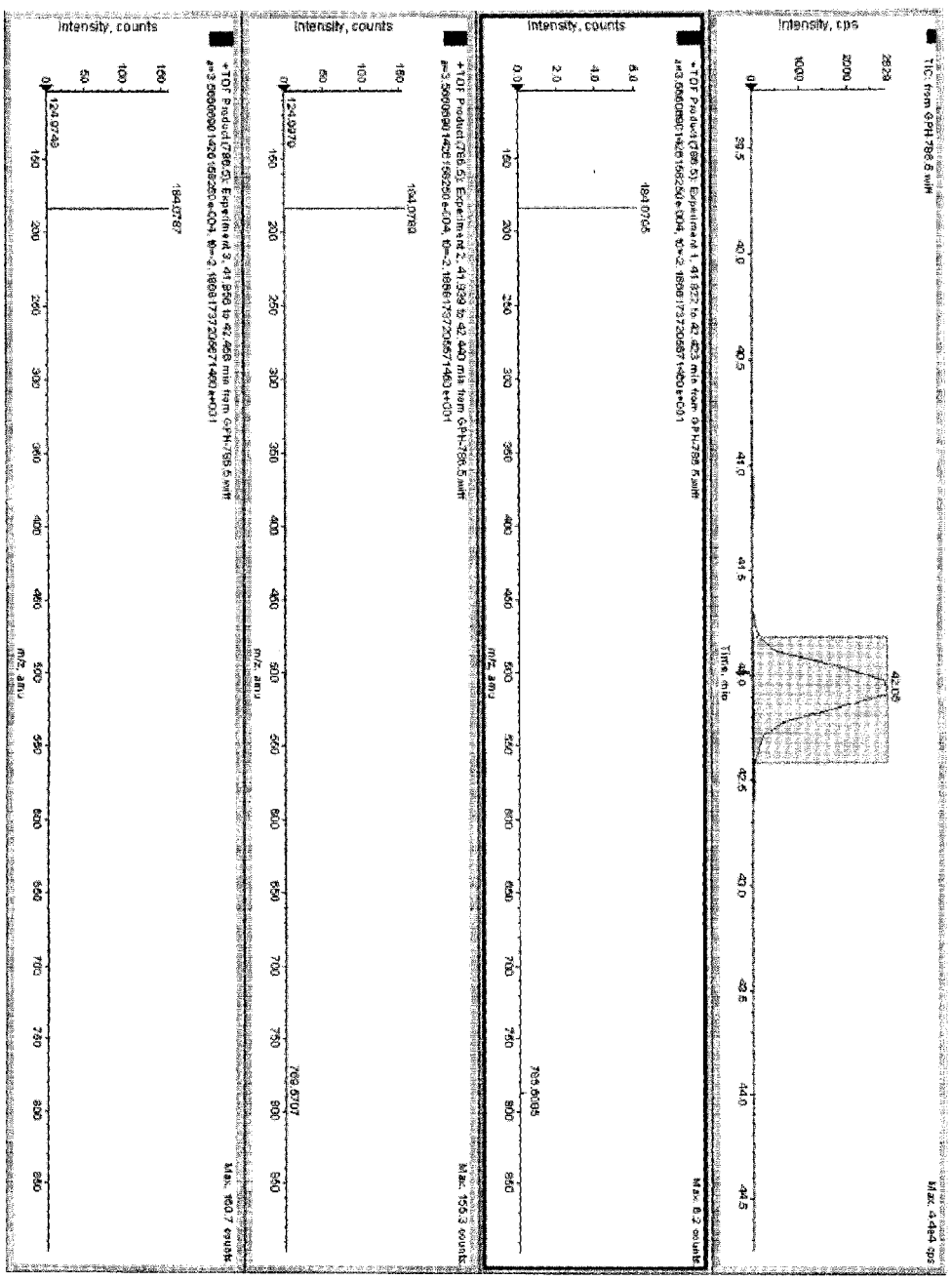
FIG. 20 illustrates the fragmentation pattern of 785.6 in positive aqueous ESI mode.

Selected aqueous extracts of serum from the control cohort used in the FTICR-MS work were re-analyzed using HPLC coupled to a quadrupole time-of-flight (Q-TOF) mass spectrometer in ESI positive ion mode (1101 mode). Multiple fragmentation patterns were observed for the three putative lysophosphatidylcholines (FIGS. 14 to 16).

TABLE 11

Fragmentation pattern of putative lysophosphatidylcholines in positive ESI mode, with daughter ion relative abundance.

| Accurate/ Exact Mass | MS/MS Parent ion (% intensity) | Daughter ions (% intensity) | Collision Energy |
|---|---|---|---|
| 519.3295 | 520 (6%) | 283 (8%), 209 (3%), 184 (100%), 177 (3%), 175 (8%), 130 (11%), 125 (8%), 109 (6%), 104 (14%), 86 (11%) | 40 V |
| 523.3661 | 524 (20%) | 506 (11%), 185 (3%), 184 (100%), 401 (62%), 86 (2%) | 30 V |
| 541.3134 | 542 (14%) Na adduct | 483 (88%), 439 (6%), 359 (8%), 337 (22%), 177 (6%), 147 (72%), 421 (6%), 104 (100%), 86 (28%) | 40 V |

The compound with a mass of 519.3 is confirmed to be a lysophosphatidylcholine with a fatty acid moiety of C18:2, and the two different retention times correspond to two different subspecies: the lower time shows the fragmentation pattern of the 1-linoleoyl-sn-glycero-3-phosphocholine (FIG. 14a) whereas the higher shows the fragmentation pattern of the 2-linoleoyl-sn-glycero-3-phosphocholine (FIG. 14b).

The compound with a mass of 523.3 is confirmed to be a lysophosphatidylcholine with a fatty acid moiety of C18:0, and different retention times correspond to two different subspecies: the lower time shows the fragmentation pattern of the 2-stearoyl-sn-glycero-3-phosphocholine (FIG. 15a) whereas the higher shows the fragmentation pattern of the 1-stearoyl-sn-glycero-3-phosphocholine (FIG. 15b).

The compounds with a mass of 541.3 seem to be a mixture of the lysophosphatidylcholines with a fatty acid moiety of C20:5 and of the sodium adduct of the compounds with a mass of 519.3 above mentioned (FIG. 16). The lowest retention time shows indeed two fragmentation patterns corresponding to 1-eicosapentaenoyl-sn-glycero-3-phosphocholine (FIG. 16a) and 2-eicosapentaenoyl-sn-glycero-3-phosphocholine (FIG. 16b). The two higher retention times observed reflect the two retention times observed for 519.3, with the lower corresponding to the fragmentation pattern of the sodium adduct of the 1-linoleoyl-sn-glycero-3-phosphocholine (FIG. 16c), and the higher corresponding to the fragmentation pattern of the sodium adduct of the 2-linoleoyl-sn-glycero-3-phosphocholine (FIG. 16d).

In order to further validate the chemical family of these putative lysophosphatidylcholines, the same samples were run in aqueous negative ESI mode (Table 12).

TABLE 12

Fragmentation pattern of putative lysophosphatidylcholines in negative ESI mode, with daughter ion relative abundance.

| Accurate/ Exact Mass | MS/MS Formic acid adduct (% intensity) | Daughter ions (% intensity) | Collision Energy |
|---|---|---|---|
| 519.3295 | 564.3 (1%) | 504 (5%), 279 (100%), 242 (2%), 224 (6%) | −35 V |
| 523.3661 | 568.3 (1%) | 508 (14%), 283 (100%), 242 (2%), 224 (6%) | −35 V |

Selected aqueous extracts of serum from the control cohort used in the FTICR-MS work were re-analyzed using HPLC coupled to a Q-TOF mass spectrometer in ESI positive ion mode (1101 mode) for the putative PtdCho (Table 13).

TABLE 13

Fragmentation pattern of putative phosphatidylcholines in positive ESI mode, with daughter ion relative abundance.

| Accurate/ Exact Mass | MS/MS Parent ion (% intensity) | Daughter ions (% intensity) | Collision Energy |
|---|---|---|---|
| 757.5560 | 758 (47%) | 184 (100%) | 30 V |
| 779.5405 | 780 (68%) | 721 (7%), 712 (4%), 597 (4%), 184 (100%) | 30 V |
| 783.5690 | 784 (55%) | 184 (100%) | 30 V |
| 785.5913 | 786 (66%) | 184 (100%) | 30 V |
| 803.5373 | 804 26% (Na adduct) | 745 (49%), 621 (100%), 599 (6%), 313 (4%), 147 (17%) | 40 V |
| 805.5549 | 806 (95%) | 747 (10%), 623 (6%), 184 (100%) | 30 V |
| 807.5734 | 808 (80%) | 749 (5%), 624 (5%), 184 (100%) | 30 V |
| 809.5796 | 810 (100%) | 751 (8%), 627 (6%), 184 (89%) | 30 V |
| 829.5516 | 830 (47%) (Na adduct) | 771 (53%), 647 (100%), 625 (10%), 147 (22%), 86 (7%) | 40 V |
| 833.5864 | 834 (96%) | 775 (6%), 651 (3%), 415, (2%), 184 (100%) | 30 V |

Figure 21:
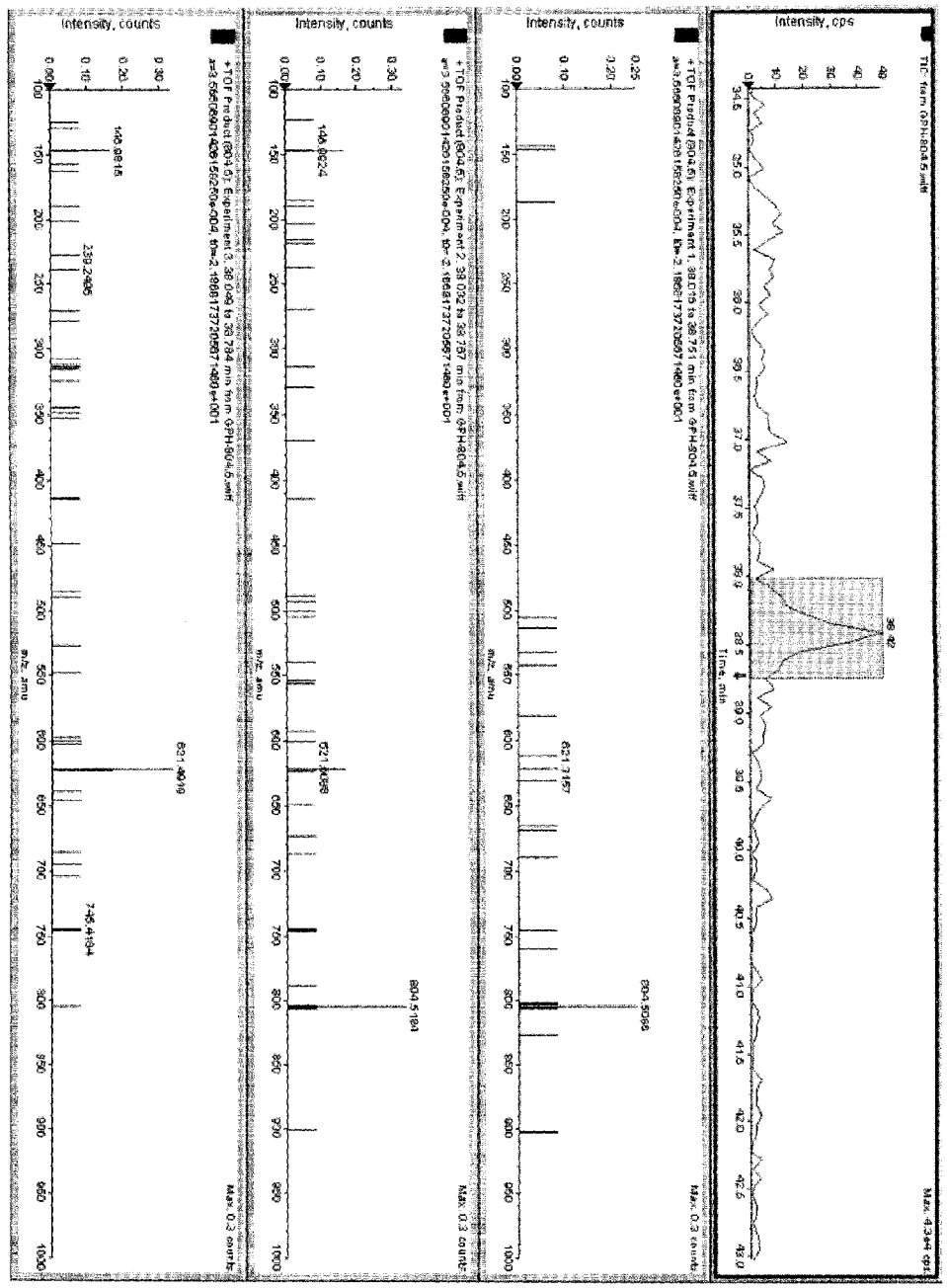
FIG. 21 illustrates the fragmentation pattern of 803.5 in positive aqueous ESI mode.
Figure 22:
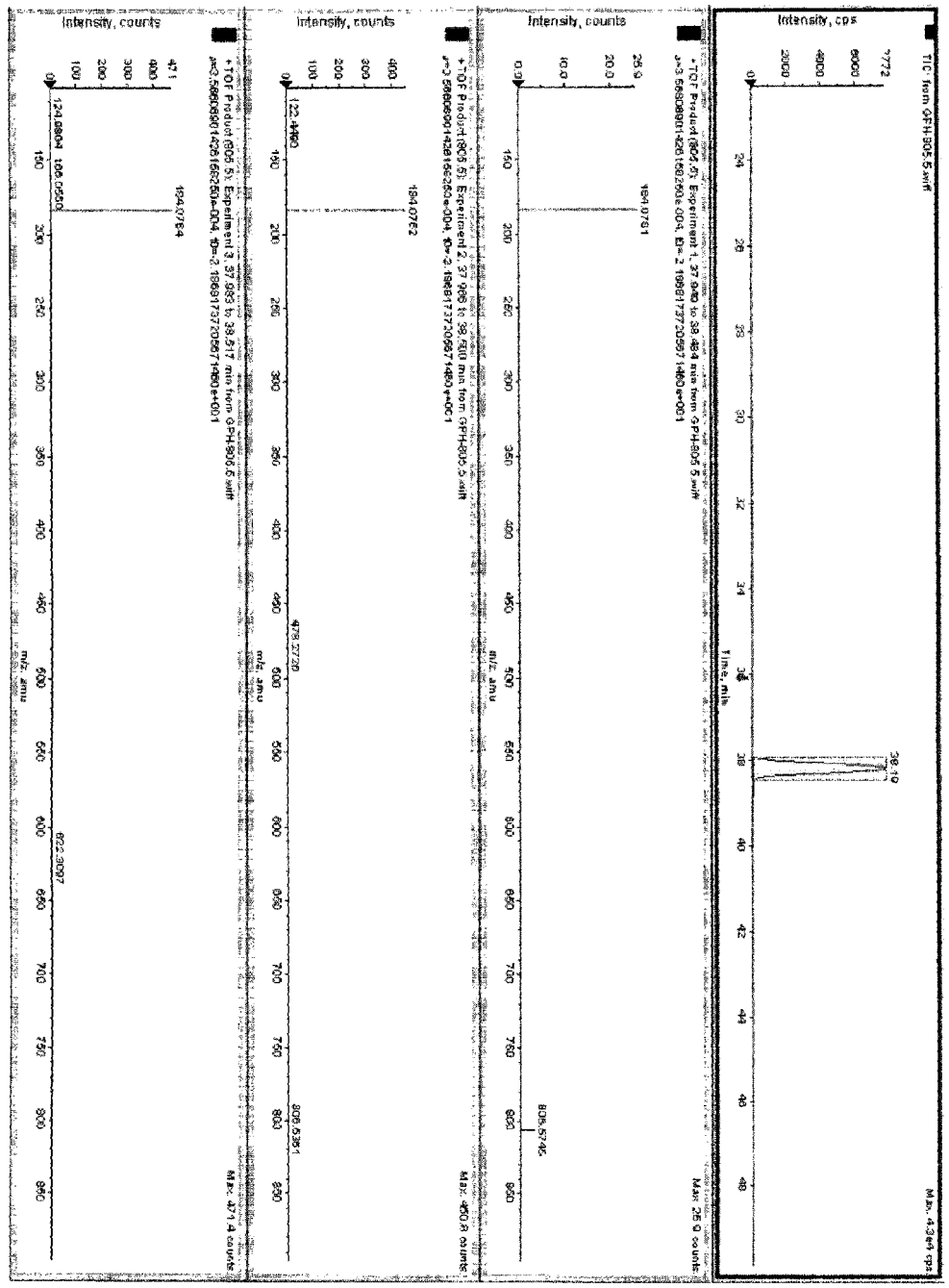
FIG. 22 illustrates the fragmentation pattern of 805.6 in positive aqueous ESI mode.
Figure 23:
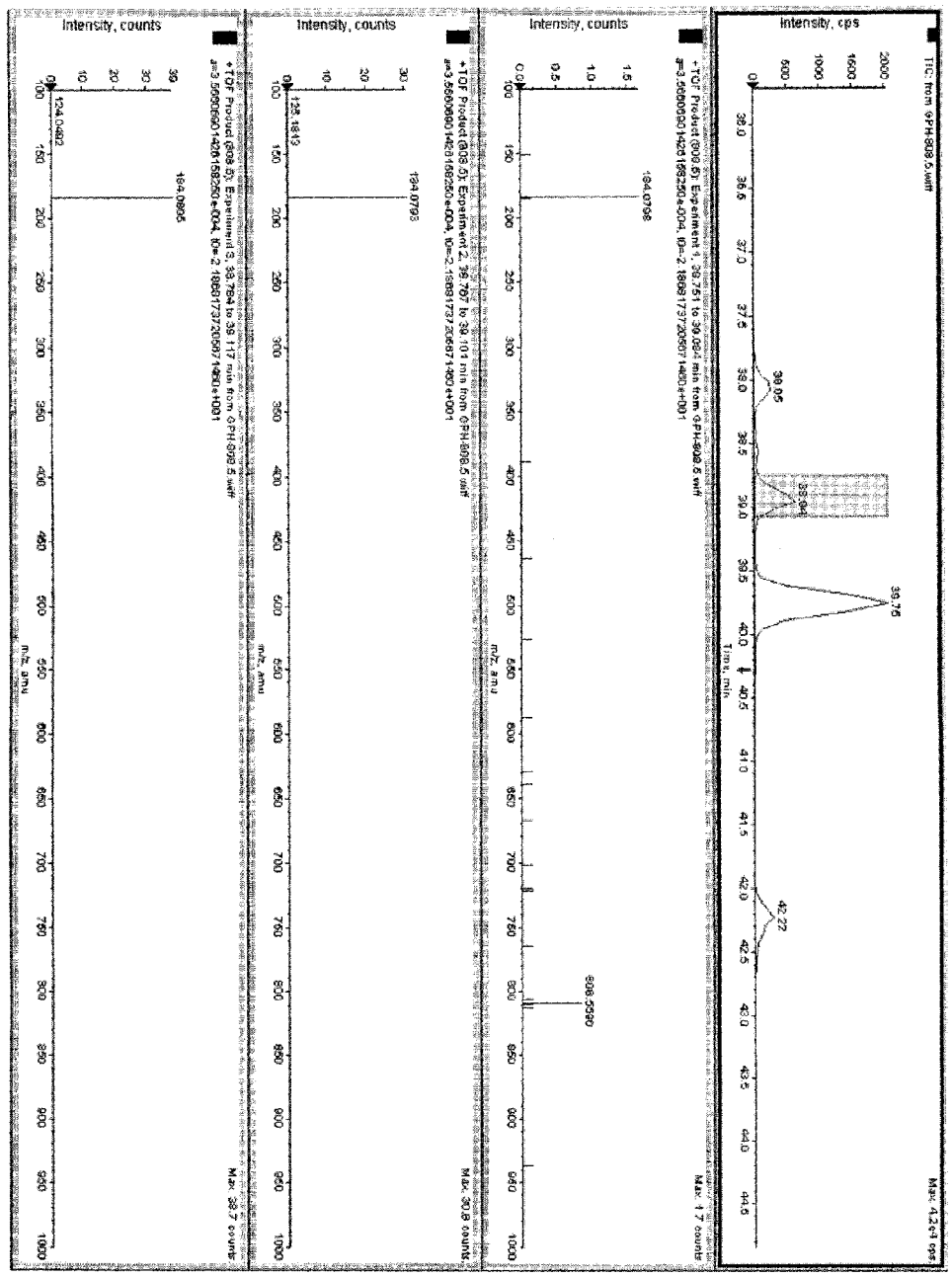
FIG. 23 illustrates the fragmentation pattern of 807.6 in positive aqueous ESI mode showing two retention times with choline fragments (a), (b).
Figure 23:
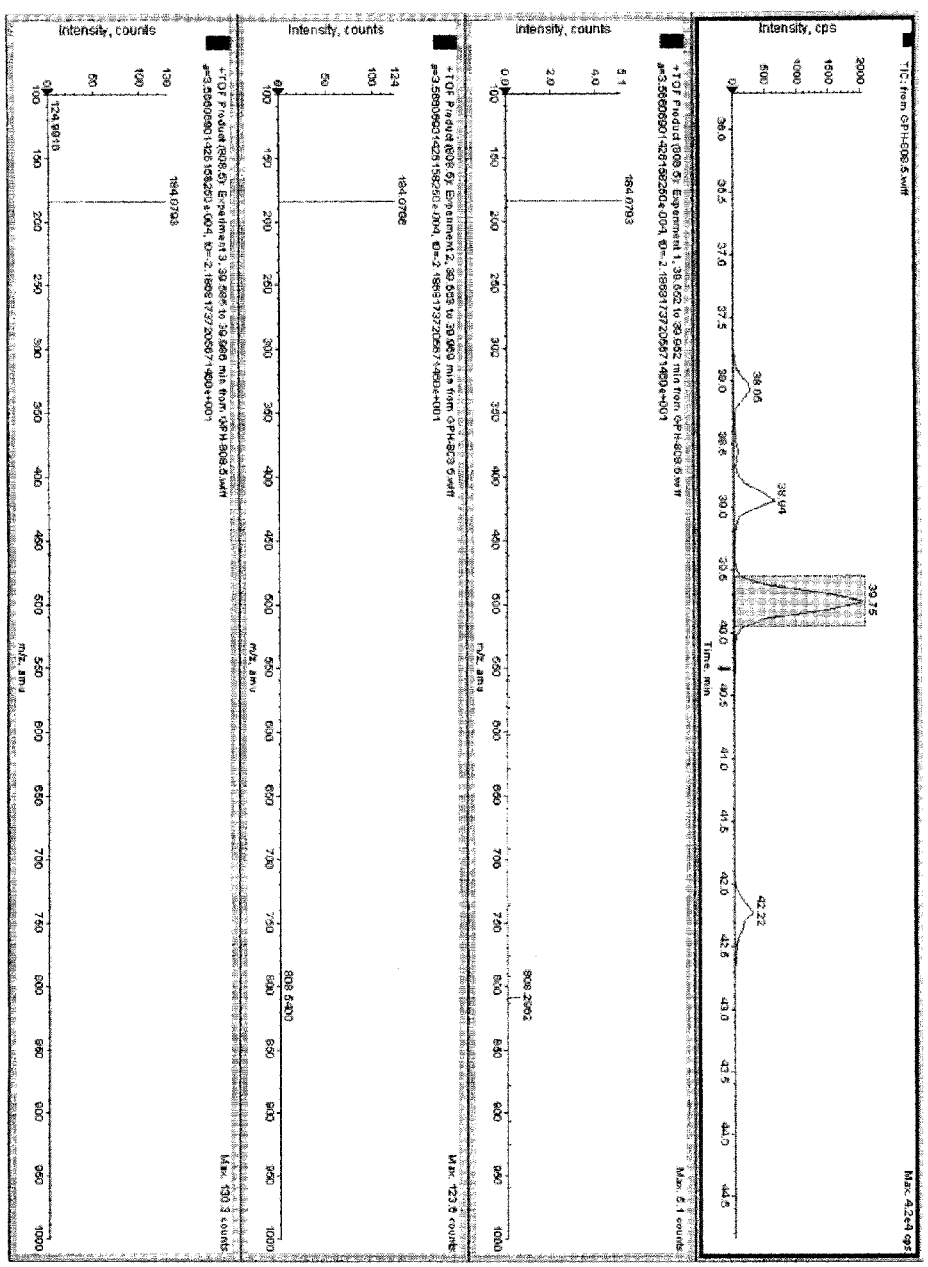
Figure 24:
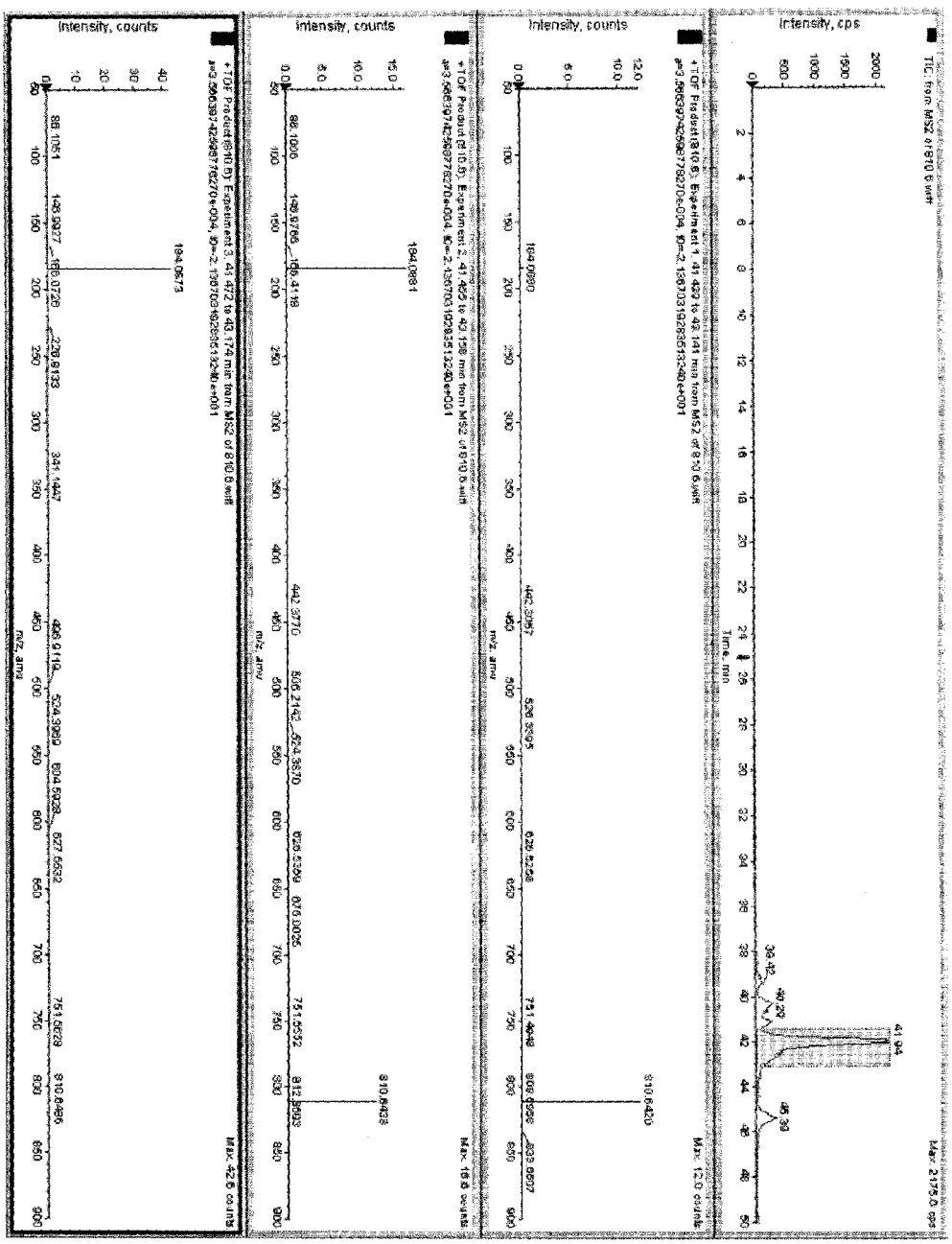
FIG. 24 illustrates the fragmentation pattern of 809.6 in positive aqueous ESI mode.
Figure 25:
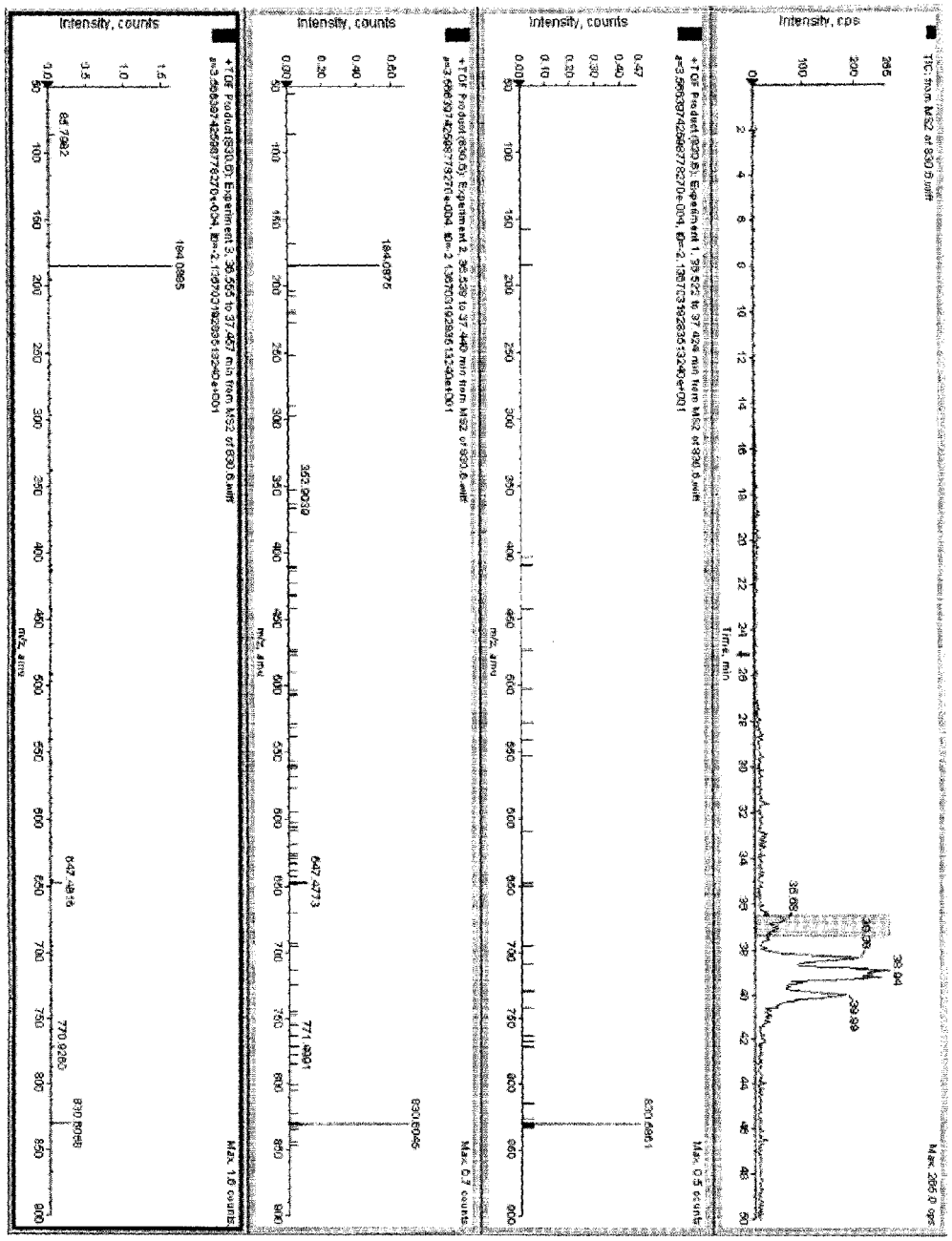
FIG. 25 illustrates the fragmentation pattern of 829.6 in positive aqueous ESI mode.
Figure 26:
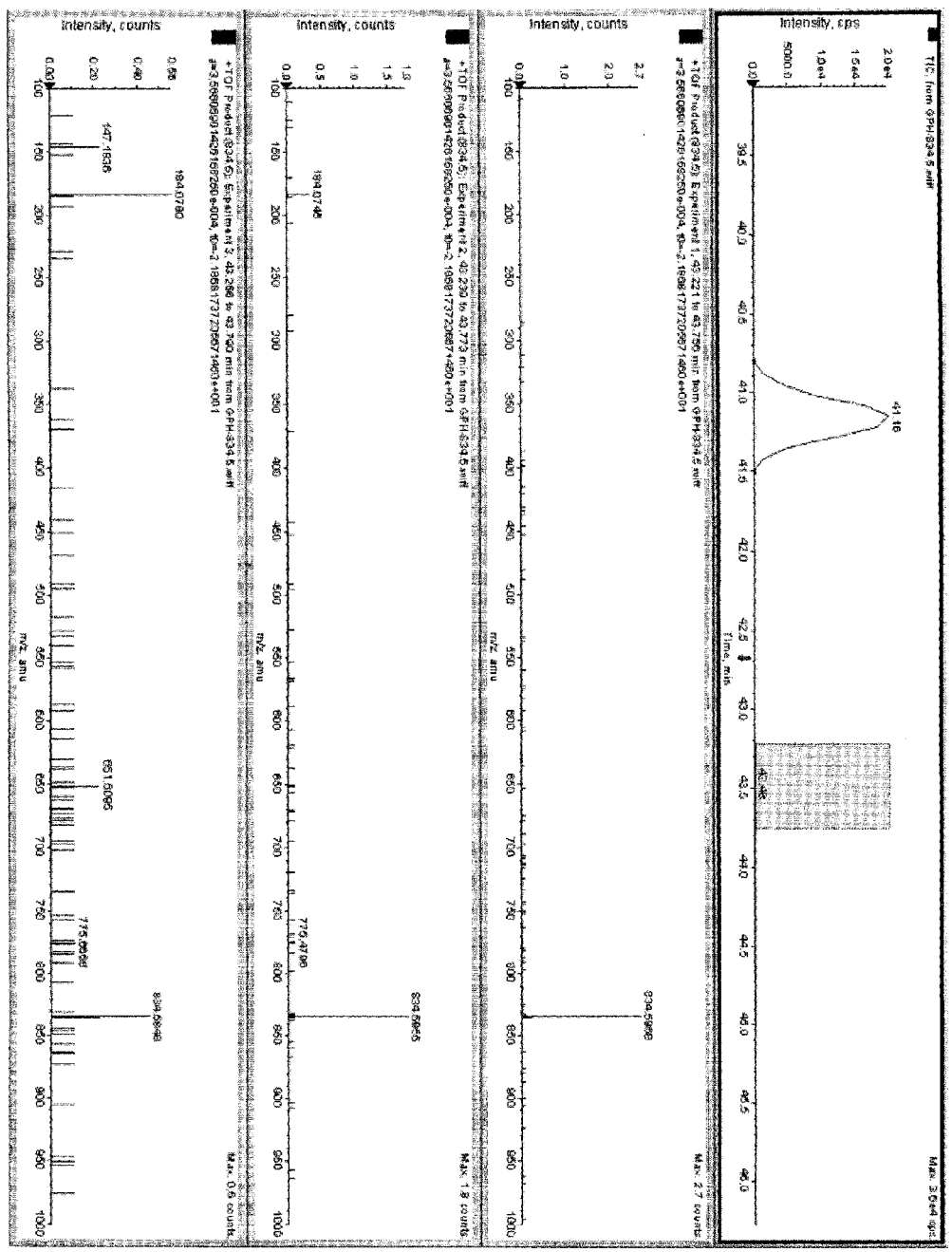
FIG. 26 illustrates the fragmentation pattern of 833.6 in positive aqueous ESI mode.
Figure 27:
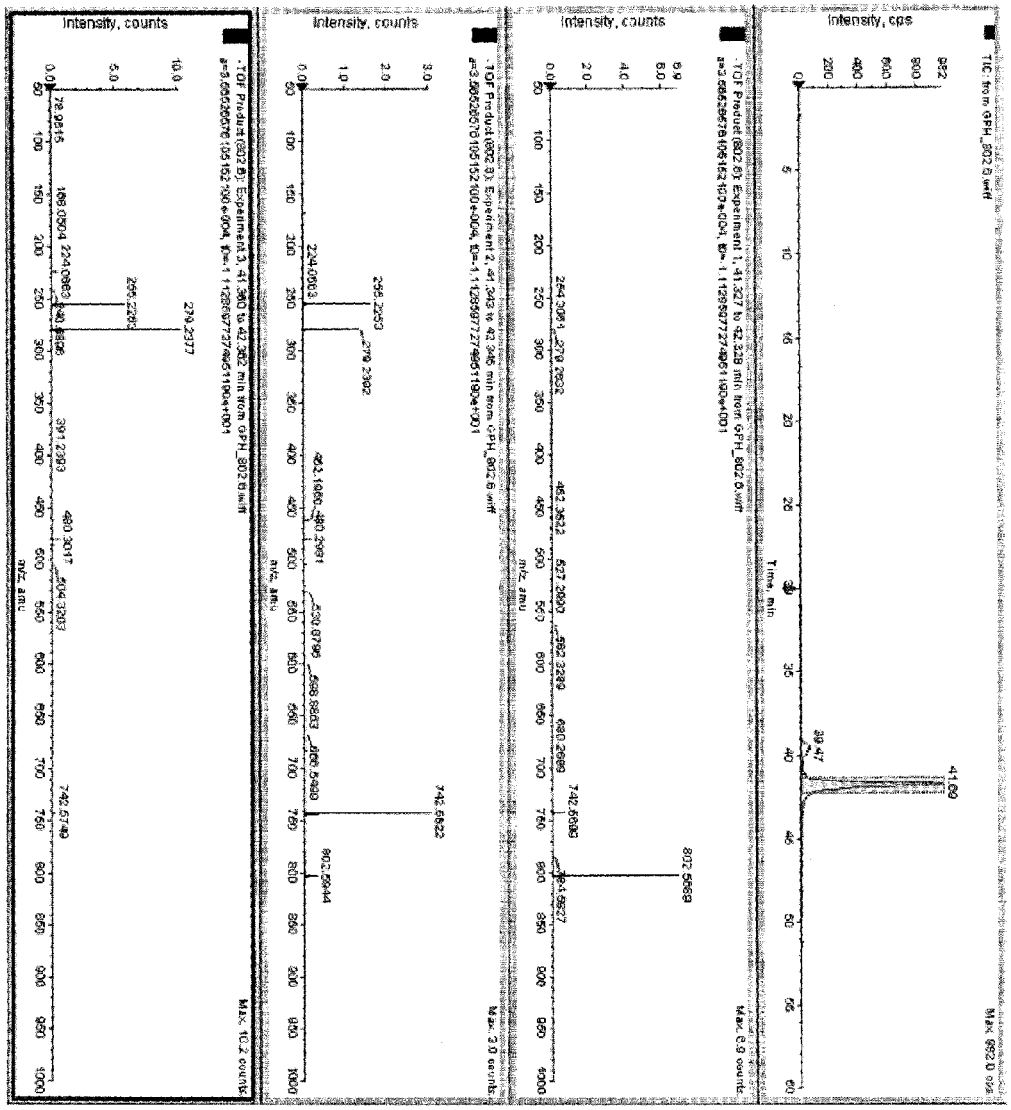
FIG. 27 illustrates the fragmentation pattern of "757.6" as a formic acid adduct in negative aqueous ESI mode, showing two main side chains, 16:0 (m/z 255.2) and 18:2 (m/z 279.2). "757.6" is therefore PtdCho 16:0/18:2 and PtdCho 18:2/16:0.
Figure 28:
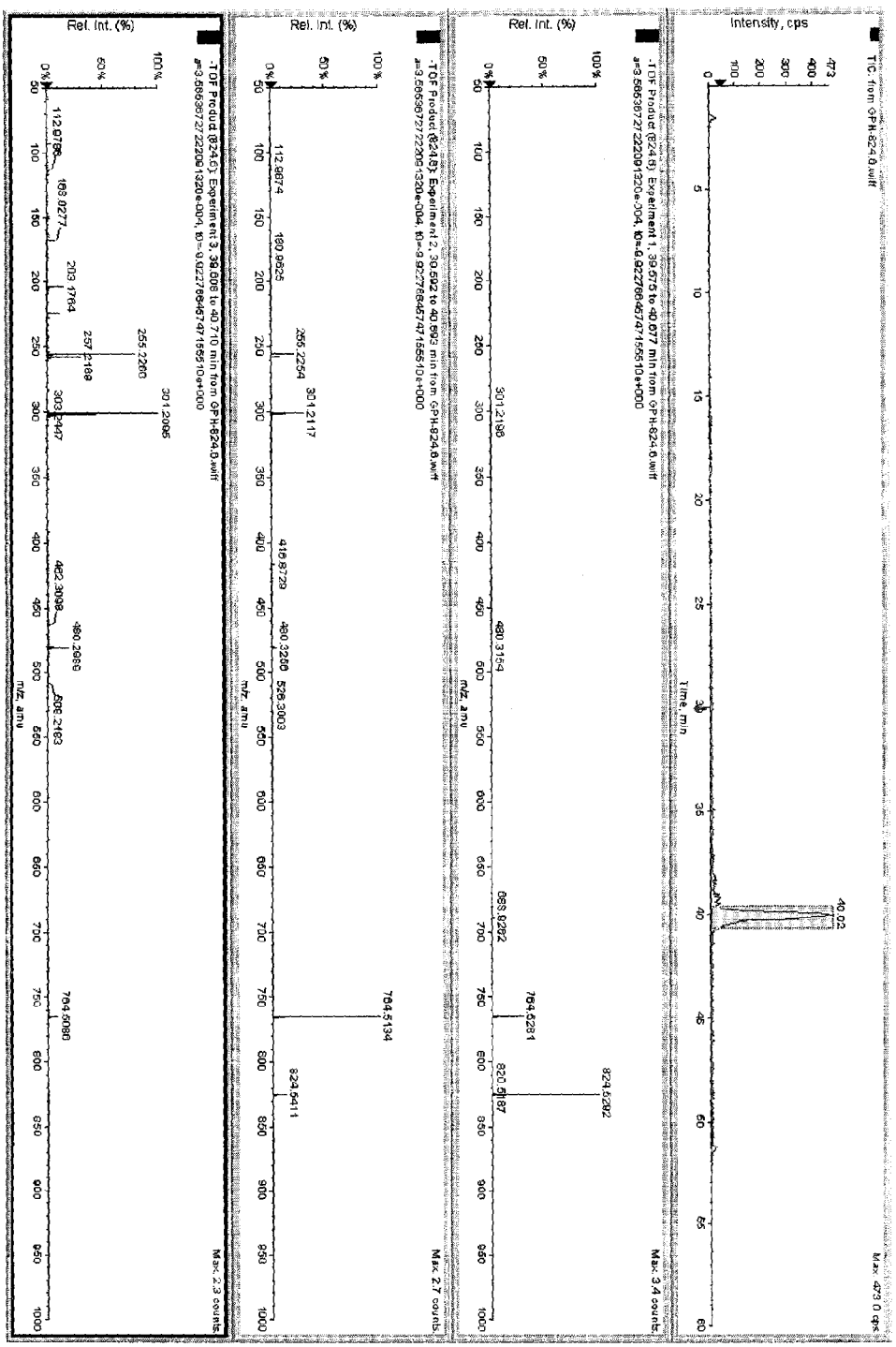
FIG. 28 illustrates the fragmentation pattern of "779.6" as a formic acid adduct in negative aqueous ESI mode, showing the side chains 16:0 (m/z 255.2), 20:5 (m/z 301.2) and 20:4 (m/z 303.2) as the most abundant. "779.6" is therefore mostly PtdCho 16:0/20:5, PtdCho 20:5/16:0 and PtdCho 18:2/20:4.
Figure 29:
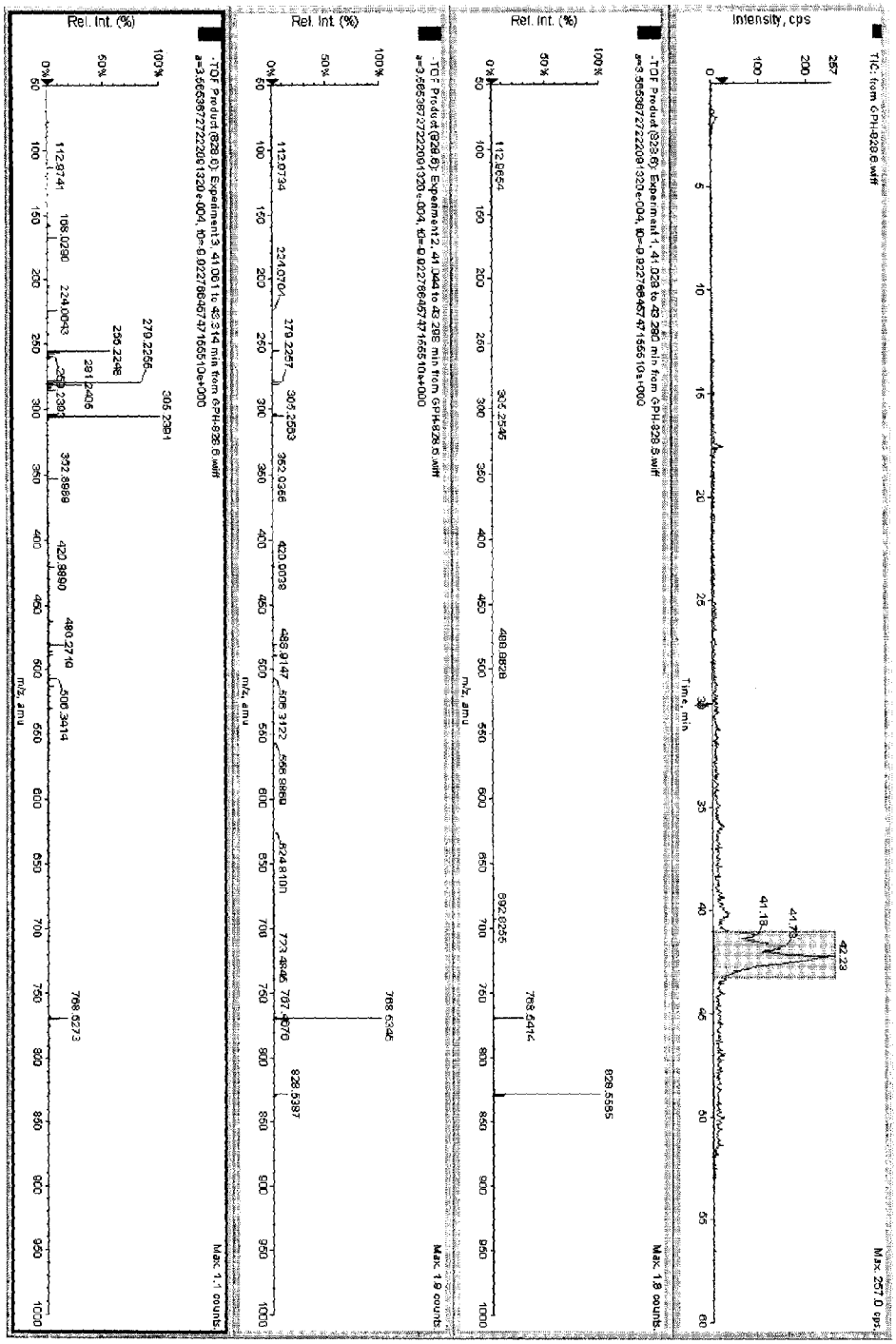
FIG. 29 illustrates the fragmentation pattern of "783.6" as a formic acid adduct in negative ESI aqueous mode, showing the side chains 20:3 (m/z 305.2), 18:2 (m/z 279.2), 18:1 (m/z 281.2) and 16:0 (m/z 255.2) as the most abundant. "783.6" therefore mostly is PtdCho 16:0/20:3 and PtdCho 18:1/18:2.
Figure 30:
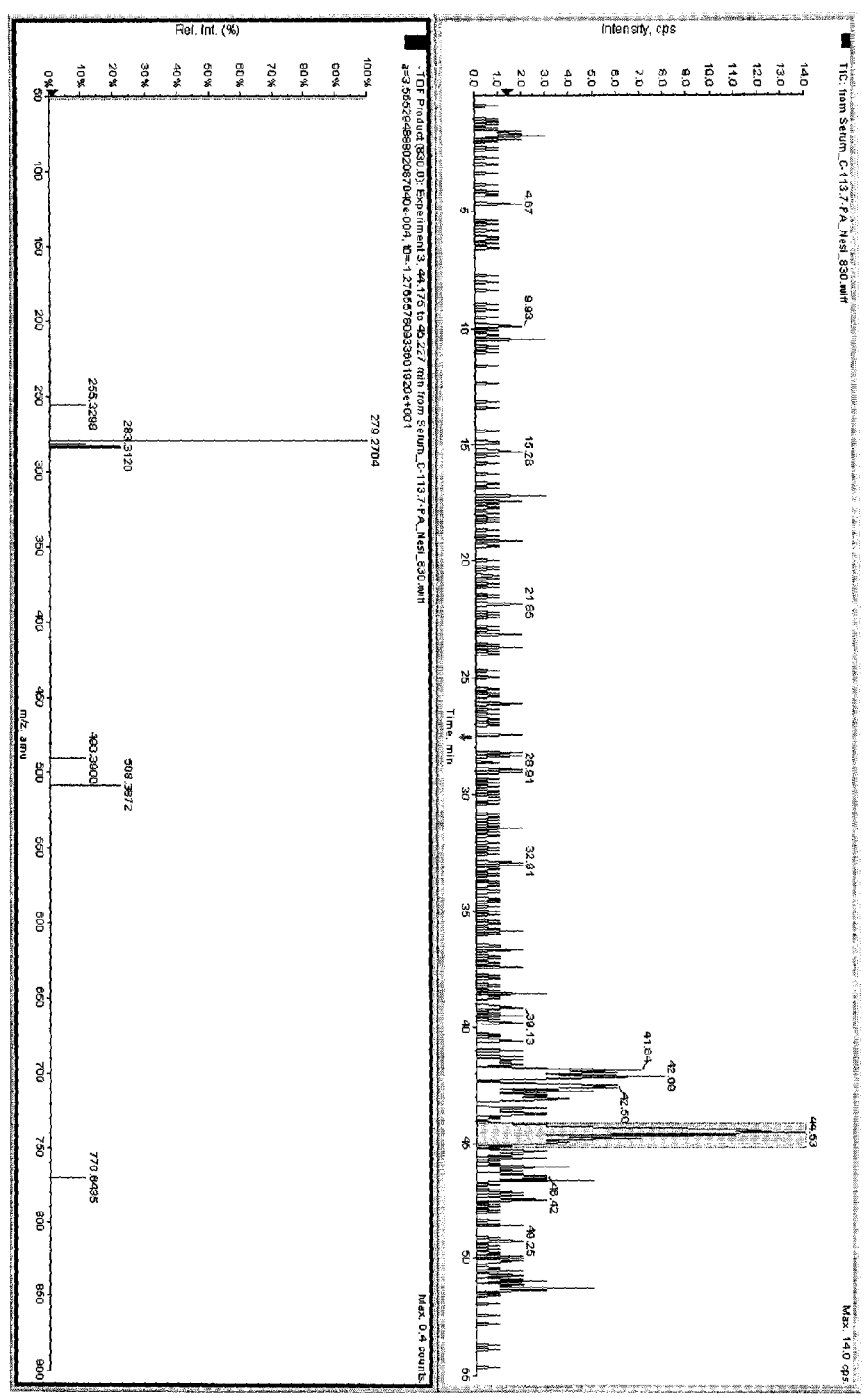
FIG. 30 illustrates the fragmentation pattern of "785.6" as a formic acid adduct in negative aqueous ESI mode, showing two side chains, 18:0 (m/z 283.3) and 18:2 (m/z 279.2)
Figure 30:
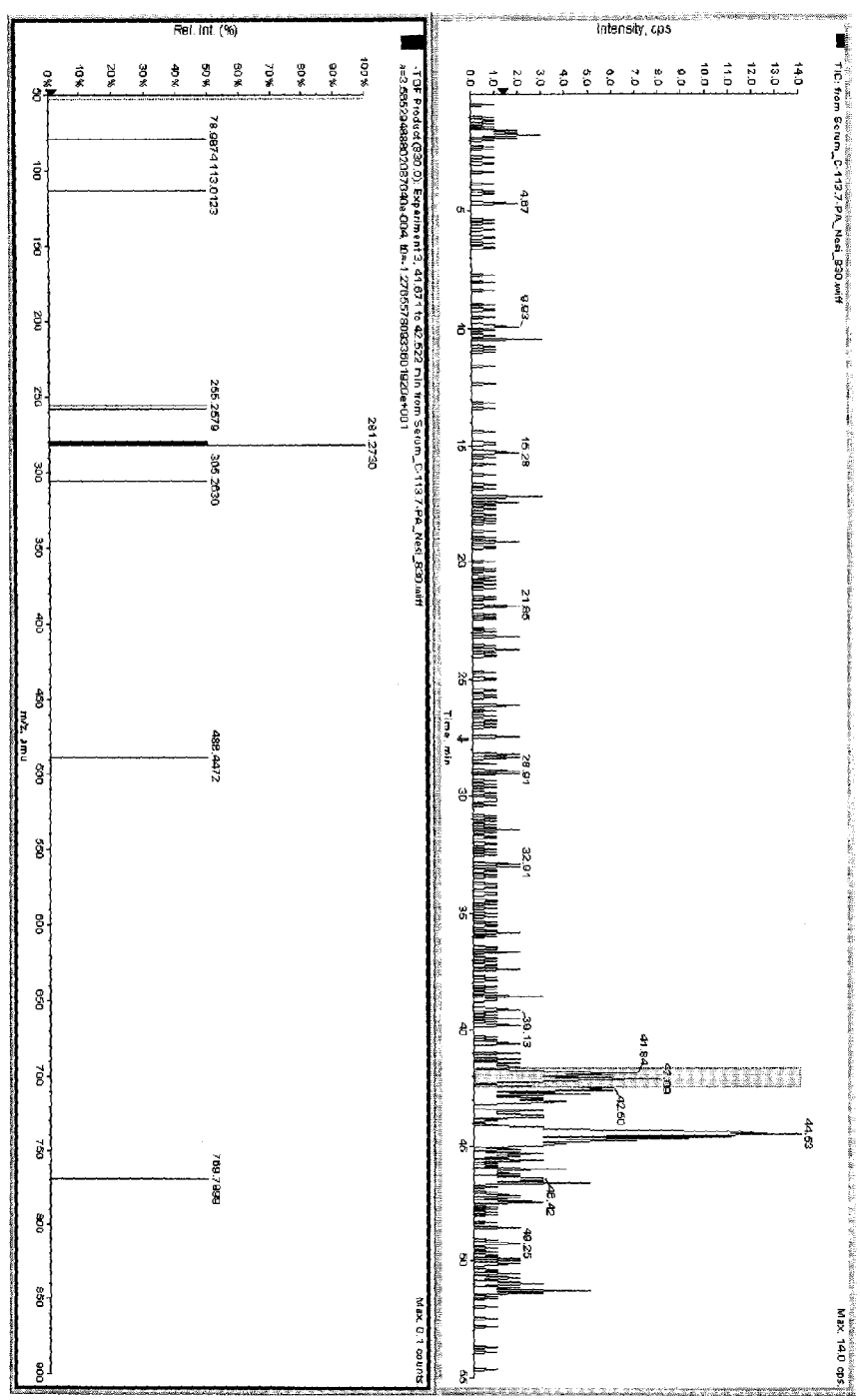

Fragmentation pattern of all compounds seems restricted to one main fragment (m/z 184) for all masses, which likely corresponds to choline phosphate (FIGS. 17 to 20, 22 to 26), except for 803.5 (FIG. 21). The fragmentation pattern of 803.5 rather suggests the majority of the compounds at this mass to be the sodium adducts of 781.5566.

In order to confirm the chemical family of these putative phosphatidylcholines, the same samples were run in aqueous negative ESI mode (Table 14). Fragmentation patterns are shown in FIGS. 27 to 32 that show how to determine the PtdCho side chains.

TABLE 14

Fragmentation pattern of putative phosphatidylcholines in negative ESI mode, with daughter ion relative abundance.

| Accurate/ Exact Mass | MS/MS Formic acid adduct (% intensity) | Daughter ions (% intensity) | Collision Energy |
|---|---|---|---|
| 757.5560 | 802.5 (1%) | 745 (9%), 480 (9%), 279 (100%), 255 (26%) | −35 V |
| 779.5405 | 824.5 (12%) | 764 (100%), 480 (4%), 301, (30%) 255 (19%) | −35 V |
| 783.5690 | 828.6 (16%) | 768 (100%), 480 (5%), 305 (15%), 279 (9%), 255 (9%), 224 (2%) | −35 V |

TABLE 14-continued

Fragmentation pattern of putative phosphatidylcholines in negative ESI mode, with daughter ion relative abundance.

| Accurate/ Exact Mass | MS/MS Formic acid adduct (% intensity) | Daughter ions (% intensity) | Collision Energy |
|---|---|---|---|
| 785.5913 | 830.6 (1%) | 770 (11%), 283 (22%), 281 (11%), 279 (100%) | −45 V |
| 803.5373 | 848.5 (1%) | 788 (100%), 576 (8%), 508 (8%), 492 (8%), 474 (8%), 440 (16%), 301 (16%) | −35 V |
| 805.5549 | 850.6 (1%) | 790 (33%), 255 (100%) | −35 V |
| 807.5734 | 852.6 (1%) | 792 (32%), 508 (16%), 480 (12%), 329 (52%), 301 (100%), 283 (56%), 257 (48%), 255 (336%), 224 (16%), 203 12%) | −45 V |
| 809.5796 | 854.6 (5%) | 794 (23%), 508 (12%), 378 (7%), 303 (100%), 283 (41%), 259 (17%), 242 (9%), 227 (7%), 205 (9%), 168 (7%) | −45 V |
| 829.5516 | 852.6 (1%) | 792 (32%), 508 (16%), 480 (12%), 329 (52%), 301 (100%), 283 (56%), 257 (48%), 255 (336%), 224 (16%), 203 12%) | −45 V |
| 833.5864 | 878.6 (1%) | 818 (33%), 508 (33%), 490 (33%), 327 (67%), 283 (100%) | −35 V |

Side chain combinations may be unique, such as in 757.6, corresponding to both PtdCho 16:0/18:2 and PtdCho 18:2/16:0 (FIG. 27), or multiple, such as in 807.6, corresponding to PtdCho 18:0/20:5, PtdCho 16:0/22:5 and PtdCho 18:1/20:4, all with the same chemical formula $C_{46}H_{82}NO_8P$ (FIG. 32). Confirmed side chains for all PtdCho biomarkers are reported in Table 15.

TABLE 15

Assignment of side chains to PtdCho according to MS/MS data analysis

| Mass | Formula | | Identity | | |
|---|---|---|---|---|---|
| 757.556 | $C_{42}H_{80}NO_8P$ | PtdCho16:0/18:2 | PtdCho18:2/16:0 | | |
| 779.5405 | $C_{44}H_{78}NO_8P$ | PtdCho18:3/18:2 | PtdCho16:0/20:5 | PtdCho20:5/16:0 | PtdCho20:4/18:1 |
| 783.569 | $C_{44}H_{82}NO_8P$ | PtdCho16:0/20:3 | PtdCho18:1/18:2 | PtdCho18:0/18:3 | |
| 785.5913 | $C_{44}H_{84}NO_8P$ | PtdCho18:0/18:2 | PtdCho18:1/18:1 | | |
| 803.5373 | $C_{46}H_{78}NO_8P$ | PtdCho20:5/18:2 | PtdCho16:1/22:6 | PtdCho22:6/16:1 | |
| 805.5549 | $C_{46}H_{80}NO_8P$ | PtdCho22:6/16:0 | PtdCho18:2/20:4 | | |
| 807.5734 | $C_{46}H_{82}NO_8P$ | PtdCho18:0/20:5 | PtdCho16:0/22:5 | PtdCho18:1/20:4 | PtdCho22:5/16:0 |
| 809.5796 | $C_{46}H_{84}NO_8P$ | PtdCho18:0/20:4 | PtdCho18:1/20:3 | PtdCho18:2/20:2 | PtdCho16:0/22:4 |
| 827.5401 | $C_{48}H_{78}NO_8P$ | Na adduct of 805.55 | PtdCho18:3/22:6 | | |
| 829.5516 | $C_{48}H_{80}NO_8P$ | PtdCho18:2/22:6 | Na adduct of 807.57 | PtdCho18:3/22:5 | |
| 833.5864 | $C_{48}H_{84}NO_8P$ | PtdCho22:6/18:0 | Na adduct of 811.6 | PtdCho18:1/22:5 | PtdCho16:0/24:6 |

The fragmentation pattern of the putative sphingomyelins confirmed the presence of a choline phosphate fragment as the major peak for 702.6 and 812.7, suggesting that these two compounds respectively are the common sphingomyelins SM(d18:1/16:0) and SM(d18:1/24:1(15Z)) with the sphingosine (18:1) as the sphingoid base (FIGS. 33 and 34). The fragmentation pattern of 724.5 suggests that the compound is the sodium adduct of 702.6 above mentioned (FIG. 35).

The sphingomyelin identity of these two compounds was confirmed by a further analysis in aqueous negative ESI mode, through the comparison between the serum compounds with a mass of 702.6 and 812.7 and the commercially available sphingomyelins SM(d18:1/16:0) and SM(d18:1/24:1(15Z)). The fragmentation pattern of the serum compound with a mass of 702.6 detected as a formic acid adduct in negative ESI mode (FIG. 36) is indeed identical to the fragmentation pattern of the synthetic SM(d18:1/16:0) (FIG. 37). Similarly, the fragmentation pattern of the serum compound with a mass of 812.7 detected as a formic acid adduct in negative ESI mode (FIG. 38) is identical to the fragmentation pattern of the synthetic SM(d18:1/24:1(15Z)) (FIG. 39).

2C. Other Compound 600.5117 compound in 1203 analysis mode was further analyzed by tandem mass spectrometry mass fragmentation. The fragmentation pattern, dominated by peaks at 545.5, 527.5 and 263.3, confirms that a compound with the molecular formula indicated in table 6 is present and can be classified as 1-alkenyl-2-acylglycerol with 18:2 at both side chains (FIG. 40).

Validation Using Multiple Reaction Monitoring Methodology

Reduced levels of choline-related compounds and C36 biomarkers in the blood of pancreatic cancer patients were further confirmed using a tandem mass spectrometry approach (see methods) in the same populations. The approach is based upon the measurement of parent-daughter fragment ion combinations (referred to as multiple-reaction monitoring; MRM) for quantifying analytes.

3A. MRM for Lysophosphatidylcholines

A tandem-MS approach based upon multiple reaction monitoring was used to confirm differences in LysoPC levels between patients and controls using the same aqueous extracts as for the FTICR-MS analysis, in both positive and negative ElectroSpray Ionization modes (see methods for formulae and transitions). FIG. 41 reports the confirmation that the levels in the 3 lysophosphatidylcholines listed in Table 6 and in 20 additional LysoPC are significantly decreased in pancreatic cancer patients relative to controls.

The lowest p-values among all LysoPC tested by MRM are obtained for LysoPC present in the 20 best FTICR biomarkers as could be expected, with the minimal value in positive ESI analysis mode, 2.69E-15, obtained for LysoPC18:2, the second best putative LysoPC by FTICR. Overall, the significant decreases observed in 23 LysoPC suggest that the whole family is down-regulated in pancreatic cancer serum.

3B. MRM for PtdCho and Plasmenylphosphocholine (PlsCho)

The same aqueous extracts as for the FTICR-MS analysis were analyzed by a targeted method for 7 PtdCho out of the 10 listed in Table 6 and 6 additional PtdCho in positive analysis mode, and for 9 PtdCho out of the 10 listed in Table 6 and many additional PtdCho in negative analysis mode. FIGS. 42a and 42b report the confirmation that the serum levels of all PtdCho tested in both positive and negative ESI analysis modes are significantly decreased in pancreatic cancer patients relative to controls. The best putative PtdCho among FTICR best biomarkers, "785.6", is also the best PtdCho among all tested by MRM in positive ESI analysis mode, with a p-value of 5.77E-18. It is interesting to note that all PtdCho tested are decreased in pancreatic cancer serum independently of their side chains, with a maximal p-value of 5.31E-10 in positive ESI analysis mode, demonstrating that the whole phosphatidylcholine family is collectively down-regulated in pancreatic cancer serum.

The decrease in PtdCho family incited us to assess the levels of their vinyl ether counterparts, plasmenylphosphocholines (PlsCho), in the same samples. FIG. 42c reports that the serum levels of all PlsCho tested in positive Electrospray Ionization analysis mode are very significantly decreased in pancreatic cancer patients relative to controls. PlsCho with a mass of 793.6, which likely is PlsCho 18:0/20:4, shows the lowest p-value, 3.9E-17.

3D. MRM for Sphingomyelins

A tandem-MS approach based upon multiple reaction monitoring was developed to confirm differences in sphingomyelin levels between patients and controls using the same aqueous extracts as for the FTICR-MS analysis. FIG. 43 reports that the serum levels of the five sphingomyelins tested (including the two identified by FTICR analysis, SM(d18:1/16:0) and SM(d18:1/24:1(15Z)) are very significantly decreased in pancreatic cancer patients relative to controls. SM(d18:1/24:0), which had not been detected by FTICR shows the strongest decrease with a p-value of 7.81E-15.

3D. MRM for C36 Biomarkers

A tandem-MS approach based upon multiple reaction monitoring was developed to confirm differences in C36 biomarker levels between patients and controls using the same ethyl acetate extracts as for the FTICR-MS analysis. As explained in 2A, among all masses listed in Table 5, several seemed to belong to a same family in C36, only differing by an $H_2O$ molecule or the number of unsaturations, and the tandem-MS method was extended to the whole "C36 family" (see methods for formulae and transitions).

FIG. 44 reports the confirmation that the levels in the seven C36 markers tested are significantly decreased in pancreatic cancer patients relative to controls. The best putative C36 marker among all FTICR biomarkers (which is also the best biomarker of pancreatic cancer), "594", is also the best biomarker among all C36 tested by MRM, with a p-value of 1.42E-11. Again, it is interesting to note that as a whole family, the C36 markers seem down-regulated in pancreatic cancer serum.

Disease Stage Analysis

Information regarding disease progression status was included. It was therefore determined whether there were a correlation between disease progression and biomarker decrease. MRM data for the 3 LysoPC, 7 PtdCho and 3 C36 markers of interest were re-analyzed according to cancer stage (FIG. 45). This preliminary study on a small amount of patients per stage does not seem to indicate any trends.

Chemoradiation Therapy Effects on Biomarkers

Information regarding chemoradiation therapy status was included. It was therefore determined whether there was a correlation between this kind of therapy and biomarker decrease. MRM data for the 3 LysoPC, 7 PtdCho and 3 C36 markers of interest were re-analyzed according to therapy status (FIG. 46). This preliminary study on a small amount of patients seems to indicate that there is no effect of chemoradiation therapy on biomarkers.

Discussion

We have performed a comprehensive non-targeted metabolomic profiling of pancreatic cancer serum samples and have identified a very strong signature of this cancer as illustrated by most AUCs above 0.90. The families of markers identified by FTICR as discriminating were validated by targeted analysis. Four families have been identified whose decrease is associated to pancreatic cancer: phosphatidylcholines, lysophosphatidylcholines, sphingomyelins and C36 markers that may be steroidal-like compounds.

Lysophosphatidylcholines 18:2, 18:3 and 20:5 show the strongest decrease of all LysoPC tested. All 27 PtdCho tested (with nine included in the top list of Table 6) show significantly decreased levels in pancreatic cancer patients relative to controls (FIG. 42a,b). Most of the 10 PtdCho in Table 8 are predicted or shown to have 18:2, 20:5 or 22:5 as one of the two side chains, as seen in Table 15. In summary, phosphatidylcholines and lysophosphatidylcholines that contain 18:2, 18:3, 20:5 and in a lesser extent, 22:5, show the strongest decrease.

The presence of sphingomyelins among the best biomarkers is extremely interesting. The role of sphingomyelin in cell death, growth and differentiation, and therefore in cancer, is well documented (25, 26) and cancer therapeutics targeted to their signaling pathways give very promising preliminary results (27, 28). For example, sphingomyelin addition to pancreatic cancer cell lines has been shown to drastically enhance chemosensitivity to anticancer agents, presumably by redirecting the cell to enter the apoptotic pathway (29).

Without wishing to be bound in any way by theory, the alteration observed in both phosphatidylcholines and sphingomyelins suggests a role for choline kinase; this cytosolic enzyme is indeed important for the generation of both species and subsequently for cell division (11). The involvement of the choline kinase during tumorigenesis (mediated by Ras effectors serine/threonine kinase (Raf-1), Ral-GDS and PI3K) and the success of its specific inhibitors in antitumoral activity make this kinase a very attractive target in cancer (11, 30). The present results therefore suggest an involvement of choline kinase in pancreatic carcinogenesis.

The C36 markers described herein have not, to our knowledge, yet been associated to pancreatic cancer. Preliminary NMR studies suggest that these compounds may be steroidal-like or conjugated bile acids. This is very interesting since bile acids are emerging as an important family in cancers of the gastrointestinal tract (31). Mechanistically speaking, although without wishing to be bound by theory, there is a complex balance in the bile between bile salts and phospholipids; the reduced levels in phosphatidylcholines observed in pancreatic cancer may be caused by a reduced export into bile, which could be reflective of MDR3 gene polymorphisms (20). An unbalance observed between phosphatidylcholines and bile acids may therefore reflect some genetic alterations underlying carcinogenesis.

A major effect of clinical variables on the alterations of biomarkers has not been identified on the whole pancreatic cancer population. Disease stages do not seem to affect the decrease in biomarkers. The observation that there are no stage effects suggests that the metabolic deficiency may precede the development of pancreatic cancer, and therefore supports the utility as an early detection risk screening method. A chemoradiation therapy effect on biomarkers was also not observed, suggesting that this therapy does not affect the underlying mechanism of pancreatic cancer; a normalization of biomarkers after treatment would therefore be a good efficacy indicator of new therapeutics.

Statistical analysis revealed how discriminating a few biomarkers could be between pancreatic cancer and healthy controls. For example, the six FTICR best biomarkers all present with a p-value lower than 1E-12 and individual AUCs above 0.90. They have been afterwards identified as most likely being a lysophosphatidylcholine, a sphingomyelin, two phosphatidylcholines and two C36 markers (one being the best biomarker, "594", with p=9.9E-14 and the highest AUC). When these markers are combined, the AUC reaches 0.985, with a specificity of 92.5% and a sensitivity of 88%, illustrating how a blood draw can be a powerful diagnostic tool in pancreatic cancer.

In summary, we have identified a metabolic dysregulation specific to pancreatic cancer. The characteristic decrease in two main metabolite families, glycerophosphocholine-related compounds (sub grouped in three subfamilies) and previously uncharacterized C36 markers. These metabolites represent useful biomarkers for sensitive and specific detection of pancreatic cancer, which remains the most dreaded cancer because of its extremely low survival rate. The described diagnostic methods, when conducted in conjunction with therapeutic optimization steps, may also be used to design more efficacious drug therapies for the disease.

One or more currently preferred embodiments have been described by way of example. It will be apparent to persons skilled in the art that a number of variations and modifications can be made without departing from the scope of the invention as defined in the claims.

REFERENCES

1. Boyle, P., and J. Ferlay. 2005. Cancer incidence and mortality in Europe, 2004. *Ann Oncol* 16: 481-488.
2. Däbritz, J., R. Preston, J. Hänfler, and H. Oettle. 2009. Follow-up study of K-ras mutations in the plasma of patients with pancreatic cancer: correlation with clinical features and carbohydrate antigen 19-9. *Pancreas* 38: 534-541.
3. Klapman, J., and M. P. Malafa. 2008. Early detection of pancreatic cancer: why, who, and how to screen. *Cancer Control.* 15: 280-287.
4. Helmstaedter, L., and J. F. Riemann. 2008. Pancreatic cancer—EUS and early diagnosis. *Langenbecks Arch Surg* 393: 923-927.
5. Gemmel, C., A. Eickhoff, L. Helmstälter, and J. F. Riemann. 2009. Pancreatic cancer screening: state of the art. *Expert Rev Gastroenterol Hepatol.* 3: 89-96.
6. Peracaula, R., S. Barrabés, A. Sarrats, P. M. Rudd, and R. de Llorens. 2008. Altered glycosylation in tumours focused to cancer diagnosis. *Dis Markers* 25: 207-218.
7. Ehmann, M., K. Felix, D. Hartmann, M. Schnölzer, M. Nees, S. Vorderwülbecke, R. Bogumil, M. W. Büchler, and H. Friess. 2007. Identification of potential markers for the detection of pancreatic cancer through comparative serum protein expression profiling. *Pancreas* 34: 205-214.
8. Barrabés, S., L. Pagés-Pons, C. M. Radcliffe, G. Tabarés, E. Fort, L. Royle, D. J. Harvey, M. Moenner, R. A. Dwek, P. M. Rudd, R. De Llorens, and R. Peracaula. 2008. Glycosylation of serum ribonuclease 1 indicates a major endothelial origin and reveals an increase in core fucosylation in pancreatic cancer. *Glycobiology* 17: 388-400.
9. Koopmann, J., C. N. White Rosenzweig, Z. Zhang, M. I. Canto, D. A. Brown, M. Hunter, C. Yeo, D. W. Chan, S, N. Breit, and M. Goggins. 2006. Serum Markers in Patients with Resectable Pancreatic Adenocarcinoma: Macrophage Inhibitory Cytokine 1 versus CA19-9 *Clinical Cancer Research* 12: 442-446.
10. Rosty, C., L. Christa, S. Kuzdzal, B. W. M., M. L. Zahurak, F. Carnot, D. W. Chan, M. Canto, K. D. Lillemoe, J. L. Cameron, C. J. Yeo, R. H. Hruban, and M. Goggins. 2002. Identification of hepatocarcinoma-intestine-pancreas/pancreatitis-associated protein I as a biomarker for pancreatic ductal adenocarcinoma by protein biochip technology. *Cancer research* 62: 1868-1875.
11. Janardhan, S., P. Srivani, and G. N. Sastry. 2006. Choline kinase: an important target for cancer. *Curr Med Chem* 13: 1169-1186.
12. Garcea, G., C. P. Neal, C. J. Pattenden, W. P. Steward, and D. P. Berry. 2005. Molecular prognostic markers in pancreatic cancer: a systematic review. *Eur J Cancer* 41: 2213-2236.
13. Bloomston, M., W. L. Frankel, F. Petrocca, S. Volinia, H. Alder, J. P. Hagan, C. G. Liu, D. Bhatt, C. Taccioli, and C. M. Croce. 2007. MicroRNA expression patterns to differentiate pancreatic adenocarcinoma from normal pancreas and chronic pancreatitis. *JAMA* 297: 1901-1908.
14. Szafranska, A. E., T. S. Davison, J. John, T. Cannon, B. Sipos, A. Maghnouj, E. Labourier, and S. A. Hahn. 2007. MicroRNA expression alterations are linked to tumorigenesis and non-neoplastic processes in pancreatic ductal adenocarcinoma. *Oncogene* 26: 4442-4452.
15. Lee, E. J., Y. Gusev, J. Jiang, G. J. Nuovo, M. R. Lerner, W. L. Frankel, D. L. Morgan, R. G. Postier, D. J. Brackett, and T. D. Schmittgen. 2007. Expression profiling identifies microRNA signature in pancreatic cancer. *Int J Cancer* 120: 1046-1054.
16. Tian, M., Y. Z. Cui, G. H. Song, M. J. Zong, X. Y. Zhou, Y. R. Chen, and J. X. Han. 2008. Proteomic analysis identifies MMP-9, DJ-1 and A1BG as overexpressed proteins in pancreatic juice from pancreatic ductal adenocarcinoma patients *BMC Cancer* 8: 241.
17. Warden, C. H., A. Daluiski, X. Bu, D. A. Purcell-Huynh, C. De Meester, B. H. Shieh, D. L. Puppione, R. M. Gray, G. M. Reaven, Y. D. Chen, and e. al. 1993. Evidence for linkage of the apolipoprotein A-II locus to plasma apolipoprotein A-II and free fatty acid levels in mice and humans. *Proceedings of the National Academy of Sciences of the United States of America* 90: 10886-10890.
18. Trougakos, I. P., and E. S. Gonos. 2002. Clusterin/apolipoprotein J in human aging and cancer. *The international journal of biochemistry & cell biology* 34: 1430-1448.
19. Zuijdgeest-van Leeuwen, S. D., M. S. van der Heijden, T. Rietveld, J. W. van den Berg, H. W. Tilanus, J. A. Burgers, J. H. Wilson, and P. C. Dagnelie. 2002. Fatty acid composition of plasma lipids in patients with pancreatic, lung and oesophageal cancer in comparison with healthy subjects. *Clinical Nutrition* 21: 225-230.
20. Khan, S. A., I. J. Cox, A. V. Thillainayagam, D. S. Bansi, H. C. Thomas, and S. D. Taylor-Robinson. 2005. Proton and phosphorus-31 nuclear magnetic resonance spectroscopy of human bile in hepatopancreaticobiliary cancer. *Eur J Gastroenterol Hepatol* 17: 733-738.
21. Kolb, A., S. Rieder, D. Born, N. A. Giese, T. Giese, G. Rudofsky, J. Werner, M. W. Büchler, H. Friess, I. Esposito, and J. Kleeff. 2009. Glucagon/insulin ratio as a potential biomarker for pancreatic cancer in patients with new-onset diabetes mellitus. *Cancer Biol Ther* 8.

22. Gray, G. R., and D. Heath. 2005. A global reorganization of the metabolome in *Arabidopsis* during cold acclimation is revealed by metabolic fingerprinting. *Physiologia Plantarum* 124: 236-248.
23. Goodenowe, D. B., L. L. Cook, J. Liu, Y. Lu, D. A. Jayasinghe, P. W. Ahiahonu, D. Heath, Y. Yamazaki, J. Flax, K. F. Krenitsky, D. L. Sparks, A. Lerner, R. P. Friedland, T. Kudo, K. Kamino, T. Morihara, M. Takeda, and P. L. Wood. 2007. Peripheral ethanolamine plasmalogen deficiency: a logical causative factor in Alzheimer's disease and dementia. *Journal of lipid research* 48: 2485-2498.
24. Aharoni, A., C. H. Ric de Vos, H. A. Verhoeven, C. A. Maliepaard, G. Kruppa, R. Bino, and D. B. Goodenowe. 2002. Nontargeted metabolome analysis by use of Fourier Transform Ion Cyclotron Mass Spectrometry. *Omics* 6: 217-234.
25. Dyatlovitskaya, E. V., and A. G. Kandyba. 2006. Role of biologically active sphingolipids in tumor growth. *Biochemistry (Mosc)*. 71: 10-17.
26. Clària, J. 2006. Regulation of cell proliferation and apoptosis by bioactive lipid mediators. *Recent Pat Anticancer Drug Discov.* 1: 369-382.
27. Billich, A., and T. Baumruker. 2008. Sphingolipid metabolizing enzymes as novel therapeutic targets. *Subcell Biochem* 49: 487-522.
28. Modrak, D. E., D. V. Gold, and D. M. Goldenberg. 2006. Sphingolipid targets in cancer therapy. *Mol Cancer Ther* 5: 200-208.
29. Modrak, D. E., E. Leon, D. M. Goldenberg, and D. V. Gold. 2009. Ceramide regulates gemcitabine-induced senescence and apoptosis in human pancreatic cancer cell lines. *Mol Cancer Res* 7: 890-896.
30. Ramírez de Molina, A., D. Gallego-Ortega, J. Sarmentero-Estrada, D. Lagares, T. Gómez Del Pulgar, E. Bandrés, J. García-Foncillas, and J. C. Lacal. 2008. Choline kinase as a link connecting phospholipid metabolism and cell cycle regulation: implications in cancer therapy. *The international journal of biochemistry & cell biology* 40: 1753-1763.
31. Bernstein, H., C. Bernstein, C. M. Payne, and K. Dvorak. 2009. Bile acids as endogenous etiologic agents in gastrointestinal cancer. *World J Gastroenterol* 15: 3329-3340.

What is claimed is:

1. An analytical method for diagnosing pancreatic cancer in a patient, comprising the steps of:
   a) performing a mass spectrometry assay on at least one blood sample from said patient using a Fourier transform ion cyclotron resonance, time of flight, magnetic sector, quadrupole or triple quadrupole mass spectrometer to obtain a collision induced dissociation (CID) MS/MS fragmentation pattern for one or more than one metabolite marker and to obtain quantifying data for said one or more than one metabolite marker;
   b) generating a result of said mass spectrometry assay, said result comprising at least the presence or absence of a decrease in the level of said one or more than one metabolite marker in said blood sample based on a comparison of said quantifying data for said one or more than one metabolite marker to corresponding data obtained for one or more than one reference blood sample; and
   c) assigning the patient as having or not having pancreatic cancer, wherein a decrease in the level of said one or more than one metabolite marker in said blood sample indicates the presence of pancreatic cancer, wherein the one or more metabolite marker is at least:
   a metabolite having the molecular formula of $C_{36}H_{66}O_6$ and which is characterized by a CID MS/MS fragmentation pattern using $N_2$ as collision gas and analyzed under negative ionization comprising the following daughter ions: 593.5, 557.5, 575.4, 549.4, 531.5, 513.4, 495.4, 433.3, 421.4, 415.2, 391.4, 371.3, 315.3, 311.1, 297.2, 281.2, 277.2, 251.2, 201.1, 195.3, 171.1, 139.1 and 133.5.

2. The method of claim 1, wherein the mass spectrometer is equipped with a chromatographic system.

3. The method of claim 1, wherein the blood sample is a blood serum sample.

4. The method of claim 1, wherein a liquid/liquid extraction is performed on the blood sample whereby non-polar metabolites are dissolved in an organic solvent and polar metabolites are dissolved in an aqueous solvent.

5. The method of claim 4, wherein the extracted samples are analyzed by: positive or negative electrospray ionization, positive or negative atmospheric pressure chemical ionization, or combinations thereof; by MS/MS transition; or by extracted ion current (EIC) chromatography and MS/MS transition.

6. The method of claim 1, wherein said one or more than one reference blood sample is from one or more pancreatic cancer-negative humans.

7. The method of claim 1, further comprising:
   performing a mass spectrometry assay on a blood sample from said patient to obtain quantifying data for one or more than one internal standard molecule; and
   obtaining a ratio for each of the levels of said one or more than one metabolite marker to the level obtained for the one or more than one internal standard molecule;
   wherein step (b) comprises generating said result based on a comparison of each ratio to one or more corresponding ratios obtained for the one or more than one reference sample.

8. The method of claim 1, wherein the one or more metabolite marker comprises a panel of at least 6 metabolite markers including the metabolite having the molecular formula of $C_{36}H_{66}O_6$ and:
   lysophosphatidylcholine LysoPC 20:5, having a molecular formula of $C_{28}H_{48}NO_7P$ and being characterized by a CID MS/MS fragmentation pattern using $N_2$ as collision gas comprising the following daughter ions: 542.3 and 184.2 in positive ionization mode 586.3 and 526.3 in negative ionization mode and 586.3 and 301.2 in negative ionization mode;
   a phosphatidylcholine having the molecular formula of $C_{44}H_{84}NO_8P$ and being characterized by a CID MS/MS fragmentation pattern using $N_2$ as collision gas comprising the following daughter ions: 786.6 and 184.2 in positive ionization mode, 830.6, 770.6 and 279.2 for PtdCho 18:0/18:2 in negative ionization mode, 830.6, 770.6 and 283.2 for PtdCho 18:2/18:0 in negative ionization mode and 830.6, 770.6 and 281.2 for PtdCho 18:1/18:1 in negative ionization mode;
   a phosphatidylcholine having the molecular formula of $C_{46}H_{82}NO_8P$ and being characterized by a CID MS/MS fragmentation pattern using $N_2$ as collision gas comprising the following daughter ions: 808.6 and 184.2 in positive ionization mode, 852.6, 792.6 and 301.3 for PtdCho 18:0/20:5 in negative ionization mode, 852.6, 792.6 and 329.3 for PtdCho 16:0/22:5 in negative ionization mode, 852.6, 792.6 and 303.2 for PtdCho 18:1/20:4 in negative ionization mode and 852.6, 792.6 and 255.2 for PtdCho 22:5/16:0 in negative ionization mode;

a sphingomyelin having a molecular formula of $C_{39}H_{79}N_2O_6P$ and being characterized by a CID MS/MS fragmentation pattern using $N_2$ as collision gas comprising the following daughter ions: 703.6 and 184.2 in positive ionization mode and 747.6, 687.6 and 168.1 in negative ionization mode; and a metabolite having the molecular formula of $C_{36}H_{64}O_5$ and which is characterized by a CID MS/MS fragmentation pattern using $N_2$ as collision gas and analyzed under negative ionization comprising the following daughter ions: 575.5, 513.5, 557.5, 539.5, 531.5, 499.5, 495.5, 459.4, 417.4, 415.3, 413.3, 403.3, 295.2, 279.2, 260.2, 251.2, 197.9, 119.4, 113.1, and 97.0.

\* \* \* \* \*